United States Patent
Yasukawa et al.

(10) Patent No.: US 11,944,009 B2
(45) Date of Patent: Mar. 26, 2024

(54) COMPOUND, MATERIAL FOR ORGANIC ELECTROLUMINESCENT ELEMENT, ORGANIC ELECTROLUMINESCENT ELEMENT, AND ELECTRONIC DEVICE

(71) Applicant: IDEMITSU KOSAN CO., LTD., Tokyo (JP)

(72) Inventors: Keiichi Yasukawa, Sodegaura (JP); Shota Sawano, Sodegaura (JP); Keiji Okinaka, Sodegaura (JP); Toshinari Ogiwara, Sodegaura (JP); Takushi Shiomi, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 568 days.

(21) Appl. No.: 17/277,928

(22) PCT Filed: Sep. 20, 2019

(86) PCT No.: PCT/JP2019/037042
§ 371 (c)(1),
(2) Date: Mar. 19, 2021

(87) PCT Pub. No.: WO2020/059862
PCT Pub. Date: Mar. 26, 2020

(65) Prior Publication Data
US 2021/0367163 A1   Nov. 25, 2021

(30) Foreign Application Priority Data
Sep. 21, 2018 (JP) .................................. 2018-178031

(51) Int. Cl.
*H10K 85/60* (2023.01)
*C07D 487/04* (2006.01)
(Continued)

(52) U.S. Cl.
CPC ....... *H10K 85/6572* (2023.02); *C07D 487/04* (2013.01); *C09K 11/06* (2013.01);
(Continued)

(58) Field of Classification Search
None
See application file for complete search history.

(56) References Cited

U.S. PATENT DOCUMENTS

| 2012/0037890 A1 | 2/2012 | Okuda et al. |
| 2014/0175419 A1 | 6/2014 | Nakano et al. |

(Continued)

FOREIGN PATENT DOCUMENTS

| CN | 108264478 A | 7/2018 |
| JP | 2016-36022 A | 3/2016 |

(Continued)

OTHER PUBLICATIONS

International Search Report dated Nov. 26, 2019 in PCT/JP2019/037042 filed Sep. 20, 2019, 2 pages.
(Continued)

*Primary Examiner* — Jeffrey D Washville
(74) *Attorney, Agent, or Firm* — Oblon, McClelland, Maier & Neustadt, L.L.P.

(57) ABSTRACT

A compound is represented by one of formulae (11) to (13). $R_1$ to $R_4$ each independently represent a group represented by a formula (1-1), a group represented by a formula (2-1), a group represented by a formula (2-2) or the like. At least one of $R_1$ to $R_4$ is the group represented by the formula (1-1) or the like. At least one of $R_1$ to $R_4$ is the group represented by the formula (2-1), (2-2) or the like. For instance, in the formula (1-1), $R_{11}$ represents a substituent, and $R_{101}$ to $R_{110}$ each independently represent a hydrogen atom or a substituent. For instance, in the formulae (2-1) to (2-2), $R_{161}$ to $R_{168}$
(Continued)

and $R_{171}$ to $R_{180}$ each independently represent a hydrogen atom or a substituent. * each independently represents a bonding position to a carbon atom in a benzene ring in each of the formulae (11) to (13), (11)

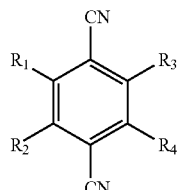

(12)

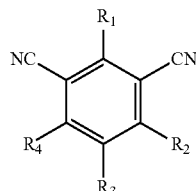

(13)

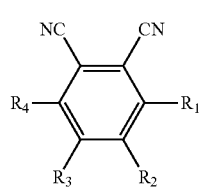

(1-1)

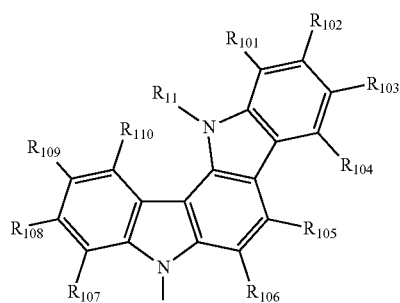

(2-1)

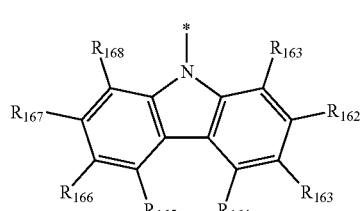

(2-2)

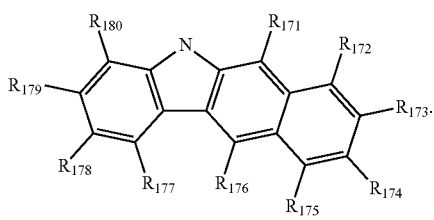

29 Claims, 6 Drawing Sheets

(51) Int. Cl.
  *C09K 11/06* (2006.01)
  *H10K 50/12* (2023.01)
(52) U.S. Cl.
  CPC .... *H10K 85/654* (2023.02); *C09K 2211/1007* (2013.01); *C09K 2211/1018* (2013.01); *H10K 50/121* (2023.02)

(56) References Cited

U.S. PATENT DOCUMENTS

| | | |
|---|---|---|
| 2014/0183486 A1 | 7/2014 | Nakano et al. |
| 2015/0105564 A1 | 4/2015 | Adachi et al. |
| 2016/0072076 A1 | 3/2016 | Stoessel et al. |
| 2016/0130225 A1 | 5/2016 | Tasaki et al. |

FOREIGN PATENT DOCUMENTS

| | | |
|---|---|---|
| WO | WO 2010/098098 A1 | 9/2010 |
| WO | WO 2012/153780 A1 | 11/2012 |
| WO | WO 2013/038650 A1 | 3/2013 |
| WO | WO 2013/154064 A1 | 10/2013 |
| WO | WO 2014/128945 A1 | 8/2014 |
| WO | WO 2014/146752 A1 | 9/2014 |
| WO | WO 2014/208698 A1 | 12/2014 |
| WO | WO 2018/237389 A1 | 12/2018 |

OTHER PUBLICATIONS

Adachi, C., "Yuki Hando-tai no Debaisu Bussei (Device Physics of Organic Semiconductors)", Kodansha, 2012, pp. 261-268, 19 total pages.
Uoyama, H., et al., "Highly efficient organic light-emitting diodes from delayed fluorescence", Nature, vol. 492, 2012, pp. 234-238, 7 total pages.

COMPOUND, MATERIAL FOR ORGANIC ELECTROLUMINESCENT ELEMENT, ORGANIC ELECTROLUMINESCENT ELEMENT, AND ELECTRONIC DEVICE

TECHNICAL FIELD

The present invention relates to a compound, a material for an organic electroluminescence device, an organic electroluminescence device, and an electronic device.

BACKGROUND

When a voltage is applied to an organic electroluminescence device (hereinafter, occasionally referred to as "organic EL device"), holes are injected from an anode and electrons are injected from a cathode into an emitting layer. The injected electrons and holes are recombined in the emitting layer to form excitons. Specifically, according to the electron spin statistics theory, singlet excitons and triplet excitons are generated at a ratio of 25%:75%.

A fluorescent organic EL device using light emission from singlet excitons has been applied to a full-color display such as a mobile phone and a television set, but an internal quantum efficiency is said to be at a limit of 25%. Accordingly, studies has been made to improve a performance of the organic EL device.

Moreover, it is expected to further efficiently emit the organic EL device using triplet excitons in addition to singlet excitons. In view of the above, a highly efficient fluorescent organic EL device using thermally activated delayed fluorescence (hereinafter, sometimes simply referred to as "delayed fluorescence") has been proposed and studied.

For instance, a TADF (Thermally Activated Delayed Fluorescence) mechanism has been studied. The TADF mechanism uses such a phenomenon that inverse intersystem crossing from triplet excitons to singlet excitons thermally occurs when a material having a small energy difference ($\Delta ST$) between singlet energy level and triplet energy level is used. Delayed fluorescence (thermally activated delayed fluorescence) is explained in "Yuki Hando-tai no Debaisu Bussei (Device Physics of Organic Semiconductors)" (edited by ADACHI, Chihaya, published by Kodansha, issued on Apr. 1, 2012, on pages 261-268).

As a compound exhibiting TADF properties (hereinafter also referred to as a TADF compound), for example, a compound in which a donor moiety and an acceptor moiety are bonded in a molecule is known.

For instance, Patent Literatures 1 and 2 disclose a compound in which a fused carbazolyl group and a cyano group are bonded to a benzene ring.

CITATION LIST

Patent Literature(s)

Patent Literature 1: International Publication No. WO2014/146752
Patent Literature 2: International Publication No. WO2014/208698

SUMMARY OF THE INVENTION

Problems to be Solved by the Invention

A compound in which a plurality of cyano groups that each have a relatively high acceptor performance and a plurality of fused carbazolyl groups that each have a relatively high donor performance are simply bonded to a benzene ring, as exemplified by the compound disclosed in Patent Literatures 1 and 2, tends to exhibit a sublimation temperature to be increased when the compound is sublimated and purified. When the sublimation temperature of the compound is increased, a purification time is prolonged to reduce a purification efficiency. In recent years, the sublimation temperature is required to be further decreased in terms of the purification efficiency.

In the meantime, it is crucial that TADF properties of the TADF compound are kept favorable.

An object of the invention is to provide a compound capable of decreasing a sublimation temperature when being sublimated and purified while maintaining TADF properties, an organic-EL-device material containing the compound, an organic EL device containing the compound, and an electronic device provided with the organic EL device.

Another object of the invention is to provide the organic EL device and the electronic device each having an excellent performance by using the compound and the organic-EL-device material containing the compound, to provide a compound capable of achieving the organic EL device and the electronic device each having an excellent performance, and to provide the organic-EL-device material containing the corn pound.

Means for Solving the Problems

According to an aspect of the invention, a compound represented by one of formulae (11) to (13) below is provided.

[Formula 1]

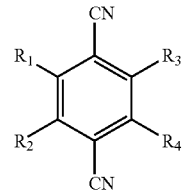

(11)

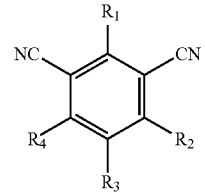

(12)

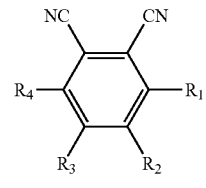

(13)

In the formulae (11) to (13): $R_1$ to $R_4$ are each independently one of groups represented by formulae (1-1) to (1-6) below or one of groups represented by formulae (2-1) to (2-10); at least one of $R_1$ to $R_4$ is one of groups represented by the formulae (1-1) to (1-6); and at least one of $R_1$ to $R_4$ is one of groups represented by the formulae (2-1) to (2-10).

[Formula 2]

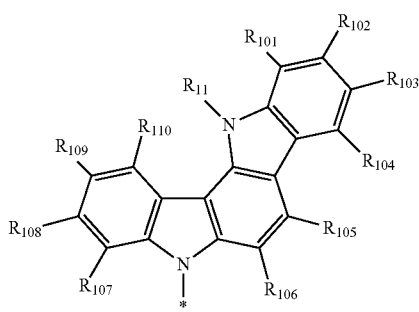
(1-1)

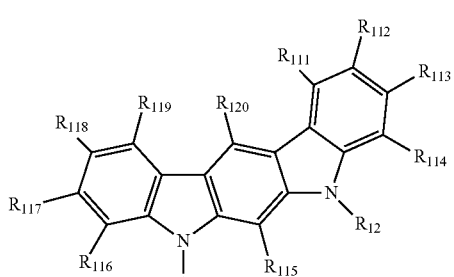
(1-2)

[Formula 3]

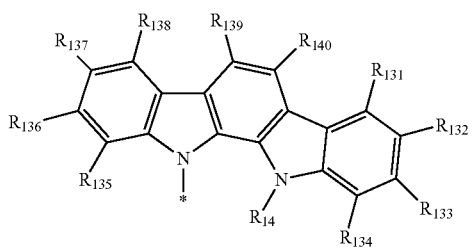
(1-3)

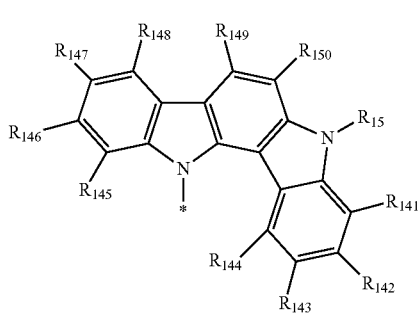
(1-4)

[Formula 4]

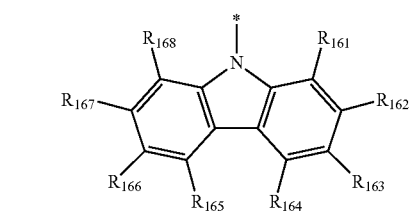
(1-5)

(1-6)

In the formulae (1-1) to (1-6), $R_{11}$ to $R_{16}$ are substituents, $R_{101}$ to $R_{150}$ and $R_{61}$ to $R_{70}$ are each independently a hydrogen atom or a substituent.

$R_{101}$ to $R_{150}$ and $R_{61}$ to $R_{70}$ as the substituent are each independently a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkysilyl group having 3 to 6 carbon atoms, a substituted or unsubstituted alkoxy group having 1 to 6 carbon atoms, a substituted or unsubstituted aryloxy group having 6 to 14 ring carbon atoms, a substituted or unsubstituted arylamino group having 6 to 28 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

$R_{11}$ to $R_{16}$ as the substituent are each independently a substituted or unsubstituted alkyl group having 1 to 6 carbon atoms, a substituted or unsubstituted aryl group having 6 to 14 ring carbon atoms, a substituted or unsubstituted heterocyclic group having 5 to 14 ring atoms, a substituted or unsubstituted alkysilyl group having 3 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

* each independently represents a bonding position to a carbon atom in a benzene ring in each of the formulae (11) to (13).

[Formula 5]

(2-1)

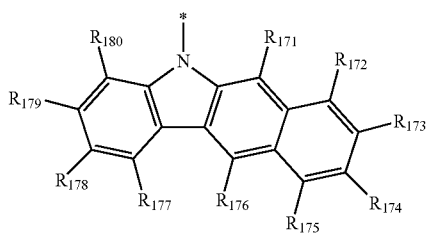

(2-2)

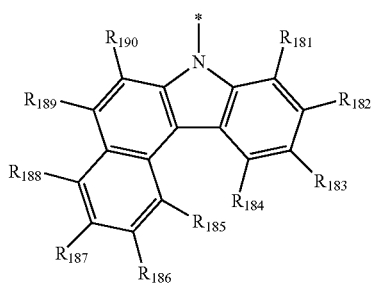

(2-3)

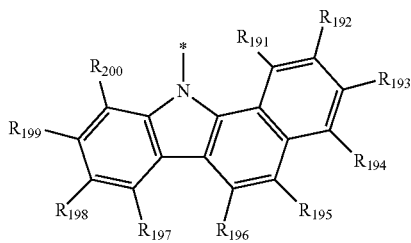

(2-4)

In the formula (2-1), $R_{161}$ to $R_{168}$ each independently represent a hydrogen atom or a substituent.

$R_{161}$ to $R_{168}$ as the substituent each independently represent a halogen atom, a substituted or unsubstituted aryl group having 6 to 14 ring carbon atoms, a substituted or unsubstituted heterocyclic group having 5 to 14 ring atoms, a substituted or unsubstituted alkyl halide group having 1 to 6 carbon atoms, a substituted or unsubstituted alkysilyl group having 3 to 6 carbon atoms, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

In the formulae (2-2) to (2-4), $R_{171}$ to $R_{200}$ each independently represent a hydrogen atom or a substituent.

$R_{171}$ to $R_{200}$ as the substituent are each independently a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 6 carbon atoms, a substituted or unsubstituted alkysilyl group having 3 to 6 carbon atoms, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

* each independently represents a bonding position to a carbon atom in a benzene ring in each of the formulae (11) to (13).

[Formula 6]

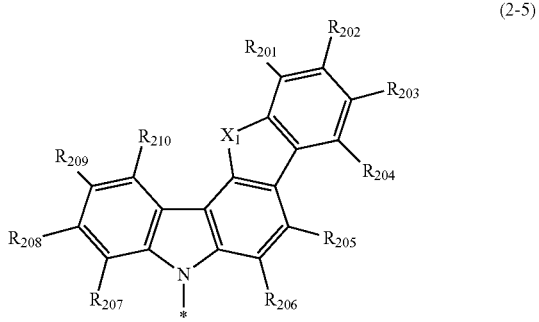

(2-5)

(2-6)

[Formula 7]

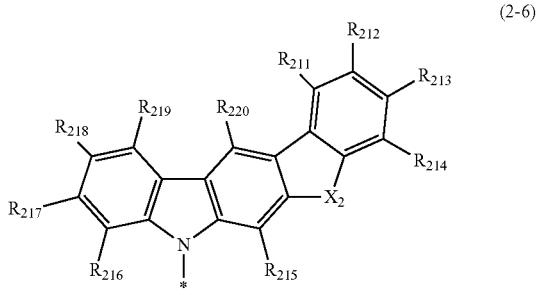

(2-7)

(2-8)

[Formula 8]

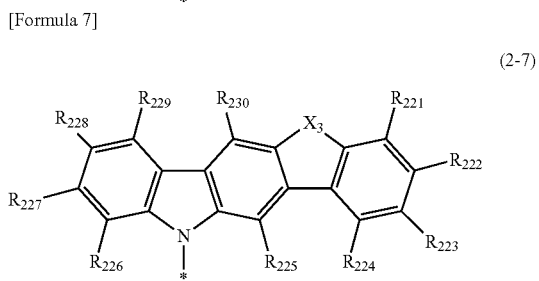

(2-9)

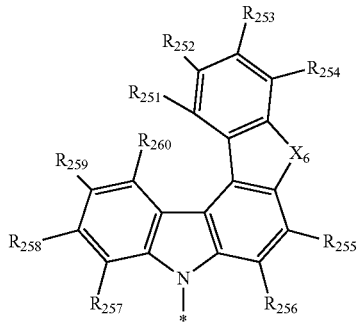

(2-10)

In the formulae (2-5) to (2-10), $X_1$ to $X_6$ each independently represent an oxygen atom, a sulfur atom, or $CR_{151}R_{152}$, $R_{201}$ to $R_{260}$ each independently represent a hydrogen atom or a substituent, and $R_{151}$ and $R_{152}$ each independently represent a hydrogen atom or a substituent or $R_{151}$ and $R_{152}$ are bonded to each other to form a ring.

$R_{201}$ to $R_{260}$, $R_{151}$ and $R_{152}$ as the substituent are each independently a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 6 carbon atoms, a substituted or unsubstituted alkylsilyl group having 3 to 6 carbon atoms, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

* each independently represents a bonding position to a carbon atom in a benzene ring in each of the formulae (11) to (13).

According to another aspect of the invention, an organic-electroluminescence-device material containing the compound according to the above aspect of the invention is provided.

According to still another aspect of the invention, an organic electroluminescence device: including an anode; a cathode; and
  a first organic layer provided between the anode and the cathode, in which
  the first organic layer contains a first compound, and the first compound is the compound according to the above aspect of the invention is provided.

According to a further aspect of the invention, an electronic device including the organic electroluminescence device according to the above aspect of the invention is provided.

According to the above aspects of the invention, a compound capable of decreasing a sublimation temperature when being sublimated and purified while maintaining TADF properties, an organic-EL-device material containing the compound, an organic EL device containing the compound, and an electronic device provided with the organic EL device can be provided.

According to the above aspects of the invention, an organic EL device and an electronic device which have an excellent performance can be provided by using the compound and the organic-EL-device material containing the compound can be provided.

According to the above aspects of the invention, a compound capable of achieving the organic EL device and the electronic device which have an excellent performance, and an organic-EL-device material containing the compound can be provided.

BRIEF DESCRIPTION OF DRAWING(S)

FIG. 1 is a figure schematically illustrating an arrangement of an organic electroluminescence device according to a third exemplary embodiment of the invention.

FIG. 2 schematically shows a device of measuring transient PL.

DESCRIPTION OF EMBODIMENT(S)

First Exemplary Embodiment

Compound

Figure 1:
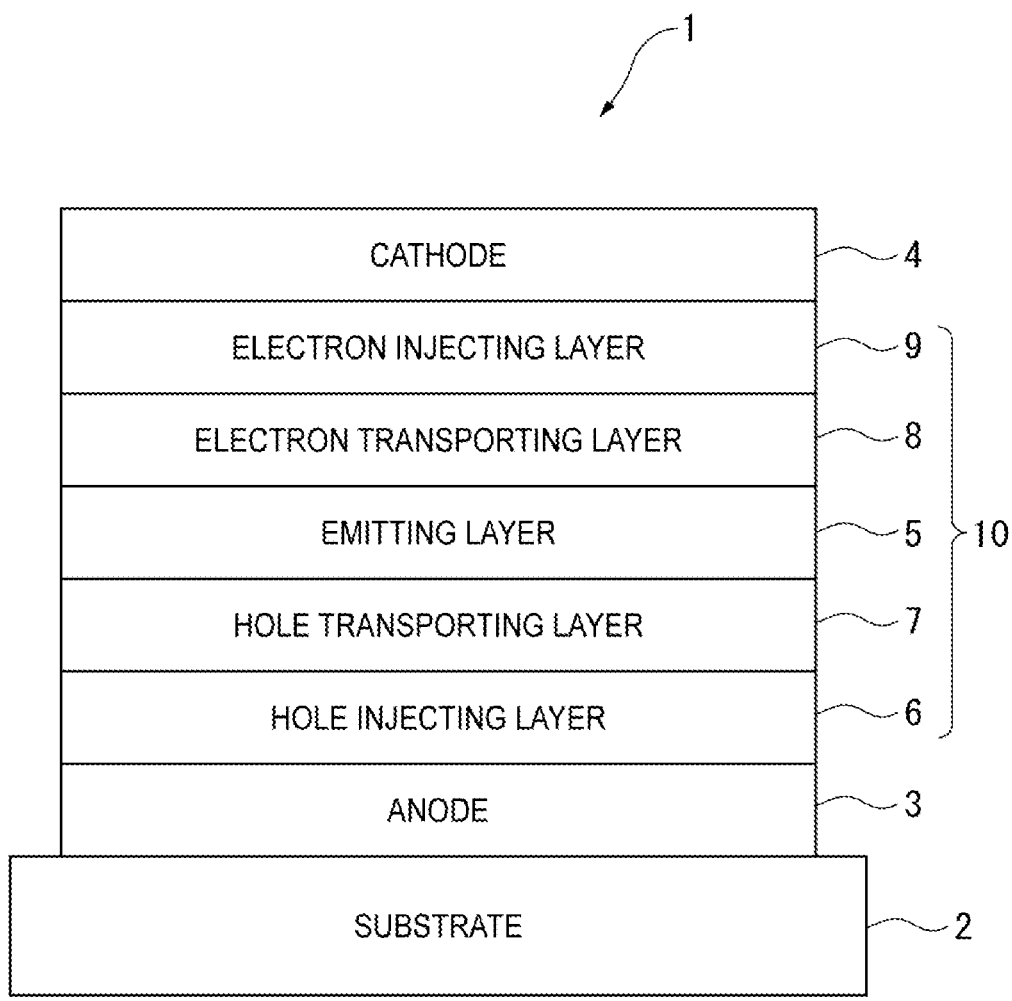

A compound according to a first exemplary embodiment is represented by one of formulae (11) to (13) below.

[Formula 9]

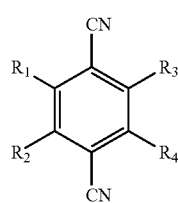

(11)

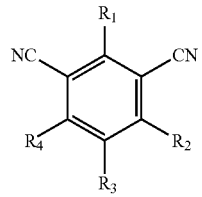

(12)

-continued (13)

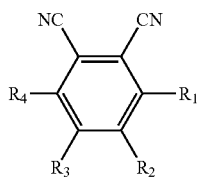

In the formulae (11) to (13): $R_1$ to $R_4$ each independently represent one of groups represent by formulae (1-1) to (1-6) below or one of groups represent by formulae (2-1) to (2-10); at least one of $R_1$ to $R_4$ is one of the groups represent by the formulae (1-1) to (1-6); and at least one of $R_1$ to $R_4$ is one of the groups represent by the formulae (2-1) to (2-10).

[Formula 10]

(1-1)

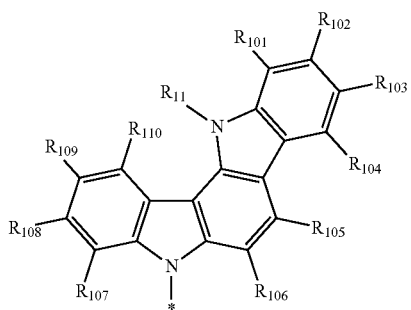

(1-2)

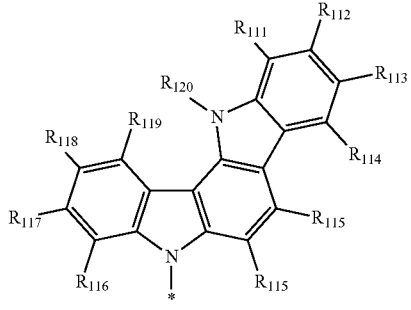

[Formula 11]

(1-3)

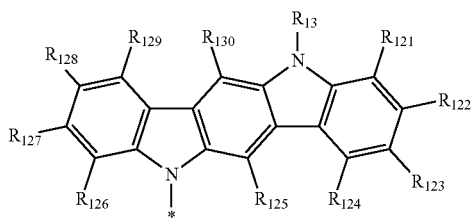

(1-4)

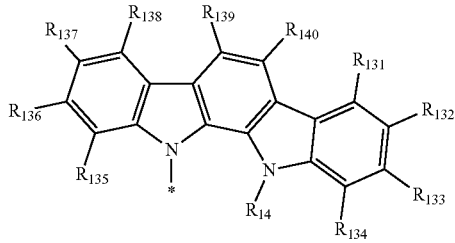

[Formula 12]

(1-5)

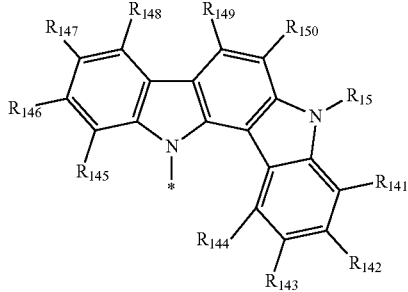

(1-6)

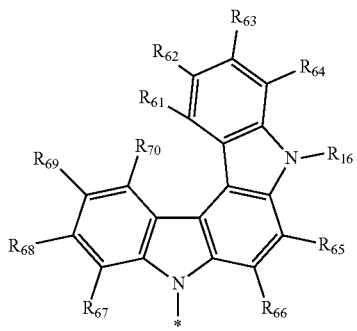

In the formulae (1-1) to (1-6), $R_{11}$ to $R_{16}$ are substituents, $R_{101}$ to $R_{150}$ and $R_{61}$ to $R_{70}$ are each independently a hydrogen atom or a substituent.

$R_{101}$ to $R_{150}$ and $R_{61}$ to $R_{70}$ as the substituent are each independently a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkysilyl group having 3 to 6 carbon atoms, a substituted or unsubstituted alkoxy group having 1 to 6 carbon atoms, a substituted or unsubstituted aryloxy group having 6 to 14 ring carbon atoms, a substituted or unsubstituted arylamino group having 6 to 28 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

$R_{11}$ to $R_{16}$ as the substituent are each independently a substituted or unsubstituted alkyl group having 1 to 6 carbon atoms, a substituted or unsubstituted aryl group having 6 to 14 ring carbon atoms, a substituted or unsubstituted heterocyclic group having 5 to 14 ring atoms, a substituted or unsubstituted alkysilyl group having 3 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

* each independently represents a bonding position to a carbon atom in a benzene ring in each of the formulae (11) to (13).

In the formulae (1-1) to (1-6), when one or more of $R_{101}$ to $R_{110}$, $R_{111}$ to $R_{120}$, $R_{121}$ to $R_{130}$, $R_{131}$ to $R_{140}$, $R_{141}$ to $R_{150}$, $R_{61}$ to $R_{70}$, $R_{11}$ to $R_{16}$ are hydrogen atom(s), it is preferable that all of the hydrogen atom(s) are protium, one or more of the hydrogen atom(s) are deuterium, or all of the hydrogen atom(s) are deuterium.

[Formula 13]

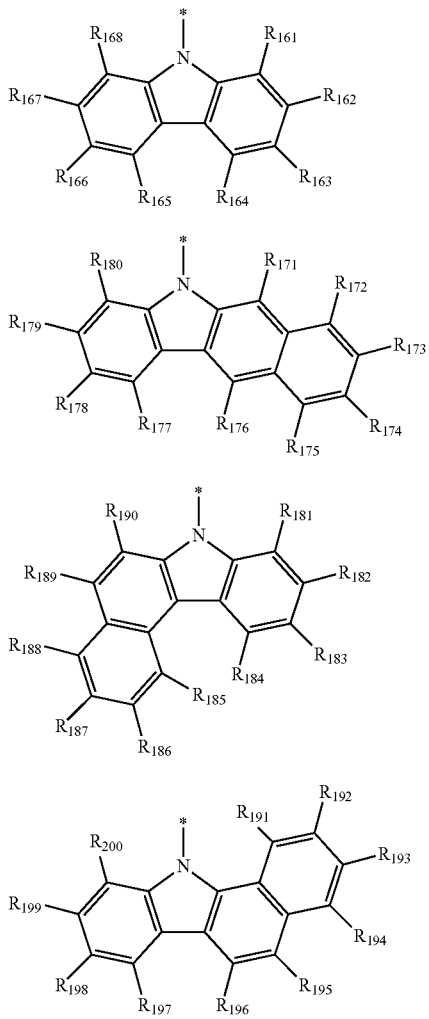

(2-1)
(2-2)
(2-3)
(2-4)

In a form A that is an exemplary form of the exemplary embodiment, $R_{161}$ to $R_{168}$ and $R_{171}$ to $R_{200}$ in the formulae (2-1) to (2-4) are each independently a hydrogen atom or a substituent.

$R_{161}$ to $R_{168}$ and $R_{171}$ to $R_{200}$ as the substituent are each independently a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 6 carbon atoms, a substituted or unsubstituted alkylsilyl group having 3 to 6 carbon atoms, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

* each independently represents a bonding position to a carbon atom of a benzene ring in each of the formulae (11) to (13).

The compound in the form A that is an exemplary form of the exemplary embodiment is also preferably a compound represented by a formula (12) or (13).

In the form A that is an exemplary form of the exemplary embodiment, it is also preferable that, when the compound represented by one of the formulae (11) to (13) has the group represented by the formula (2-1), $R_{161}$ to $R_{168}$ each independently represent a hydrogen atom or a substituent, and $R_{161}$ to $R_{168}$ as the substituent are each independently a halogen atom, a substituted or unsubstituted aryl group having 6 to 14 ring carbon atoms, a substituted or unsubstituted heterocyclic group having 5 to 14 ring atoms, a substituted or unsubstituted alkyl group having 2 to 6 carbon atoms, a substituted or unsubstituted alkyl halide group having 1 to 6 carbon atoms, a substituted or unsubstituted alkylsilyl group having 3 to 6 carbon atoms, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

In the form A that is an exemplary form of the exemplary embodiment, it is also preferable that, when the compound represented by one of the formulae (11) to (13) has the group represented by the formula (2-1), $R_{161}$ to $R_{168}$ each independently represent a hydrogen atom or a substituent, $R_{161}$, $R_{162}$, $R_{164}$, $R_{165}$, $R_{167}$ and $R_{168}$ as the substituent each independently represent a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 6 carbon atoms, a substituted or unsubstituted alkylsilyl group having 3 to 6 carbon atoms, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

It is also preferable that $R_{163}$ and $R_{166}$ as the substituent are each independently a halogen atom, a substituted or unsubstituted aryl group having 6 to 14 ring carbon atoms, a substituted or unsubstituted heterocyclic group having 5 to 14 ring atoms, a substituted or unsubstituted alkyl group having 2 to 6 carbon atoms, a substituted or unsubstituted alkyl halide group having 1 to 6 carbon atoms, a substituted or unsubstituted alkylsilyl group having 3 to 6 carbon atoms, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

In the formula (2-1), $R_{161}$ to $R_{168}$ each independently represent a hydrogen atom or a substituent.

$R_{161}$ to $R_{168}$ as the substituent each independently represent a halogen atom, a substituted or unsubstituted aryl group having 6 to 14 ring carbon atoms, a substituted or unsubstituted heterocyclic group having 5 to 14 ring atoms, a substituted or unsubstituted alkyl halide group having 1 to 6 carbon atoms, a substituted or unsubstituted alkysilyl group having 3 to 6 carbon atoms, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

In the formulae (2-2) to (2-4), $R_{171}$ to $R_{200}$ each independently represent a hydrogen atom or a substituent.

$R_{171}$ to $R_{200}$ as the substituent are each independently a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 6 carbon atoms, a substituted or unsubstituted alkysilyl group having 3 to 6 carbon atoms, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

* each independently represents a bonding position to a carbon atom of a benzene ring in each of the formulae (11) to (13).

In the formulae (2-1) to (2-4), when one or more of $R_{161}$ to $R_{168}$, $R_{171}$ to $R_{180}$, $R_{181}$ to $R_{190}$ and $R_{191}$ to $R_{200}$ are hydrogen atom(s), it is preferable that all of the hydrogen atom(s) are protium, one or more of the hydrogen atom(s) are deuterium, or all of the hydrogen atom(s) are deuterium.

A compound in a form B that is an exemplary form of the exemplary embodiment is also preferably a compound represented by the formula (12) or (13).

[Formula 14]

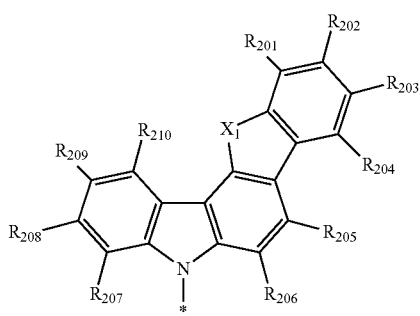

(2-5)

(2-6)

[Formula 15]

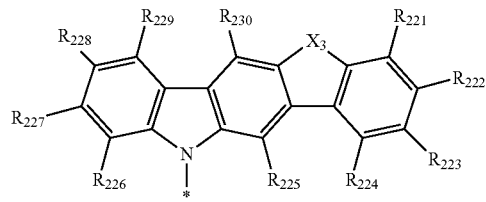

(2-7)

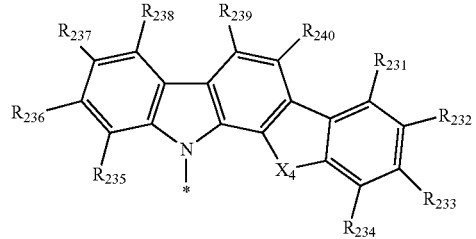

(2-8)

[Formula 16]

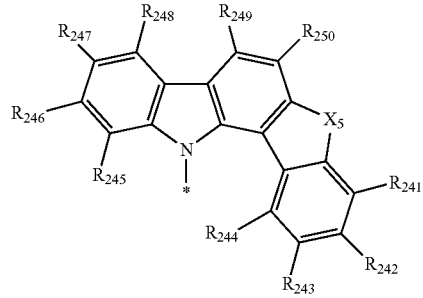

(2-9)

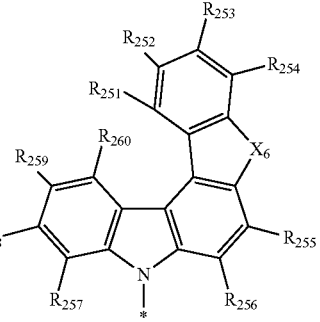

(2-10)

In the formulae (2-5) to (2-10): $X_1$ to $X_6$ each independently represent an oxygen atom, a sulfur atom, or $CR_{151}R_{152}$, $R_{201}$ to $R_{260}$ each independently represent a hydrogen atom or a substituent; and $R_{151}$ and $R_{152}$ each independently represent a hydrogen atom or a substituent or $R_{151}$ and $R_{152}$ are bonded to each other to form a ring.

$R_{201}$ to $R_{260}$, $R_{151}$ and $R_{152}$ as the substituent are each independently a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 6 carbon atoms, a substituted or unsubstituted alkysilyl group having 3 to 6 carbon atoms, a substituted or unsubstituted alkoxy group having 1 to 6 carbon atoms, a substituted or unsubstituted alkoxy halide group having 1 to 6 carbon atoms, a substituted or unsub-

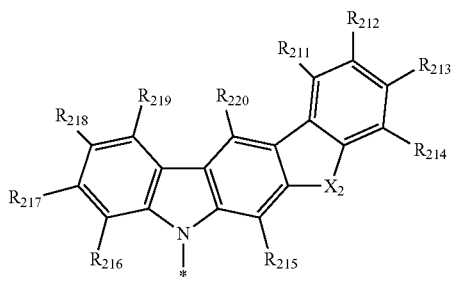

stituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms.

* each independently represents a bonding position to a carbon atom in a benzene ring in each of the formulae (11) to (13).

All of groups represented by formulae (1-1) to (1-6) (hereinafter, also referred to as a "carbazolyl derivative group $C_1$"), groups represented by formulae (2-1) to (2-4) (hereinafter, also referred to as a "carbazolyl derivative group $C_{2A}$"), and groups represented by formulae (2-5) to (2-10) (hereinafter, also referred to as a "carbazolyl derivative group $C_{2B}$") have been known as a group having donor properties.

Among the above groups, since a conjugation length of the carbazolyl derivative group $C_1$ extends longer than that of the carbazolyl derivative group $C_{2A}$, an ionization potential tends to become low (an absolute value tends to become small).

Moreover, since an electron donating property of the carbazolyl derivative group $C_1$ is higher than that of the carbazolyl derivative group $C_{2B}$, an ionization potential tends to become low (an absolute value tends to become small).

Accordingly, when the compound having the carbazolyl derivative group $C_1$ is contained, for instance, in the emitting layer, it is considered that hole injectability from the hole transporting layer to the emitting layer is improved to improve charge transportability to the emitting layer. It is considered that the effects of improving the hole injectability and charge transportability is more easily expressed with use of a compound including a cyano group having relatively high acceptor properties as well as a carbazolyl derivative group $C_1$.

In contrast, for instance, for a compound formed by bonding four carbazolyl derivative groups $C_1$ to a benzene ring of dicyanobenzene, the sublimation temperature for sublimation purification is likely to be increased. A phenomenon that the sublimation temperature of this compound is likely to be increased is more likely to occur than when using a compound in which four carbazolyl derivative groups $C_{2A}$ are bonded to a benzene ring of dicyanobenzene. This phenomenon is also more likely to occur than when using a compound in which four carbazolyl derivative groups $C_{2B}$ are bonded to a benzene ring of dicyanobenzene.

When the sublimation temperature of the compound is increased, a purifying time is prolonged resulting in reduced purification efficiency.

The inventors have found a compound capable of decreasing the sublimation temperature while keeping TADF properties. The compound is formed by bonding four groups in total, selected from the carbazolyl derivative group $C_1$, $C_{2A}$ and $C_{2B}$ and including the carbazolyl derivative group $C_1$ and at least one of the carbazolyl derivative group $C_{2A}$ and the carbazolyl derivative group $C_{2B}$, to a benzene ring of dicyanobenzene.

In addition, since the carbazolyl derivative group $C_{2A}$ has a skeleton having a higher triplet energy than the carbazolyl derivative group $C_1$, it is expected that, for instance, presence of the compound having the carbazolyl derivative group $C_{2A}$ in the emitting layer can express the function of inhibiting energy deactivation from the triplet state.

In addition, since the carbazolyl derivative group $C_{2B}$ also has a skeleton having a higher triplet energy than the carbazolyl derivative group $C_1$, it is expected that, for instance, presence of the compound having the carbazolyl derivative group $C_{2B}$ in the emitting layer can express the function of inhibiting energy deactivation from the triplet state.

Thus, according to the exemplary embodiment, it is expected that the combined use of the carbazolyl derivative group $C_1$ and at least one of the carbazolyl derivative group $C_{2A}$ and the carbazolyl derivative group $C_{2B}$ can keep a balance between the decrease in the sublimation temperature and the maintenance of the TADF properties. As a result, it is expected that the compound capable of decreasing the sublimation temperature for sublimation purification while maintaining the TADF properties can be obtained.

Maintaining of the TADF properties herein means, for instance, specifically the "value of $X_D/X_P$", which is measured in Examples, is 0.05 or more.

The amount of Prompt emission is denoted by $X_P$ and the amount of Delay emission is denoted by $X_D$. Details of the measurement method is described in the description about Examples.

In the compound of the exemplary embodiment, when a plurality of groups represented by the formula (1-1) are present as the group for $R_1$ to $R_4$, the plurality of groups represented by the formula (1-1) are preferably the same group having the same substituent.

In the compound of the exemplary embodiment, when a plurality of groups represented by the formula (1-2) are present as the group for $R_1$ to $R_4$, the plurality of groups represented by the formula (1-2) are preferably the same group having the same substituent.

In the compound of the exemplary embodiment, when a plurality of groups represented by the formula (1-3) are present as the group for $R_1$ to $R_4$, the plurality of groups represented by the formula (1-3) are preferably the same group having the same substituent.

In the compound of the exemplary embodiment, when a plurality of groups represented by the formula (1-4) are present as the group of $R_1$ to $R_4$, the plurality of groups represented by the formula (1-4) are preferably the same group having the same substituent.

In the compound of the exemplary embodiment, when a plurality of groups represented by the formula (1-5) are present as the group for $R_1$ to $R_4$, the plurality of groups represented by the formula (1-5) are preferably the same group having the same substituent.

When a plurality of groups represented by the formula (1-6) are present as groups for $R_1$ to $R_4$, the plurality of groups represented by the formula (1-6) are preferably the same group having the same substituent.

For instance, when two groups each represented by the formula (1-1) are selected as the groups for $R_1$ and $R_2$ and one group represented by the formula (1-2) is selected as the group for $R_3$, and one group represented by the formula (2-1) is selected as the group for $R_4$, the two groups each represented by the formula (1-1) (group for $R_1$ and $R_2$) are the same group having the same substituent.

For instance, when three groups each represented by the formula (1-1) are selected as the groups for $R_1$ to $R_3$, the three groups represented by the formula (1-1) are preferably the same group having the same substituent.

In the compound of the exemplary embodiment, when three of the groups represented by the formulae (1-1) to (1-6) are selected as the groups for $R_1$ to $R_4$, it is preferable that all of the three groups are represented by one of the formulae (1-1) to (1-6) and are the same group including the substituent.

When two of the groups for $R_1$ to $R_4$ are represented by the formulae (1-1) to (1-6), it is preferable that all of the two groups are represented by one of the formulae (1-1) to (1-6) and are the same group including the substituent.

For instance, when two of the groups for $R_1$ to $R_4$ are selected from the groups represented by the formulae (1-1) to (1-6) and the remaining two thereof are selected from the groups represented by the formulae (2-1) to (2-10), it is preferable that the two groups represented by the formulae (1-1) to (1-6) are represented by one of the formulae (1-1) to (1-6) and are the same group having the same substituent.

When three of the groups for $R_1$ to $R_4$ are selected from the groups represented by the formulae (1-1) to (1-6) and the remaining one thereof is selected from the groups represented by the formulae (2-1) to (2-10), it is preferable that the three groups represented by the formulae (1-1) to (1-6) are represented by one of the formulae (1-1) to (1-6) and are the same group having the same substituent.

For instance, when three groups each represented by the formula (1-1) are selected as the groups for $R_1$ to $R_4$, it is preferable that the three groups are represented by the formula (1-1) and are the same group having the same substituent.

In the compound of the exemplary embodiment, when a plurality of groups each represented by the formula (2-1) are present as the group of $R_1$ to $R_4$, the plurality of groups represented by the formula (2-1) are preferably the same group having the same substituent.

When a plurality of groups each represented by the formula (2-2) are present as the group for $R_1$ to $R_4$, the plurality of groups represented by the formula (2-2) are preferably the same group having the same substituent.

When a plurality of groups each represented by the formula (2-3) are present as the group for $R_1$ to $R_4$, the plurality of groups represented by the formula (2-3) are preferably the same group having the same substituent.

When a plurality of groups each represented by the formula (2-4) are present as groups for $R_1$ to $R_4$, the plurality of groups represented by the formula (2-4) are preferably the same group having the same substituent.

When a plurality of groups represented by the formula (2-5) are present as the group for $R_1$ to $R_4$, the plurality of groups represented by the formula (2-5) are preferably the same group having the same substituent.

When a plurality of groups represented by the formula (2-6) are present as the group for $R_1$ to $R_4$, the plurality of groups represented by the formula (2-6) are preferably the same group having the same substituent.

When a plurality of groups represented by the formula (2-7) are present as the group for $R_1$ to $R_4$, the plurality of groups represented by the formula (2-7) are preferably the same group having the same substituent.

When a plurality of groups represented by the formula (2-8) are present as the group for $R_1$ to $R_4$, the plurality of groups represented by the formula (2-8) are preferably the same group having the same substituent.

When a plurality of groups represented by the formula (2-9) are present as the group for $R_1$ to $R_4$, the plurality of groups represented by the formula (2-9) are preferably the same group having the same substituent.

When a plurality of groups represented by the formula (2-10) are present as the group for $R_1$ to $R_4$, the plurality of groups represented by the formula (2-10) are preferably the same group having the same substituent.

For instance, when two groups represented by the formula (2-1) are selected as the groups for $R_1$ and $R_2$ and one group represented by the formula (2-2) is selected as the group for $R_3$, and one group represented by the formula (1-1) is selected as the group for $R_4$, the two groups represented by the formula (2-1) (group for $R_1$ and $R_2$) are the same group having the same substituent.

Moreover, for instance, when three groups represented by the formula (2-1) are selected as the groups for $R_1$ to $R_3$, the three groups represented by the formula (2-1) (the groups for $R_1$ to $R_3$) are preferably the same group having the same substituent.

In the compound of the exemplary embodiment, it is preferable that, when three of the groups for $R_1$ to $R_4$ are represented by the formulae (2-1) to (2-10), all of the three groups are represented by one of the formulae (2-1) to (2-10) and are the same group including the substituent, and when two of the groups for $R_1$ to $R_4$ are represented by the formulae (2-1) to (2-10), all of the two groups are represented by one of the formulae (2-1) to (2-10) and are the same group including the substituent.

For instance, when two of the groups for $R_1$ to $R_4$ are selected from the groups represented by the formulae (2-1) to (2-10) and the remaining two thereof are selected from the groups represented by the formulae (1-1) to (1-6), it is preferable that the two groups represented by the formulae (2-1) to (2-10) are represented by one of the formulae (2-1) to (2-10) and are the same group having the same substituent.

When three of the groups for $R_1$ to $R_4$ are selected from the groups represented by the formulae (2-1) to (2-10) and the remaining one thereof is selected from the groups represented by the formulae (1-1) to (1-6), it is preferable that the three groups represented by the formulae (2-1) to (2-10) are represented by one of the formulae (2-1) to (2-10) and are the same group having the same substituent.

For instance, when three groups each represented by the formula (2-1) are selected as the groups for $R_1$ to $R_4$, it is preferable that the three groups are represented by the formula (2-1) and are the same group having the same substituent.

The compound of the exemplary embodiment is preferably a compound represented by one of formulae (101) to (123).

[Formula 17]

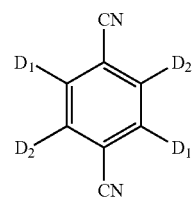

(101)

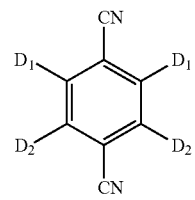

(102)

(103) 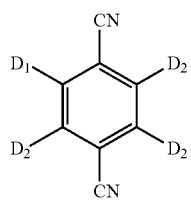
(104) 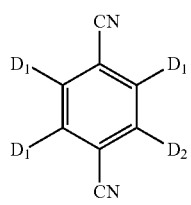
(105) 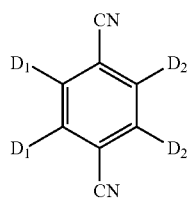
(106) 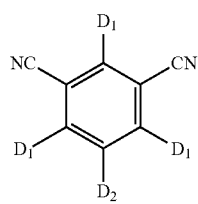
[Formula 18]
(107) 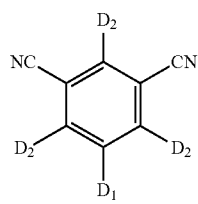
(108) 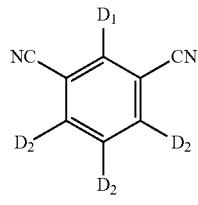
(109) 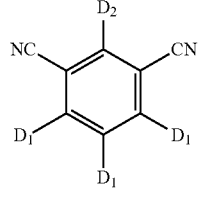
(110) 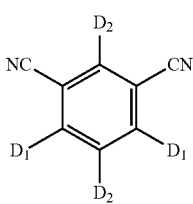
(111) 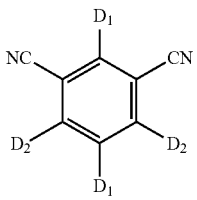
(112) 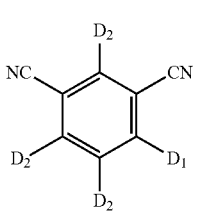
(113) 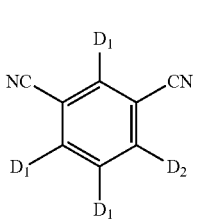
(114) 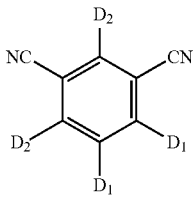
(115) 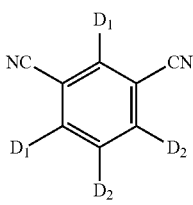
[Formula 19]
(116) 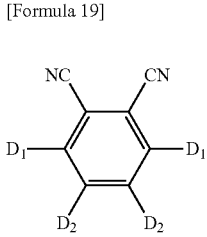

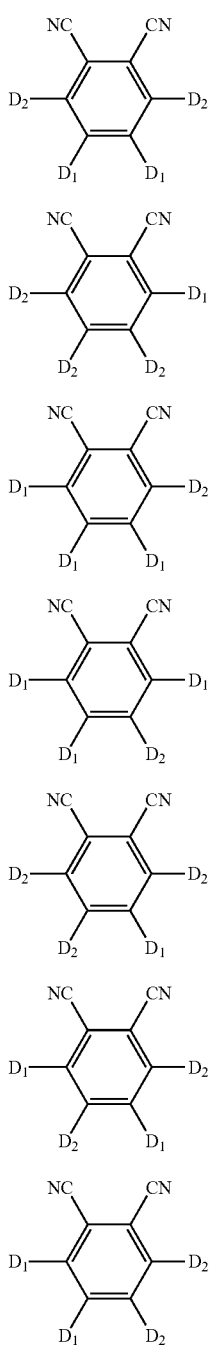

(117)

(118)

(119)

(120)

(121)

(122)

(123)

In the formulae (101) to (123): $D_1$ is each independently one of the groups represented by the formulae (1-1) to (1-6); $D_2$ is each independently one of the groups represented by the formulae (2-1) to (2-10); a plurality of $D_1$ are mutually the same or different; and a plurality of $D_2$ are mutually the same or different.

In the compound of the exemplary embodiment, $D_1$ in the formulae (101) to (123) are preferably mutually the same group.

In the compound of the exemplary embodiment, $D_2$ in the formulae (101) to (123) are preferably mutually the same group.

In the compound of the exemplary embodiment, it is more preferable that $D_1$ is the same group and $D_2$ is the same group in the formulae (101) to (123).

The compound of the exemplary embodiment is preferably the compound represented by the formula (101), (103), (106) to (108), (110) to (112), (116) to (119), or (121).

The compound of the exemplary embodiment is more preferably the compound represented by the formula (103), (107), (108), (112), (118), or (121).

In the compound of the exemplary embodiment, each of the groups that are to be represented by the formulae (1-1) to (1-6) is preferably the group represented by one of the formulae (1-1), (1-2), (1-4), (1-5), and (1-6).

In the compound of the exemplary embodiment, each of the groups that are to be represented by the formulae (1-1) to (1-6) are more preferably the group represented by one of the formulae (1-2), (1-4), and (1-6).

In the compound of the exemplary embodiment, each of the groups that are to be represented by the formulae (2-1) to (2-10) is preferably the group represented by one of the formulae (2-2) to (2-10).

In the compound of the exemplary embodiment, each of the groups that are to be represented by the formulae (2-1) to (2-10) is more preferably the group represented by the formula (2-2), the group represented by the formula (2-3), or the group represented by the formula (2-4).

In the compound of the exemplary embodiment, all the groups represented by the formulae (2-1) to (2-10) are also preferably the group represented by the formulae (2-1).

When the compound in the exemplary embodiment has a group represented by the formula (2-1), $R_{161}$ to $R_{168}$ each independently preferably represent a hydrogen atom, or a substituted or unsubstituted aryl group having 6 to 14 ring carbon atoms.

When the compound in the exemplary embodiment has a group represented by the formula (2-1), it is also preferable that at least one of $R_{161}$, $R_{163}$, $R_{166}$ and $R_{168}$ is a substituent, and the substituent each independently is a substituted or unsubstituted aryl group having 6 to 14 ring carbon atoms, and $R_{162}$, $R_{164}$, $R_{165}$ and $R_{167}$ are hydrogen atoms.

In the compound of the exemplary embodiment, the group represented by each of the formulae (2-1) to (2-10) is preferably one of the groups represented by the formulae (2A-1) to (2A-7).

[Formula 20]

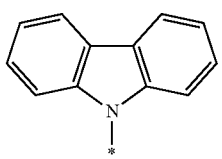

(2A-1)

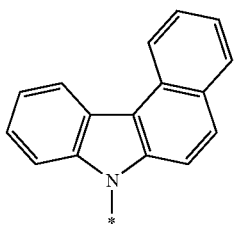

(2A-2)

-continued (2A-3)
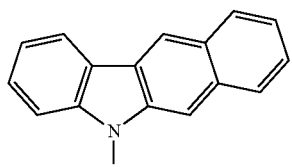

(2A-4)
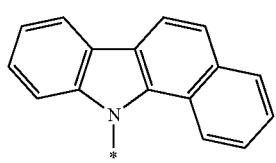

[Formula 21]

(2A-5)
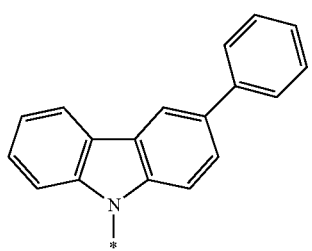

(2A-6)
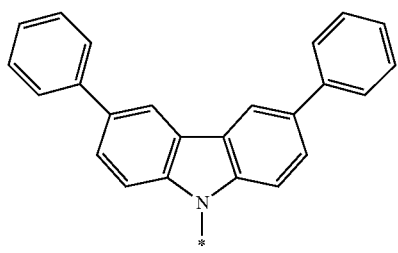

[Formula 22]

(2A-7)
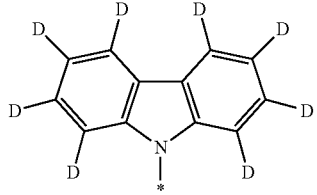

In the formulae (2A-1) to (2A-7), * each independently represents a bonding position to a carbon atom of a benzene ring in each of the formulae (11) to (13). D represents deuterium.

More preferably, the compound of the exemplary embodiment is the compound represented by one of the formulae (101), (103), (106) to (108), (110) to (112), (116) to (119), and (121), $D_1$ is each independently the group represented by one of the formulae (1-1), (1-2), (1-4), (1-5), and (1-6), and $D_2$ is each independently the group represented by one of the formulae (2A-1) to (2A-6). It should be noted that a plurality of $D_1$ are mutually the same or different and a plurality of $D_2$ are mutually the same or different.

Further preferably, the compound of the exemplary embodiment is the compound represented by one of the formulae (103), (107), (108), (112), (118), and (121), $D_1$ is each independently the group represented by one of the formulae (1-1), (1-2), (1-4), (1-5), and (1-6), and $D_2$ is independently the group represented by one of the formulae (2A-1) to (2A-6). It should be noted that a plurality of $D_1$ are mutually the same or different and a plurality of $D_2$ are mutually the same or different.

Also preferably, the compound of the exemplary embodiment is the compound represented by one of the formulae (103), (107), (108), (112), (118), and (121), $D_1$ is each independently the group represented by one of the formulae (1-1), (1-2), (1-4), (1-5), and (1-6), and $D_2$ is the group represented by the formula (2A-1). It should be noted that a plurality of $D_1$ are mutually the same or different.

The compound of the exemplary embodiment is also preferably the compound represented by the formula (11).

The compound of the exemplary embodiment is also preferably the compound represented by the formula (12).

The compound in the exemplary embodiment is also preferably the compound represented by the formula (13).

In the compound of the exemplary embodiment, $R_{101}$ to $R_{150}$ and $R_{61}$ to $R_{70}$ as the substituent are each independently preferably an unsubstituted aryl group having 6 to 14 ring carbon atoms, an unsubstituted heterocyclic group having 5 to 14 ring atoms, an unsubstituted alkyl group having 1 to 6 carbon atoms, an unsubstituted alkoxy group having 1 to 6 carbon atoms, an unsubstituted aryloxy group having 6 to 14 ring carbon atoms, an unsubstituted arylamino group having 6 to 28 ring carbon atoms, or an unsubstituted alkylamino group 2 to 12 carbon atoms.

In the compound of the exemplary embodiment, $R_{11}$ to $R_{16}$ as the substituent are each independently preferably an unsubstituted aryl group having 6 to 14 ring carbon atoms, an unsubstituted heterocyclic group having 5 to 14 ring atoms, an unsubstituted aryloxy group having 6 to 14 ring carbon atoms, or an unsubstituted arylthio group having 6 to 14 ring carbon atoms.

$R_{11}$ to $R_{16}$ as the substituent are each independently more preferably an unsubstituted aryl group having 6 to 14 ring carbon atoms or an unsubstituted heterocyclic group having 5 to 14 ring atoms.

In the compound of the exemplary embodiment, it is further preferable that $R_{101}$ to $R_{150}$ and $R_{61}$ to $R_{70}$ as the substituent are each an unsubstituted aryl group having 6 to 14 ring carbon atoms, an unsubstituted heterocyclic group having 5 to 14 ring atoms, an unsubstituted alkyl group having 1 to 6 carbon atoms, an unsubstituted alkoxy group having 1 to 6 carbon atoms, an unsubstituted aryloxy group having 6 to 14 ring carbon atoms, or an unsubstituted arylamino group having 6 to 28 ring carbon atoms, and $R_{11}$ to $R_{16}$ as the substituent are each independently an unsubstituted aryl group having 6 to 14 ring carbon atoms or an unsubstituted heterocyclic group having 5 to 14 ring atoms.

In the compound of the exemplary embodiment, $R_{101}$ to $R_{150}$ and $R_{61}$ to $R_{70}$ as the substituent are each independently more preferably an unsubstituted aryl group having 6 to 14 ring carbon atoms or an unsubstituted alkyl group 1 to 6 carbon atoms.

In the compound of the exemplary embodiment, it is more preferable that Rios to $R_{150}$ and $R_{61}$ to $R_{70}$ as the substituent are each an unsubstituted aryl group having 6 to 14 ring carbon atoms or an unsubstituted alkyl group having 1 to 6 carbon atoms, and $R_{11}$ to $R_{16}$ as the substituent are each independently an unsubstituted aryl group having 6 to 14 ring carbon atoms or an unsubstituted heterocyclic group having 5 to 14 ring atoms.

In the compound of the exemplary embodiment, it is more preferable that $R_{161}$ to $R_{168}$ and $R_{171}$ to $R_{260}$ as the substituent may be each independently a halogen atom, an unsubstituted aryl group having 6 to 14 ring carbon atoms, an unsubstituted heterocyclic group having 5 to 14 ring atoms, an unsubstituted alkyl group having 1 to 6 carbon atoms, an unsubstituted alkyl halide group having 1 to 6 carbon atoms, an unsubstituted alkoxy group having 1 to 6 carbon atoms, an unsubstituted alkoxy halide group having 1 to 6 carbon atoms, an unsubstituted aryloxy group having 6 to 14 ring carbon atoms, or an unsubstituted alkylamino group having 2 to 12 carbon atoms.

In the compound of the exemplary embodiment, $R_{161}$ to $R_{168}$ and $R_{171}$ to $R_{260}$ as the substituent are each independently preferably a halogen atom, an unsubstituted aryl group having 6 to 14 ring carbon atoms, an unsubstituted heterocyclic group having 5 to 14 ring atoms, an unsubstituted alkyl halide group having 1 to 6 carbon atoms, an unsubstituted alkoxy group having 1 to 6 carbon atoms, an unsubstituted alkoxy halide group having 1 to 6 carbon atoms, an unsubstituted aryloxy group having 6 to 14 ring carbon atoms, or an unsubstituted alkylamino group 2 to 12 carbon atoms.

In the compound of the exemplary embodiment, it is preferable that $R_{151}$ and $R_{152}$ as the substituent are each independently an unsubstituted aryl group having 6 to 14 ring carbon atoms or an unsubstituted alkyl group having 1 to 6 carbon atoms.

In the compound of the exemplary embodiment, it is preferable that $R_{161}$ to $R_{168}$ and $R_{171}$ to $R_{260}$ as the substituent are each independently a halogen atom, an unsubstituted aryl group having 6 to 14 ring carbon atoms, an unsubstituted heterocyclic group having 5 to 14 ring atoms, an unsubstituted alkyl halide group having 1 to 6 carbon atoms, an unsubstituted alkoxy group having 1 to 6 carbon atoms, an unsubstituted alkoxy halide group having 1 to 6 carbon atoms, an unsubstituted aryloxy group having 6 to 14 ring carbon atoms, or an unsubstituted alkylamino group having 2 to 12 carbon atoms, and $R_{151}$ and $R_{152}$ as the substituent are each independently an unsubstituted aryl group having 6 to 14 ring carbon atoms or an unsubstituted alkyl group having 1 to 6 carbon atoms.

In the compound of the exemplary embodiment, it is more preferable that $R_{161}$ to $R_{168}$, $R_{171}$ to $R_{260}$, $R_{151}$ and $R_{152}$ as the substituent are each independently an unsubstituted aryl group 6 to 14 ring carbon atoms.

In the compound of the exemplary embodiment, it is more preferable that $R_{161}$ to $R_{168}$ and $R_{171}$ to $R_{260}$ as the substituent are each independently an unsubstituted aryl group having 6 to 14 ring carbon atoms, and $R_{151}$ and $R_{152}$ as the substituent are each independently an unsubstituted aryl group having 6 to 14 ring carbon atoms or an unsubstituted alkyl group 1 to 6 carbon atoms.

In the compound of the exemplary embodiment, it is also preferable that $R_{101}$ to $R_{150}$ and $R_{61}$ to $R_{70}$ are hydrogen atoms.

In the compound of the exemplary embodiment, it is also preferable that $R_{101}$ to $R_{150}$ and $R_{61}$ to $R_{70}$ are hydrogen atoms and $R_{11}$ to $R_{16}$ are each independently an unsubstituted aryl group having 6 to 14 ring carbon atoms or an unsubstituted heterocyclic group having 5 to 14 ring atoms.

In the compound of the exemplary embodiment, it is also preferable that $R_{161}$ to $R_{168}$ and $R_{171}$ to $R_{260}$ are hydrogen atoms.

In the compound of the exemplary embodiment, when $R_{161}$ to $R_{168}$ and $R_{171}$ to $R_{260}$ are hydrogen atoms, it is preferable that all of the hydrogen atoms are protium, one or more of the hydrogen atoms are deuterium, or all of the hydrogen atoms are deuterium.

In the compound of the exemplary embodiment, it is also preferable that $R_{161}$ to $R_{168}$ and $R_{171}$ to $R_{260}$ are hydrogen atoms and $R_{151}$ and $R_{152}$ as a substituent are each independently an unsubstituted aryl group having 6 to 14 ring carbon atoms or an unsubstituted alkyl group having 1 to 6 carbon atoms.

In the compound of the exemplary embodiment, it is preferable that, on a basis of a calculation of a sum of atomic weights of atoms forming each of $R_1$ to $R_4$,
 a minimum sum M1(min) among the sums of the groups corresponding to the groups represented by the formulae (1-1) to (1-6) and a maximum sum M2(max) among the sums of the groups corresponding to the groups represented by the formulae (2-1) to (2-10) satisfy a relationship represented by a numerical formula (Numerical Formula 1).

Moreover, it is further preferable that the minimum sum M1(min) among the sums and the maximum sum M2(max) among the sums of the groups corresponding to the groups represented by the formulae (2-1) to (2-10) satisfy a relationship represented by a numerical formula (Numerical Formula 1X) below.

Moreover, it is particularly preferable that the minimum sum M1(min) among the sums and the maximum sum M2(max) among the sums of the groups corresponding to the groups represented by the formulae (2-1) to (2-10) satisfy a relationship represented by a numerical formula (Numerical Formula 1Y) below.

By satisfying the relationship represented by the numerical formula (Numerical Formula 1), (Numerical Formula 1X) or (Numerical Formula 1Y), the TADF properties are kept favorable and the sublimation temperature when the compound is sublimated and purified is easily lowered.

| | |
|---|---|
| M1(min) > M2(max) | (Numerical Formula 1) |
| 200 > M1(min) − M2(max) | (Numerical Formula 1X) |
| 170 > M1(min) − M2(max) | (Numerical Formula 1Y) |

A numerical formula (Numerical Formula 1) will be described.

The compound in the exemplary embodiment will be described with an exemplary compound represented by the formula (12). In the formula (12), when $R_1$ and $R_3$ are unsubstituted 11,12-dihydro-11-phenylindolo[2,3-a]carbazolyl groups ($C_{24}H_{15}N_2$), and $R_2$ and $R_4$ are unsubstituted carbazolyl groups ($C_{12}H_8N$), the compound of the exemplary embodiment is a compound A below.

[Formula 23]

Compound A

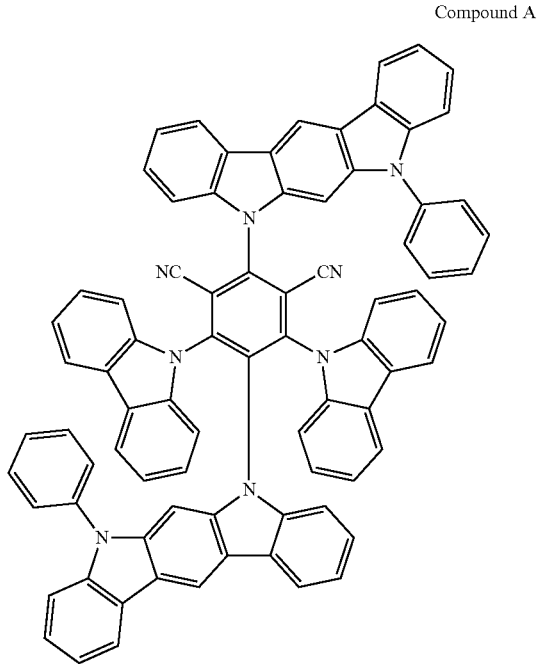

In this case, a sum of atomic weights of atoms forming $R_1$ and $R_3$ ($C_{24}H_{15}N_2$) (hereinafter, also referred to as a "sum $M_{R1}$") is calculated as $12\times24+15+14\times2=331$. Also, a sum of atomic weights of atoms forming $R_2$ and $R_4$ ($C_{12}H_8N$) (hereinafter, also referred to as a "sum $M_{R2}$") is calculated as $12\times12+8+14=166$.

$R_1$ and $R_3$ each are a group corresponding to the group represented by one of the formulae (1-1) to (1-6).

In a comparison between $R_1$ and $R_3$ in terms of the sum of the atomic weights, the sum $M_{R1}$=the sum $M_{R3}$, indicating that the minimum sum M1(min) is equal to the SUM $M_{R1}$ Or $M_{R3}$.

$R_2$ and $R_4$ each are a group corresponding to the group represented by one of the formulae (2-1) to (2-10).

In a comparison between $R_2$ and $R_4$ in terms of the sum of the atomic weights, the sum $M_{R2}$=the sum $M_{R4}$, indicating that the maximum sum M2(max) is equal to the sum $M_{R2}$ or $M_{R4}$.

According, since the compound A satisfies "sum $M_{R1}$ or sum $M_{R3}$>sum $M_{R2}$ or sum $M_{R4}$", the compound A is a compound satisfying the relationship of the numerical formula (Numerical Formula 1).

Manufacturing Method of Compound According to Exemplary Embodiment

The compound according to the first exemplary embodiment can be prepared through, for instance, a process described later in Examples. The compound of the exemplary embodiment can be manufactured, for instance, by application of known substitution reactions and/or materials depending on a target compound according to reactions described later in Examples.

Examples of the compound of the exemplary embodiment include compounds represented by formulae (11-1), (12-1) to (12-2) and (13-1) to (13-2).

[Formula 24]

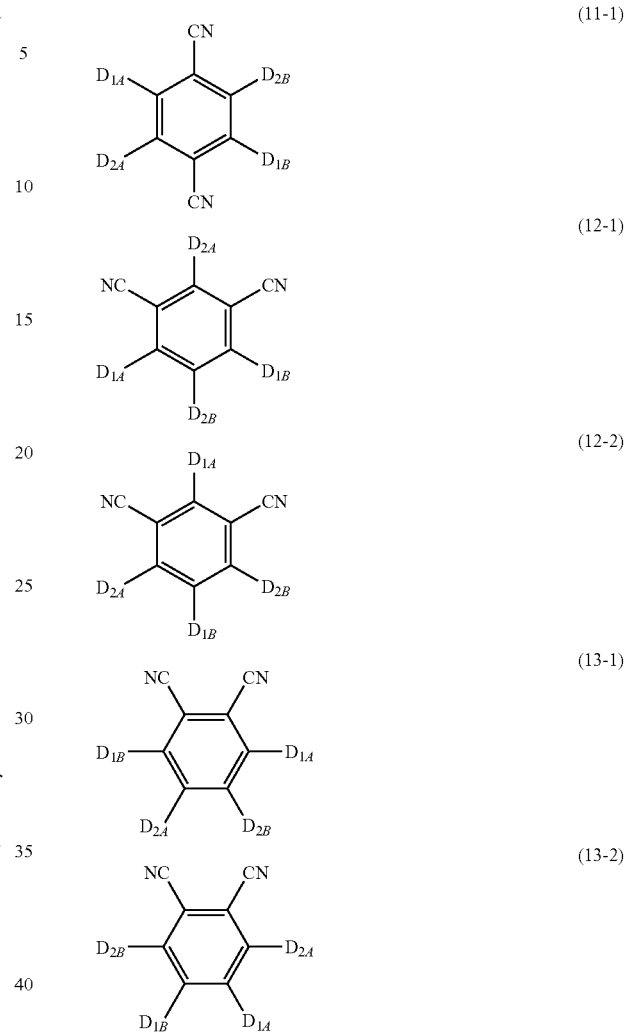

In the formula (11-1), $D_{1A}$, $D_{2A}$, $D_{1B}$, and $D_{2B}$ respectively represent groups corresponding to numbers given to columns of $D_{1A}$, $D_{2A}$, $D_{1B}$, and $D_{2B}$ in Tables 3 to 10.

In the formula (12-1), $D_{1A}$, $D_{2A}$, $D_{1B}$, and $D_{2B}$ respectively represent groups corresponding to numbers given to columns of $D_{1A}$, $D_{2A}$, $D_{1B}$, and $D_{2B}$ in Tables 3 to 10.

In the formula (12-2), $D_{1A}$, $D_{2A}$, $D_{1B}$, and $D_{2B}$ respectively represent groups corresponding to numbers given to columns of $D_{1A}$, $D_{2A}$, $D_{1B}$, and $D_{2B}$ in Tables 3 to 10.

In the formula (13-1), $D_{1A}$, $D_{2A}$, $D_{1B}$, and $D_{2B}$ respectively represent groups corresponding to numbers given to columns of $D_{1A}$, $D_{2A}$, $D_{1B}$, and $D_{2B}$ in Tables 3 to 10.

In the formula (13-2), $D_{1A}$, $D_{2A}$, $D_{1B}$, and $D_{2B}$ respectively represent groups corresponding to numbers given to columns of $D_{1A}$, $D_{2A}$, $D_{1B}$, and $D_{2B}$ in Tables 3 to 10.

In Tables 3 to 11 below, the numbers given to columns of $D_{1A}$, $D_{2A}$, $D_{1B}$, and $D_{2B}$ correspond to numbers of later-described groups 1 to 6 and groups 1' to 47'.

The groups 1 to 6 and groups 1' to 47' are shown below. * each independently represents a bonding position to a carbon atom of a benzene ring in each of the formulae (11-1), (12-1) to (12-2) and (13-1) to (13-2) and later-described formulae (11-2), (12-3) to (12-5) and (13-3) to (13-4). Me represents a methyl group.

The groups 1 to 6 and groups 1' to 47' are shown below. * each independently represents a bonding position to a carbon atom of a benzene ring in each of the formulae (11-1), (12-1) to (12-2) and (13-1) to (13-2) and later-described formulae (11-2), (12-3) to (12-5) and (13-3) to (13-4). Me represents a methyl group.
[Formula 25]
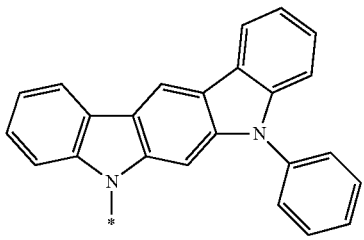
1
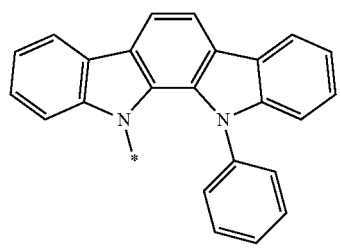
2
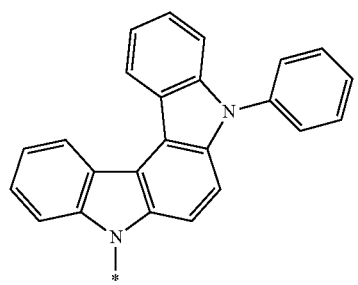
3
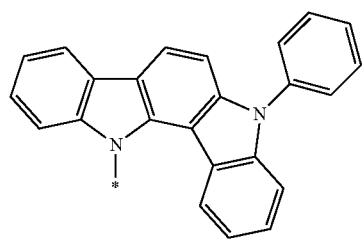
4
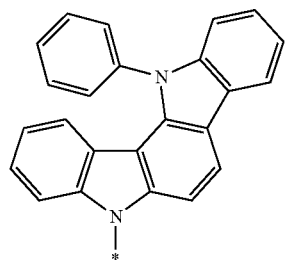
5
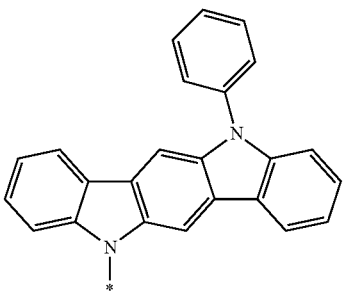
6
[Formula 26]
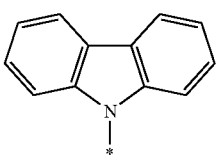
1'
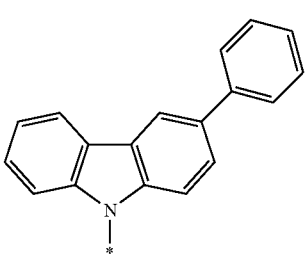
2'
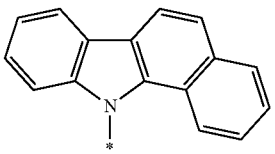
3'
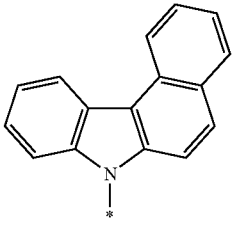
4'
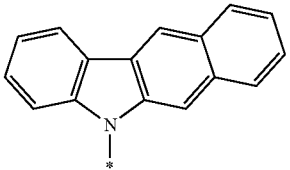
5'
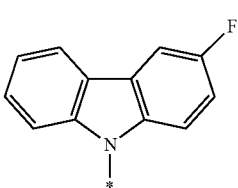
6'

[Formula 27]
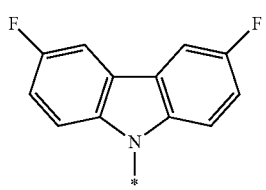
7'
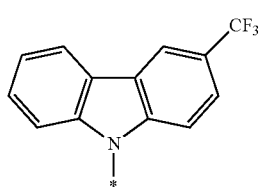
8'
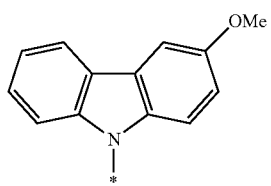
9'
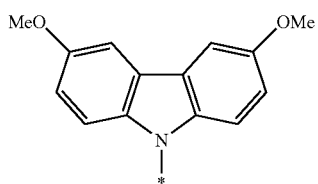
10'
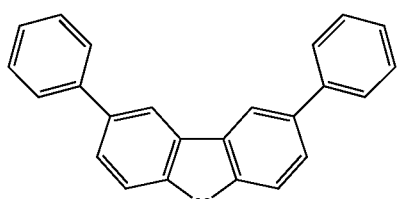
11'
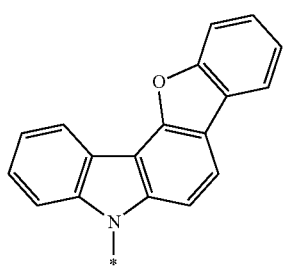
12'
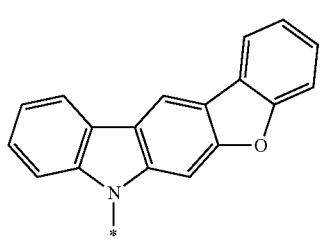
13'
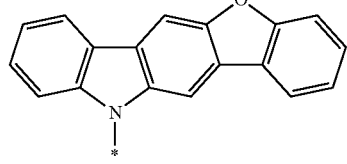
14'
[Formula 28]
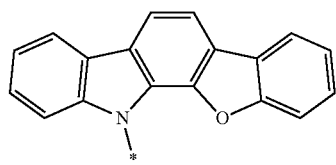
15'
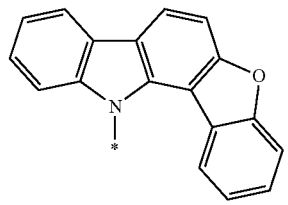
16'
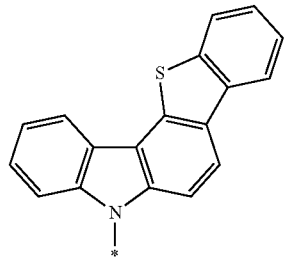
17'
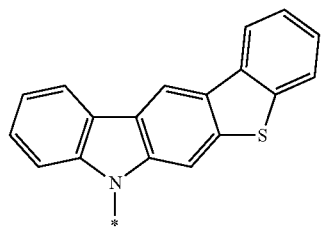
18'
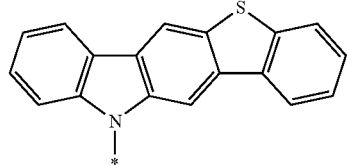
19'
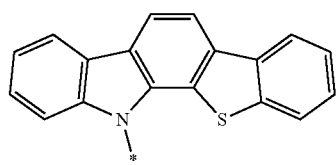
20'

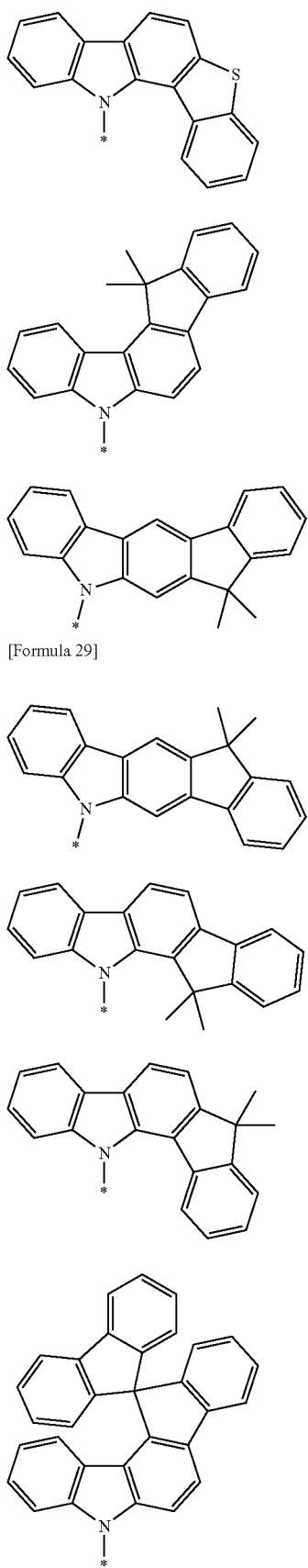
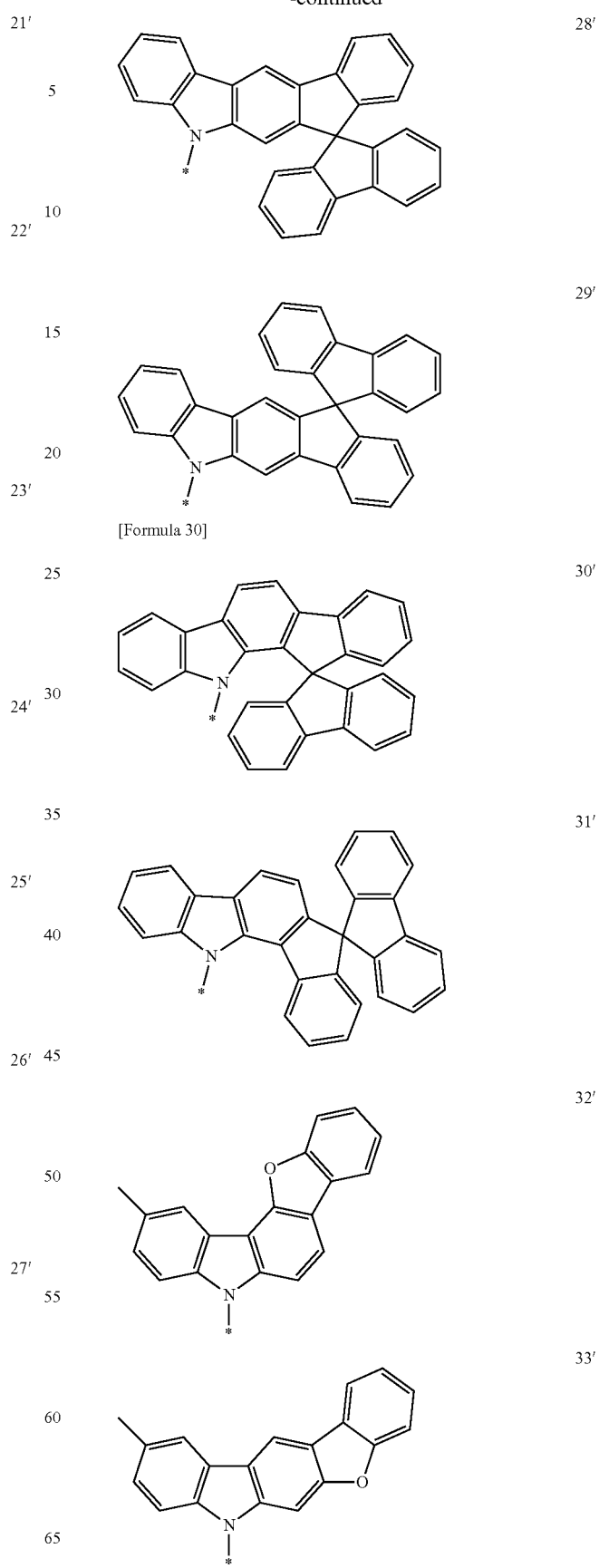
[Formula 29]
[Formula 30]

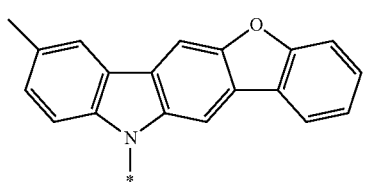
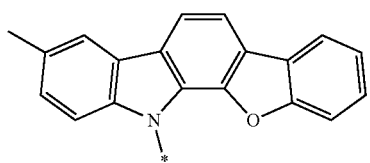
[Formula 31]
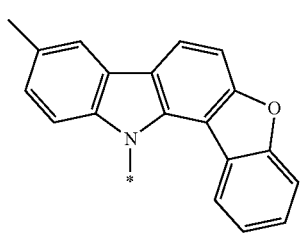
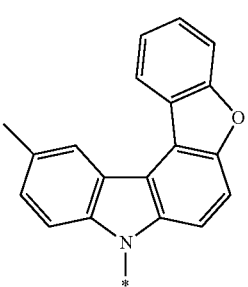
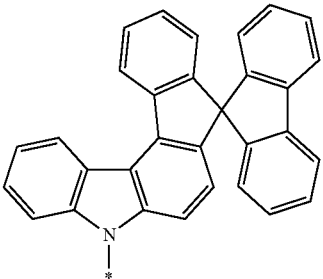
[Formula 32]
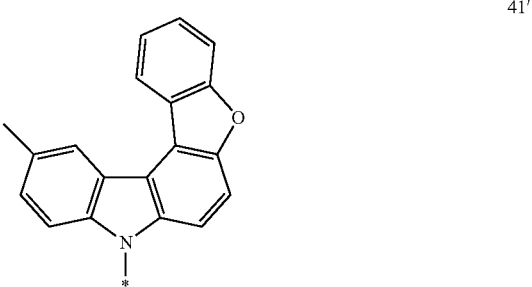
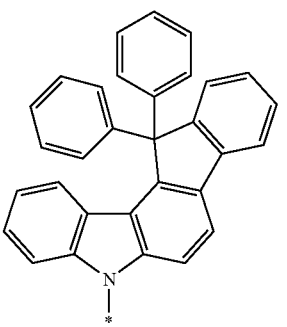
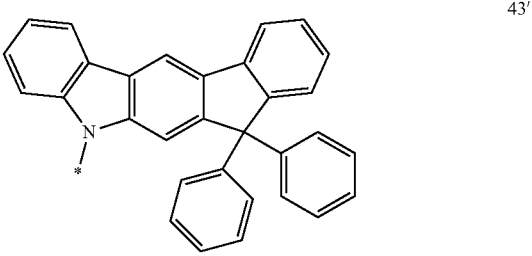
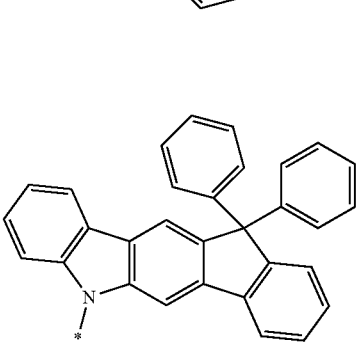

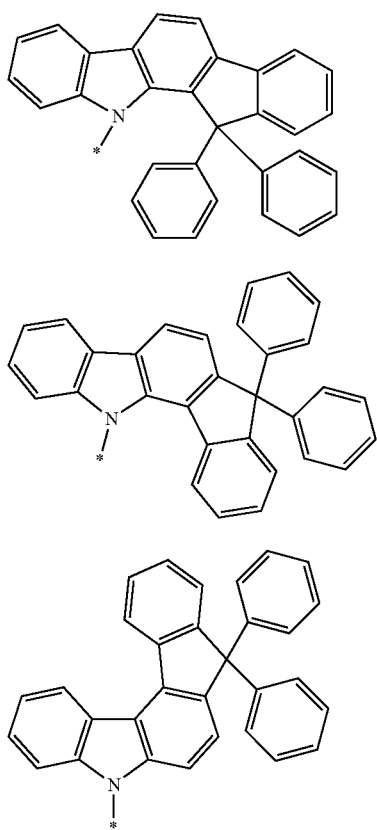

45'

46'

47'

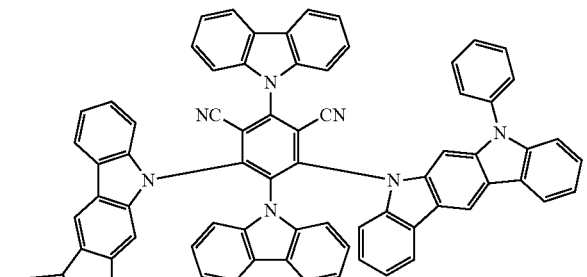

Compound 1b

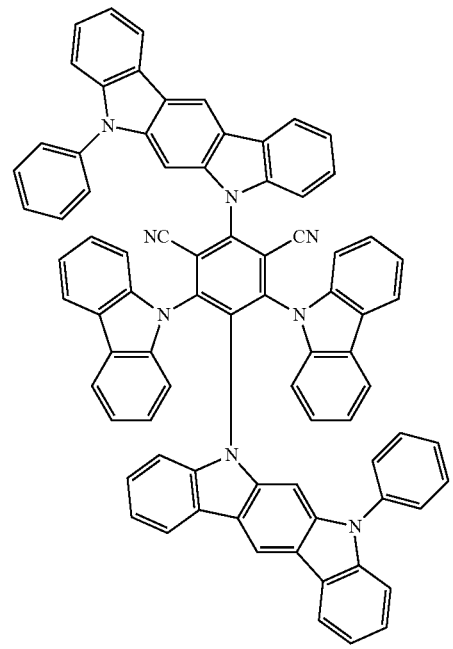

Compound 1c

For instance, in Table 3, a compound 1 represents a compound 1a represented by the formula (11-1) in which $D_{1A}$ and $D_{1B}$ are groups 1 and $D_{2A}$ and $D_{2B}$ are groups 1', a compound 1 b represented by the formula (12-1) in which $D_{1A}$ and $D_{1B}$ are groups 1 and $D_{2A}$ and $D_{2B}$ are groups 1', a compound 1c represented by the formula (12-2) in which $D_{1A}$ and $D_{1B}$ are groups 1 and $D_{2A}$ and $D_{2B}$ are groups 1', a compound 1d represented by the formula (13-1) in which $D_{1A}$ and $D_{1B}$ are groups 1 and $D_{2A}$ and $D_{2B}$ are groups 1', or a compound 1e represented by the formula (13-2) in which $D_{1A}$ and $D_{1B}$ are groups 1 and $D_{2A}$ and $D_{2B}$ are groups 1'.

In other words, the compound 1 is any one of the compounds 1a to 1e.

[Formula 33]

Compound 1a

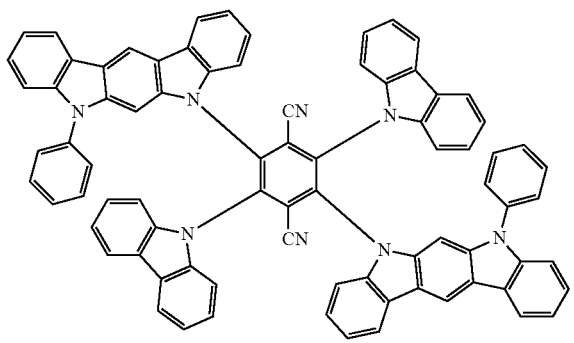

Compound 1d

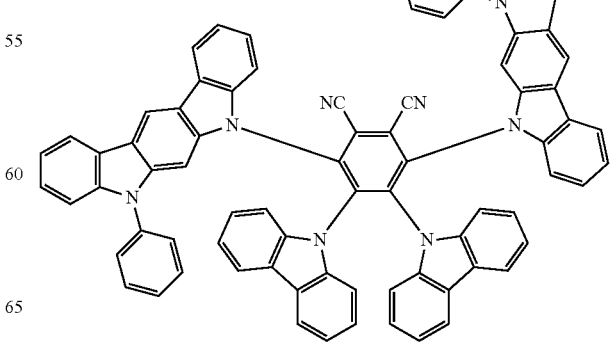

-continued

Compound 1e

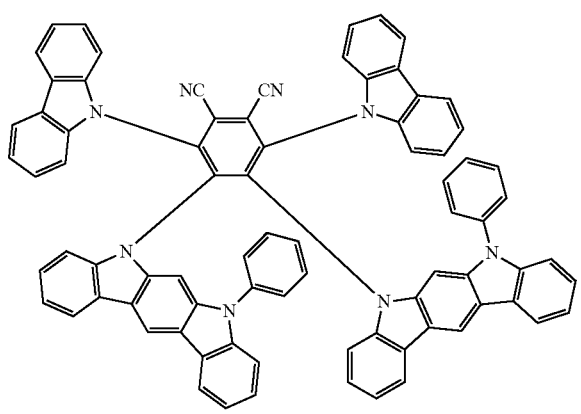

A relationship between the compound 1 and the compounds 1a to 1e is shown in Table 1 below.

Herein, the compounds 1 to 282 are also referred to as a compound X. X is an integer from 1 to 282. Specifically, the compound X represents compounds Xa to Xe.

A relationship between the compound X and the compounds Xa to Xe is shown in Table 2 below.

TABLE 1

| Compound No. | Type | Formula No. | $D_{1A}$ | $D_{1B}$ | $D_{2A}$ | $D_{2B}$ |
|---|---|---|---|---|---|---|
| Compound 1 | Compound 1a | (11-1) | 1 | 1 | 1' | 1' |
|  | Compound 1b | (12-1) | 1 | 1 | 1' | 1' |
|  | Compound 1c | (12-2) | 1 | 1 | 1' | 1' |
|  | Compound 1d | (13-1) | 1 | 1 | 1' | 1' |
|  | Compound 1e | (13-2) | 1 | 1 | 1' | 1' |

TABLE 2

| Compound No. | Type | Formula No. |
|---|---|---|
| Compound X | Compound Xa | (11-1) |
|  | Compound Xb | (12-1) |
|  | Compound Xc | (12-2) |
|  | Compound Xd | (13-1) |
|  | Compound Xe | (13-2) |

TABLE 3

| Compound No. | $D_{1A}$ | $D_{1B}$ | $D_{2A}$ | $D_{2B}$ |
|---|---|---|---|---|
| Compound 1 | 1 | 1 | 1' | 1' |
| Compound 2 | 2 | 2 | 1' | 1' |
| Compound 3 | 3 | 3 | 1' | 1' |
| Compound 4 | 4 | 4 | 1' | 1' |
| Compound 5 | 5 | 5 | 1' | 1' |
| Compound 6 | 6 | 6 | 1' | 1' |
| Compound 7 | 1 | 1 | 2' | 2' |
| Compound 8 | 2 | 2 | 2' | 2' |
| Compound 9 | 3 | 3 | 2' | 2' |
| Compound 10 | 4 | 4 | 2' | 2' |
| Compound 11 | 5 | 5 | 2' | 2' |
| Compound 12 | 6 | 6 | 2' | 2' |
| Compound 13 | 1 | 1 | 3' | 3' |
| Compound 14 | 2 | 2 | 3' | 3' |
| Compound 15 | 3 | 3 | 3' | 3' |
| Compound 16 | 4 | 4 | 3' | 3' |
| Compound 17 | 5 | 5 | 3' | 3' |
| Compound 18 | 6 | 6 | 3' | 3' |
| Compound 19 | 1 | 1 | 4' | 4' |
| Compound 20 | 2 | 2 | 4' | 4' |

TABLE 3-continued

| Compound No. | $D_{1A}$ | $D_{1B}$ | $D_{2A}$ | $D_{2B}$ |
|---|---|---|---|---|
| Compound 21 | 3 | 3 | 4' | 4' |
| Compound 22 | 4 | 4 | 4' | 4' |
| Compound 23 | 5 | 5 | 4' | 4' |
| Compound 24 | 6 | 6 | 4' | 4' |
| Compound 25 | 1 | 1 | 5' | 5' |
| Compound 26 | 2 | 2 | 5' | 5' |
| Compound 27 | 3 | 3 | 5' | 5' |
| Compound 28 | 4 | 4 | 5' | 5' |
| Compound 29 | 5 | 5 | 5' | 5' |
| Compound 30 | 6 | 6 | 5' | 5' |
| Compound 31 | 1 | 1 | 6' | 6' |
| Compound 32 | 2 | 2 | 6' | 6' |
| Compound 33 | 3 | 3 | 6' | 6' |
| Compound 34 | 4 | 4 | 6' | 6' |
| Compound 35 | 5 | 5 | 6' | 6' |
| Compound 36 | 6 | 6 | 6' | 6' |

TABLE 4

| Compound No. | $D_{1A}$ | $D_{1B}$ | $D_{2A}$ | $D_{2B}$ |
|---|---|---|---|---|
| Compound 37 | 1 | 1 | 7' | 7' |
| Compound 38 | 2 | 2 | 7' | 7' |
| Compound 39 | 3 | 3 | 7' | 7' |
| Compound 40 | 4 | 4 | 7' | 7' |
| Compound 41 | 5 | 5 | 7' | 7' |
| Compound 42 | 6 | 6 | 7' | 7' |
| Compound 43 | 1 | 1 | 8' | 8' |
| Compound 44 | 2 | 2 | 8' | 8' |
| Compound 45 | 3 | 3 | 8' | 8' |
| Compound 46 | 4 | 4 | 8' | 8' |
| Compound 47 | 5 | 5 | 8' | 8' |
| Compound 48 | 6 | 6 | 8' | 8' |
| Compound 49 | 1 | 1 | 9' | 9' |
| Compound 50 | 2 | 2 | 9' | 9' |
| Compound 51 | 3 | 3 | 9' | 9' |
| Compound 52 | 4 | 4 | 9' | 9' |
| Compound 53 | 5 | 5 | 9' | 9' |
| Compound 54 | 6 | 6 | 9' | 9' |
| Compound 55 | 1 | 1 | 10' | 10' |
| Compound 56 | 2 | 2 | 10' | 10' |
| Compound 57 | 3 | 3 | 10' | 10' |
| Compound 58 | 4 | 4 | 10' | 10' |
| Compound 59 | 5 | 5 | 10' | 10' |
| Compound 60 | 6 | 6 | 10' | 10' |
| Compound 61 | 1 | 1 | 11' | 11' |
| Compound 62 | 2 | 2 | 11' | 11' |
| Compound 63 | 3 | 3 | 11' | 11' |
| Compound 64 | 4 | 4 | 11' | 11' |
| Compound 65 | 5 | 5 | 11' | 11' |
| Compound 66 | 6 | 6 | 11' | 11' |
| Compound 67 | 1 | 1 | 12' | 12' |
| Compound 68 | 2 | 2 | 12' | 12' |
| Compound 69 | 3 | 3 | 12' | 12' |
| Compound 70 | 4 | 4 | 12' | 12' |
| Compound 71 | 5 | 5 | 12' | 12' |
| Compound 72 | 6 | 6 | 12' | 12' |

TABLE 5

| Compound No. | $D_{1A}$ | $D_{1B}$ | $D_{2A}$ | $D_{2B}$ |
|---|---|---|---|---|
| Compound 73 | 1 | 1 | 13' | 13' |
| Compound 74 | 2 | 2 | 13' | 13' |
| Compound 75 | 3 | 3 | 13' | 13' |
| Compound 76 | 4 | 4 | 13' | 13' |
| Compound 77 | 5 | 5 | 13' | 13' |
| Compound 78 | 6 | 6 | 13' | 13' |
| Compound 79 | 1 | 1 | 14' | 14' |
| Compound 80 | 2 | 2 | 14' | 14' |
| Compound 81 | 3 | 3 | 14' | 14' |
| Compound 82 | 4 | 4 | 14' | 14' |
| Compound 83 | 5 | 5 | 14' | 14' |

TABLE 5-continued

| Compound No. | $D_{1A}$ | $D_{1B}$ | $D_{2A}$ | $D_{2B}$ |
|---|---|---|---|---|
| Compound 84 | 6 | 6 | 14' | 14' |
| Compound 85 | 1 | 1 | 15' | 15' |
| Compound 86 | 2 | 2 | 15' | 15' |
| Compound 87 | 3 | 3 | 15' | 15' |
| Compound 88 | 4 | 4 | 15' | 15' |
| Compound 89 | 5 | 5 | 15' | 15' |
| Compound 90 | 6 | 6 | 15' | 15' |
| Compound 91 | 1 | 1 | 16' | 16' |
| Compound 92 | 2 | 2 | 16' | 16' |
| Compound 93 | 3 | 3 | 16' | 16' |
| Compound 94 | 4 | 4 | 16' | 16' |
| Compound 95 | 5 | 5 | 16' | 16' |
| Compound 96 | 6 | 6 | 16' | 16' |
| Compound 97 | 1 | 1 | 17' | 17' |
| Compound 98 | 2 | 2 | 17' | 17' |
| Compound 99 | 3 | 3 | 17' | 17' |
| Compound 100 | 4 | 4 | 17' | 17' |
| Compound 101 | 5 | 5 | 17' | 17' |
| Compound 102 | 6 | 6 | 17' | 17' |
| Compound 103 | 1 | 1 | 18' | 18' |
| Compound 104 | 2 | 2 | 18' | 18' |
| Compound 105 | 3 | 3 | 18' | 18' |
| Compound 106 | 4 | 4 | 18' | 18' |
| Compound 107 | 5 | 5 | 18' | 18' |
| Compound 108 | 6 | 6 | 18' | 18' |

TABLE 6

| Compound No. | $D_{1A}$ | $D_{1B}$ | $D_{2A}$ | $D_{2B}$ |
|---|---|---|---|---|
| Compound 109 | 1 | 1 | 19' | 19' |
| Compound 110 | 2 | 2 | 19' | 19' |
| Compound 111 | 3 | 3 | 19' | 19' |
| Compound 112 | 4 | 4 | 19' | 19' |
| Compound 113 | 5 | 5 | 19' | 19' |
| Compound 114 | 6 | 6 | 19' | 19' |
| Compound 115 | 1 | 1 | 20' | 20' |
| Compound 116 | 2 | 2 | 20' | 20' |
| Compound 117 | 3 | 3 | 20' | 20' |
| Compound 118 | 4 | 4 | 20' | 20' |
| Compound 119 | 5 | 5 | 20' | 20' |
| Compound 120 | 6 | 6 | 20' | 20' |
| Compound 121 | 1 | 1 | 21' | 21' |
| Compound 122 | 2 | 2 | 21' | 21' |
| Compound 123 | 3 | 3 | 21' | 21' |
| Compound 124 | 4 | 4 | 21' | 21' |
| Compound 125 | 5 | 5 | 21' | 21' |
| Compound 126 | 6 | 6 | 21' | 21' |
| Compound 127 | 1 | 1 | 22' | 22' |
| Compound 128 | 2 | 2 | 22' | 22' |
| Compound 129 | 3 | 3 | 22' | 22' |
| Compound 130 | 4 | 4 | 22' | 22' |
| Compound 131 | 5 | 5 | 22' | 22' |
| Compound 132 | 6 | 6 | 22' | 22' |
| Compound 133 | 1 | 1 | 23' | 23' |
| Compound 134 | 2 | 2 | 23' | 23' |
| Compound 135 | 3 | 3 | 23' | 23' |
| Compound 136 | 4 | 4 | 23' | 23' |
| Compound 137 | 5 | 5 | 23' | 23' |
| Compound 138 | 6 | 6 | 23' | 23' |
| Compound 139 | 1 | 1 | 24' | 24' |
| Compound 140 | 2 | 2 | 24' | 24' |
| Compound 141 | 3 | 3 | 24' | 24' |
| Compound 142 | 4 | 4 | 24' | 24' |
| Compound 143 | 5 | 5 | 24' | 24' |
| Compound 144 | 6 | 6 | 24' | 24' |

TABLE 7

| Compound No. | $D_{1A}$ | $D_{1B}$ | $D_{2A}$ | $D_{2B}$ |
|---|---|---|---|---|
| Compound 145 | 1 | 1 | 25' | 25' |
| Compound 146 | 2 | 2 | 25' | 25' |

TABLE 7-continued

| Compound No. | $D_{1A}$ | $D_{1B}$ | $D_{2A}$ | $D_{2B}$ |
|---|---|---|---|---|
| Compound 147 | 3 | 3 | 25' | 25' |
| Compound 148 | 4 | 4 | 25' | 25' |
| Compound 149 | 5 | 5 | 25' | 25' |
| Compound 150 | 6 | 6 | 25' | 25' |
| Compound 151 | 1 | 1 | 26' | 26' |
| Compound 152 | 2 | 2 | 26' | 26' |
| Compound 153 | 3 | 3 | 26' | 26' |
| Compound 154 | 4 | 4 | 26' | 26' |
| Compound 155 | 5 | 5 | 26' | 26' |
| Compound 156 | 6 | 6 | 26' | 26' |
| Compound 157 | 1 | 1 | 27' | 27' |
| Compound 158 | 2 | 2 | 27' | 27' |
| Compound 159 | 3 | 3 | 27' | 27' |
| Compound 160 | 4 | 4 | 27' | 27' |
| Compound 161 | 5 | 5 | 27' | 27' |
| Compound 162 | 6 | 6 | 27' | 27' |
| Compound 163 | 1 | 1 | 28' | 28' |
| Compound 164 | 2 | 2 | 28' | 28' |
| Compound 165 | 3 | 3 | 28' | 28' |
| Compound 166 | 4 | 4 | 28' | 28' |
| Compound 167 | 5 | 5 | 28' | 28' |
| Compound 168 | 6 | 6 | 28' | 28' |
| Compound 169 | 1 | 1 | 29' | 29' |
| Compound 170 | 2 | 2 | 29' | 29' |
| Compound 171 | 3 | 3 | 29' | 29' |
| Compound 172 | 4 | 4 | 29' | 29' |
| Compound 173 | 5 | 5 | 29' | 29' |
| Compound 174 | 6 | 6 | 29' | 29' |
| Compound 175 | 1 | 1 | 30' | 30' |
| Compound 176 | 2 | 2 | 30' | 30' |
| Compound 177 | 3 | 3 | 30' | 30' |
| Compound 178 | 4 | 4 | 30' | 30' |
| Compound 179 | 5 | 5 | 30' | 30' |
| Compound 180 | 6 | 6 | 30' | 30' |

TABLE 8

| Compound No. | $D_{1A}$ | $D_{1B}$ | $D_{2A}$ | $D_{2B}$ |
|---|---|---|---|---|
| Compound 181 | 1 | 1 | 31' | 31' |
| Compound 182 | 2 | 2 | 31' | 31' |
| Compound 183 | 3 | 3 | 31' | 31' |
| Compound 184 | 4 | 4 | 31' | 31' |
| Compound 185 | 5 | 5 | 31' | 31' |
| Compound 186 | 6 | 6 | 31' | 31' |
| Compound 187 | 1 | 1 | 32' | 32' |
| Compound 188 | 2 | 2 | 32' | 32' |
| Compound 189 | 3 | 3 | 32' | 32' |
| Compound 190 | 4 | 4 | 32' | 32' |
| Compound 191 | 5 | 5 | 32' | 32' |
| Compound 192 | 6 | 6 | 32' | 32' |
| Compound 193 | 1 | 1 | 33' | 33' |
| Compound 194 | 2 | 2 | 33' | 33' |
| Compound 195 | 3 | 3 | 33' | 33' |
| Compound 196 | 4 | 4 | 33' | 33' |
| Compound 197 | 5 | 5 | 33' | 33' |
| Compound 198 | 6 | 6 | 33' | 33' |
| Compound 199 | 1 | 1 | 34' | 34' |
| Compound 200 | 2 | 2 | 34' | 34' |
| Compound 201 | 3 | 3 | 34' | 34' |
| Compound 202 | 4 | 4 | 34' | 34' |
| Compound 203 | 5 | 5 | 34' | 34' |
| Compound 204 | 6 | 6 | 34' | 34' |
| Compound 205 | 1 | 1 | 35' | 35' |
| Compound 206 | 2 | 2 | 35' | 35' |
| Compound 207 | 3 | 3 | 35' | 35' |
| Compound 208 | 4 | 4 | 35' | 35' |
| Compound 209 | 5 | 5 | 35' | 35' |
| Compound 210 | 6 | 6 | 35' | 35' |
| Compound 211 | 1 | 1 | 36' | 36' |
| Compound 212 | 2 | 2 | 36' | 36' |
| Compound 213 | 3 | 3 | 36' | 36' |
| Compound 214 | 4 | 4 | 36' | 36' |

TABLE 8-continued

| Compound No. | $D_{1A}$ | $D_{1B}$ | $D_{2A}$ | $D_{2B}$ |
| --- | --- | --- | --- | --- |
| Compound 215 | 5 | 5 | 36' | 36' |
| Compound 216 | 6 | 6 | 36' | 36' |

TABLE 9

| Compound No. | $D_{1A}$ | $D_{1B}$ | $D_{2A}$ | $D_{2B}$ |
| --- | --- | --- | --- | --- |
| Compound 217 | 1 | 1 | 37' | 37' |
| Compound 218 | 2 | 2 | 37' | 37' |
| Compound 219 | 3 | 3 | 37' | 37' |
| Compound 220 | 4 | 4 | 37' | 37' |
| Compound 221 | 5 | 5 | 37' | 37' |
| Compound 222 | 6 | 6 | 37' | 37' |
| Compound 223 | 1 | 1 | 38' | 38' |
| Compound 224 | 2 | 2 | 38' | 38' |
| Compound 225 | 3 | 3 | 38' | 38' |
| Compound 226 | 4 | 4 | 38' | 38' |
| Compound 227 | 5 | 5 | 38' | 38' |
| Compound 228 | 6 | 6 | 38' | 38' |
| Compound 229 | 1 | 1 | 39' | 39' |
| Compound 230 | 2 | 2 | 39' | 39' |
| Compound 231 | 3 | 3 | 39' | 39' |
| Compound 232 | 4 | 4 | 39' | 39' |
| Compound 233 | 5 | 5 | 39' | 39' |
| Compound 234 | 6 | 6 | 39' | 39' |
| Compound 235 | 1 | 1 | 40' | 40' |
| Compound 236 | 2 | 2 | 40' | 40' |
| Compound 237 | 3 | 3 | 40' | 40' |
| Compound 238 | 4 | 4 | 40' | 40' |
| Compound 239 | 5 | 5 | 40' | 40' |
| Compound 240 | 6 | 6 | 40' | 40' |
| Compound 241 | 1 | 1 | 41' | 41' |
| Compound 242 | 2 | 2 | 41' | 41' |
| Compound 243 | 3 | 3 | 41' | 41' |
| Compound 244 | 4 | 4 | 41' | 41' |
| Compound 245 | 5 | 5 | 41' | 41' |
| Compound 246 | 6 | 6 | 41' | 41' |
| Compound 247 | 1 | 1 | 42' | 42' |
| Compound 248 | 2 | 2 | 42' | 42' |
| Compound 249 | 3 | 3 | 42' | 42' |
| Compound 250 | 4 | 4 | 42' | 42' |
| Compound 251 | 5 | 5 | 42' | 42' |
| Compound 252 | 6 | 6 | 42' | 42' |

TABLE 10

| Compound No. | $D_{1A}$ | $D_{1B}$ | $D_{2A}$ | $D_{2B}$ |
| --- | --- | --- | --- | --- |
| Compound 253 | 1 | 1 | 43' | 43' |
| Compound 254 | 2 | 2 | 43' | 43' |
| Compound 255 | 3 | 3 | 43' | 43' |
| Compound 256 | 4 | 4 | 43' | 43' |
| Compound 257 | 5 | 5 | 43' | 43' |
| Compound 258 | 6 | 6 | 43' | 43' |
| Compound 259 | 1 | 1 | 44' | 44' |
| Compound 260 | 2 | 2 | 44' | 44' |
| Compound 261 | 3 | 3 | 44' | 44' |
| Compound 262 | 4 | 4 | 44' | 44' |
| Compound 263 | 5 | 5 | 44' | 44' |
| Compound 264 | 6 | 6 | 44' | 44' |
| Compound 265 | 1 | 1 | 45' | 45' |
| Compound 266 | 2 | 2 | 45' | 45' |
| Compound 267 | 3 | 3 | 45' | 45' |
| Compound 268 | 4 | 4 | 45' | 45' |
| Compound 269 | 5 | 5 | 45' | 45' |
| Compound 270 | 6 | 6 | 45' | 45' |
| Compound 271 | 1 | 1 | 46' | 46' |
| Compound 272 | 2 | 2 | 46' | 46' |
| Compound 273 | 3 | 3 | 46' | 46' |
| Compound 274 | 4 | 4 | 46' | 46' |
| Compound 275 | 5 | 5 | 46' | 46' |
| Compound 276 | 6 | 6 | 46' | 46' |
| Compound 277 | 1 | 1 | 47' | 47' |

TABLE 10-continued

| Compound No. | $D_{1A}$ | $D_{1B}$ | $D_{2A}$ | $D_{2B}$ |
| --- | --- | --- | --- | --- |
| Compound 278 | 2 | 2 | 47' | 47' |
| Compound 279 | 3 | 3 | 47' | 47' |
| Compound 280 | 4 | 4 | 47' | 47' |
| Compound 281 | 5 | 5 | 47' | 47' |
| Compound 282 | 6 | 6 | 47' | 47' |

Examples of the compound according to the exemplary embodiment include compounds represented by the formulae (11-2), (12-3) to (12-5), and (13-3) to (13-4).

[Formula 34]

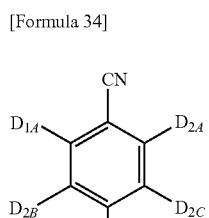

(11-2)

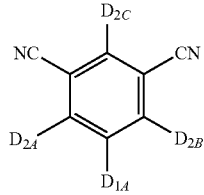

(12-3)

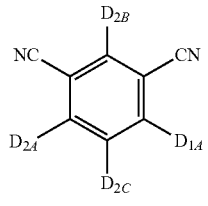

(12-4)

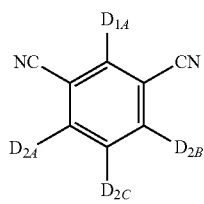

(12-5)

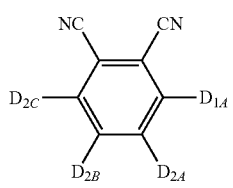

(13-3)

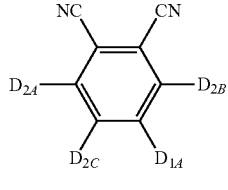

(13-4)

In the formula (11-2), $D_{1A}$, $D_{2A}$, $D_{2B}$, and $D_{2C}$ respectively represent the groups denoted by the numbers shown in Tables 12 to 19.

In the formula (12-3), $D_{1A}$, $D_{2A}$, $D_{2B}$, and $D_{2C}$ respectively represent the groups denoted by the numbers shown in Tables 12 to 19.

In the formula (12-4), $D_{1A}$, $D_{2A}$, $D_{2B}$, and $D_{2C}$ respectively represent the groups denoted by the numbers shown in Tables 12 to 19.

In the formula (12-5), $D_{1A}$, $D_{2A}$, $D_{2B}$, and $D_{2C}$ respectively represent the groups denoted by the numbers shown in Tables 12 to 19.

In the formula (13-3), $D_{1A}$, $D_{2A}$, $D_{2B}$, and $D_{2C}$ respectively represent the groups denoted by the numbers shown in Tables 12 to 19.

In the formula (13-4), $D_{1A}$, $D_{2A}$, $D_{2B}$, and $D_{2C}$ respectively represent the groups denoted by the numbers shown in Tables 12 to 19.

In Tables 12 to 19 below, the numbers given to columns of $D_{1A}$, $D_{2A}$, $D_{1B}$, and $D_{2B}$ correspond to numbers of the above-described groups 1 to 6 and groups 1' to 47'.

For instance, in Table 12, a compound 283 represents a compound 283a represented by the formula (11-2) in which $D_{1A}$ is a group 1 and $D_{2A}$, $D_{2B}$ and $D_{2C}$ are groups 1', a compound 283b represented by the formula (12-3) in which $D_{1A}$ is a group 1 and $D_{2A}$, $D_{2B}$ and $D_{2C}$ are groups 1', a compound 283c represented by the formula (12-4) in which $D_{1A}$ is a group 1 and $D_{2A}$, $D_{2B}$ and $D_{2C}$ are groups 1', a compound 283d represented by the formula (12-5) in which $D_{1A}$ is a group 1 and $D_{2A}$, $D_{2B}$ and $D_{2C}$ are groups 1', a compound 283e represented by the formula (13-3) in which $D_{1A}$ is a group 1 and $D_{2A}$, $D_{2B}$ and $D_{2C}$ are groups 1', or a compound 283f represented by the formula (13-4) in which $D_{1A}$ is a group 1 and $D_{2A}$, $D_{2B}$ and $D_{2C}$ are groups 1'.

In other words, the compound 283 is any one of the compounds 283a to 283f.

[Formula 35]

Compound 283a

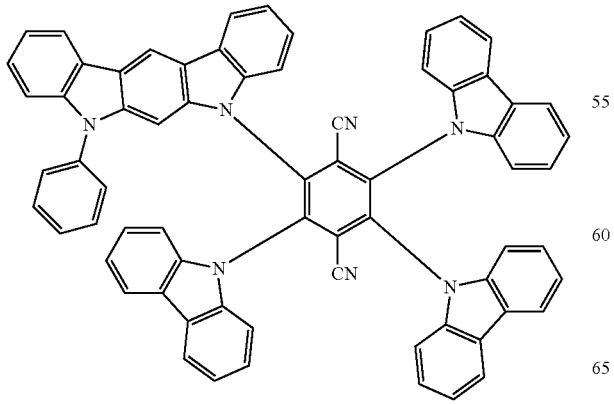

Compound 283b

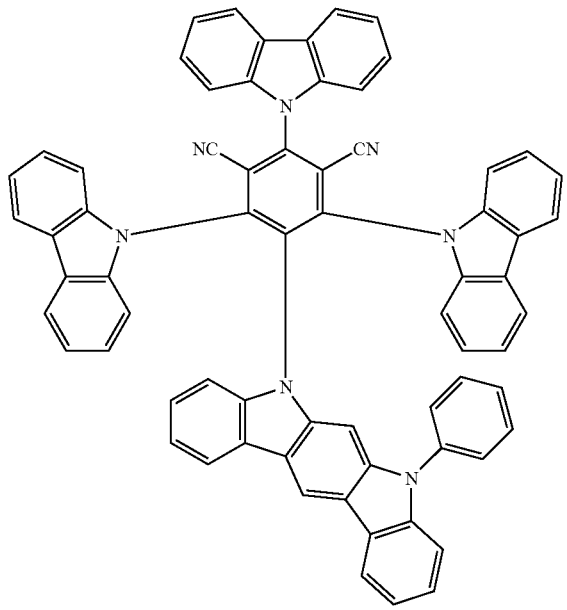

Compound 283c

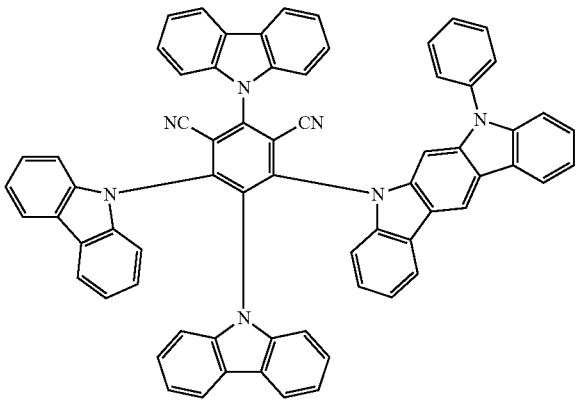

Compound 283d

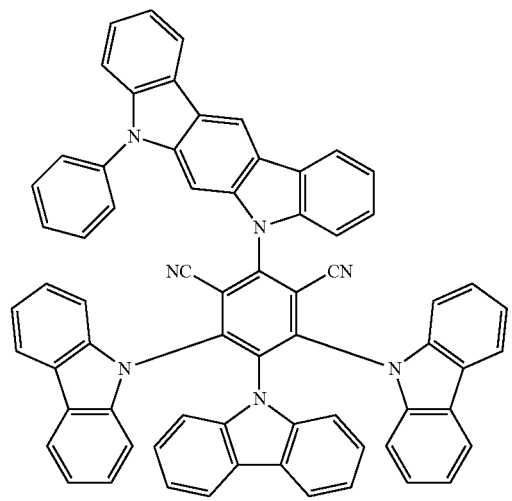

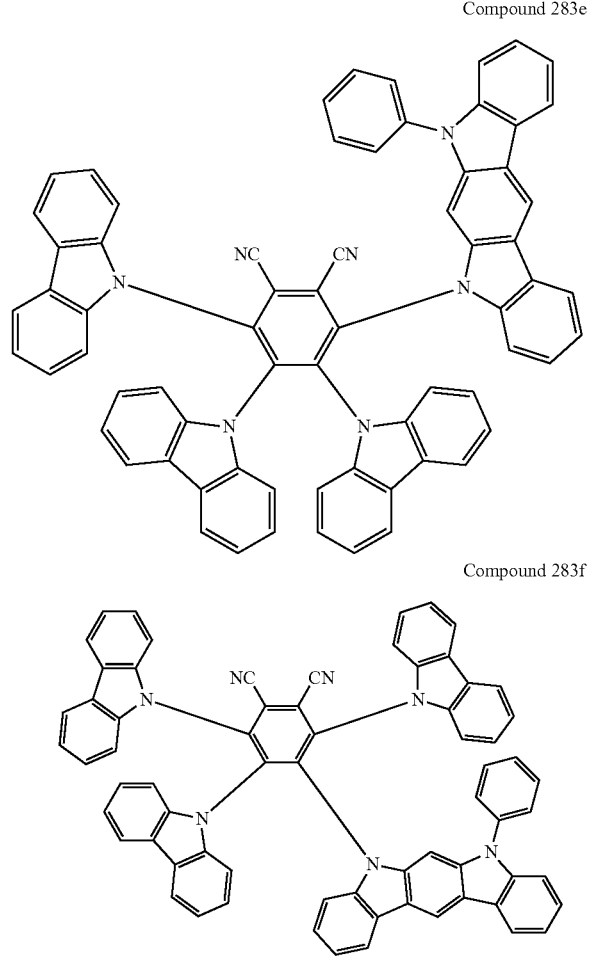

Compound 283e

Compound 283f

Herein, the compound 283 to the compound 564 are also referred to as a compound Y. Y is an integer from 283 to 564. Specifically, the compound Y represents a compound Ya, Yb, Yc, Yd, Ye or Yf.

A relationship between the compound Y and the compounds Ya to Yf is shown in Table 11 below.

TABLE 11

| Compound No. | Type | Formula No. |
|---|---|---|
| Compound Y | Compound Ya | (11-2) |
| | Compound Yb | (12-3) |
| | Compound Yc | (12-4) |
| | Compound Yd | (12-5) |
| | Compound Ye | (13-3) |
| | Compound Yf | (13-4) |

TABLE 12

| Compound No. | $D_{1A}$ | $D_{2A}$ | $D_{2B}$ | $D_{2C}$ |
|---|---|---|---|---|
| Compound 283 | 1 | 1' | 1' | 1' |
| Compound 284 | 2 | 1' | 1' | 1' |
| Compound 285 | 3 | 1' | 1' | 1' |
| Compound 286 | 4 | 1' | 1' | 1' |
| Compound 287 | 5 | 1' | 1' | 1' |
| Compound 288 | 6 | 1' | 1' | 1' |
| Compound 289 | 1 | 2' | 2' | 2' |
| Compound 290 | 2 | 2' | 2' | 2' |

TABLE 12-continued

| Compound No. | $D_{1A}$ | $D_{2A}$ | $D_{2B}$ | $D_{2C}$ |
|---|---|---|---|---|
| Compound 291 | 3 | 2' | 2' | 2' |
| Compound 292 | 4 | 2' | 2' | 2' |
| Compound 293 | 5 | 2' | 2' | 2' |
| Compound 294 | 6 | 2' | 2' | 2' |
| Compound 295 | 1 | 3' | 3' | 3' |
| Compound 296 | 2 | 3' | 3' | 3' |
| Compound 297 | 3 | 3' | 3' | 3' |
| Compound 298 | 4 | 3' | 3' | 3' |
| Compound 299 | 5 | 3' | 3' | 3' |
| Compound 300 | 6 | 3' | 3' | 3' |
| Compound 301 | 1 | 4' | 4' | 4' |
| Compound 302 | 2 | 4' | 4' | 4' |
| Compound 303 | 3 | 4' | 4' | 4' |
| Compound 304 | 4 | 4' | 4' | 4' |
| Compound 305 | 5 | 4' | 4' | 4' |
| Compound 306 | 6 | 4' | 4' | 4' |
| Compound 307 | 1 | 5' | 5' | 5' |
| Compound 308 | 2 | 5' | 5' | 5' |
| Compound 309 | 3 | 5' | 5' | 5' |
| Compound 310 | 4 | 5' | 5' | 5' |
| Compound 311 | 5 | 5' | 5' | 5' |
| Compound 312 | 6 | 5' | 5' | 5' |
| Compound 313 | 1 | 6' | 6' | 6' |
| Compound 314 | 2 | 6' | 6' | 6' |
| Compound 315 | 3 | 6' | 6' | 6' |
| Compound 316 | 4 | 6' | 6' | 6' |
| Compound 317 | 5 | 6' | 6' | 6' |
| Compound 318 | 6 | 6' | 6' | 6' |

TABLE 13

| Compound No. | $D_{1A}$ | $D_{2A}$ | $D_{2B}$ | $D_{2C}$ |
|---|---|---|---|---|
| Compound 319 | 1 | 7' | 7' | 7' |
| Compound 320 | 2 | 7' | 7' | 7' |
| Compound 321 | 3 | 7' | 7' | 7' |
| Compound 322 | 4 | 7' | 7' | 7' |
| Compound 323 | 5 | 7' | 7' | 7' |
| Compound 324 | 6 | 7' | 7' | 7' |
| Compound 325 | 1 | 8' | 8' | 8' |
| Compound 326 | 2 | 8' | 8' | 8' |
| Compound 327 | 3 | 8' | 8' | 8' |
| Compound 328 | 4 | 8' | 8' | 8' |
| Compound 329 | 5 | 8' | 8' | 8' |
| Compound 330 | 6 | 8' | 8' | 8' |
| Compound 331 | 1 | 9' | 9' | 9' |
| Compound 332 | 2 | 9' | 9' | 9' |
| Compound 333 | 3 | 9' | 9' | 9' |
| Compound 334 | 4 | 9' | 9' | 9' |
| Compound 335 | 5 | 9' | 9' | 9' |
| Compound 336 | 6 | 9' | 9' | 9' |
| Compound 337 | 1 | 10' | 10' | 10' |
| Compound 338 | 2 | 10' | 10' | 10' |
| Compound 339 | 3 | 10' | 10' | 10' |
| Compound 340 | 4 | 10' | 10' | 10' |
| Compound 341 | 5 | 10' | 10' | 10' |
| Compound 342 | 6 | 10' | 10' | 10' |
| Compound 343 | 1 | 11' | 11' | 11' |
| Compound 344 | 2 | 11' | 11' | 11' |
| Compound 345 | 3 | 11' | 11' | 11' |
| Compound 346 | 4 | 11' | 11' | 11' |
| Compound 347 | 5 | 11' | 11' | 11' |
| Compound 348 | 6 | 11' | 11' | 11' |
| Compound 349 | 1 | 12' | 12' | 12' |
| Compound 350 | 2 | 12' | 12' | 12' |
| Compound 351 | 3 | 12' | 12' | 12' |
| Compound 352 | 4 | 12' | 12' | 12' |
| Compound 353 | 5 | 12' | 12' | 12' |
| Compound 354 | 6 | 12' | 12' | 12' |

TABLE 14

| Compound No. | $D_{1A}$ | $D_{2A}$ | $D_{2B}$ | $D_{2C}$ |
|---|---|---|---|---|
| Compound 355 | 1 | 13' | 13' | 13' |
| Compound 356 | 2 | 13' | 13' | 13' |
| Compound 357 | 3 | 13' | 13' | 13' |
| Compound 358 | 4 | 13' | 13' | 13' |
| Compound 359 | 5 | 13' | 13' | 13' |
| Compound 360 | 6 | 13' | 13' | 13' |
| Compound 361 | 1 | 14' | 14' | 14' |
| Compound 362 | 2 | 14' | 14' | 14' |
| Compound 363 | 3 | 14' | 14' | 14' |
| Compound 364 | 4 | 14' | 14' | 14' |
| Compound 365 | 5 | 14' | 14' | 14' |
| Compound 366 | 6 | 14' | 14' | 14' |
| Compound 367 | 1 | 15' | 15' | 15' |
| Compound 368 | 2 | 15' | 15' | 15' |
| Compound 369 | 3 | 15' | 15' | 15' |
| Compound 370 | 4 | 15' | 15' | 15' |
| Compound 371 | 5 | 15' | 15' | 15' |
| Compound 372 | 6 | 15' | 15' | 15' |
| Compound 373 | 1 | 16' | 16' | 16' |
| Compound 374 | 2 | 16' | 16' | 16' |
| Compound 375 | 3 | 16' | 16' | 16' |
| Compound 376 | 4 | 16' | 16' | 16' |
| Compound 377 | 5 | 16' | 16' | 16' |
| Compound 378 | 6 | 16' | 16' | 16' |
| Compound 379 | 1 | 17' | 17' | 17' |
| Compound 380 | 2 | 17' | 17' | 17' |
| Compound 381 | 3 | 17' | 17' | 17' |
| Compound 382 | 4 | 17' | 17' | 17' |
| Compound 383 | 5 | 17' | 17' | 17' |
| Compound 384 | 6 | 17' | 17' | 17' |
| Compound 385 | 1 | 18' | 18' | 18' |
| Compound 386 | 2 | 18' | 18' | 18' |
| Compound 387 | 3 | 18' | 18' | 18' |
| Compound 388 | 4 | 18' | 18' | 18' |
| Compound 389 | 5 | 18' | 18' | 18' |
| Compound 390 | 6 | 18' | 18' | 18' |

TABLE 15

| Compound No. | $D_{1A}$ | $D_{2A}$ | $D_{2B}$ | $D_{2C}$ |
|---|---|---|---|---|
| Compound 391 | 1 | 19' | 19' | 19' |
| Compound 392 | 2 | 19' | 19' | 19' |
| Compound 393 | 3 | 19' | 19' | 19' |
| Compound 394 | 4 | 19' | 19' | 19' |
| Compound 395 | 5 | 19' | 19' | 19' |
| Compound 396 | 6 | 19' | 19' | 19' |
| Compound 397 | 1 | 20' | 20' | 20' |
| Compound 398 | 2 | 20' | 20' | 20' |
| Compound 399 | 3 | 20' | 20' | 20' |
| Compound 400 | 4 | 20' | 20' | 20' |
| Compound 401 | 5 | 20' | 20' | 20' |
| Compound 402 | 6 | 20' | 20' | 20' |
| Compound 403 | 1 | 21' | 21' | 21' |
| Compound 404 | 2 | 21' | 21' | 21' |
| Compound 405 | 3 | 21' | 21' | 21' |
| Compound 406 | 4 | 21' | 21' | 21' |
| Compound 407 | 5 | 21' | 21' | 21' |
| Compound 408 | 6 | 21' | 21' | 21' |
| Compound 409 | 1 | 22' | 22' | 22' |
| Compound 410 | 2 | 22' | 22' | 22' |
| Compound 411 | 3 | 22' | 22' | 22' |
| Compound 412 | 4 | 22' | 22' | 22' |
| Compound 413 | 5 | 22' | 22' | 22' |
| Compound 414 | 6 | 22' | 22' | 22' |
| Compound 415 | 1 | 23' | 23' | 23' |
| Compound 416 | 2 | 23' | 23' | 23' |
| Compound 417 | 3 | 23' | 23' | 23' |
| Compound 418 | 4 | 23' | 23' | 23' |
| Compound 419 | 5 | 23' | 23' | 23' |
| Compound 420 | 6 | 23' | 23' | 23' |
| Compound 421 | 1 | 24' | 24' | 24' |
| Compound 422 | 2 | 24' | 24' | 24' |
| Compound 423 | 3 | 24' | 24' | 24' |
| Compound 424 | 4 | 24' | 24' | 24' |
| Compound 425 | 5 | 24' | 24' | 24' |
| Compound 426 | 6 | 24' | 24' | 24' |

TABLE 16

| Compound No. | $D_{1A}$ | $D_{2A}$ | $D_{2B}$ | $D_{2C}$ |
|---|---|---|---|---|
| Compound 427 | 1 | 25' | 25' | 25' |
| Compound 428 | 2 | 25' | 25' | 25' |
| Compound 429 | 3 | 25' | 25' | 25' |
| Compound 430 | 4 | 25' | 25' | 25' |
| Compound 431 | 5 | 25' | 25' | 25' |
| Compound 432 | 6 | 25' | 25' | 25' |
| Compound 433 | 1 | 26' | 26' | 26' |
| Compound 434 | 2 | 26' | 26' | 26' |
| Compound 435 | 3 | 26' | 26' | 26' |
| Compound 436 | 4 | 26' | 26' | 26' |
| Compound 437 | 5 | 26' | 26' | 26' |
| Compound 438 | 6 | 26' | 26' | 26' |
| Compound 439 | 1 | 27' | 27' | 27' |
| Compound 440 | 2 | 27' | 27' | 27' |
| Compound 441 | 3 | 27' | 27' | 27' |
| Compound 442 | 4 | 27' | 27' | 27' |
| Compound 443 | 5 | 27' | 27' | 27' |
| Compound 444 | 6 | 27' | 27' | 27' |
| Compound 445 | 1 | 28' | 28' | 28' |
| Compound 446 | 2 | 28' | 28' | 28' |
| Compound 447 | 3 | 28' | 28' | 28' |
| Compound 448 | 4 | 28' | 28' | 28' |
| Compound 449 | 5 | 28' | 28' | 28' |
| Compound 450 | 6 | 28' | 28' | 28' |
| Compound 451 | 1 | 29' | 29' | 29' |
| Compound 452 | 2 | 29' | 29' | 29' |
| Compound 453 | 3 | 29' | 29' | 29' |
| Compound 454 | 4 | 29' | 29' | 29' |
| Compound 455 | 5 | 29' | 29' | 29' |
| Compound 456 | 6 | 29' | 29' | 29' |
| Compound 457 | 1 | 30' | 30' | 30' |
| Compound 458 | 2 | 30' | 30' | 30' |
| Compound 459 | 3 | 30' | 30' | 30' |
| Compound 460 | 4 | 30' | 30' | 30' |
| Compound 461 | 5 | 30' | 30' | 30' |
| Compound 462 | 6 | 30' | 30' | 30' |

TABLE 17

| Compound No. | $D_{1A}$ | $D_{2A}$ | $D_{2B}$ | $D_{2C}$ |
|---|---|---|---|---|
| Compound 463 | 1 | 31' | 31' | 31' |
| Compound 464 | 2 | 31' | 31' | 31' |

TABLE 17-continued

| Compound No. | $D_{1A}$ | $D_{2A}$ | $D_{2B}$ | $D_{2C}$ |
|---|---|---|---|---|
| Compound 465 | 3 | 31' | 31' | 31' |
| Compound 466 | 4 | 31' | 31' | 31' |
| Compound 467 | 5 | 31' | 31' | 31' |
| Compound 468 | 6 | 31' | 31' | 31' |
| Compound 469 | 1 | 32' | 32' | 32' |
| Compound 470 | 2 | 32' | 32' | 32' |
| Compound 471 | 3 | 32' | 32' | 32' |
| Compound 472 | 4 | 32' | 32' | 32' |
| Compound 473 | 5 | 32' | 32' | 32' |
| Compound 474 | 6 | 32' | 32' | 32' |
| Compound 475 | 1 | 33' | 33' | 33' |
| Compound 476 | 2 | 33' | 33' | 33' |
| Compound 477 | 3 | 33' | 33' | 33' |
| Compound 478 | 4 | 33' | 33' | 33' |
| Compound 479 | 5 | 33' | 33' | 33' |
| Compound 480 | 6 | 33' | 33' | 33' |
| Compound 481 | 1 | 34' | 34' | 34' |
| Compound 482 | 2 | 34' | 34' | 34' |
| Compound 483 | 3 | 34' | 34' | 34' |
| Compound 484 | 4 | 34' | 34' | 34' |
| Compound 485 | 5 | 34' | 34' | 34' |
| Compound 486 | 6 | 34' | 34' | 34' |
| Compound 487 | 1 | 35' | 35' | 35' |
| Compound 488 | 2 | 35' | 35' | 35' |
| Compound 489 | 3 | 35' | 35' | 35' |
| Compound 490 | 4 | 35' | 35' | 35' |
| Compound 491 | 5 | 35' | 35' | 35' |
| Compound 492 | 6 | 35' | 35' | 35' |
| Compound 493 | 1 | 36' | 36' | 36' |
| Compound 494 | 2 | 36' | 36' | 36' |
| Compound 495 | 3 | 36' | 36' | 36' |
| Compound 496 | 4 | 36' | 36' | 36' |
| Compound 497 | 5 | 36' | 36' | 36' |
| Compound 498 | 6 | 36' | 36' | 36' |

TABLE 18

| Compound No. | $D_{1A}$ | $D_{2A}$ | $D_{2B}$ | $D_{2C}$ |
|---|---|---|---|---|
| Compound 499 | 1 | 37' | 37' | 37' |
| Compound 500 | 2 | 37' | 37' | 37' |
| Compound 501 | 3 | 37' | 37' | 37' |
| Compound 502 | 4 | 37' | 37' | 37' |
| Compound 503 | 5 | 37' | 37' | 37' |
| Compound 504 | 6 | 37' | 37' | 37' |
| Compound 505 | 1 | 38' | 38' | 38' |
| Compound 506 | 2 | 38' | 38' | 38' |
| Compound 507 | 3 | 38' | 38' | 38' |
| Compound 508 | 4 | 38' | 38' | 38' |
| Compound 509 | 5 | 38' | 38' | 38' |
| Compound 510 | 6 | 38' | 38' | 38' |
| Compound 511 | 1 | 39' | 39' | 39' |
| Compound 512 | 2 | 39' | 39' | 39' |
| Compound 513 | 3 | 39' | 39' | 39' |
| Compound 514 | 4 | 39' | 39' | 39' |
| Compound 515 | 5 | 39' | 39' | 39' |
| Compound 516 | 6 | 39' | 39' | 39' |
| Compound 517 | 1 | 40' | 40' | 40' |
| Compound 518 | 2 | 40' | 40' | 40' |
| Compound 519 | 3 | 40' | 40' | 40' |
| Compound 520 | 4 | 40' | 40' | 40' |
| Compound 521 | 5 | 40' | 40' | 40' |
| Compound 522 | 6 | 40' | 40' | 40' |
| Compound 523 | 1 | 41' | 41' | 41' |
| Compound 524 | 2 | 41' | 41' | 41' |
| Compound 525 | 3 | 41' | 41' | 41' |
| Compound 526 | 4 | 41' | 41' | 41' |
| Compound 527 | 5 | 41' | 41' | 41' |
| Compound 528 | 6 | 41' | 41' | 41' |
| Compound 529 | 1 | 42' | 42' | 42' |
| Compound 530 | 2 | 42' | 42' | 42' |
| Compound 531 | 3 | 42' | 42' | 42' |
| Compound 532 | 4 | 42' | 42' | 42' |
| Compound 533 | 5 | 42' | 42' | 42' |
| Compound 534 | 6 | 42' | 42' | 42' |

TABLE 19

| Compound No. | $D_{1A}$ | $D_{2A}$ | $D_{2B}$ | $D_{2C}$ |
|---|---|---|---|---|
| Compound 535 | 1 | 43' | 43' | 43' |
| Compound 536 | 2 | 43' | 43' | 43' |
| Compound 537 | 3 | 43' | 43' | 43' |
| Compound 538 | 4 | 43' | 43' | 43' |
| Compound 539 | 5 | 43' | 43' | 43' |
| Compound 540 | 6 | 43' | 43' | 43' |
| Compound 541 | 1 | 44' | 44' | 44' |
| Compound 542 | 2 | 44' | 44' | 44' |
| Compound 543 | 3 | 44' | 44' | 44' |
| Compound 544 | 4 | 44' | 44' | 44' |
| Compound 545 | 5 | 44' | 44' | 44' |
| Compound 546 | 6 | 44' | 44' | 44' |
| Compound 547 | 1 | 45' | 45' | 45' |
| Compound 548 | 2 | 45' | 45' | 45' |
| Compound 549 | 3 | 45' | 45' | 45' |
| Compound 550 | 4 | 45' | 45' | 45' |
| Compound 551 | 5 | 45' | 45' | 45' |
| Compound 552 | 6 | 45' | 45' | 45' |
| Compound 553 | 1 | 46' | 46' | 46' |
| Compound 554 | 2 | 46' | 46' | 46' |
| Compound 555 | 3 | 46' | 46' | 46' |
| Compound 556 | 4 | 46' | 46' | 46' |
| Compound 557 | 5 | 46' | 46' | 46' |
| Compound 558 | 6 | 46' | 46' | 46' |
| Compound 559 | 1 | 47' | 47' | 47' |
| Compound 560 | 2 | 47' | 47' | 47' |
| Compound 561 | 3 | 47' | 47' | 47' |
| Compound 562 | 4 | 47' | 47' | 47' |
| Compound 563 | 5 | 47' | 47' | 47' |
| Compound 564 | 6 | 47' | 47' | 47' |

Examples of the compound of the exemplary embodiment are shown below. The compound of the invention is by no means limited to the Examples.

[Formula 36]
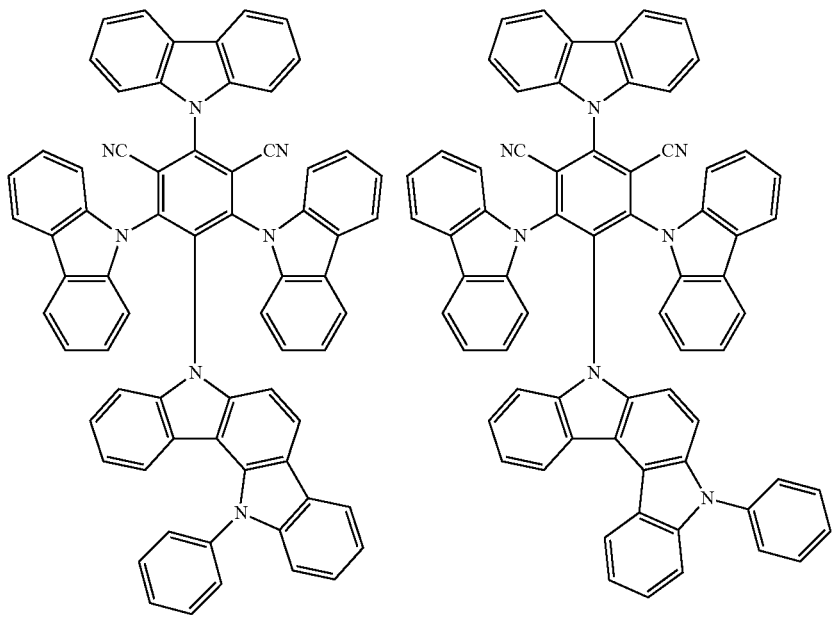
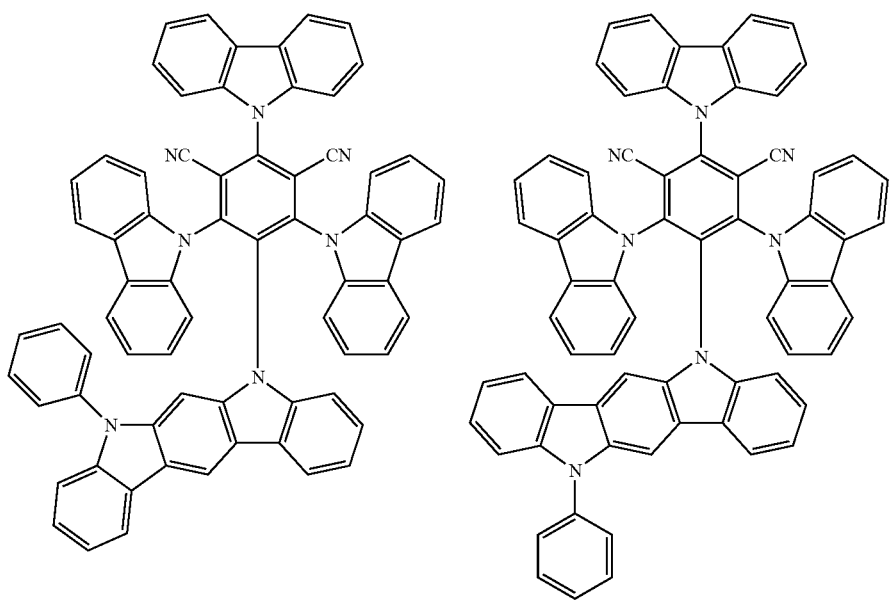

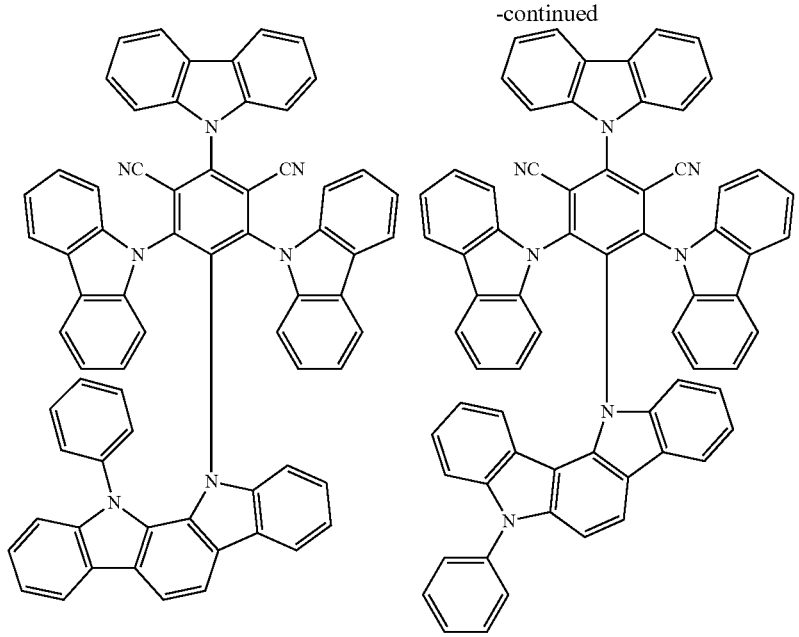
[Formula 37]
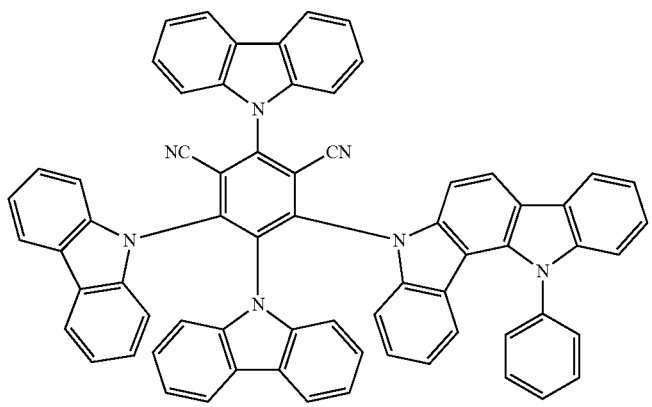
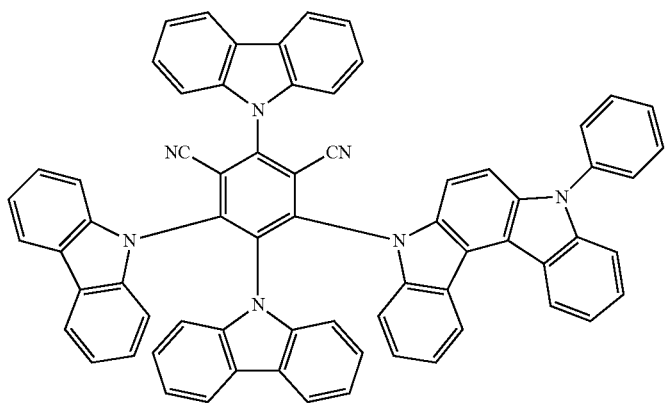

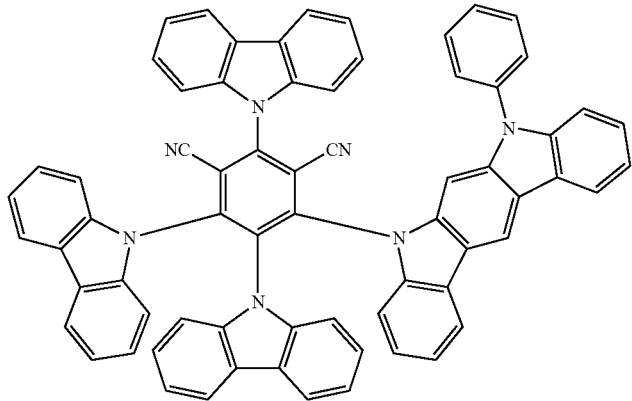
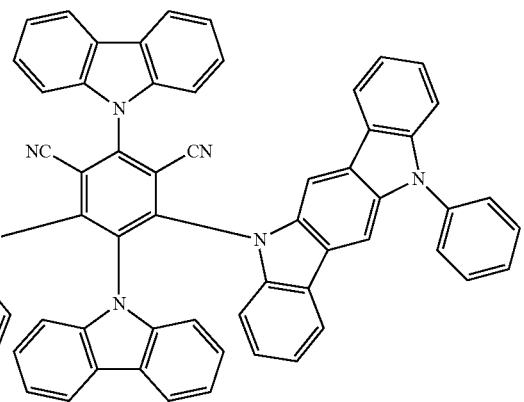
[Formula 38]
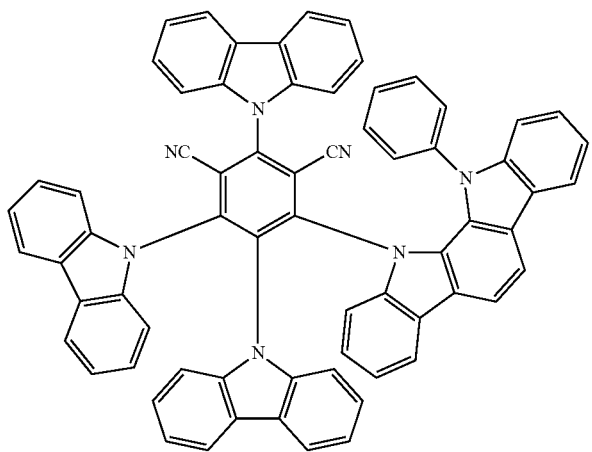

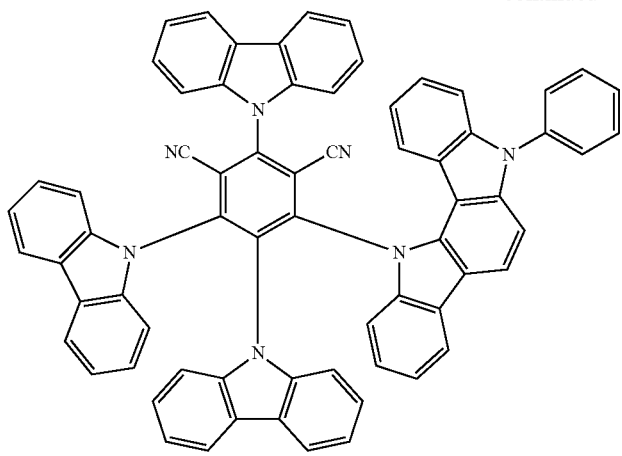
[Formula 39]
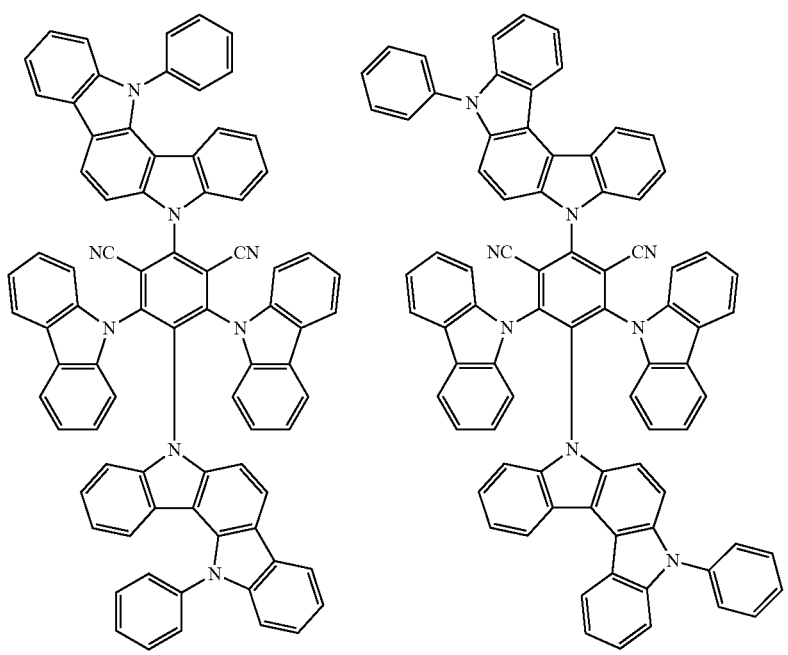

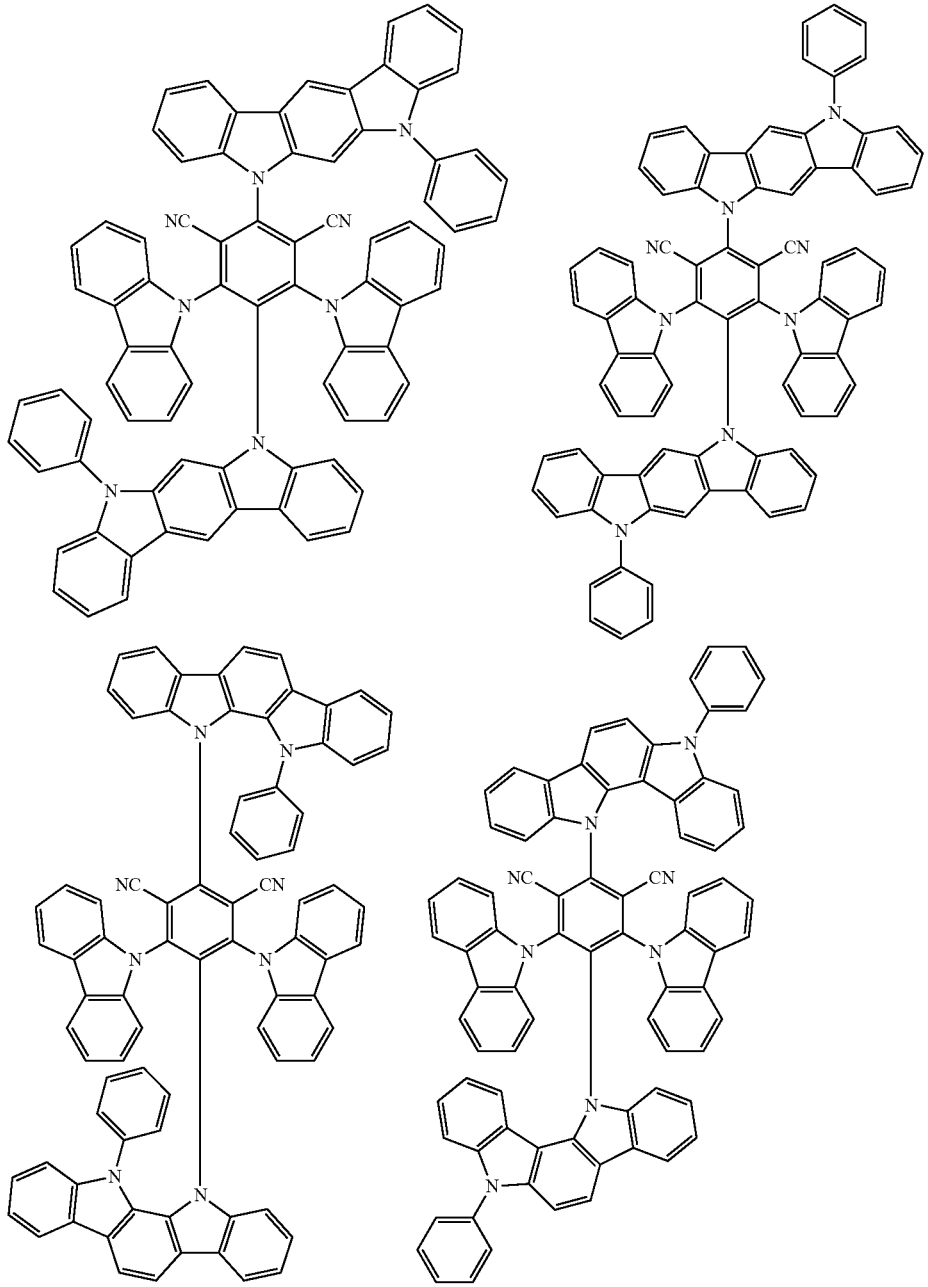
[Formula 40]
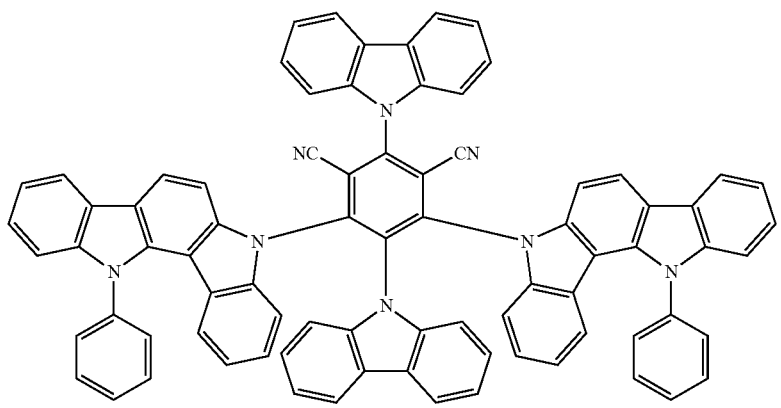

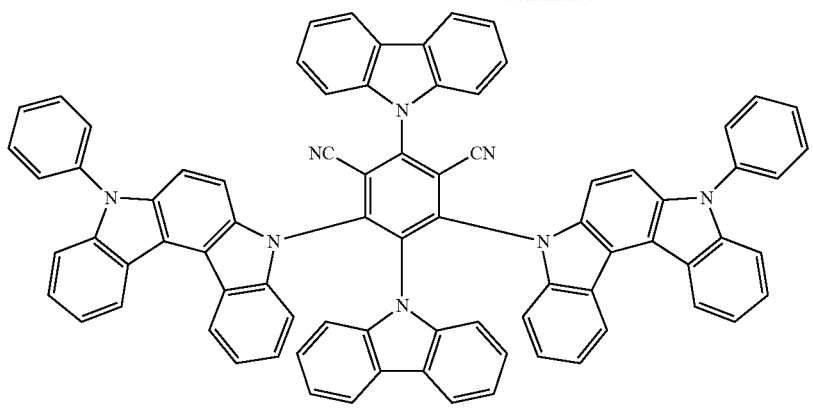
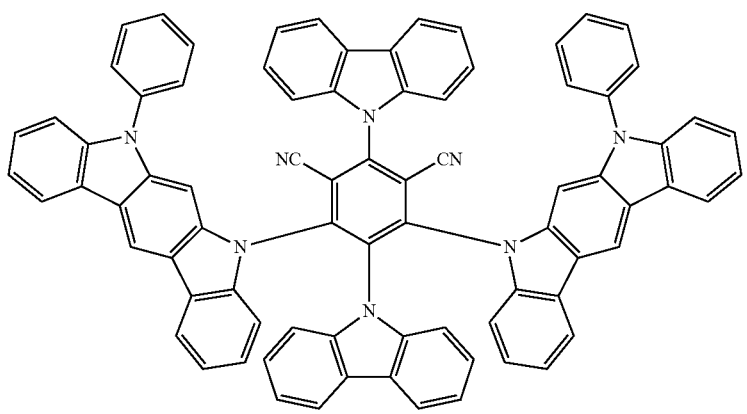
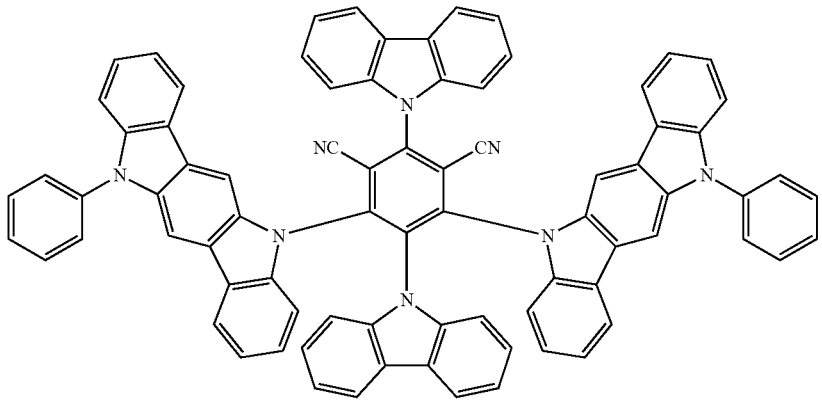
[Formula 41]
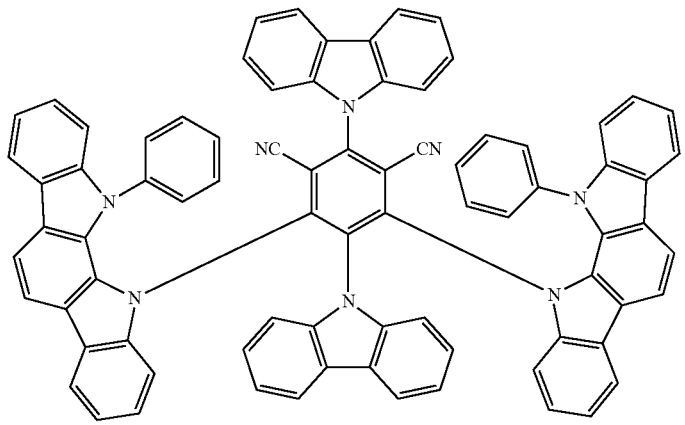

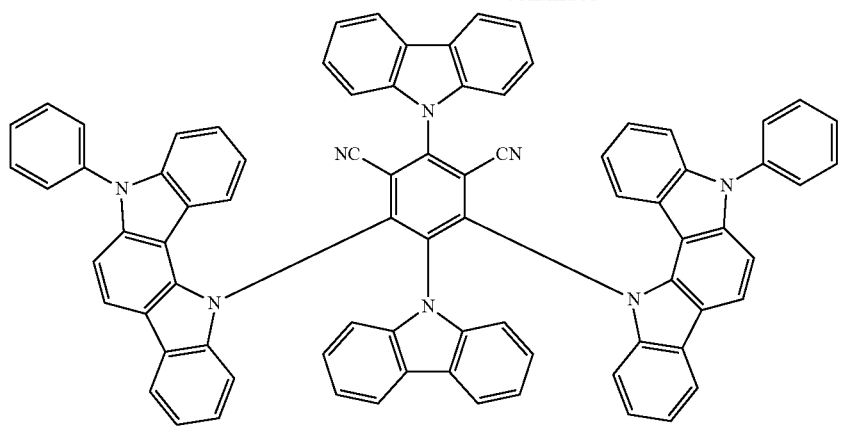
[Formula 42]
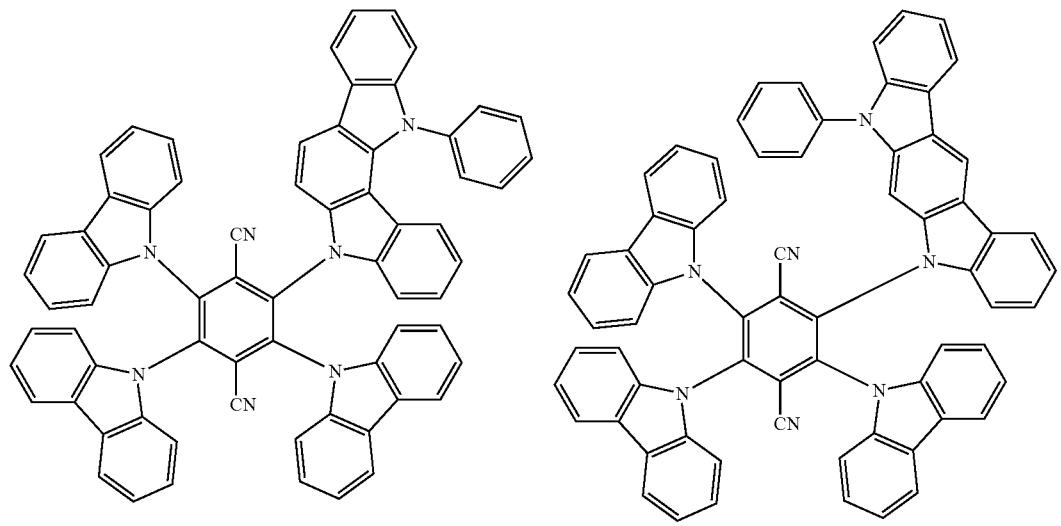
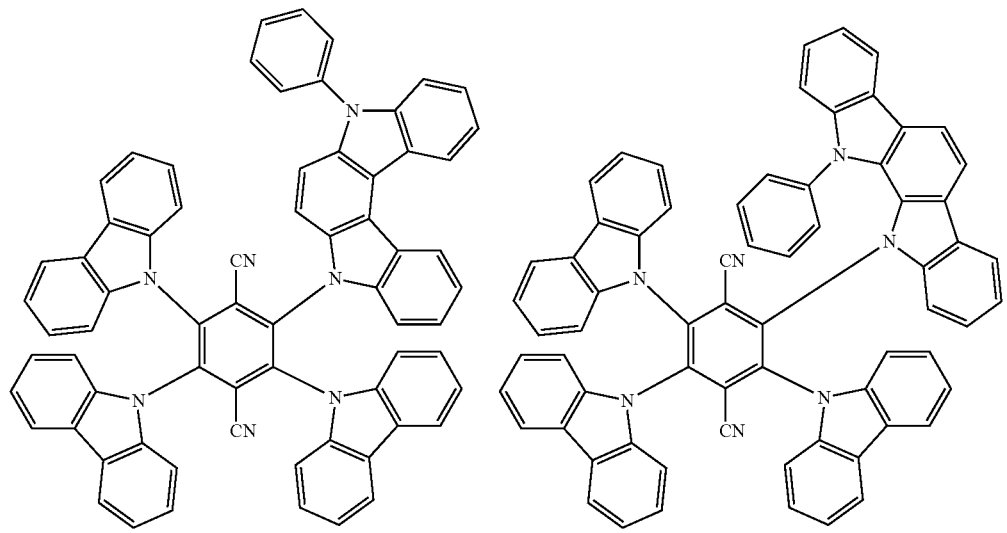

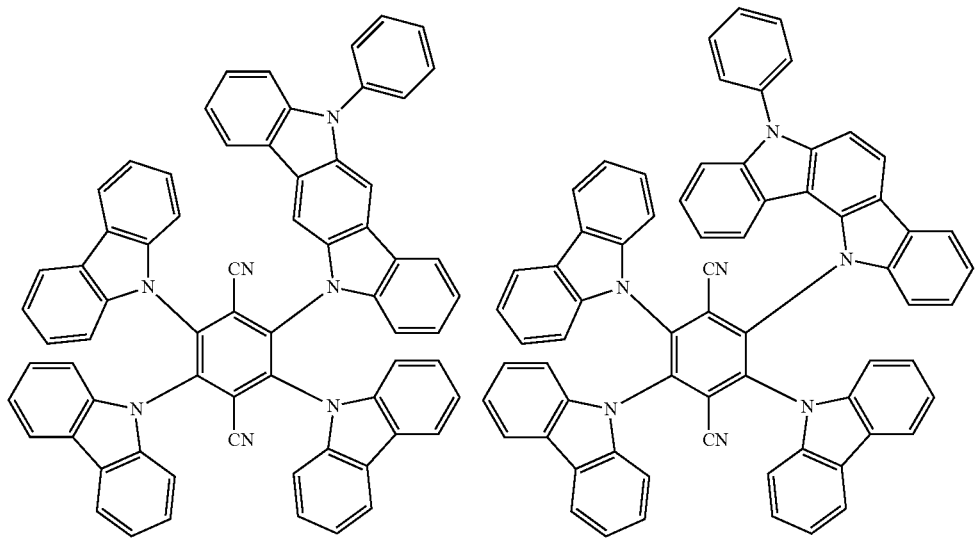
[Formula 43]
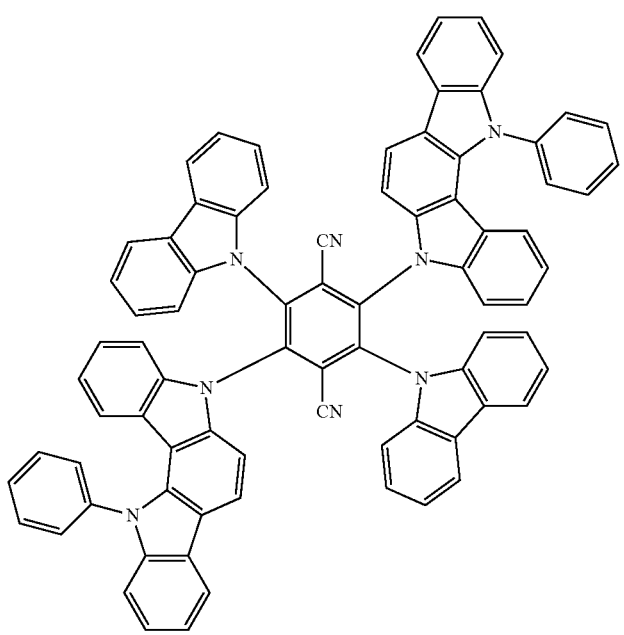

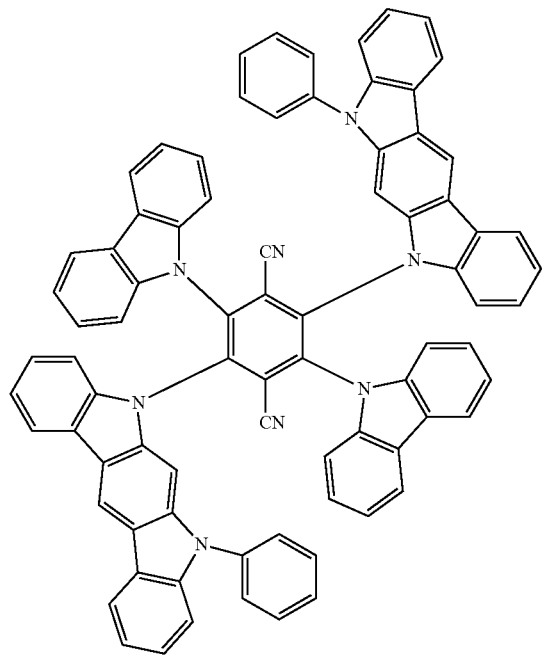
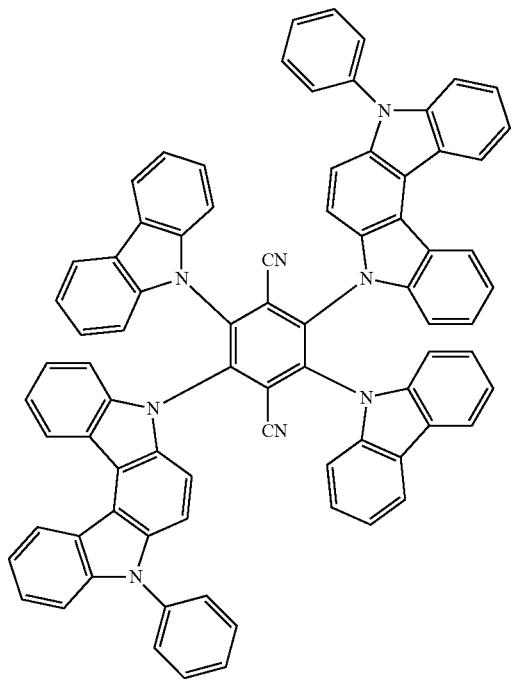
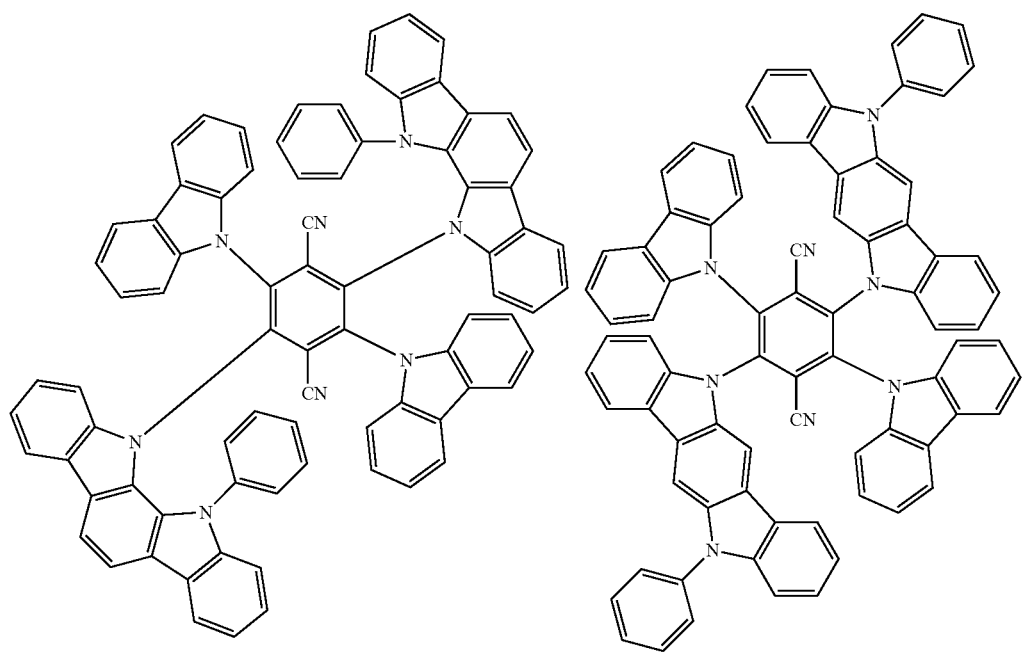

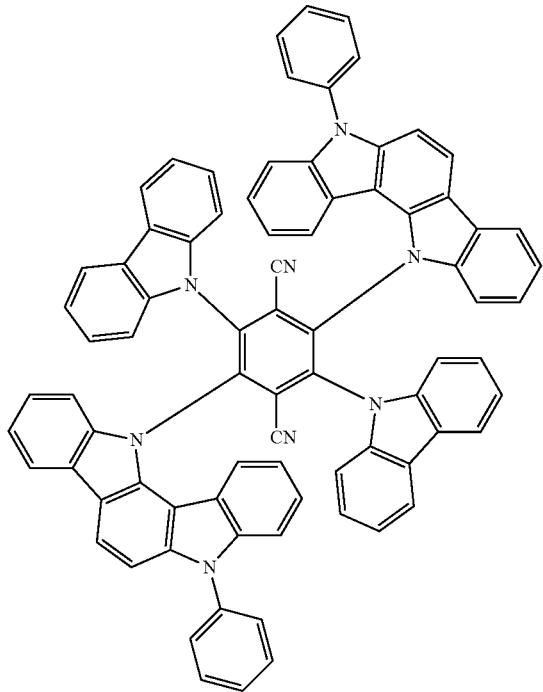
[Formula 44]
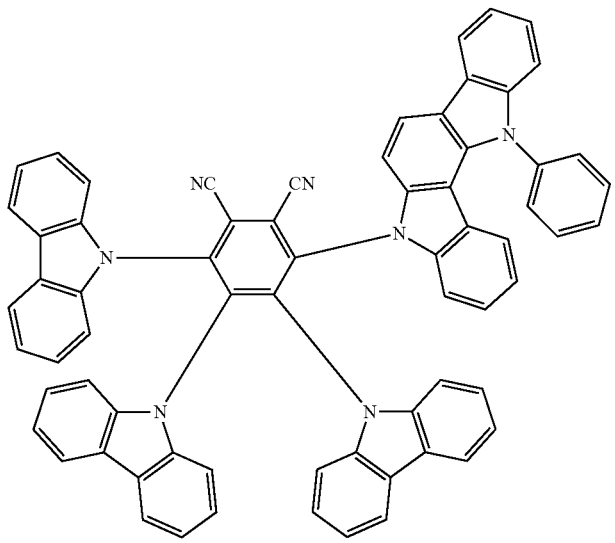

73 74
-continued
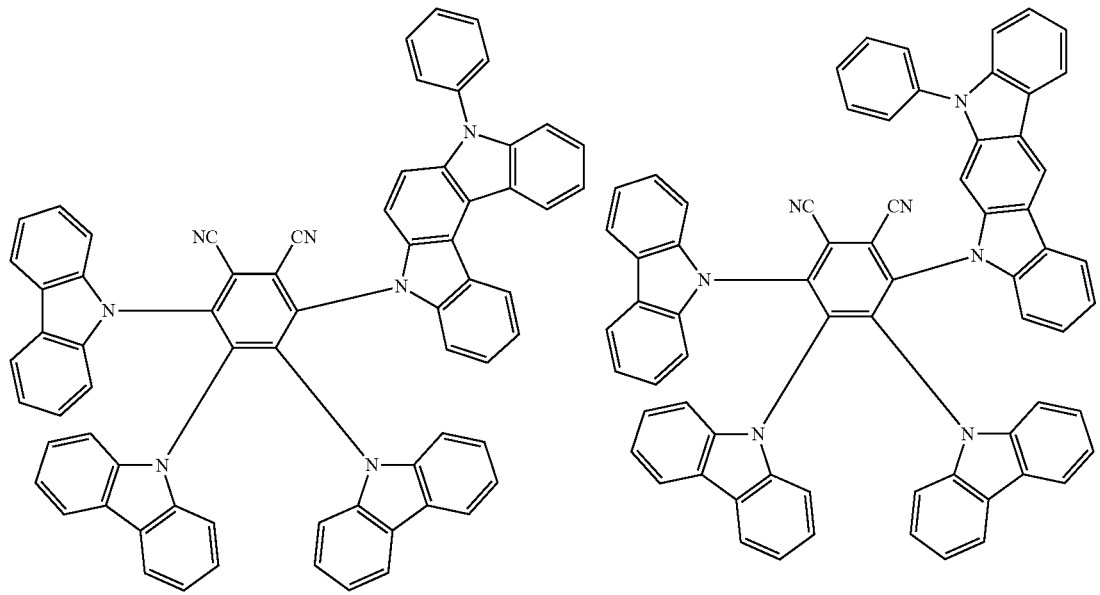
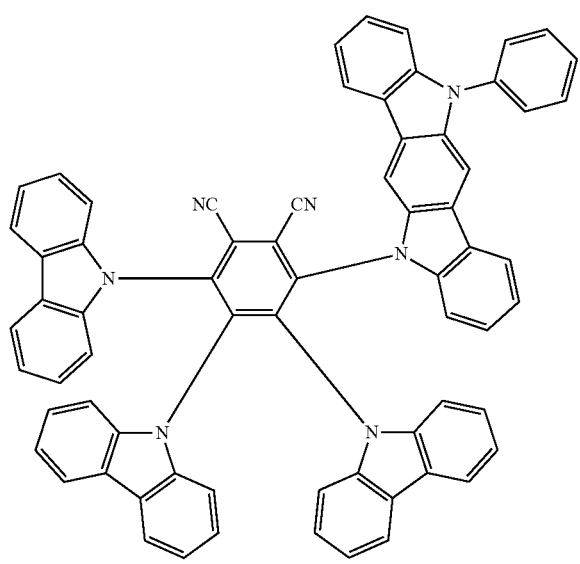

[Formula 45]
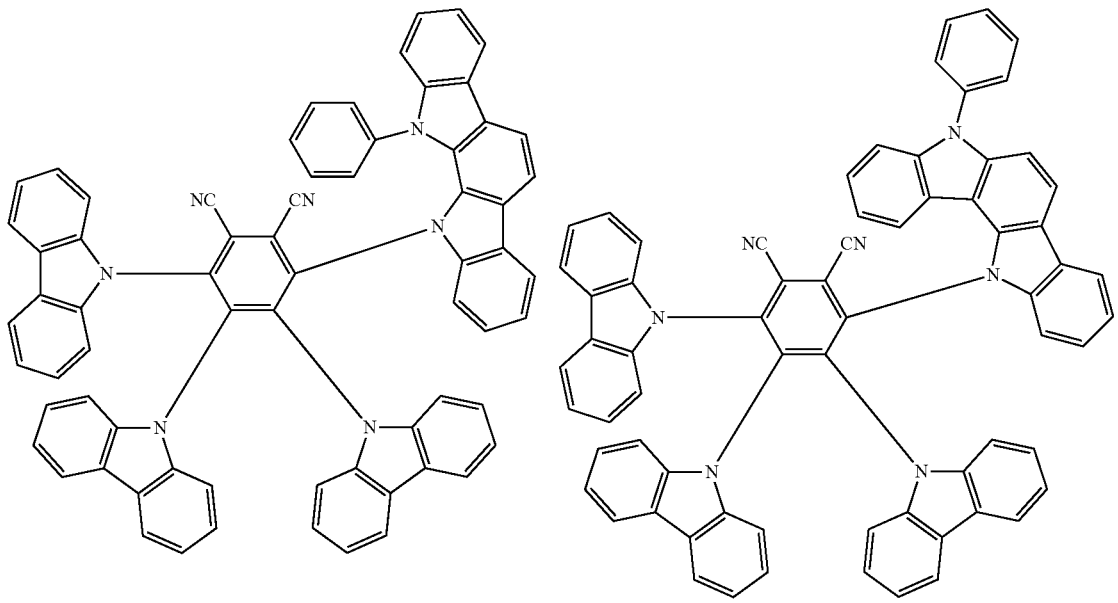
[Formula 46]
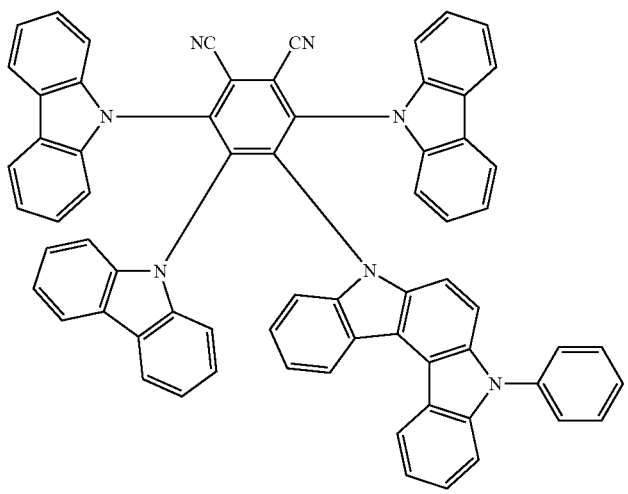
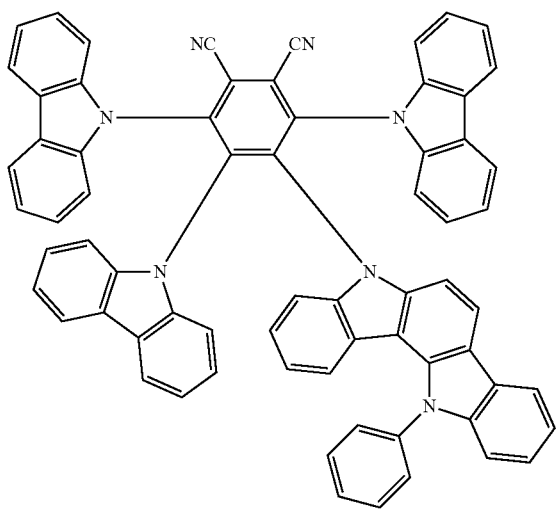

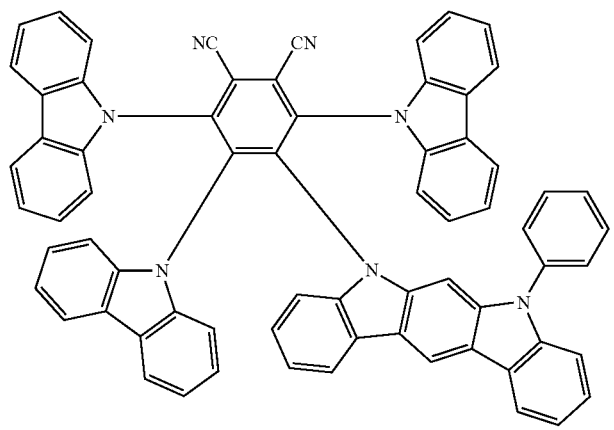
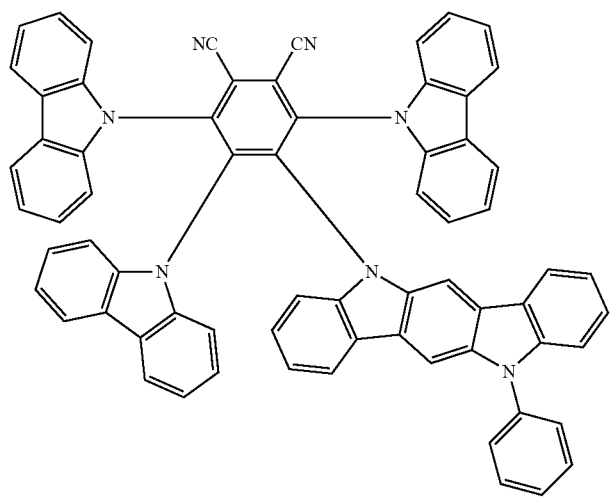
[Formula 47]
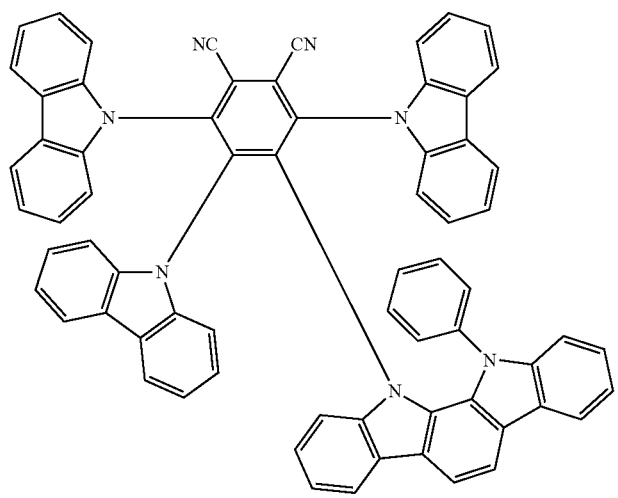

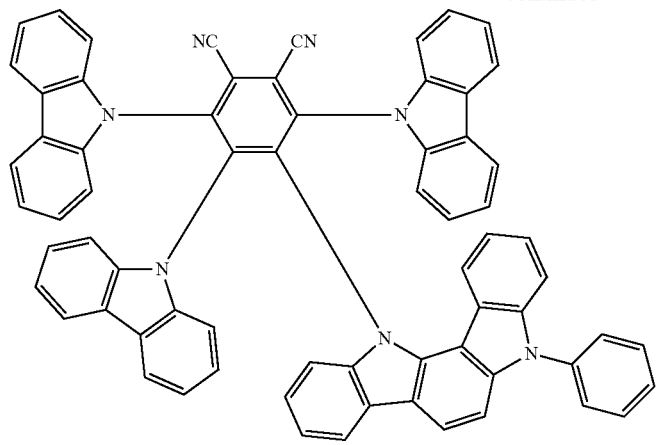
[Formula 48]
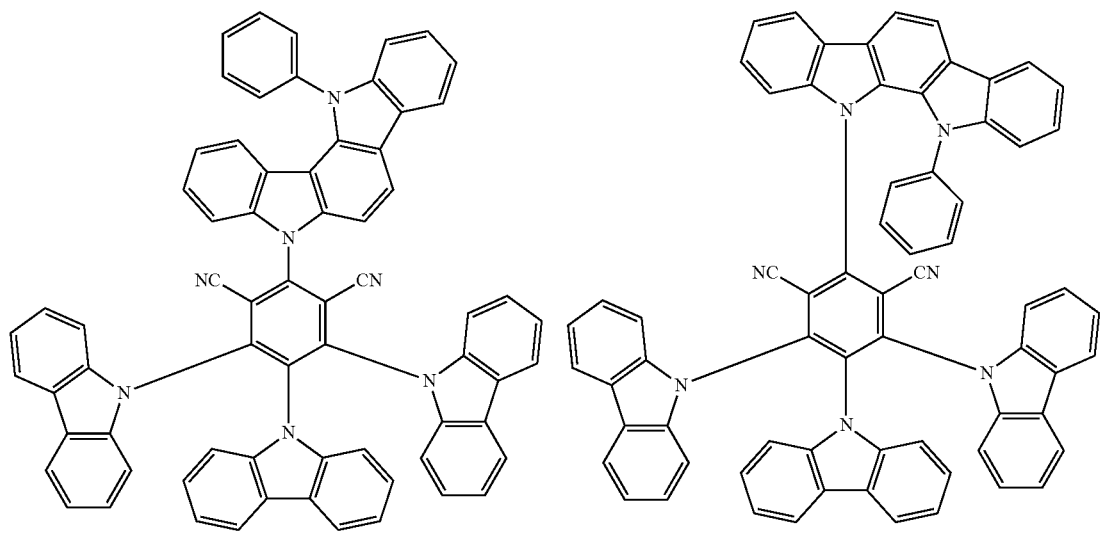
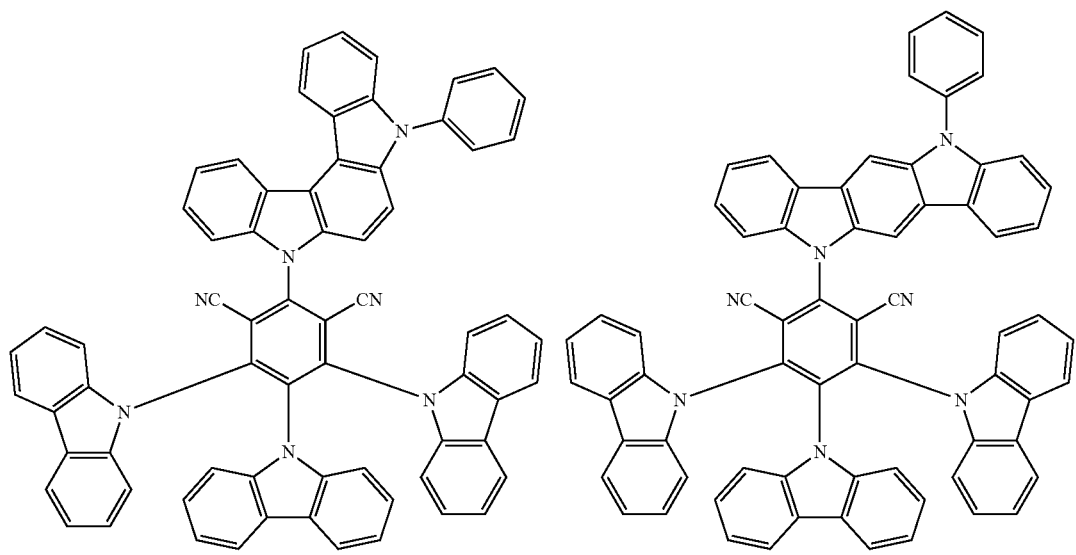

81    82
-continued
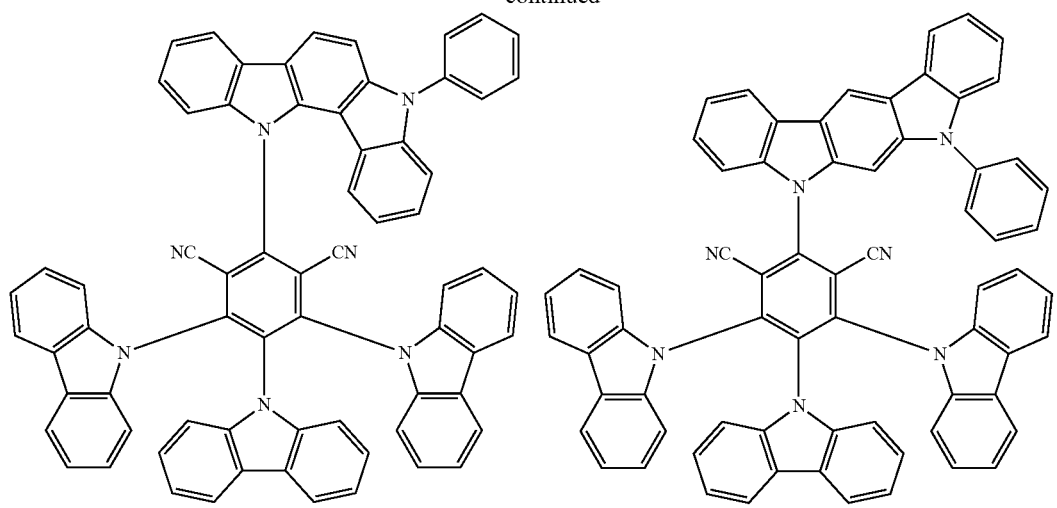
[Formula 49]
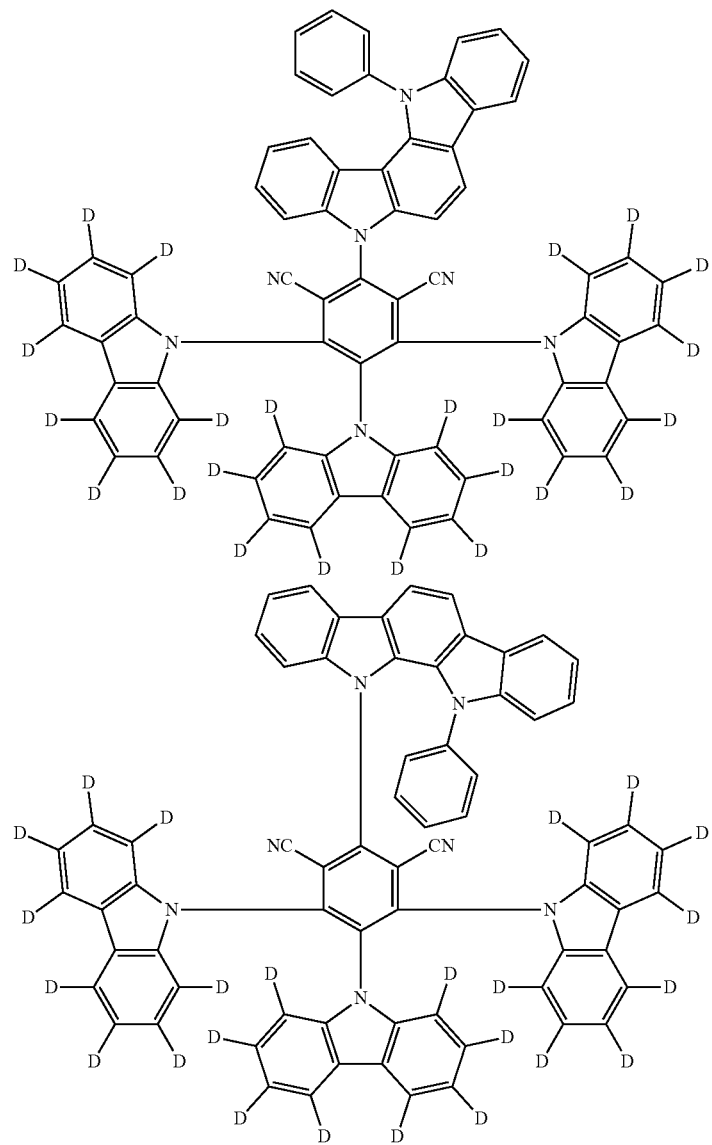

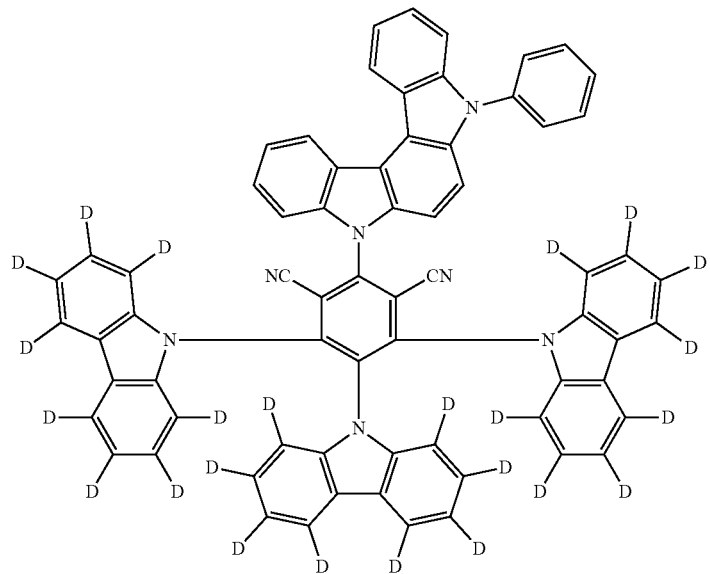
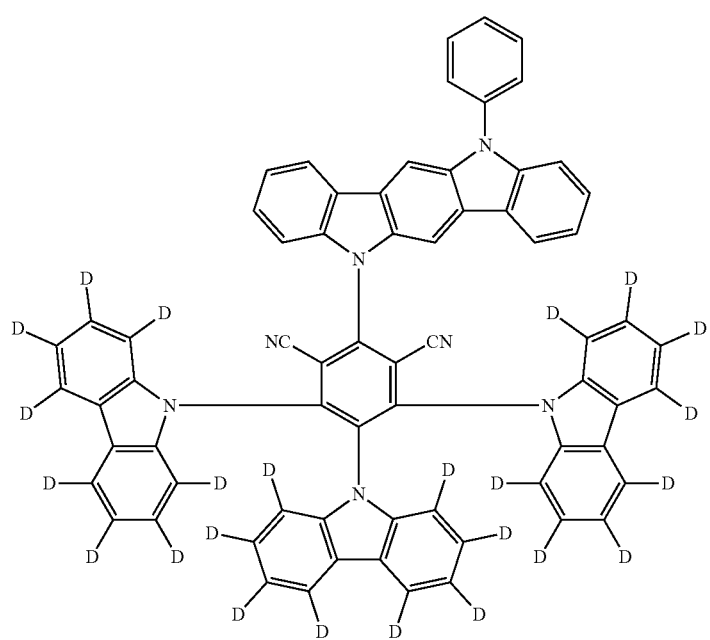

-continued
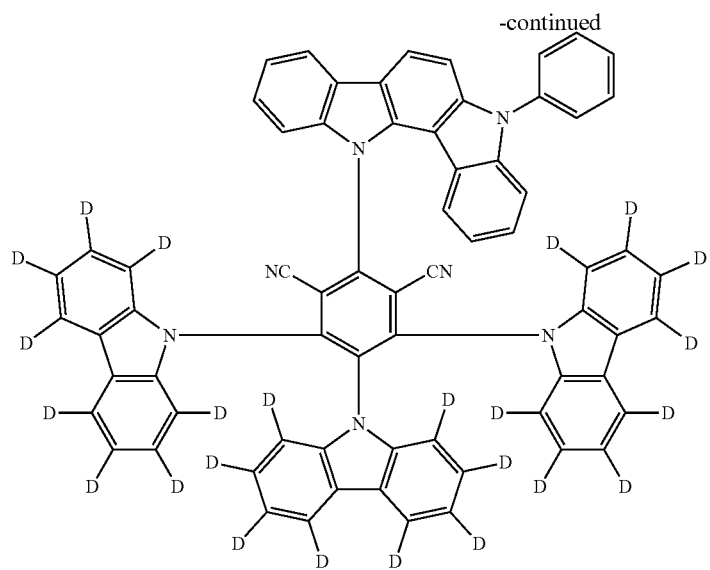
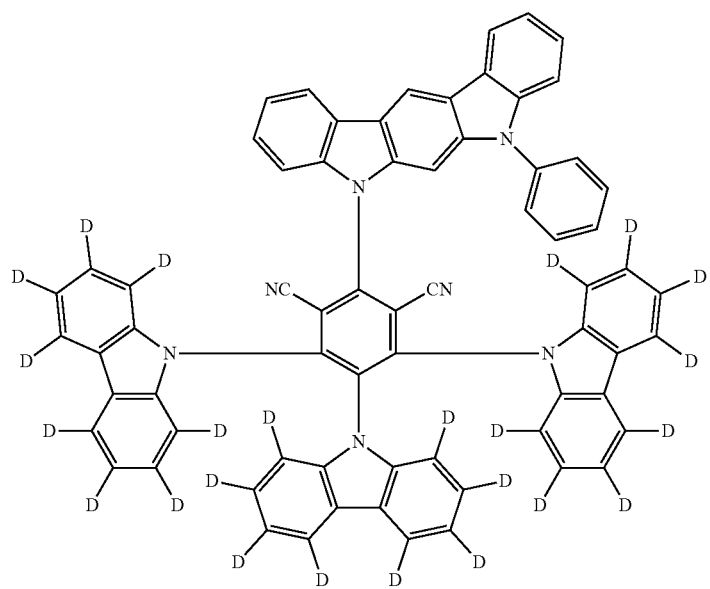

-continued
[Formula 50]
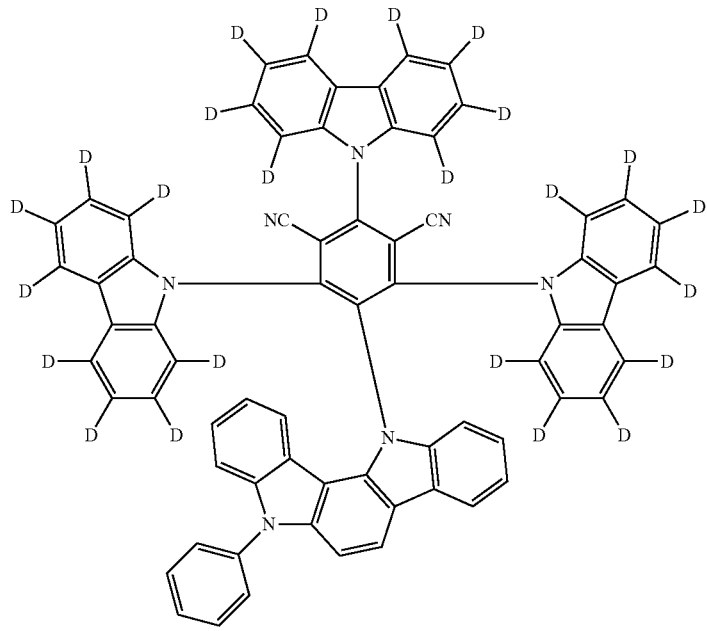
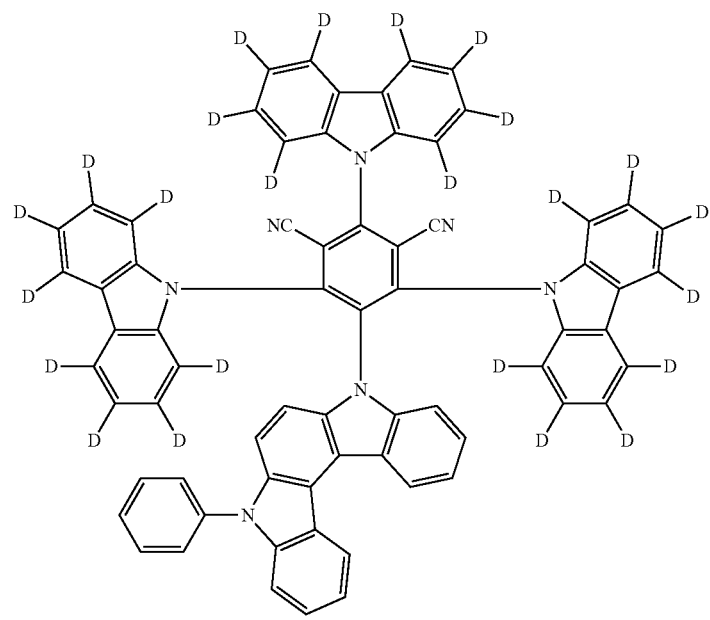

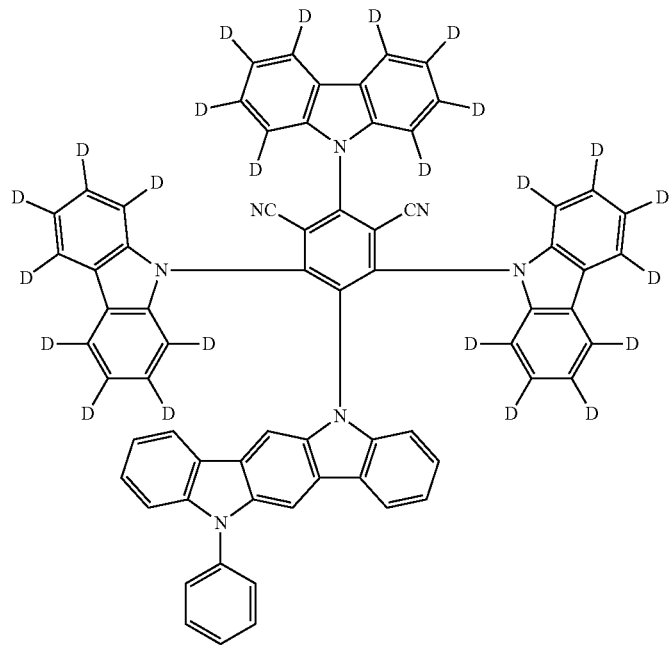
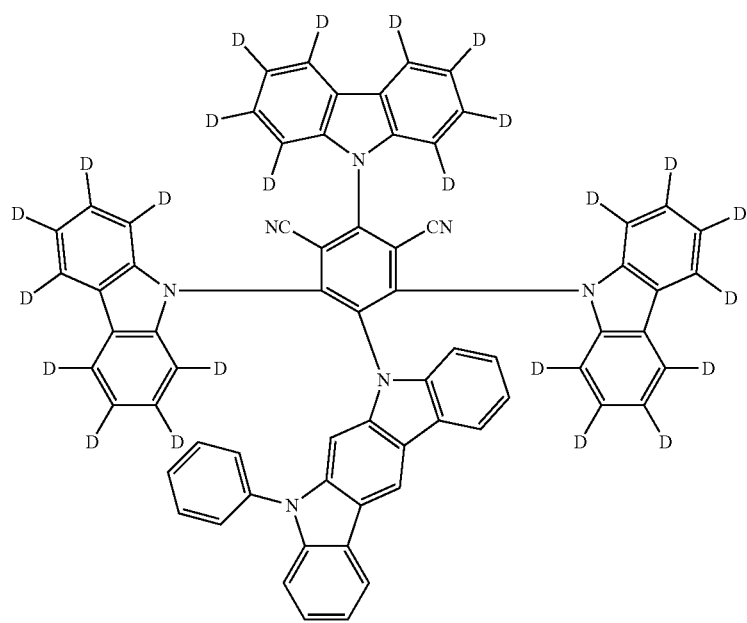

-continued

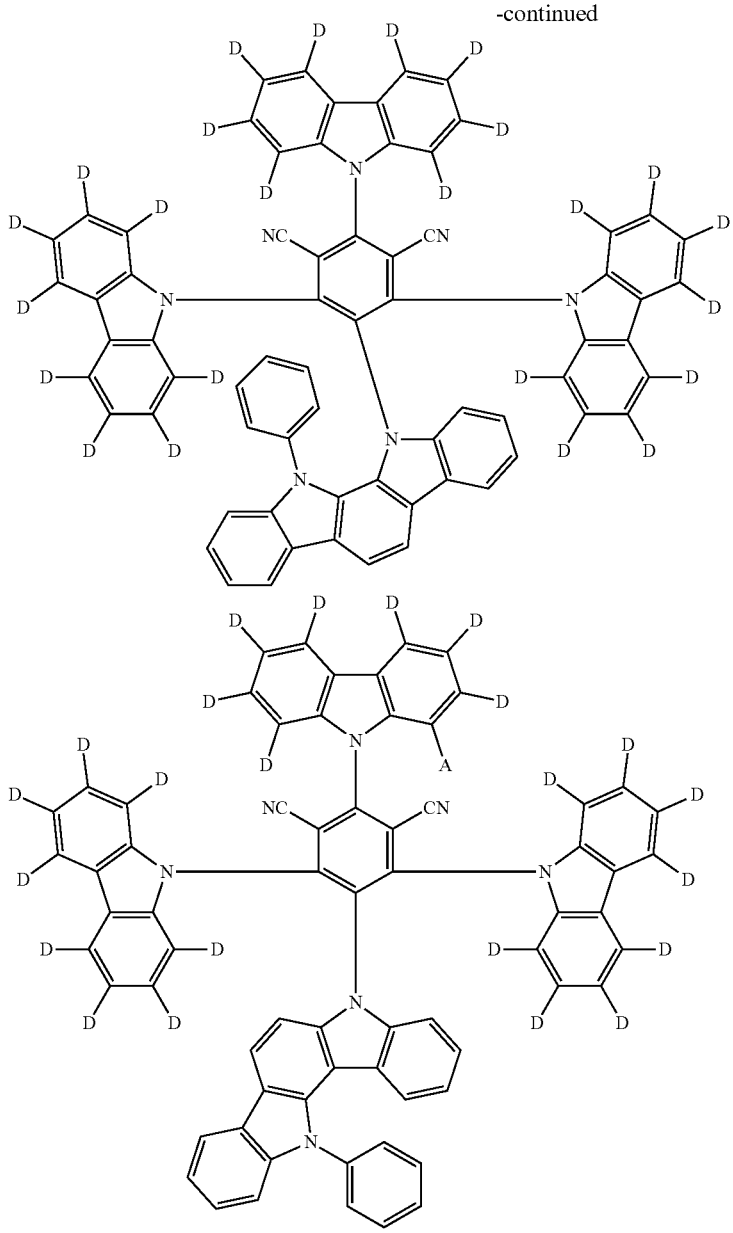

Second Exemplary Embodiment

Organic-EL-Device Material

An organic-EL-device material according to a second exemplary embodiment contains the compound according to the first exemplary embodiment (at least one of the compounds represented by the formulae (11) to (13).)

According to the second exemplary embodiment, the organic-EL-device material capable of decreasing a sublimation temperature when being sublimated and purified while maintaining TADF properties can be obtained.

The organic-EL-device material according to the second exemplary embodiment may further contain a compound other than the compound according to the first exemplary embodiment. When organic-EL-device material according to the second exemplary embodiment contains the compound other than the compound according to the first exemplary embodiment, the compound in the second exemplary embodiment may be solid or liquid.

Third Exemplary Embodiment

Organic EL Device

An arrangement of an organic EL device according to a third exemplary embodiment will be described below.

The organic EL device includes an anode, a cathode, and an at least one organic layer between the anode and the cathode. The organic layer typically includes a plurality of layers formed of an organic compound(s). The organic layer may further include an inorganic compound. The organic EL device according to the exemplary embodiment includes a first organic layer between the anode and the cathode. The first organic layer contains at least one of the compounds represented by the formulae (11) to (13).

The first organic layer is, for instance, at least one layer selected from the group consisting of a hole injecting layer, a hole transporting layer, an emitting layer, an electron injecting layer, an electron transporting layer, a hole blocking layer and an electron blocking layer.

The first organic layer is preferably the emitting layer.

In the organic EL device of the exemplary embodiment, the first organic layer is the emitting layer.

In the exemplary embodiment, the organic layer may consist of the emitting layer as the first organic layer. Alternatively, the organic layer may further include, for instance, at least one layer selected from the group consisting of the hole injecting layer, the hole transporting layer, the electron injecting layer, the electron transporting layer, the hole blocking layer, and the electron blocking layer.

FIG. 1 schematically shows an exemplary structure of the organic EL device of the exemplary embodiment.

The organic EL device 1 includes a light-transmissive substrate 2, an anode 3, a cathode 4, and an organic layer 10 provided between the anode 3 and the cathode 4. The organic layer 10 includes a hole injecting layer 6, a hole transporting layer 7, an emitting layer 5 (the first organic layer), an electron transporting layer 8, and an electron injecting layer 9, which are sequentially layered on the anode 3.

In the organic EL device 1 according to the exemplary embodiment, the emitting layer 5 contains the first compound.

The first compound is the compound according to the first exemplary embodiment (at least one of the compounds represented by the formulae (11) to (13)).

It is preferable that the emitting layer 5 does not contain a phosphorescent material (dopant material).

It is preferable that the emitting layer 5 does not contain a heavy metal complex and a phosphorescent rare-metal complex. Examples of the heavy metal complex herein include iridium complex, osmium complex, and platinum complex.

It is also preferable that the emitting layer 5 does not contain a metal complex.

In the organic EL device 1 according to the exemplary embodiment, the emitting layer 5 contains the first compound and further a second compound.

In this embodiment, the first compound is preferably a host material (sometimes referred to as a matrix material hereinafter), and the second compound is preferably a dopant material (sometimes referred to as a guest material, an emitter, or a luminescent material hereinafter).

First Compound

The first compound is according to the first exemplary embodiment.

The first compound is preferably a delayed fluorescent compound.

Delayed Fluorescence

Delayed fluorescence is explained in "Yuki Hando-tai no Debaisu Bussei (Device Physics of Organic Semiconductors)" (edited by ADACHI, Chihaya, published by Kodansha, on pages 261-268). This document describes that, if an energy gap $\Delta E_{13}$ of a fluorescent material between a singlet state and a triplet state is reducible, a reverse energy transfer from the triplet state to the singlet state, which usually occurs at a low transition probability, would occur at a high efficiency to express thermally activated delayed fluorescence (TADF). Further, a mechanism of generating delayed fluorescence is explained in FIG. 10.38 in the document. The first compound in the exemplary embodiment is preferably a compound exhibiting thermally activated delayed fluorescence generated by such a mechanism.

In general, emission of delayed fluorescence can be confirmed by measuring the transient PL (Photo Luminescence).

The behavior of delayed fluorescence can also be analyzed based on the decay curve obtained from the transient PL measurement. The transient PL measurement is a method of irradiating a sample with a pulse laser to excite the sample, and measuring the decay behavior (transient characteristics) of PL emission after the irradiation is stopped. PL emission in TADF materials is classified into a light emission component from a singlet exciton generated by the first PL excitation and a light emission component from a singlet exciton generated via a triplet exciton. The lifetime of the singlet exciton generated by the first PL excitation is on the order of nanoseconds and is very short. Therefore, light emission from the singlet exciton rapidly attenuates after irradiation with the pulse laser.

On the other hand, the delayed fluorescence is gradually attenuated due to light emission from a singlet exciton generated via a triplet exciton having a long lifetime. As described above, there is a large temporal difference between the light emission from the singlet exciton generated by the first PL excitation and the light emission from the singlet exciton generated via the triplet exciton. Therefore, the luminous intensity derived from delayed fluorescence can be determined.

Figure 2:
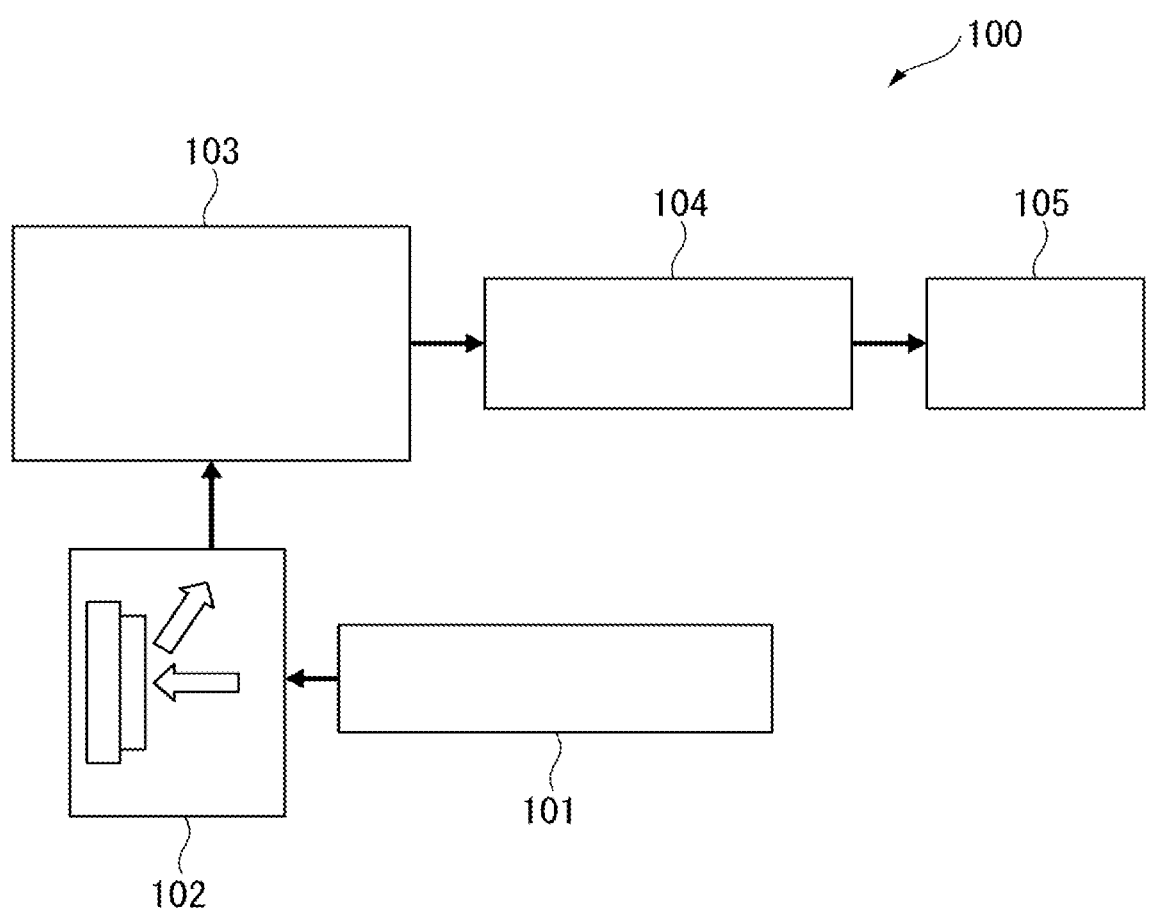

FIG. 2 shows a schematic diagram of an exemplary device for measuring the transient PL. An example of a method of measuring a transient PL using FIG. 2 and an example of behavior analysis of delayed fluorescence will be described.

A transient PL measuring device 100 in FIG. 2 includes: a pulse laser 101 capable of radiating a light having a predetermined wavelength; a sample chamber 102 configured to house a measurement sample; a spectrometer 103 configured to divide a light radiated from the measurement sample; a streak camera 104 configured to provide a two-dimensional image; and a personal computer 105 configured to import and analyze the two-dimensional image. A device for measuring the transient PL is not limited to the device described in the exemplary embodiment.

The sample to be housed in the sample chamber 102 is obtained by doping a matrix material with a doping material at a concentration of 12 mass % and forming a thin film on a quartz substrate.

The thin film sample housed in the sample chamber 102 is radiated with a pulse laser from the pulse laser 101 to excite the doping material. Emission is extracted in a direction of 90 degrees with respect to a radiation direction of the excited light. The extracted emission is divided by the spectrometer 103 to form a two-dimensional image in the streak camera 104. As a result, the two-dimensional image is obtainable in which the ordinate axis represents a time, the abscissa axis represents a wavelength, and a bright spot represents a luminous intensity. When this two-dimensional image is taken out at a predetermined time axis, an emission spectrum in which the ordinate axis represents the luminous intensity and the abscissa axis represents the wavelength is obtainable. Moreover, when this two-dimensional image is taken out at the wavelength axis, a decay curve (transient PL) in which the ordinate axis represents a logarithm of the luminous intensity and the abscissa axis represents the time is obtainable.

For instance, a thin film sample A was manufactured as described above from a reference compound H1 as the matrix material and a reference compound D1 as the doping material and was measured in terms of the transient PL.

[Formula 51]

Reference Compound H1

Reference Compound D1

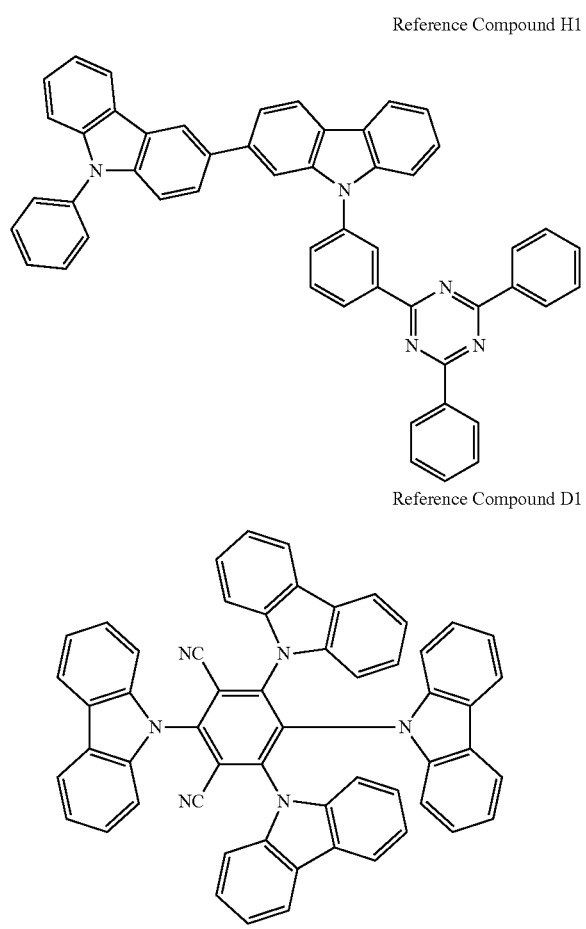

The decay curve was analyzed with respect to the above thin film sample A and a thin film sample B. The thin film sample B was manufactured in the same manner as described above from a reference compound H2 as the matrix material and the reference compound D1 as the doping material.

Figure 3:
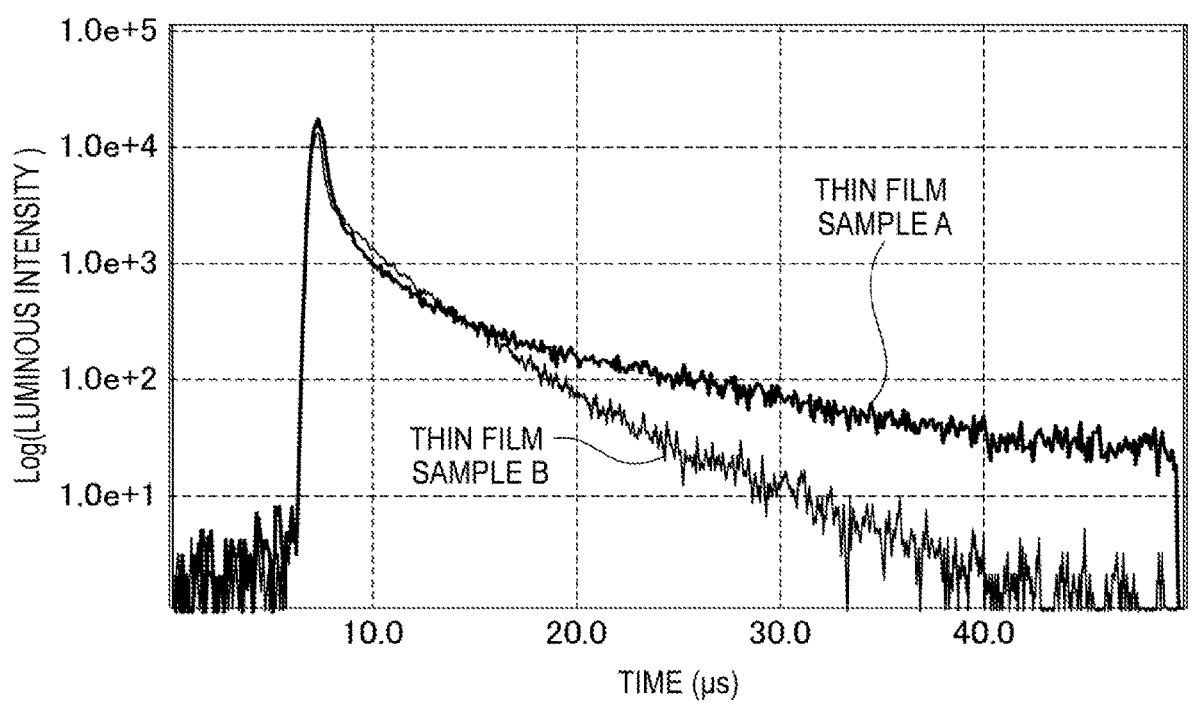
FIG. 3 shows an example of a decay curve of the transient PL.

FIG. 3 shows decay curves obtained from transient PL obtained by measuring the thin film samples A and B.

[Formula 52]

Reference Compound H2

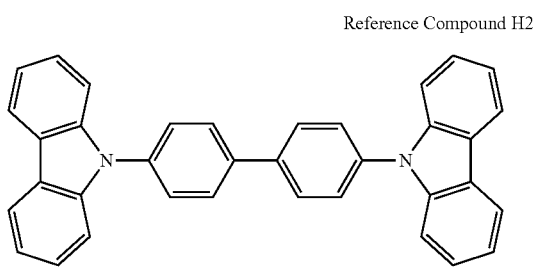

As described above, an emission decay curve in which the ordinate axis represents the luminous intensity and the abscissa axis represents the time can be obtained by the transient PL measurement. Based on the emission decay curve, a fluorescence intensity ratio between fluorescence emitted from a singlet state generated by photo-excitation and delayed fluorescence emitted from a singlet state generated by inverse energy transfer via a triplet state can be estimated. In a delayed fluorescent material, a ratio of the intensity of the slowly decaying delayed fluorescence to the intensity of the promptly decaying fluorescence is relatively large.

Specifically, Prompt emission and Delay emission are present as emission from the delayed fluorescent material. Prompt emission is observed promptly when the excited state is achieved by exciting the compound of the exemplary embodiment with a pulse beam (i.e., a beam emitted from a pulse laser) having a wavelength absorbable by the delayed fluorescent material. Delay emission is observed not promptly when the excited state is achieved but after the excited state is achieved.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 2.

In the exemplary embodiment, a sample manufactured by a method shown below is used for measuring delayed fluorescence of the first compound. For instance, the first compound is dissolved in toluene to prepare a dilute solution with an absorbance of 0.05 or less at the excitation wavelength to eliminate the contribution of self-absorption. In order to prevent quenching due to oxygen, the sample solution is frozen and degassed and then sealed in a cell with a lid under an argon atmosphere to obtain an oxygen-free sample solution saturated with argon.

The fluorescence spectrum of the sample solution is measured with a spectrofluorometer FP-8600 (manufactured by JASCO Corporation), and the fluorescence spectrum of a 9,10-diphenylanthracene ethanol solution is measured under the same conditions. Using the fluorescence area intensities of both spectra, the total fluorescence quantum yield is calculated by an equation (1) in Morris et al. J. Phys. Chem. 80 (1976) 969.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 2.

In the exemplary embodiment, a measurement target compound (the first compound) preferably has a value of $X_D/X_P$ is 0.05 or more, provided that the amount of Prompt emission is denoted by $X_P$ and the amount of Delay emission is denoted by $X_D$.

Amounts of Prompt emission and Delay emission and a ratio of the amounts thereof in compounds other than the first compound herein are measured in the same manner as those of the first compound.

Second Compound

The second compound is preferably a fluorescent compound. The second compound may be a thermally activated delayed fluorescent compound or a compound exhibiting no thermally activated delayed fluorescence.

A fluorescent material is usable as the second compound in the exemplary embodiment. Specific examples of the fluorescent material include a bisarylaminonaphthalene derivative, aryl-substituted naphthalene derivative, bisarylaminoanthracene derivative, aryl-substituted anthracene derivative, bisarylaminopyrene derivative, aryl-substituted pyrene derivative, and bisarylamino Chrysene derivative, aryl-substituted chrysene derivative, bisarylaminofluoranthene derivative, aryl-substituted fluoranthene derivative, indenoperylene derivative, acenaphthofluoranthene derivative, pyromethene boron complex compound, compound having a pyromethene skeleton, metal complex of the compound having a pyrromethene skeleton, diketopyrrolopyrrole derivative, perylene derivative, and naphthacene derivative.

The second compound in the exemplary embodiment is also preferably represented by a formula (20) below.

The second compound is represented by the formula (20) below.

The second compound is preferably a fluorescent compound.

[Formula 53]

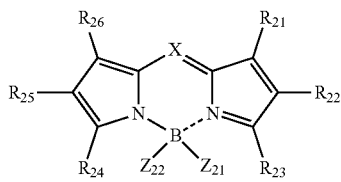
(20)

In the formula (20), In the formula (20), X is a nitrogen atom, or a carbon atom bonded to Y.

Y is a hydrogen atom or a substituent; $R_{21}$ to $R_{26}$ are each independently a hydrogen atom or a substituent, or at least one of a pair of $R_{21}$ and $R_{22}$, a pair of $R_{22}$ and $R_{23}$, a pair of $R_{24}$ and $R_{25}$, or a pair of $R_{25}$ and $R_{26}$ are mutually bonded to form a ring.

Y and $R_{21}$ to $R_{26}$ each being the substituent are each independently selected from the group consisting of a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, a substituted or unsubstituted alkylthio group having 1 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted alkenyl group having 2 to 30 carbon atoms, a substituted or unsubstituted aralkyl group having 7 to 30 carbon atoms, a substituted or unsubstituted heteroaryl group having 5 to 30 ring atoms, a halogen atom, a carboxy group, a substituted or unsubstituted ester group, a substituted or unsubstituted carbamoyl group, a substituted or unsubstituted amino group, a nitro group, a cyano group, a substituted or unsubstituted silyl group, and a substituted or unsubstituted siloxanyl group.

$Z_{21}$ and $Z_{22}$ are each independently a substituent, or are mutually bonded to form a ring, $Z_{21}$ and $Z_{22}$ as the substituent are each independently selected from the group consisting of a halogen atom, a substituted or unsubstituted alkyl group having 1 to 30 carbon atoms, a substituted or unsubstituted alkyl halide group having 1 to 30 carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, and a substituted or unsubstituted aryloxy group having 6 to 30 ring carbon atoms.

For instance, when a pair of $R_{25}$ and $R_{26}$ in the formula (20) is mutually bonded to form a ring, the second compound is represented by a formula (21) below.

[Formula 54]

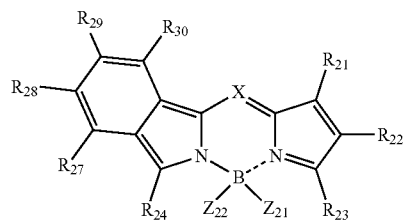
(21)

In the formula (21), X, Y, $R_{21}$ to $R_{24}$, $Z_{21}$ and $Z_{22}$ respectively represent the same as X, Y, $R_{21}$ to $R_{24}$, $Z_{21}$ and $Z_{22}$ in the formula (20). $R_{27}$ to Rao each independently represent a hydrogen atom or a substituent. When $R_{27}$ to Rao are each independently the substituent, the substituent represents the same as the substituents for $R_{21}$ to $R_{24}$.

When a pair of R21 and R22 in the formula (20) is mutually bonded to form a ring, the second compound is represented by a formula (20A) or (20B) below. However, a structure of the second compound is not limited to structures below.

[Formula 55]

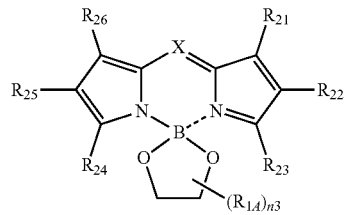
(20A)

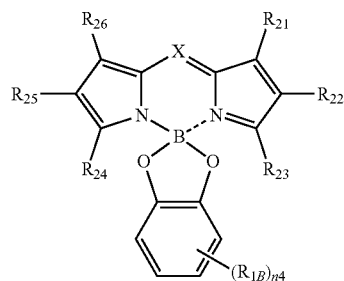
(20B)

In the formula (20A), X, Y and $R_{21}$ to $R_{26}$ respectively represent the same as X, Y and $R_{21}$ to $R_{26}$ in the formula (20). $R_{1A}$ each independently represent a hydrogen atom or a substituent. When $R_{1A}$ is the substituent, the substituent represents the same as the substituents for $R_{21}$ to $R_{26}$. n3 is 4.

In the formula (20B), X, Y and $R_{21}$ to $R_{26}$ respectively represent the same as X, Y and $R_{21}$ to $R_{26}$ in the formula (20). $R_{1B}$ each independently represent a hydrogen atom or a substituent. When RIB is the substituent, the substituent represents the same as the substituents for $R_{21}$ to $R_{26}$. n4 is 4.

It is preferable that at least one of $Z_{21}$ or $Z_{22}$ (preferably both of $Z_{21}$ and $Z_{22}$) is a group selected from the group consisting of a substituted or unsubstituted alkyl group having 1 to 30 carbon atoms, substituted or unsubstituted alkyl halide group having 1 to 30 carbon atoms, substituted or unsubstituted aryl group having 6 to 30 ring carbon atoms, substituted or unsubstituted alkoxy group having 1 to 30 carbon atoms, substituted or unsubstituted alkoxy halide group having 1 to 30 carbon atoms, and substituted or unsubstituted aryloxy group having 6 to 30 ring carbon atoms.

It is more preferable that at least one of $Z_{21}$ or $Z_{22}$ is a group selected from the group consisting of a fluorine-substituted alkoxy group having 1 to 30 carbon atoms, a fluorine-substituted aryloxy group having 6 to 30 ring carbon atoms, and an aryloxy group having 6 to 30 ring carbon atoms and substituted with a fluoroalkyl group having 1 to 30 carbon atoms.

Further preferably, at least one of $Z_{21}$ or $Z_{22}$ is a fluorine-substituted alkoxy group having 1 to 30 carbon atoms. Furthermore preferably, both of $Z_{21}$ and $Z_{22}$ are a fluorine-substituted alkoxy group having 1 to 30 carbon atoms.

It is also preferable that both of $Z_{21}$ and $Z_{22}$ are the same to each other.

Meanwhile, it is also preferable that at least one of $Z_{21}$ or $Z_{22}$ is a fluorine atom. It is also more preferable that both of $Z_{21}$ and $Z_{22}$ are fluorine atoms.

It is also preferable that at least one of $Z_{21}$ or $Z_{22}$ is a group represented by a formula (20a).

[Formula 56]

(20a)

In the formula (20a): A represents a substituted or unsubstituted alkyl group having 1 to 6 carbon atoms, substituted or unsubstituted alkyl halide group having 1 to 6 carbon atoms, or substituted or unsubstituted aryl group having 6 to 12 ring carbon atoms; $L_2$ represents a substituted or unsubstituted alkylene group having 1 to 6 carbon atoms, or substituted or unsubstituted arylene group having 6 to 12 ring carbon atoms; and m is 0, 1, 2, 3, 4, 5, 6 or 7. When m is 2, 3, 4, 5, 6 or 7, a plurality of $L_2$ are mutually the same or different. m is preferably 0, 1 or 2. When m is O, A is directly bonded to O (oxygen atom).

When $Z_{21}$ and $Z_{22}$ of the formula (20) are each the group represented by the formula (20a), the second compound is represented by a formula (22).

The second compound is also preferably represented by the formula (22).

[Formula 57]

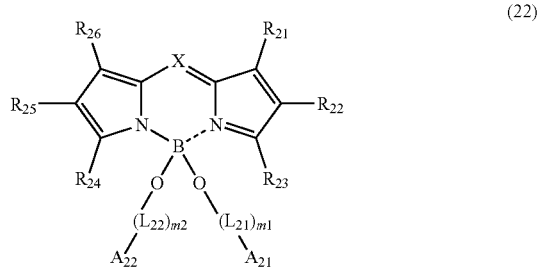

(22)

In the formula (22), X, Y bonded to a carbon atom as X, and $R_{21}$ to $R_{26}$ represent the same as X, Y and $R_{21}$ to $R_{26}$ in the formulae (20). A21 and A22 represent the same as A in the formula (20a) and may be mutually the same or different. $L_{21}$ and $L_{22}$ represent the same as $L_2$ in the formula (20a) and may be mutually the same or different. m1 and m2 are each independently 0, 1, 2, 3, 4, 5, 6 or 7, preferably 0, 1 or 2. When m1 is 2, 3, 4, 5, 6 or 7, a plurality of $L_{21}$ are mutually the same or different. When m2 is 2, 3, 4, 5, 6 or 7, a plurality of $L_{22}$ are mutually the same or different. When m1 is 0, $A_{21}$ is directly bonded to O (oxygen atom). When m2 is 0, $A_{22}$ is directly bonded to O (oxygen atom).

At least one of A or $L_2$ in the formula (20a) is preferably substituted with a halogen atom, more preferably substituted with a fluorine atom.

A in the formula (20a) is more preferably a perfluoroalkyl group having 1 to 6 carbon atoms or a perfluoroaryl group having 6 to 12 carbon atoms, further preferably a perfluoroalkyl group having 1 to 6 carbon atoms.

$L_2$ in the formula (20a) is more preferably a perfluoroalkylene group having 1 to 6 carbon atoms or a perfluoroarylene group having 6 to 12 carbon atoms, further preferably a perfluoroalkylene group having 1 to 6 carbon atoms.

Specifically, it is also preferable that the second compound is a compound represented by a formula (22a).

[Formula 58]

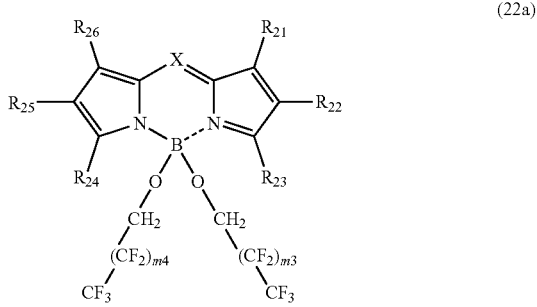

(22a)

In the formula (22a): X represents the same as X in the formula (20). Y bonded to a carbon atom as X represents the same as Y in the formula (20).

$R_{21}$ to $R_{26}$ each independently represent the same as $R_{21}$ to $R_{26}$ in the formula (20).

m3 is in a range from 0 to 4.

m4 is in a range from 0 to 4.

m3 and m4 are mutually the same or different.

In the formulae (20), (21), (22) and (22a), X is a carbon atom bonded to Y; Y is a hydrogen atom or a substituent; Y as the substituent is preferably a substituent selected from the group consisting of a substituted or unsubstituted alkyl group having 1 to 30 carbon atoms, substituted or unsubstituted alkyl halide group having 1 to 30 carbon atoms and substituted or unsubstituted aryl group having 6 to 30 ring carbon atoms, more preferably a substituted or unsubstituted aryl group having 6 to 30 ring carbon atoms.

In the formulae (20), (21), (22) and (22a), it is more preferable that X is a carbon atom bonded to Y; Y is a hydrogen atom or a substituent; Y as the substituent is a substituted or unsubstituted aryl group having 6 to 30 ring carbon atoms; when Y as the substituent is an aryl group having 6 to 30 ring carbon atoms having a substituent, the substituent is a substituted or unsubstituted alkyl group having 1 to 30 carbon atoms, a substituted or unsubstituted alkyl halide group having 1 to 30 carbon atoms, a substituted or unsubstituted alkoxy group having 1 to 30 carbon atoms, a substituted or unsubstituted alkoxy halide group having 1 to 30 carbon atoms, or an aryl group having 6 to 30 ring carbon atoms and substituted by an alkyl group having 1 to 30 carbon atoms.

In the second compound, $Z_{21}$ and $Z_{22}$ may be mutually bonded to form a ring. However, it is preferable that $Z_{21}$ and $Z_{22}$ are not mutually bonded.

In the formulae (20), (22) and (22a), at least one of $R_{21}$, $R_{23}$, $R_{24}$ or $R_{26}$ is preferably a substituted or unsubstituted alkyl group having 1 to 30 carbon atoms or a substituted or unsubstituted alkyl halide group having 1 to 30 carbon atoms.

In the formulae (20), (22) and (22a), $R_{21}$, $R_{23}$, $R_{24}$ and $R_{26}$ are more preferably each a substituted or unsubstituted alkyl group having 1 to 30 carbon atoms or a substituted or unsubstituted alkyl halide group having 1 to 30 carbon atoms. In this case, $R_{22}$ and $R_{25}$ are preferably hydrogen atoms.

In the formulae (20), (22) and (22a), at least one of $R_{21}$, $R_{23}$, $R_{24}$ or $R_{26}$ is preferably a substituted or unsubstituted aryl group having 6 to 30 ring carbon atoms.

In the formulae (20), (22) and (22a), $R_{21}$, $R_{23}$, $R_{24}$ and $R_{26}$ are more preferably each a substituted or unsubstituted aryl group having 6 to 30 ring carbon atoms. In this case, $R_{22}$ and $R_{25}$ are preferably hydrogen atoms.

In the formulae (20), (22) and (22a), it is more preferable that $R_{21}$, $R_{23}$, $R_{24}$ and $R_{26}$ are each independently a substituted or unsubstituted alkyl group having 1 to 30 carbon atoms (preferably 1 to 6 carbon atoms), a substituted or unsubstituted alkyl halide group having 1 to 30 carbon atoms (preferably 1 to 6 carbon atoms), or an aryl group having 6 to 30 ring carbon atoms (preferably 6 to 12 ring carbon atoms) and substituted with an alkyl group having 1 to 30 carbon atoms; and $R_{22}$ and $R_{25}$ are hydrogen atoms.

In the formula (21), at least one of $R_{21}$, $R_{23}$ or $R_{24}$ is preferably a substituted or unsubstituted alkyl group having 1 to 30 carbon atoms or a substituted or unsubstituted alkyl halide group having 1 to 30 carbon atoms.

In the formula (21), $R_{21}$, $R_{23}$ and $R_{24}$ are more preferably a substituted or unsubstituted alkyl group having 1 to 30 carbon atoms or a substituted or unsubstituted alkyl halide group having 1 to 30 carbon atoms. In this case, $R_{22}$ is preferably a hydrogen atom.

In the formula (21), at least one of $R_{21}$, $R_{23}$ or $R_{24}$ is preferably a substituted or unsubstituted aryl group having 6 to 30 ring carbon atoms.

In the formula (21), $R_{21}$, $R_{23}$ and $R_{24}$ are more preferably a substituted or unsubstituted aryl group having 6 to 30 ring carbon atoms. In this case, $R_{22}$ is preferably a hydrogen atom.

In the formula (21): it is more preferable that $R_{21}$, $R_{23}$, and $R_{24}$ are each independently a substituted or unsubstituted alkyl group having 1 to 30 carbon atoms (preferably 1 to 6 carbon atoms), a substituted or unsubstituted alkyl halide group having 1 to 30 carbon atoms (preferably 1 to 6 carbon atoms), or an aryl group having 6 to 30 ring carbon atoms (preferably 6 to 12 ring carbon atoms) and substituted with an alkyl group having 1 to 30 carbon atoms; and $R_{22}$ is a hydrogen atom.

In the second compound, examples of the fluorine-substituted alkoxy group include 2,2,2-trifluoroethoxy group, 2,2-difluoroethoxy group, 2,2,3,3,3-pentafluoro-1-propoxy group, 2,2,3,3-tetrafluoro-1-propoxy group, 1,1,1,3,3,3-hexafluoro-2-propoxy group, 2,2,3,3,4,4,4-heptafluoro-1-butyloxy group, 2,2,3,3,4,4-hexafluoro-1-butyloxy group, nonafluoro-tertiary-butyloxy group, 2,2,3,3,4,4,5,5,5-nonafluoropentanoxy group, 2,2,3,3,4,4,5,5,6,6,6-undecafluorohexanoxy group, 2,3 bis(trifluoromethyl)-2,3-butanedioxy group, 1,1,2,2-tetra(trifluoromethyl)ethylene glycoxy group, 4,4,5,5,6,6,6-heptafluorohexane-1,2-dioxy group, and 4,4,5,5,6,6,7,7,8,8,9,9,9-tridecafluorononane-1,2-dioxy group.

In the second compound, examples of the fluorine-substituted aryloxy group or the aryloxy group substituted with a fluoroalkyl group include a pentafluorophenoxy group, 3,4,5-trifluorophenoxy group, 4-trifluoromethylphenoxy group, 3,5-bistrifluoromethylphenoxy group, 3-fluoro-4-trifluoromethylphenoxy group, 2,3,5,6-tetrafluoro-4-trifluoromethylphenoxy group, 4-fluorocatecholato group, 4-trifluoromethylcatecholato group, and 3,5-bistrifluoromethylcatecholato group.

When the second compound is a fluorescent compound, the second compound preferably emits light having a main peak wavelength in a range from 400 nm to 700 nm.

Herein, the main peak wavelength means a peak wavelength of an emission spectrum exhibiting a maximum luminous intensity among fluorescence spectra measured in a toluene solution in which a measurement target compound is dissolved at a concentration ranging from $10^{-6}$ mol/l to $10^{-5}$ mol/l. A spectrophotofluorometer (F-7000 manufactured by Hitachi High-Tech Science Corporation) is used as a measurement device.

The second compound preferably exhibits red or green light emission.

Herein, the red light emissions refers to a light emission in which a main peak wavelength of fluorescence spectrum is in a range from 600 nm to 660 nm.

When the second compound is a red fluorescent compound, the main peak wavelength of the second compound is preferably in a range from 600 nm to 660 nm, more preferably in a range from 600 nm to 640 nm, further preferably in a range from 610 nm to 630 nm.

Herein, the green light emissions refers to a light emission in which a main peak wavelength of fluorescence spectrum is in a range from 500 nm to 560 nm.

When the second compound is a green fluorescent compound, the main peak wavelength of the second compound is preferably in a range from 500 nm to 560 nm, more preferably in a range from 500 nm to 540 nm, further preferably in a range from 510 nm to 530 nm.

Herein, the blue light emissions refers to a light emission in which a main peak wavelength of fluorescence spectrum is in a range from 430 nm to 480 nm.

When the second compound is a blue fluorescent compound, the main peak wavelength of the second compound is preferably in a range from 430 nm to 480 nm, more preferably in a range from 445 nm to 480 nm.

Manufacturing Method of Second Compound

The second compound can be manufactured by a known method.

Examples of the second compound according to the exemplary embodiment are shown below. The second compound of the invention is by no means limited to the Examples.

A coordinate bond between a boron atom and a nitrogen atom in a pyrromethene skeleton is shown by various means such as a solid line, a broken line, an arrow, and omission. Herein, the coordinate bond is shown by a solid line or a broken line, or the description of the coordinate bond is omitted.

[Formula 59]
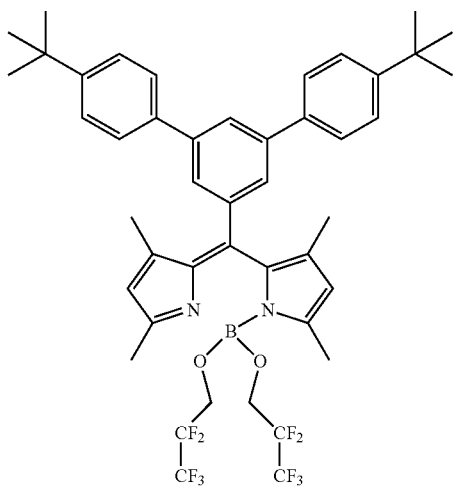
[Formula 60]
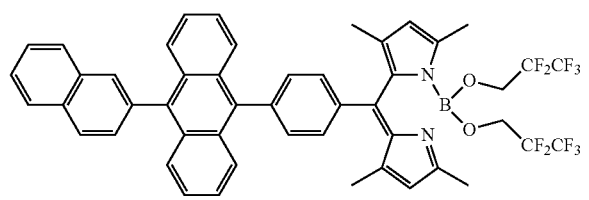
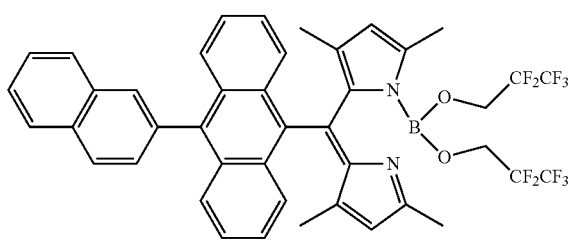
[Formula 61]
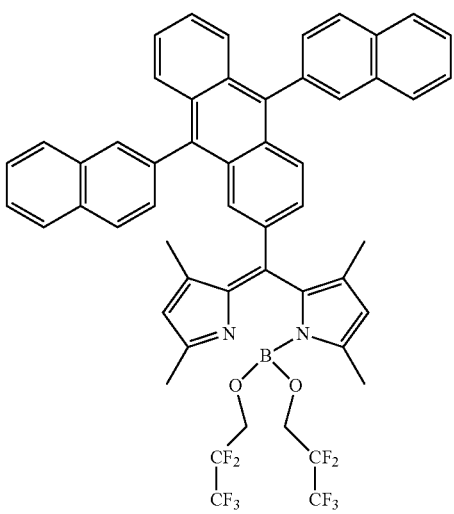
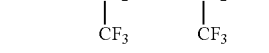
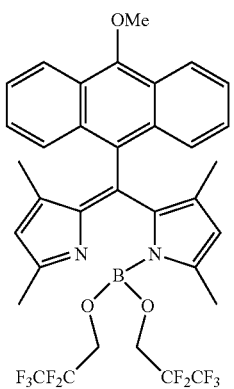

105
-continued
[Formula 62]
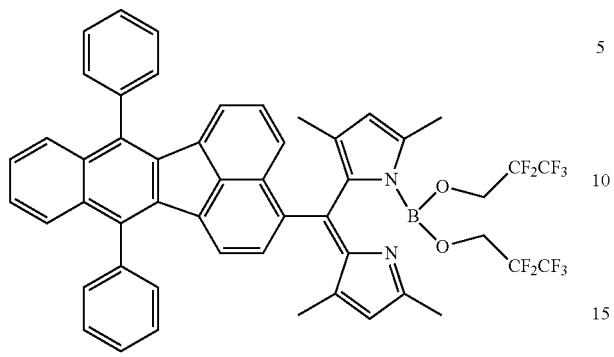
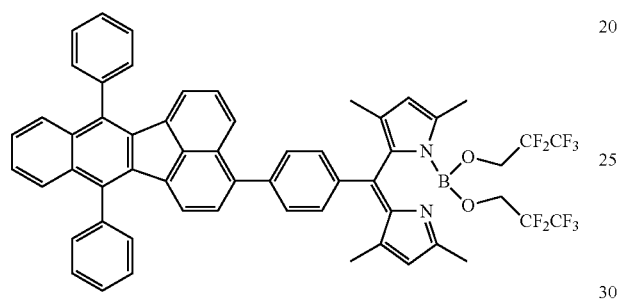
[Formula 63]
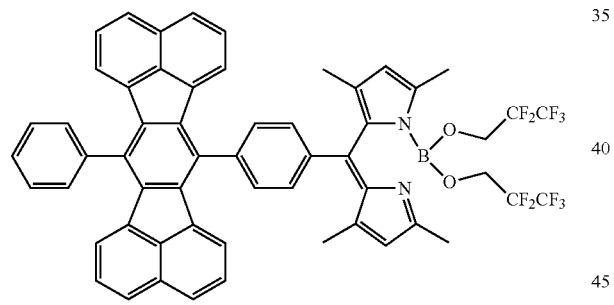
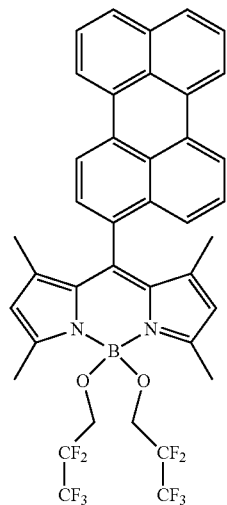
106
-continued
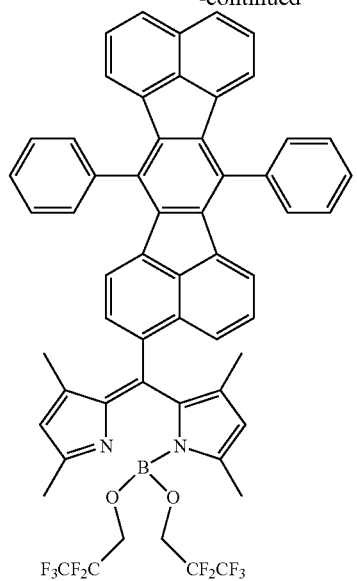
[Formula 64]
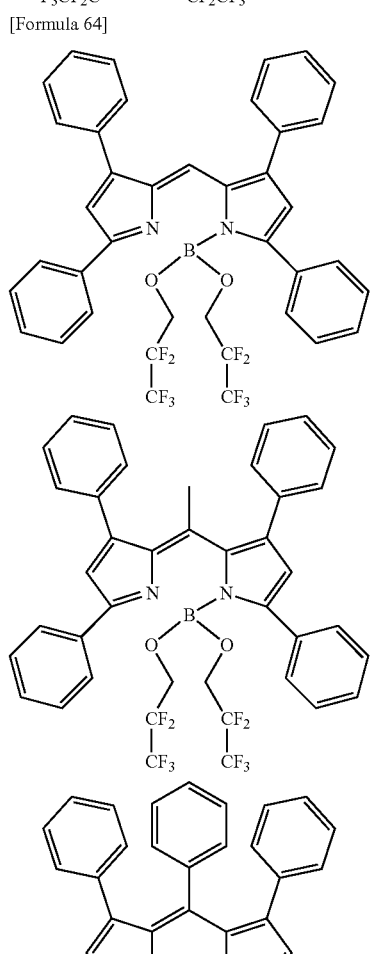

107
-continued
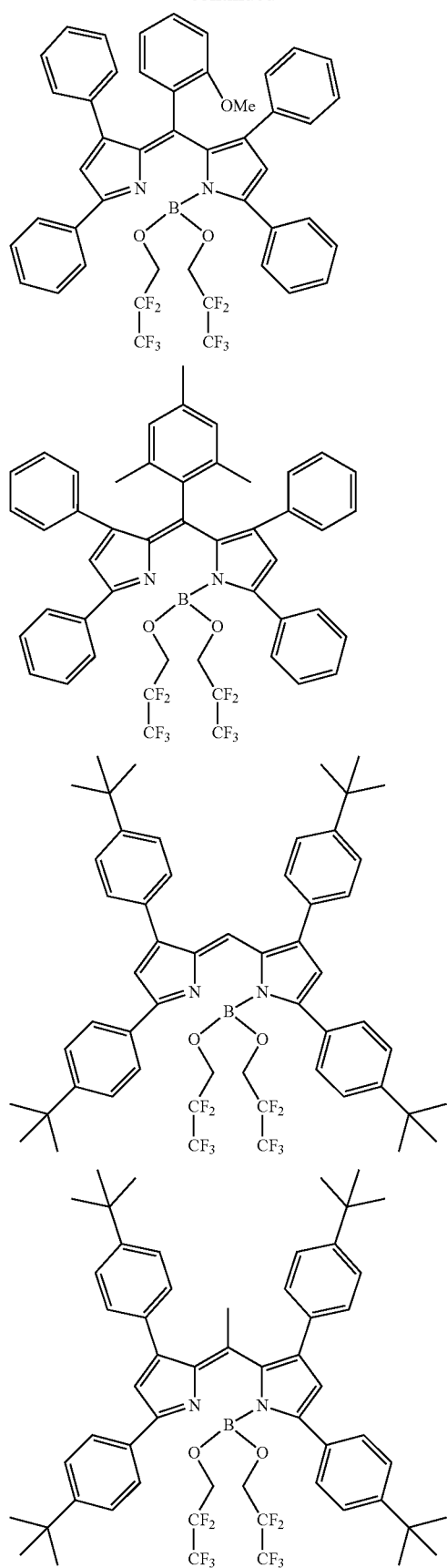
108
-continued
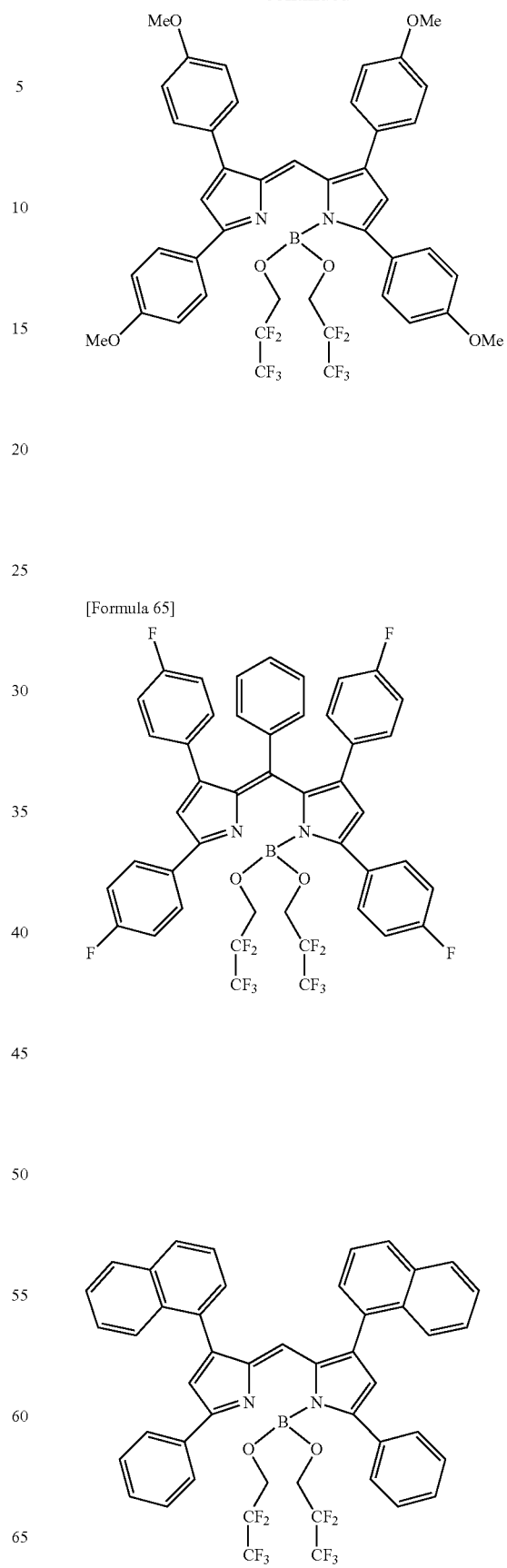
[Formula 65]

109
-continued
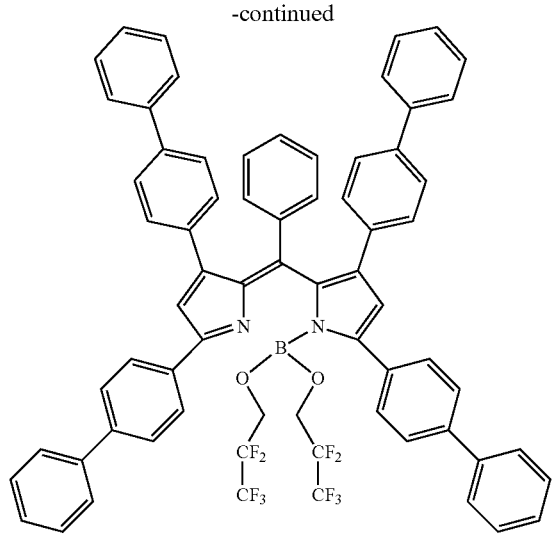
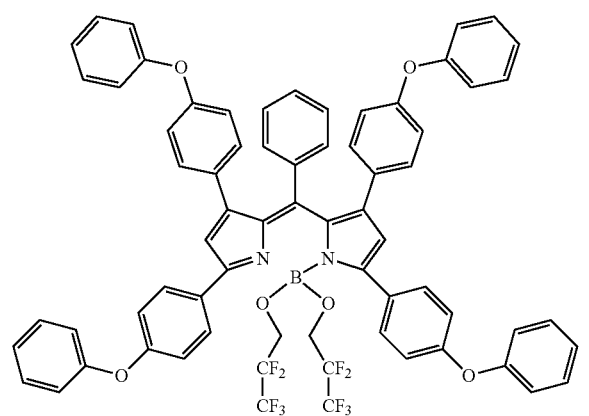
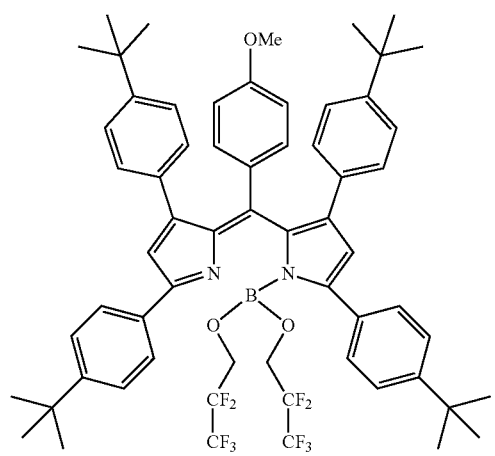
110
-continued
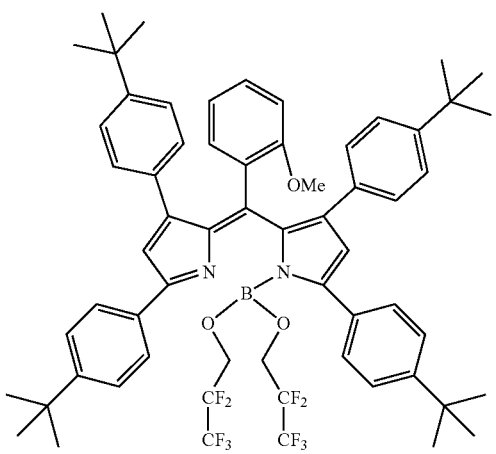
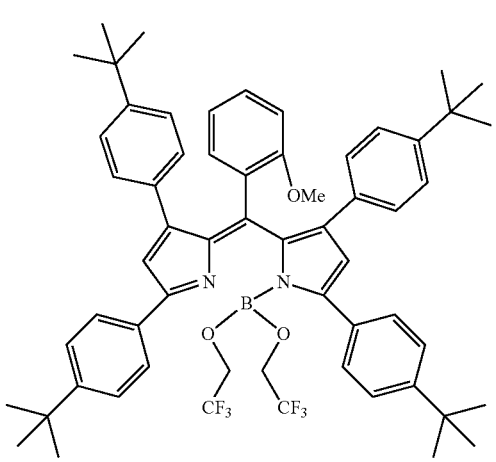
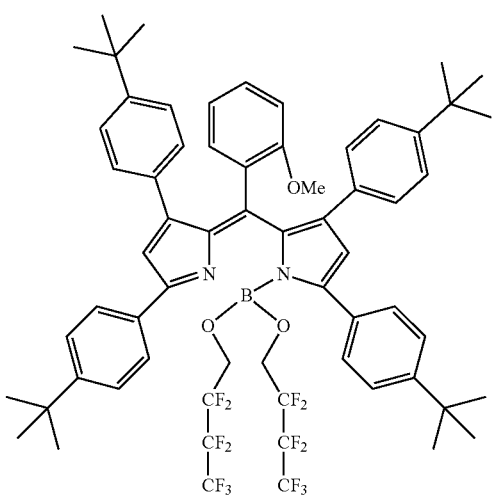

111
-continued
[Formula 66]
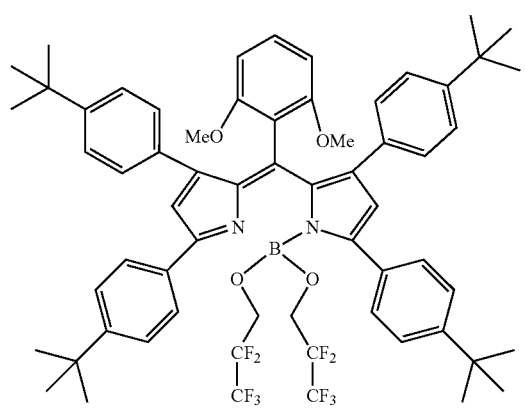
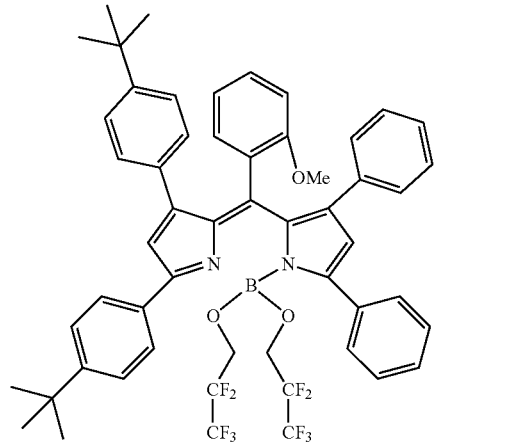
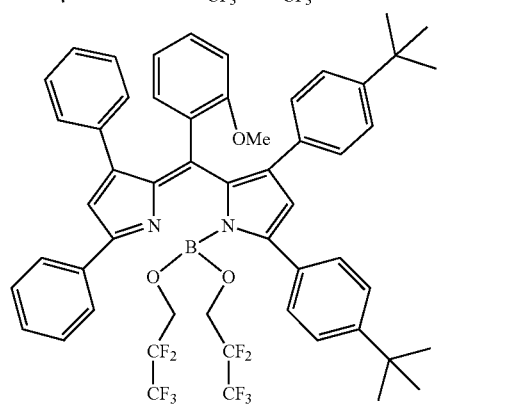
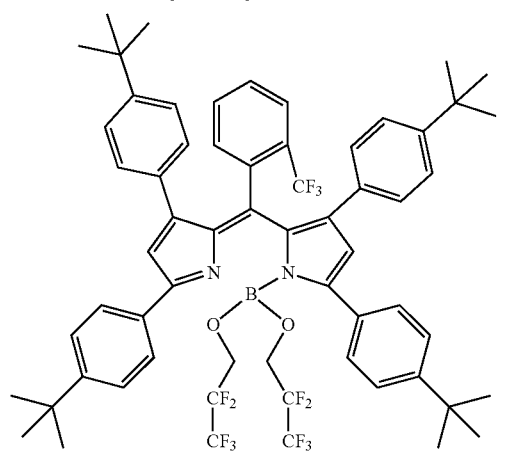
112
-continued
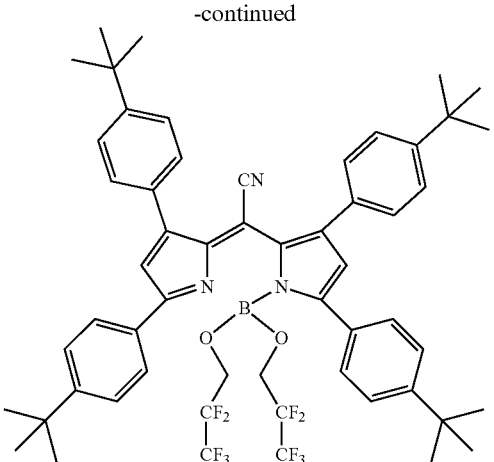
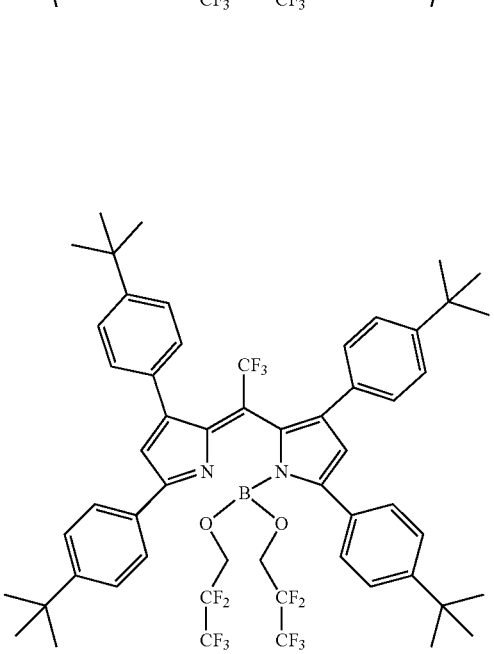
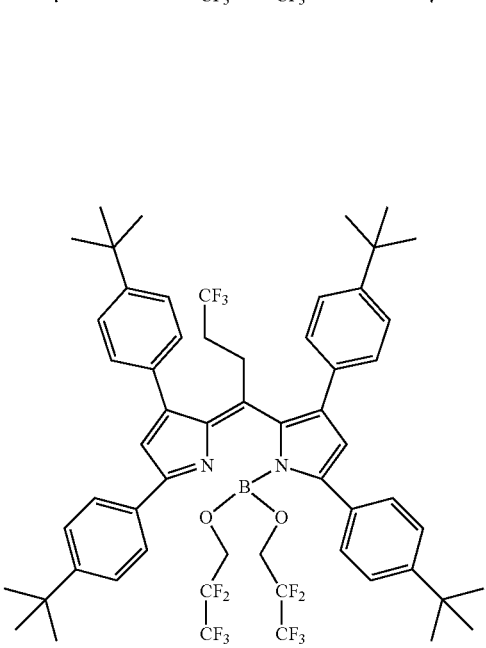

113
-continued
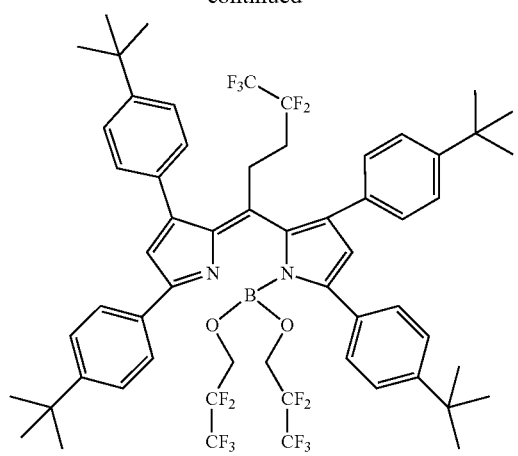
[Formula 67]
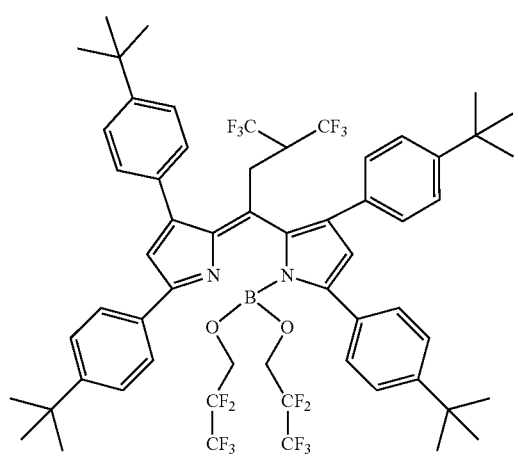
114
-continued
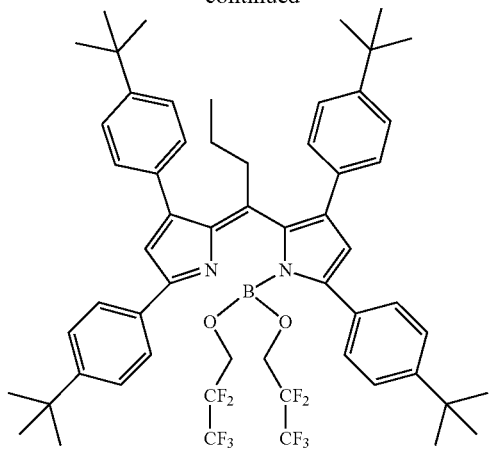
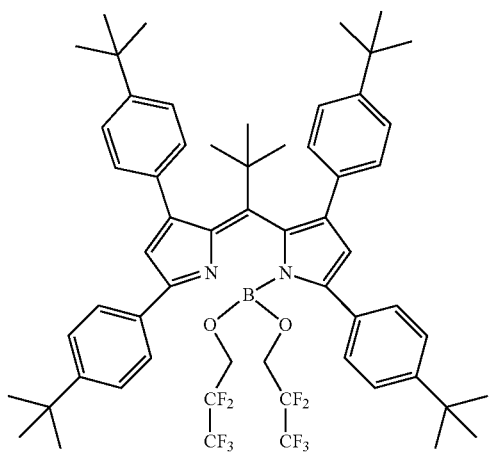
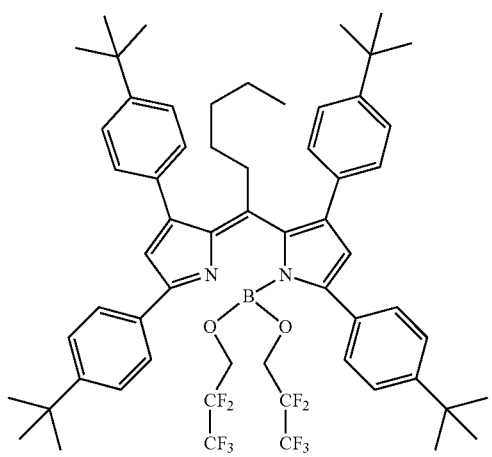

115
-continued
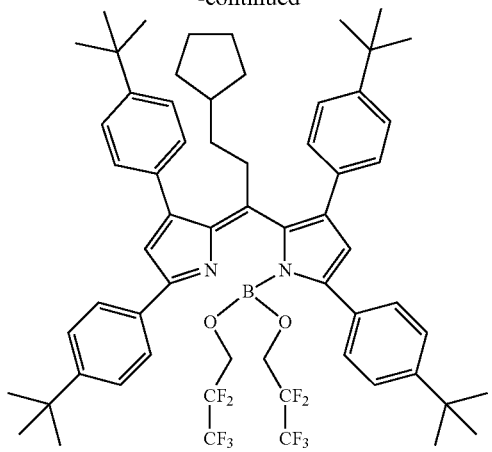
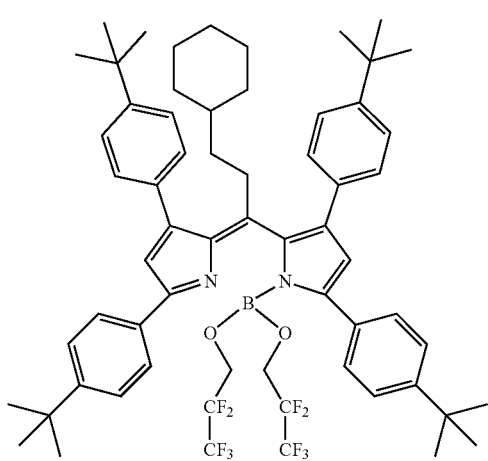
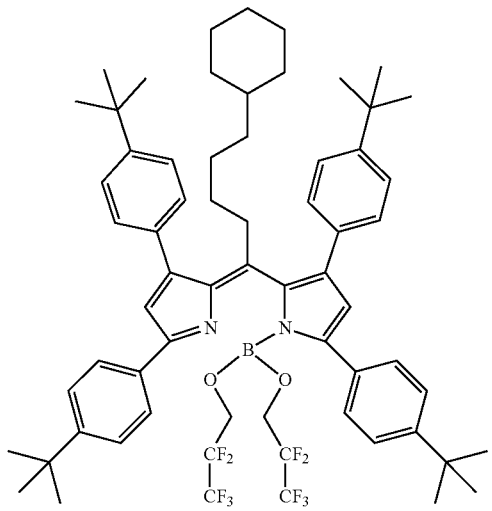
116
-continued
[Formula 68]
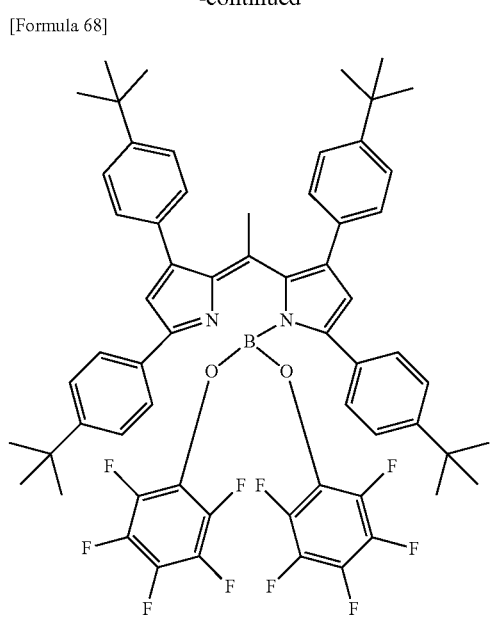
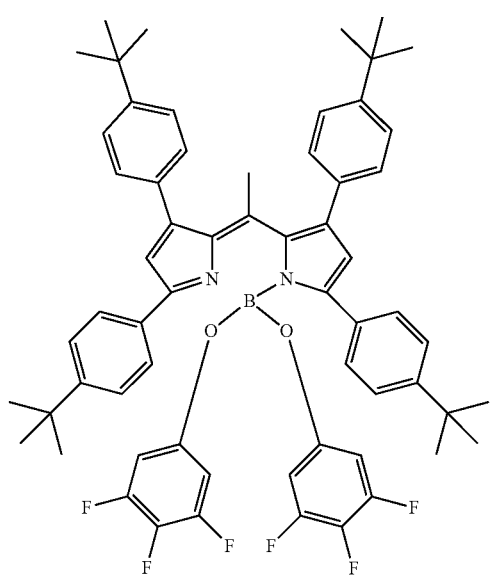

117
-continued
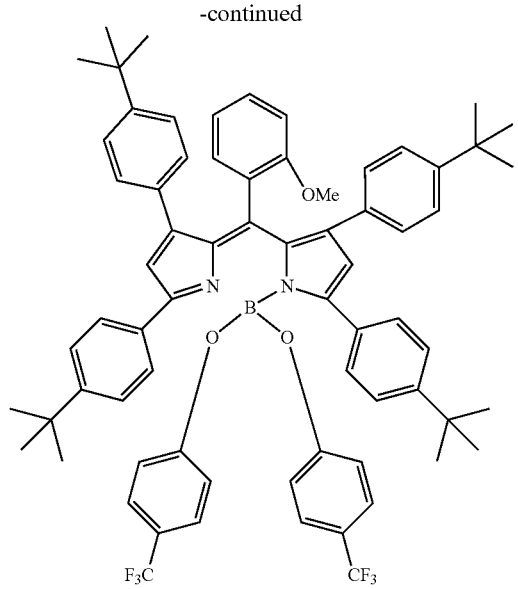
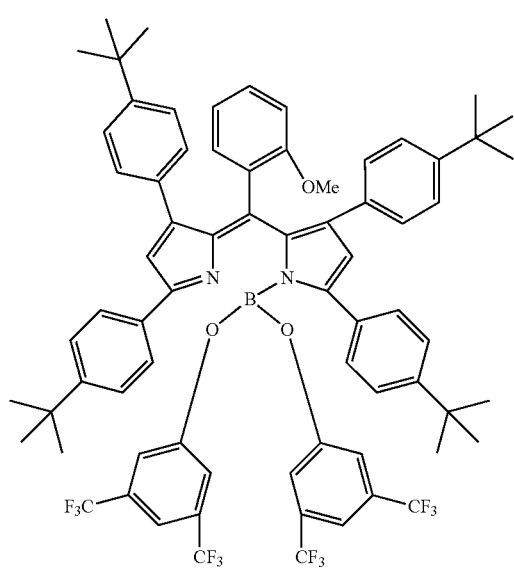
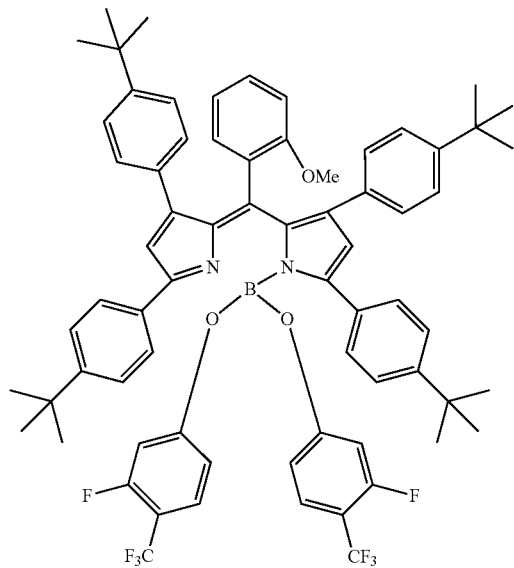
118
-continued
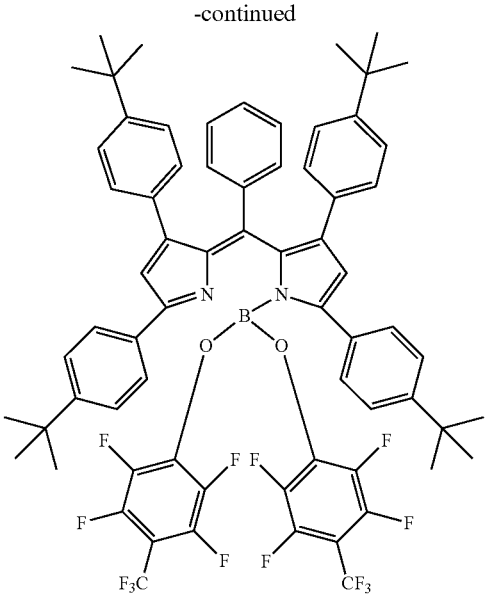
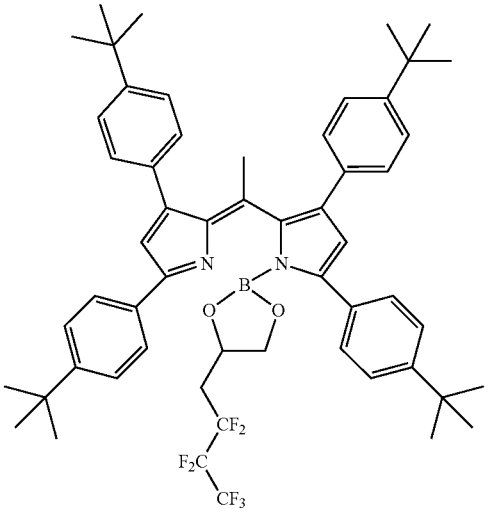
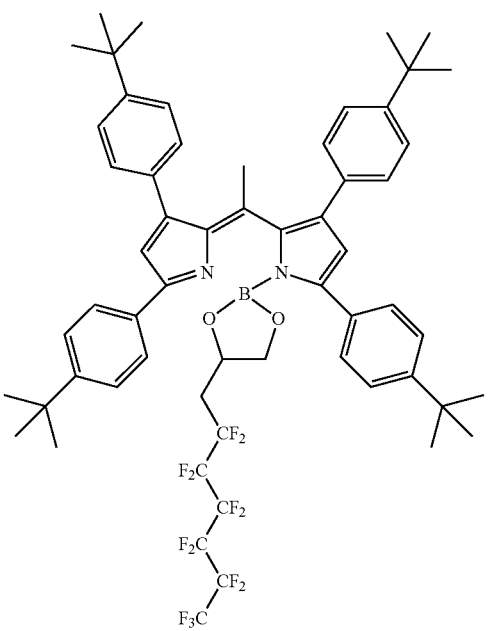

[Formula 69]
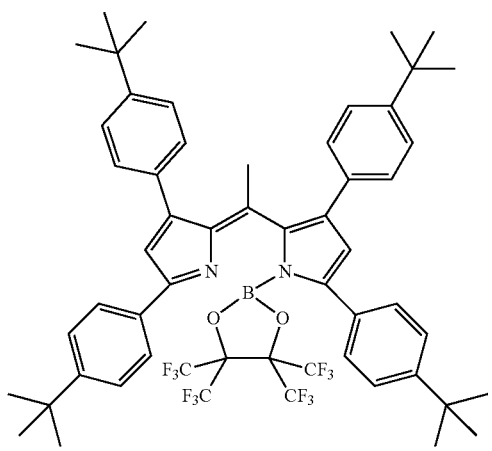
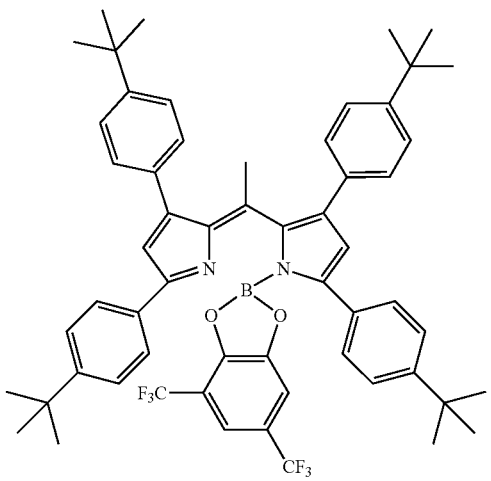
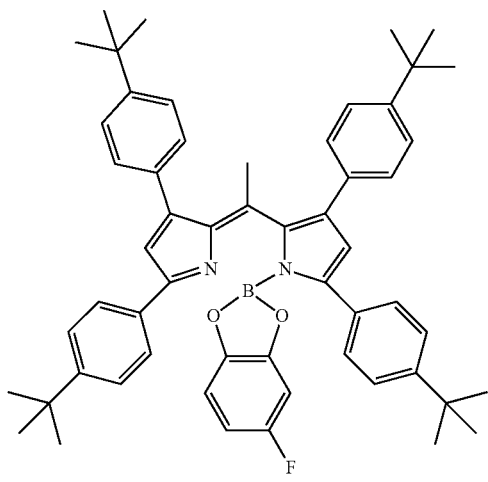
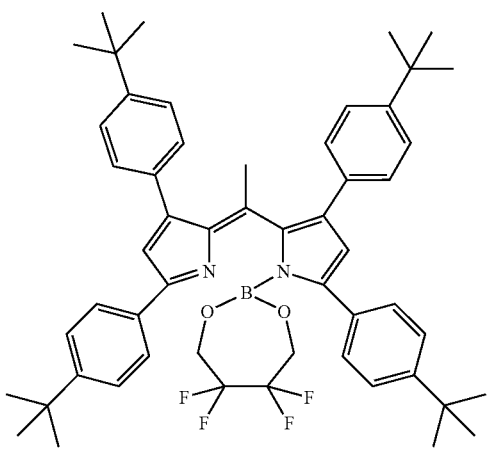
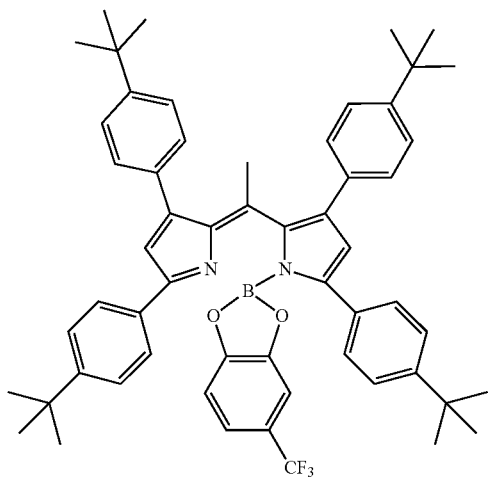
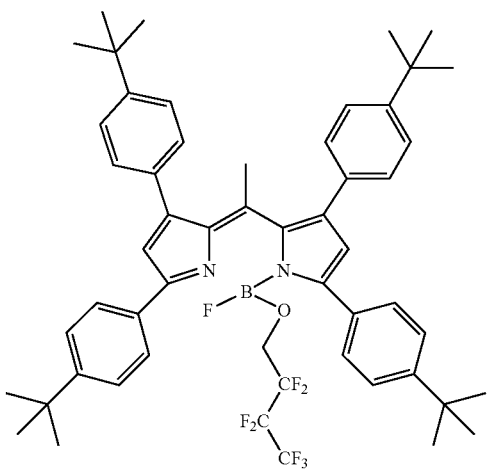

121
-continued
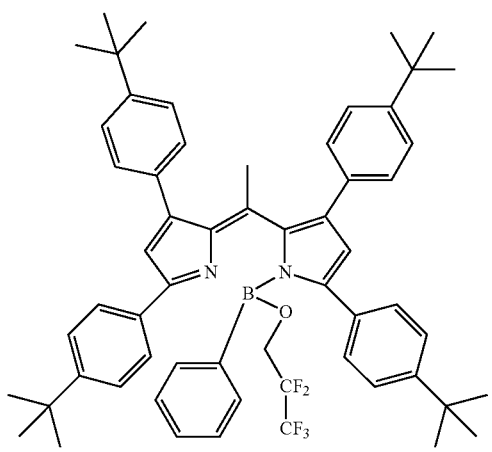
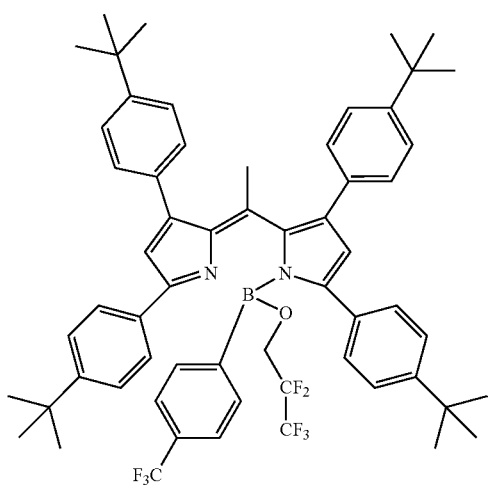
[Formula 70]
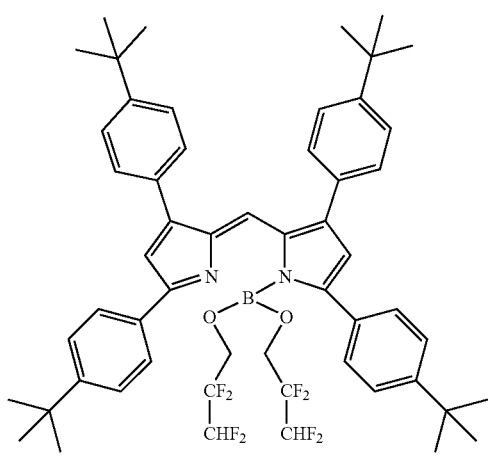
122
-continued
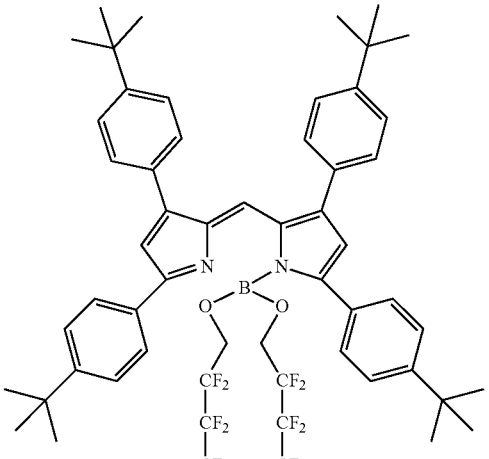
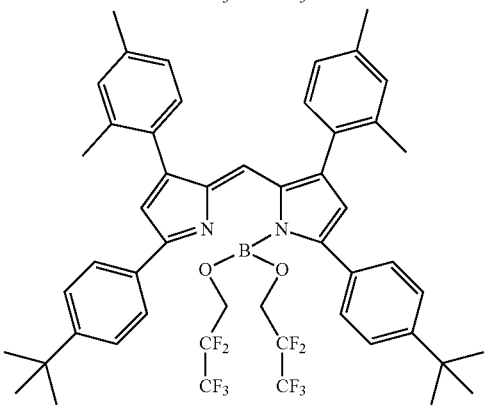
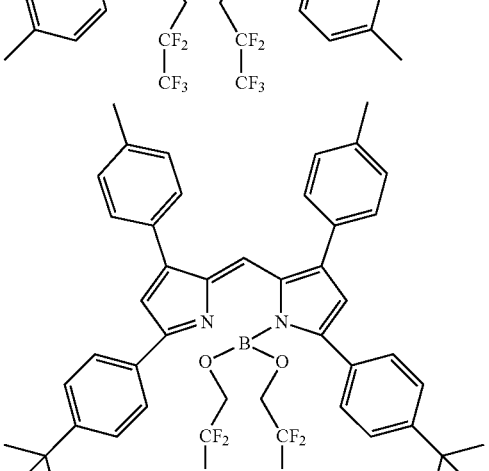
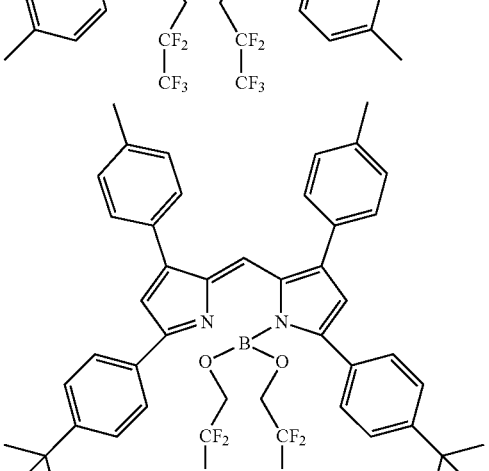

123
-continued
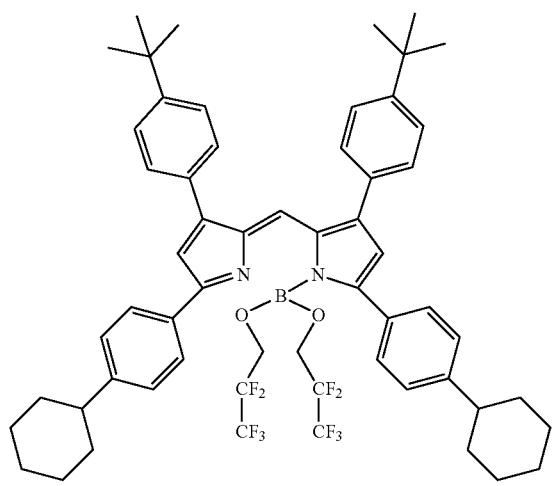
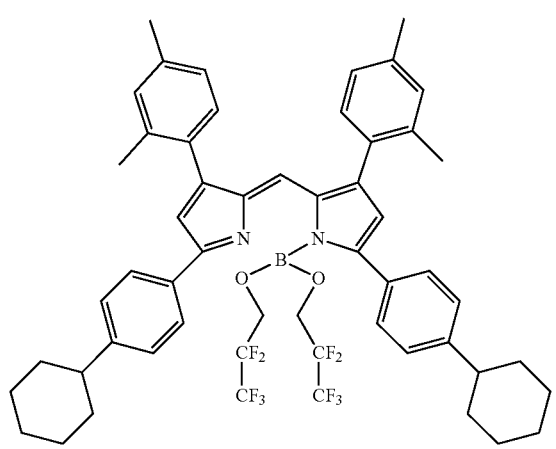
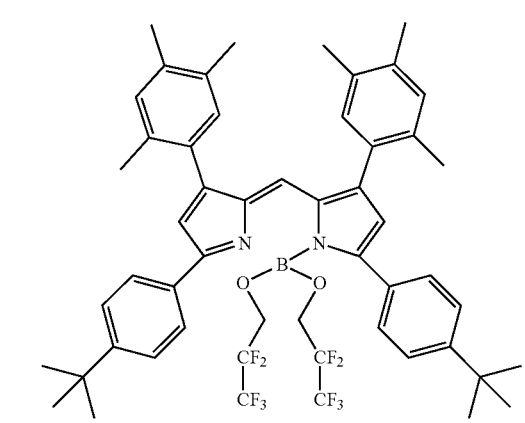
124
-continued
[Formula 71]
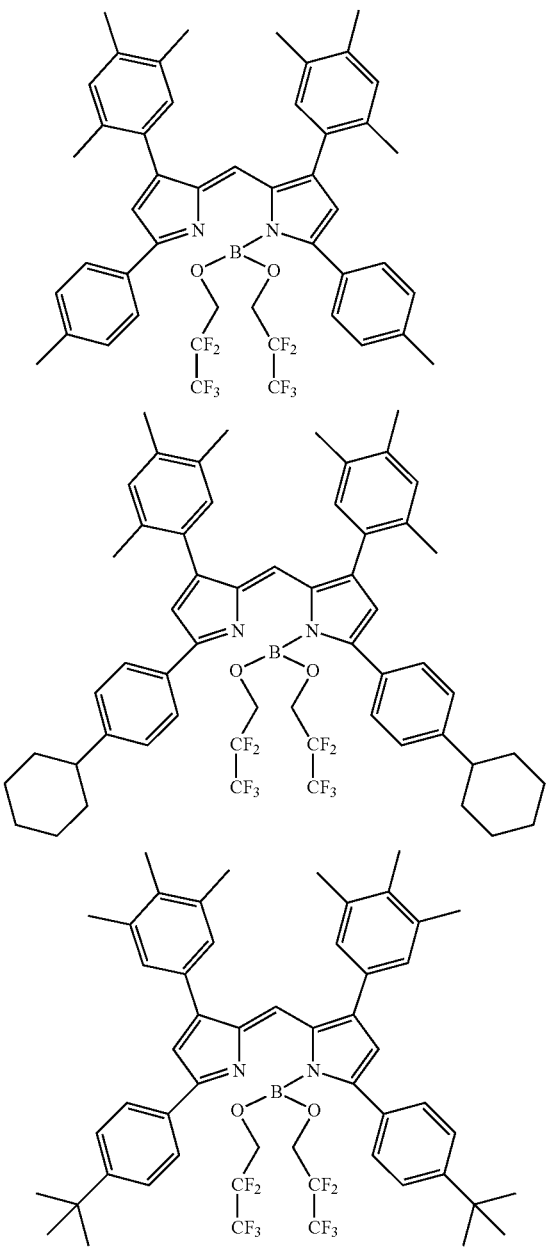

125
-continued
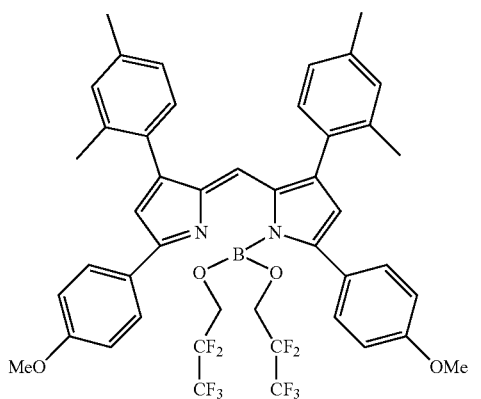
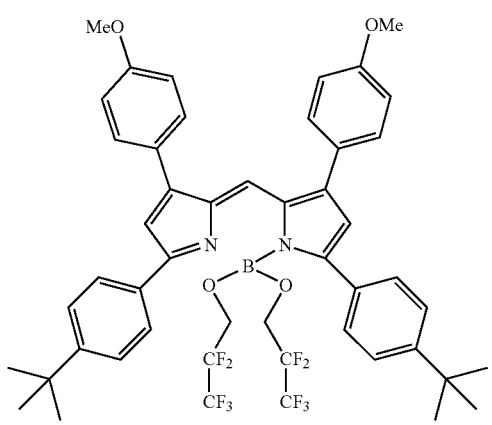
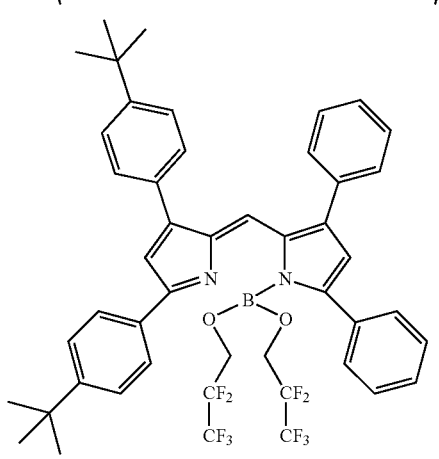
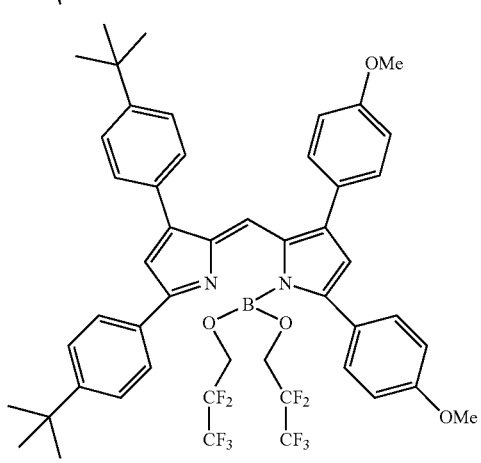
126
-continued
[Formula 72]
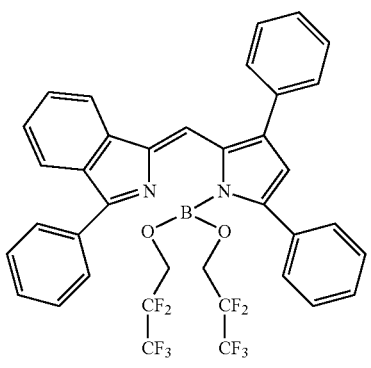
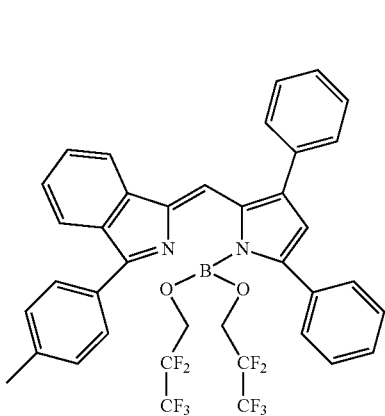
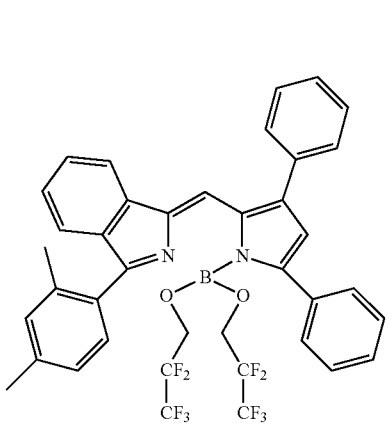
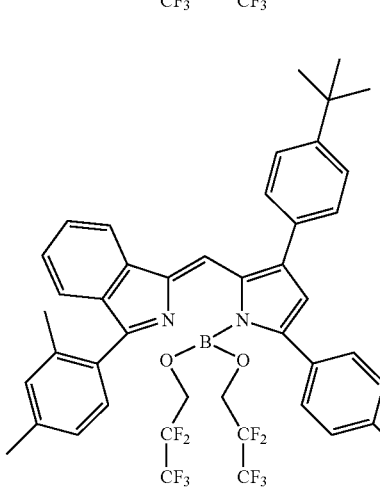

127
-continued
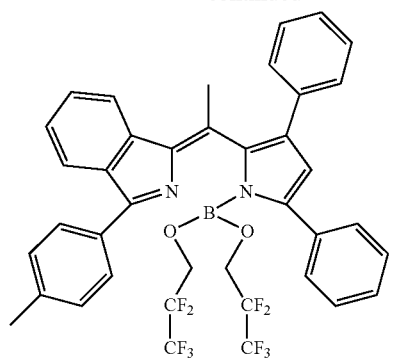
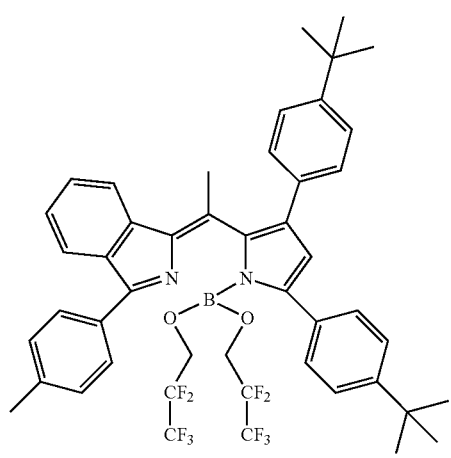
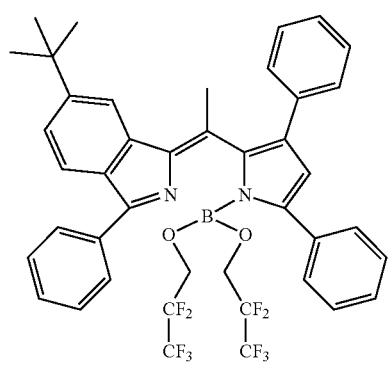
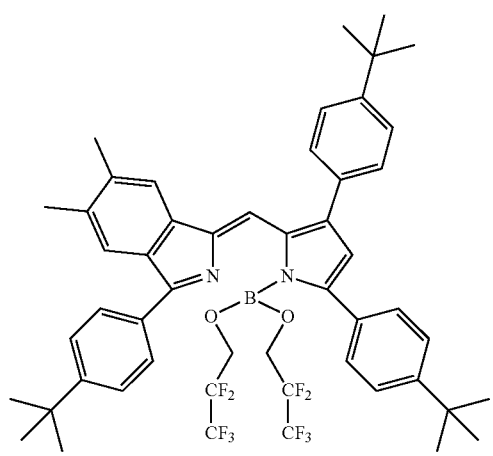
128
-continued
[Formula 73]
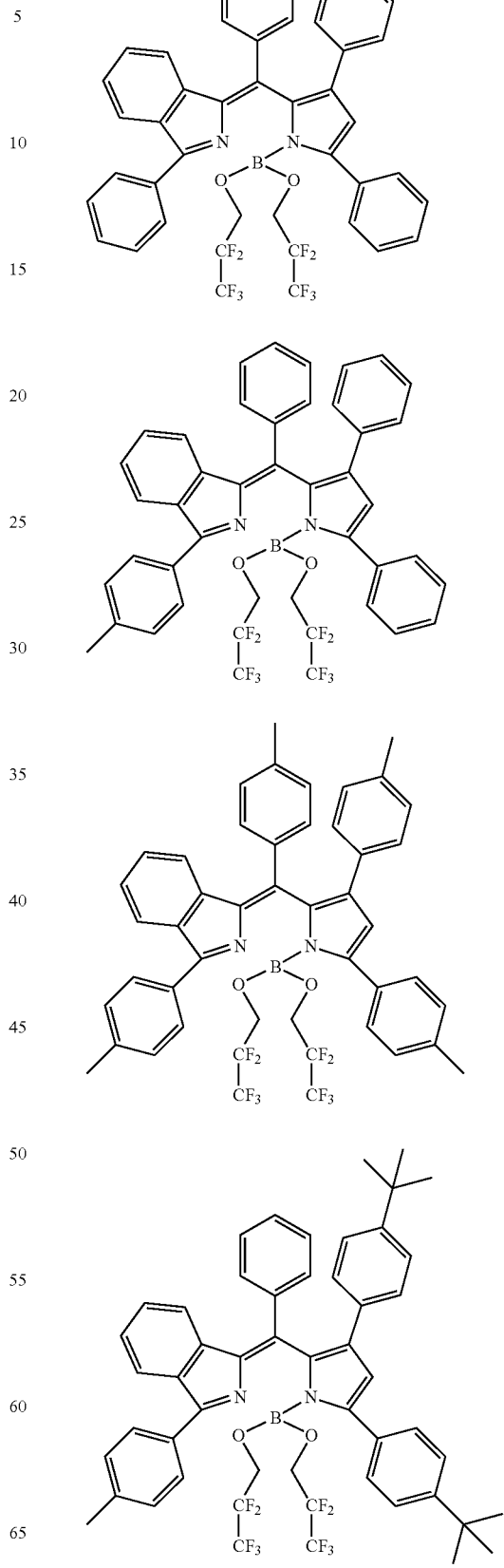

129
-continued
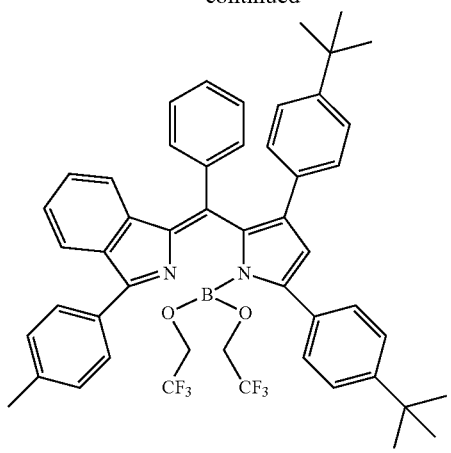
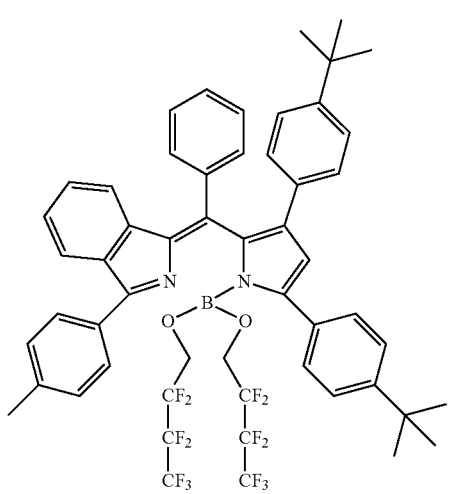
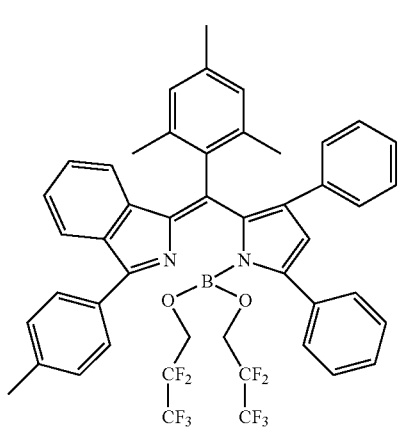
130
-continued
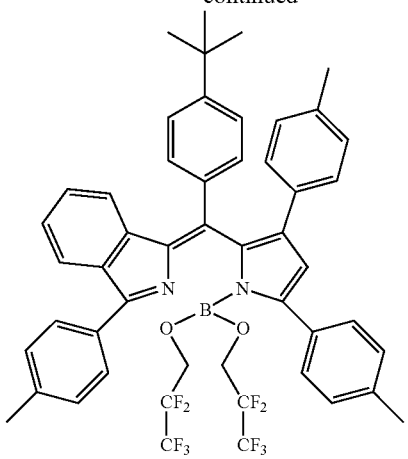
[Formula 74]
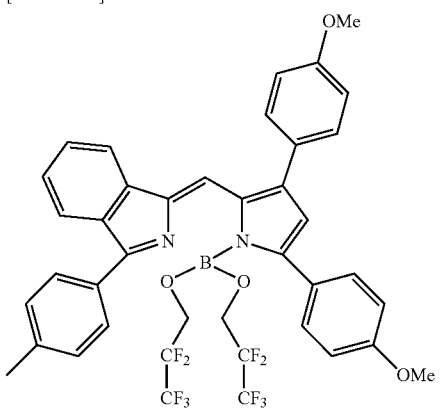
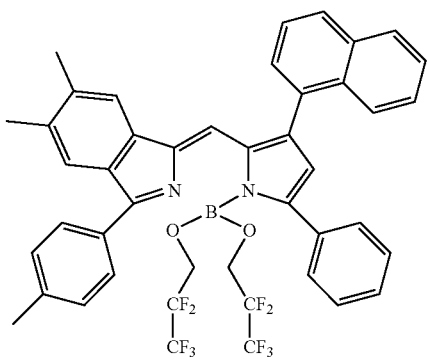

-continued
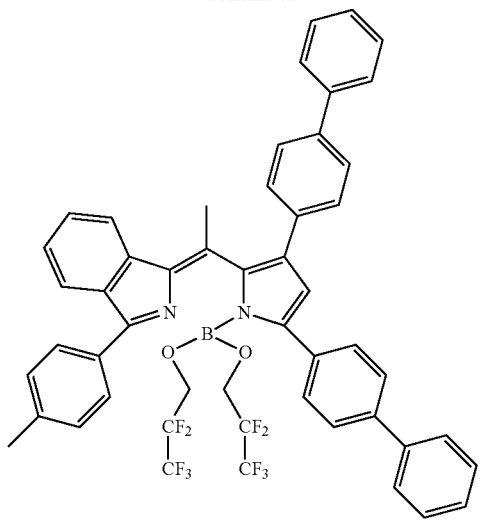
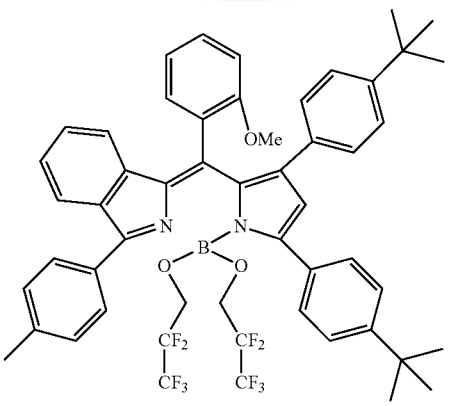
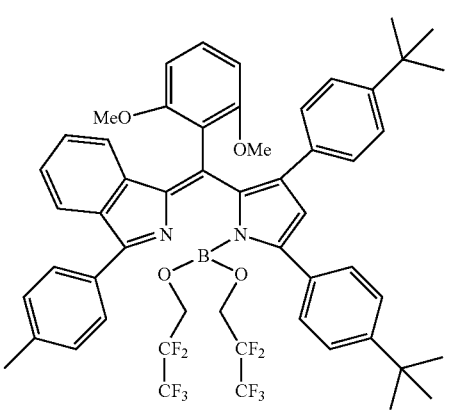
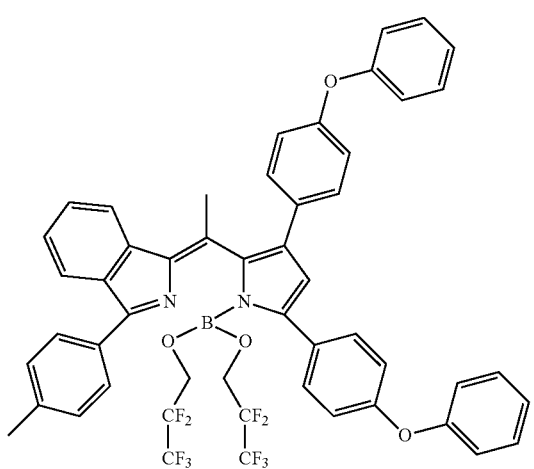
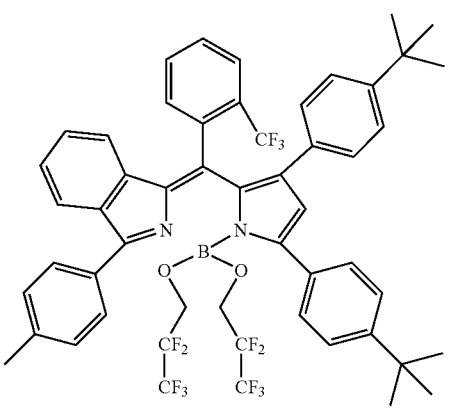
[Formula 75]
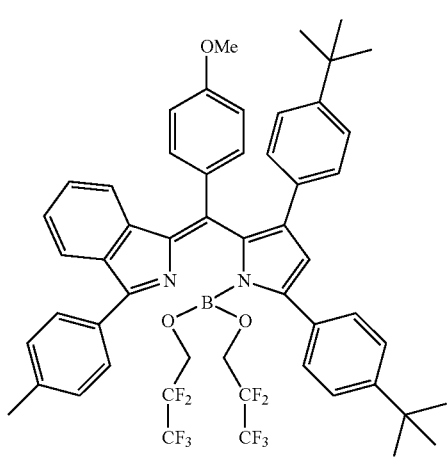
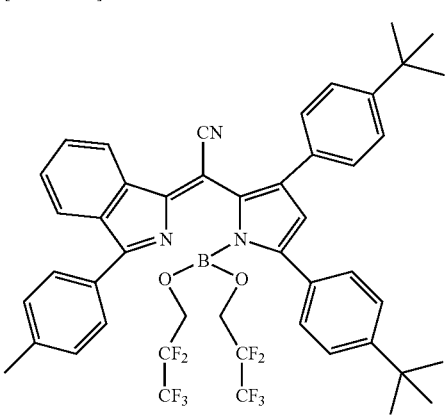

133
-continued
134
-continued
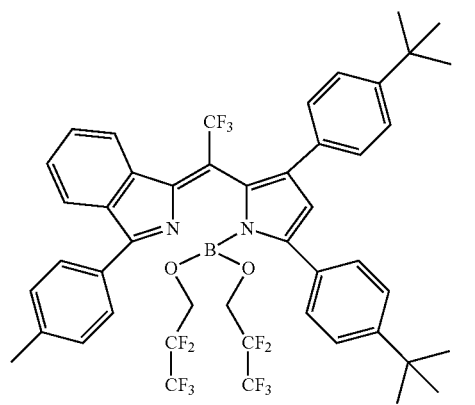
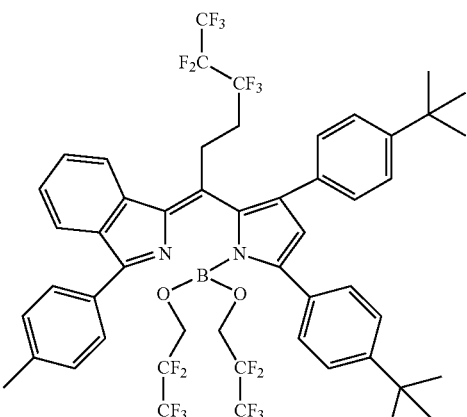

[Formula 76]
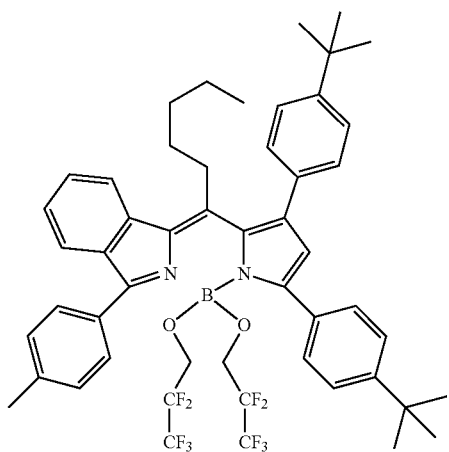
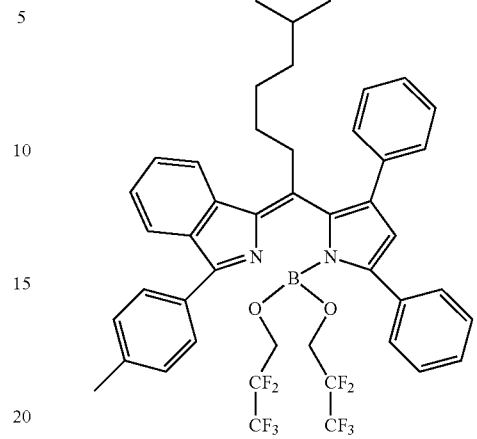
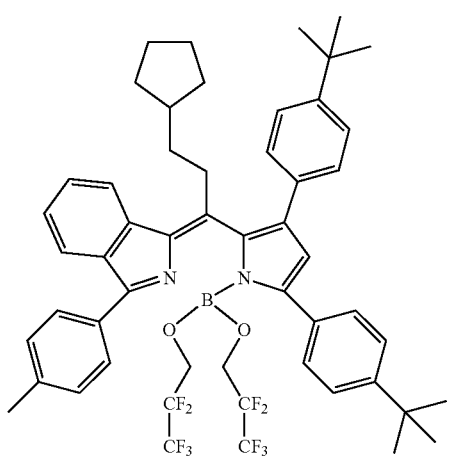
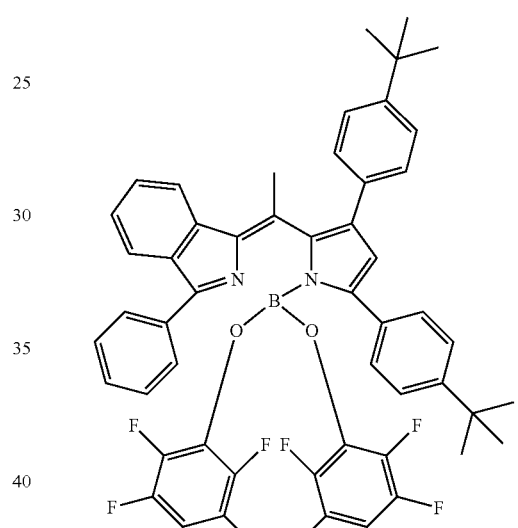
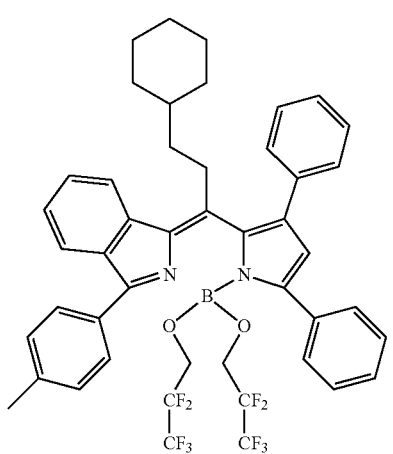
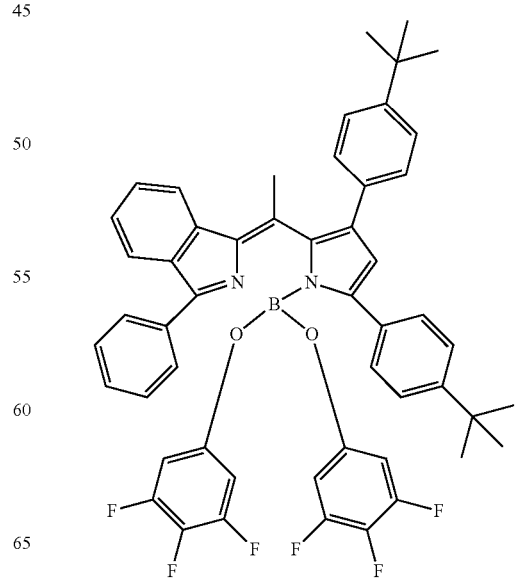

137
-continued
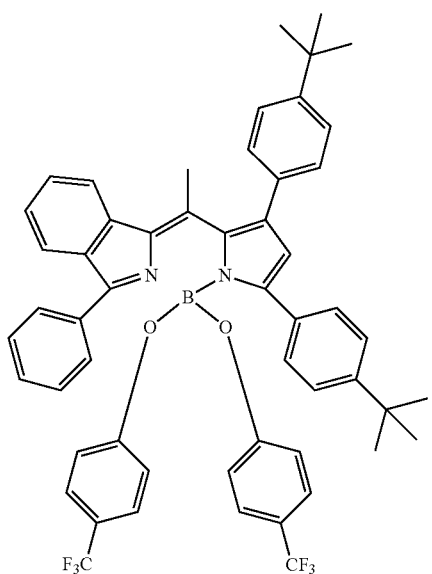
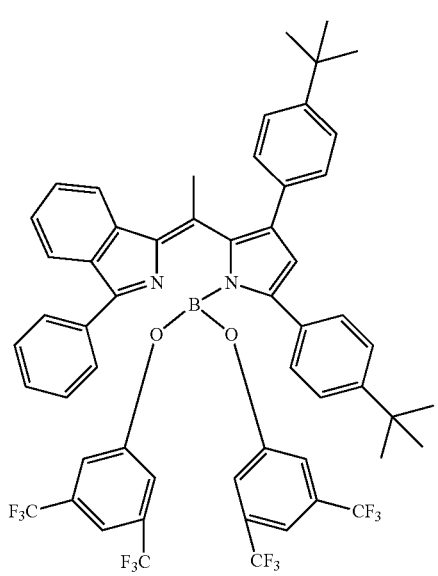
138
-continued
[Formula 77]
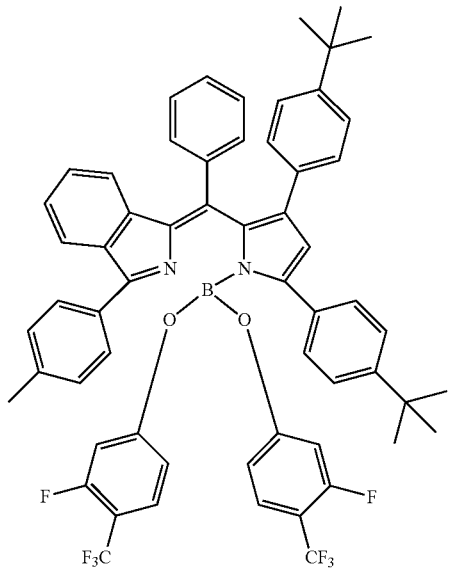
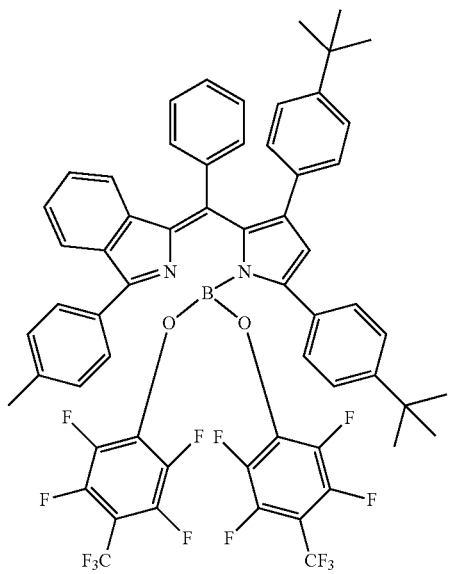
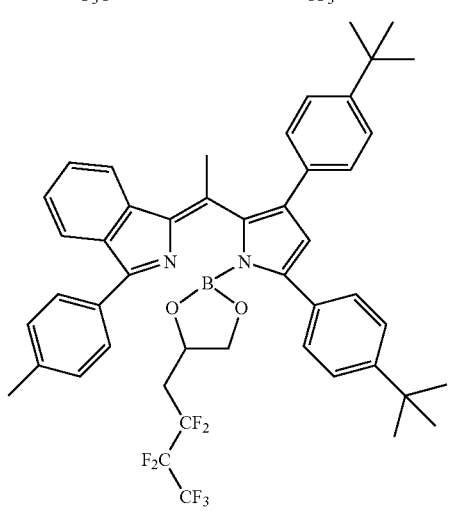

139
-continued
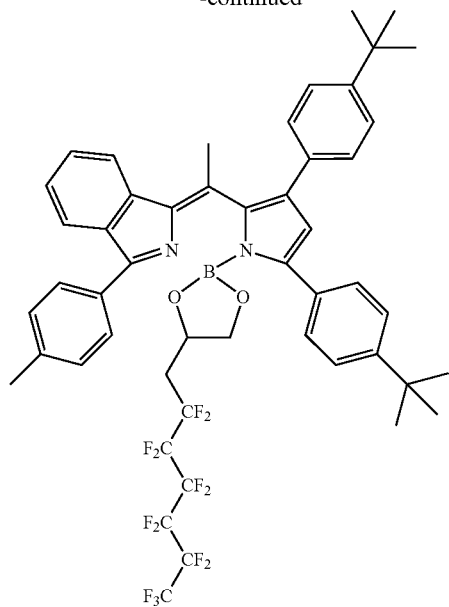
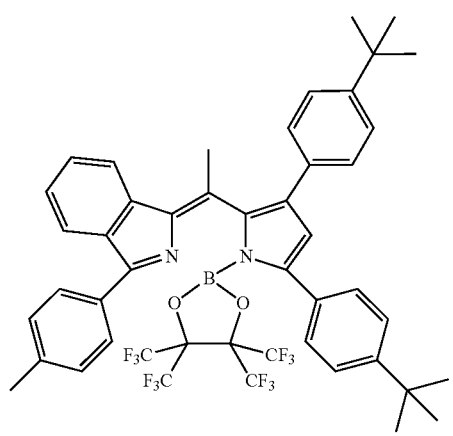
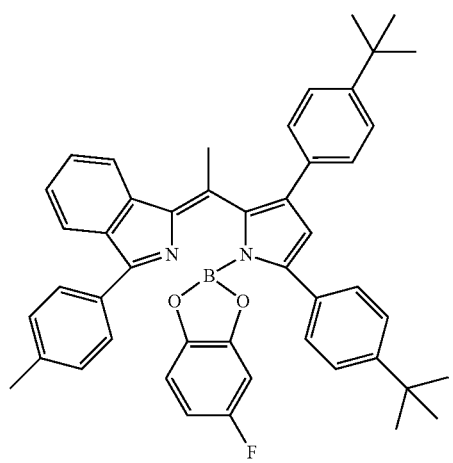
140
-continued
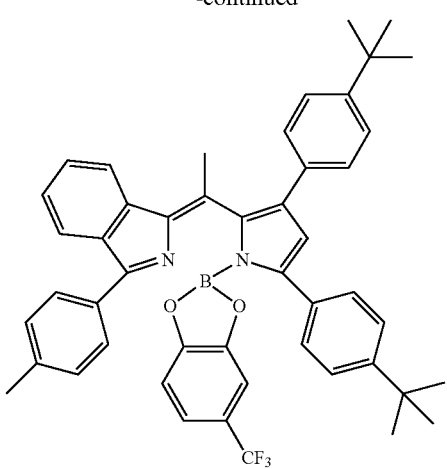
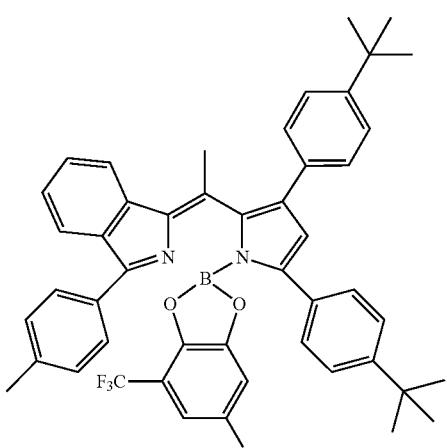
[Formula 78]
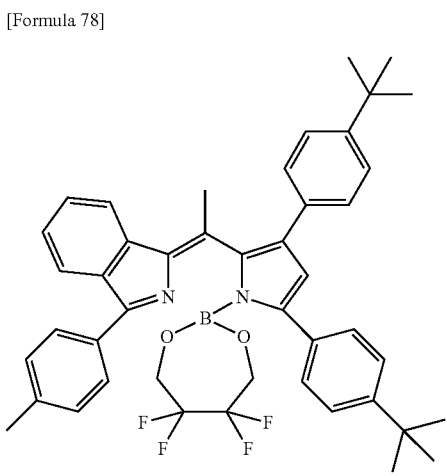

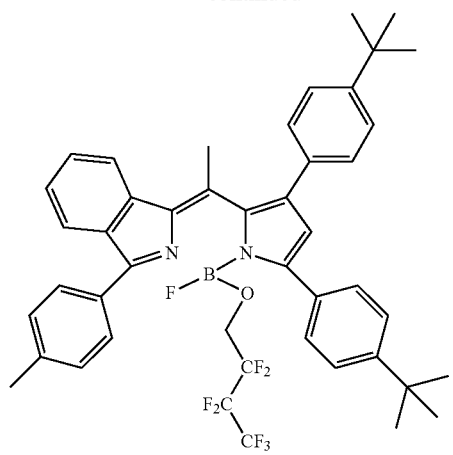
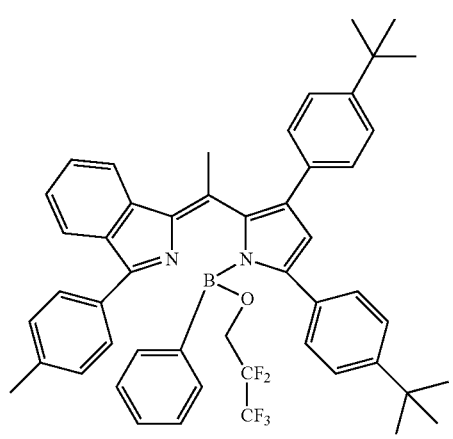
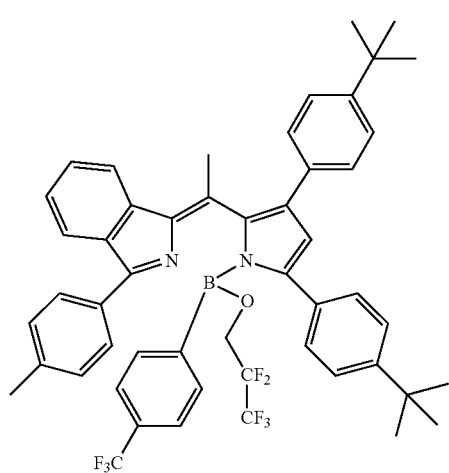
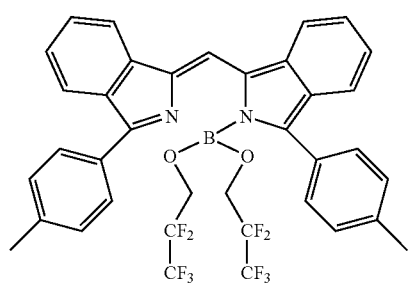
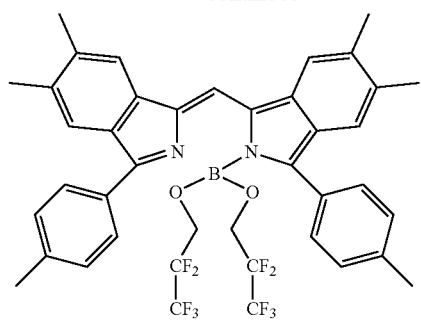
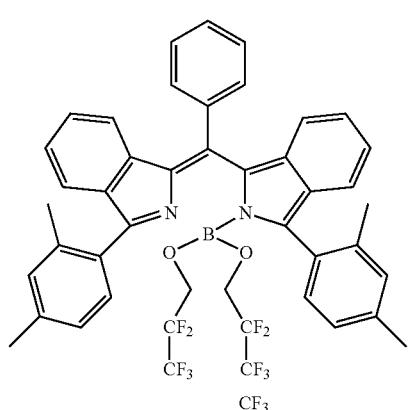
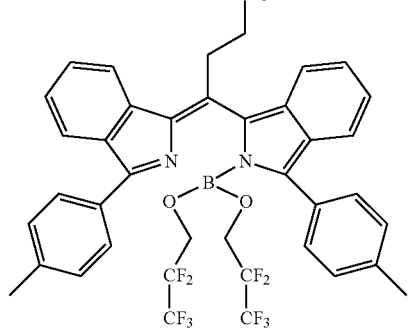
[Formula 79]
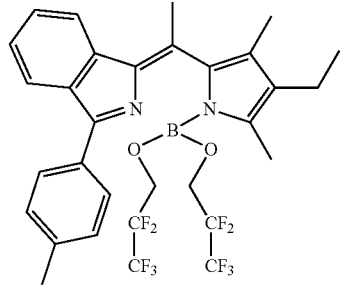
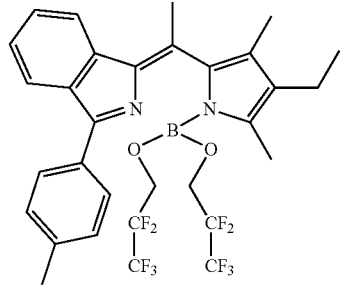

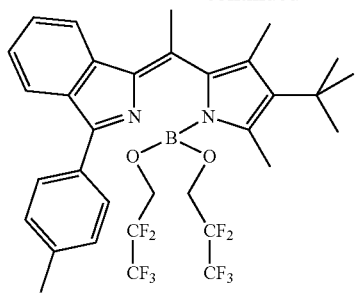
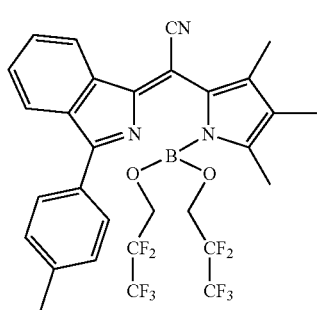
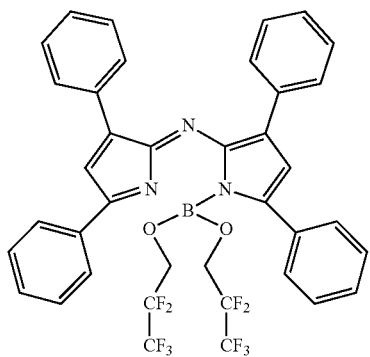
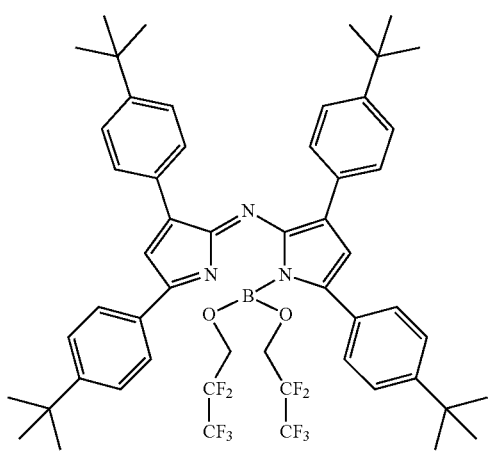
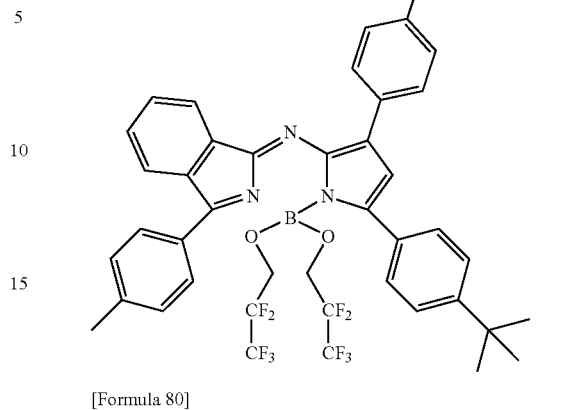
[Formula 80]
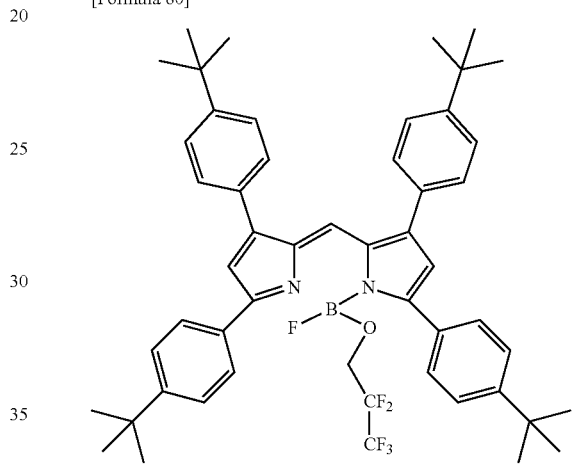
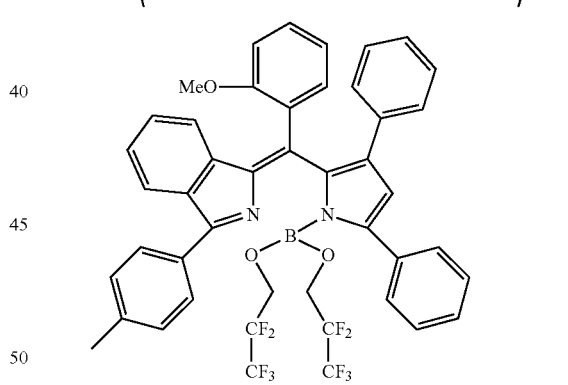
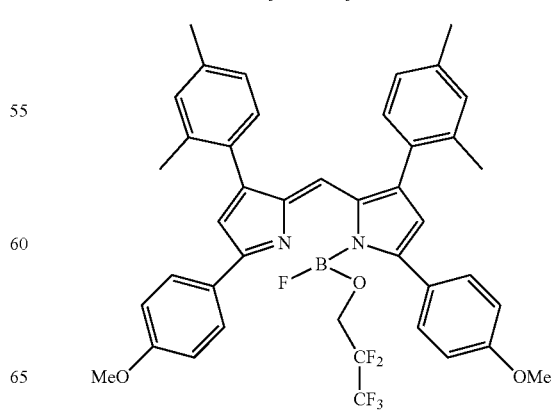

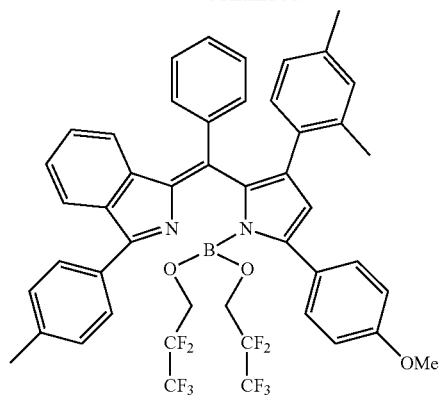
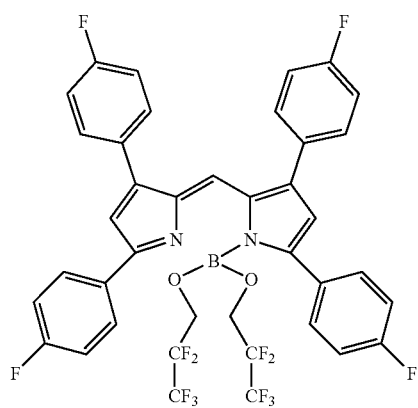
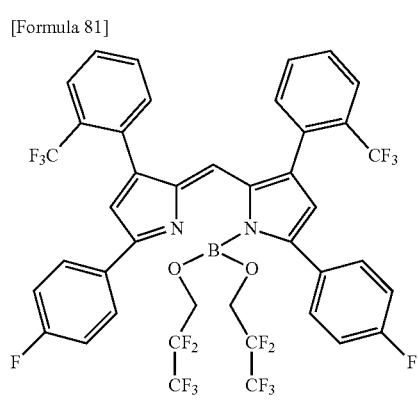
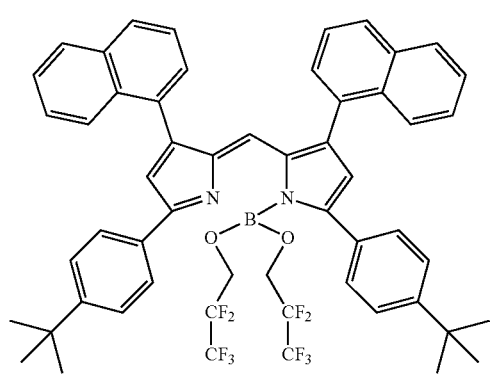
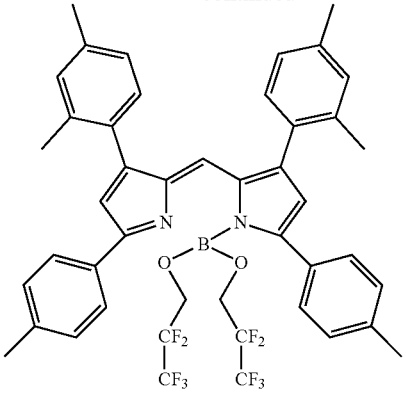
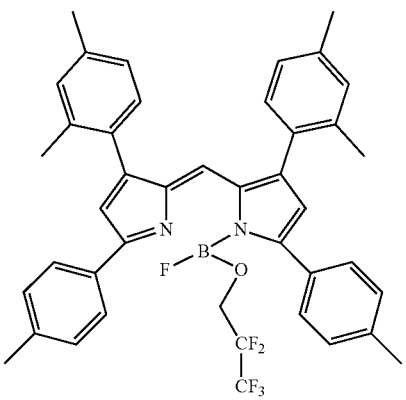
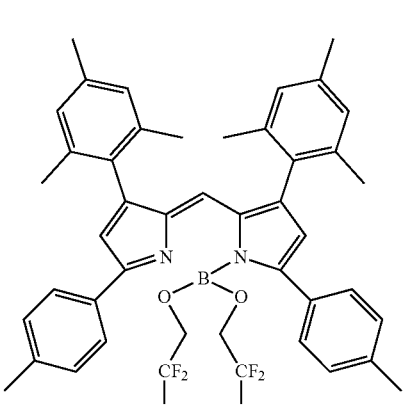
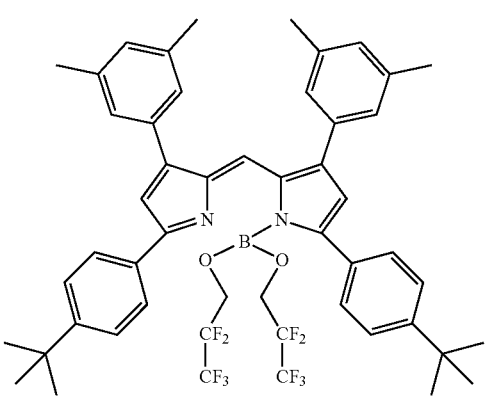
[Formula 81]

[Formula 82]
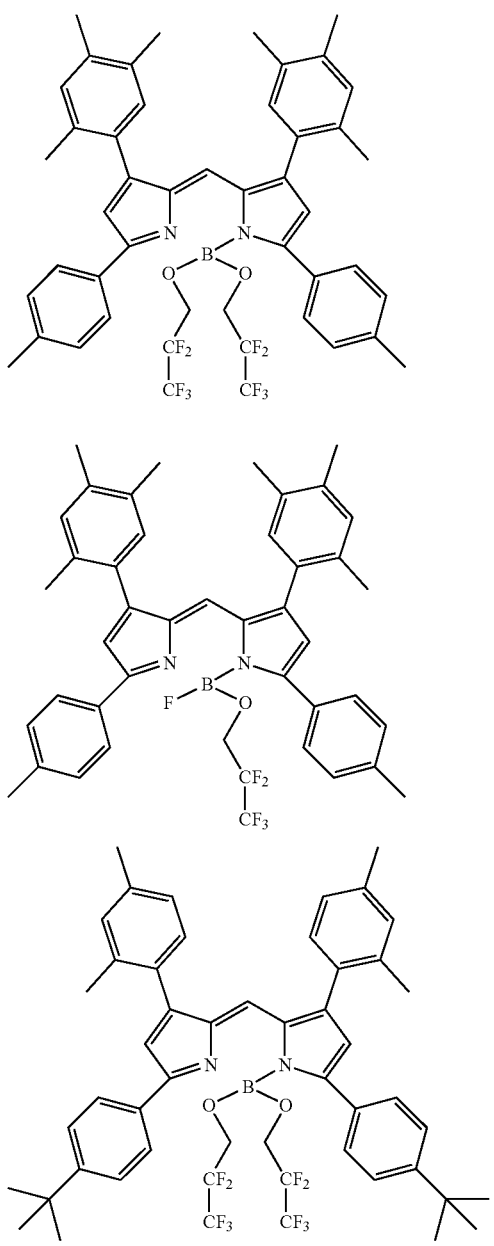
[Formula 83]
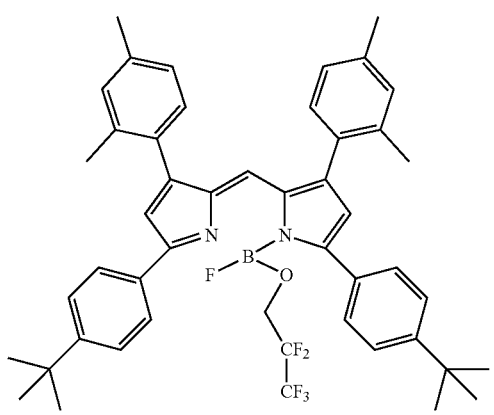
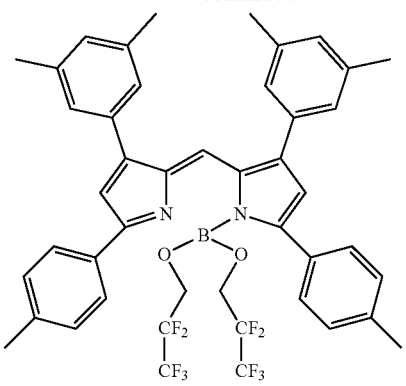
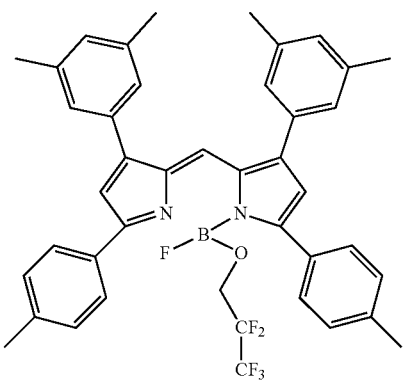
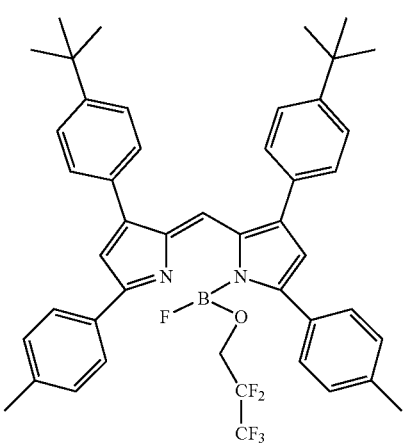
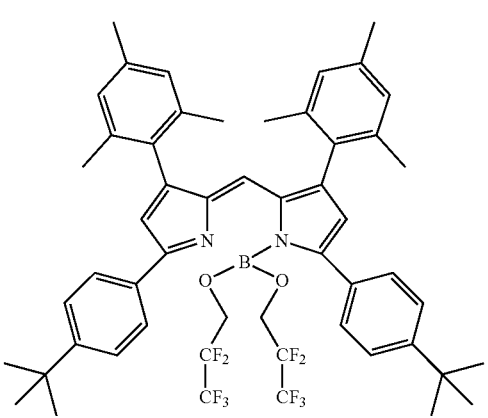

-continued
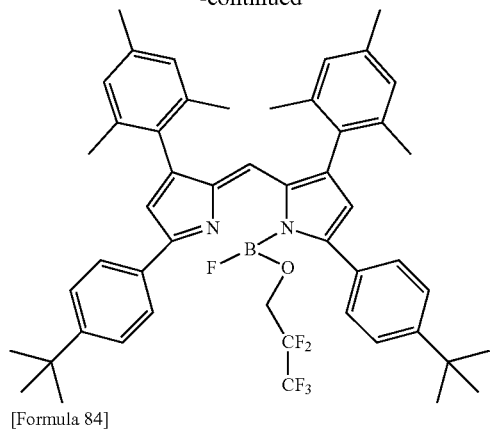
[Formula 84]
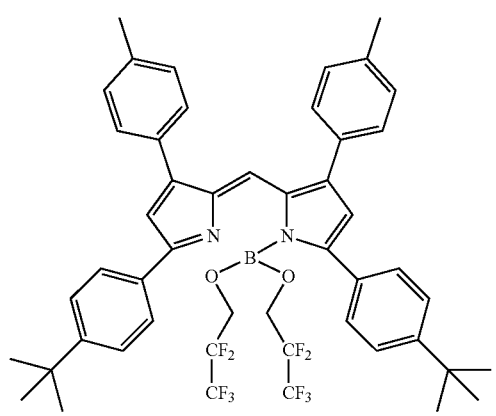
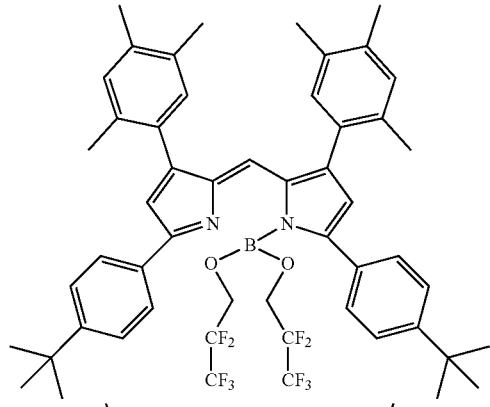
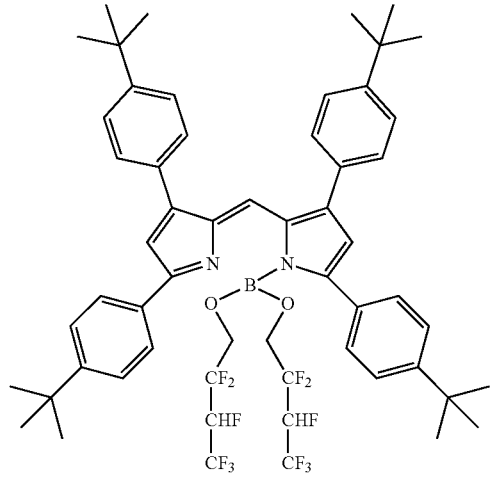
-continued
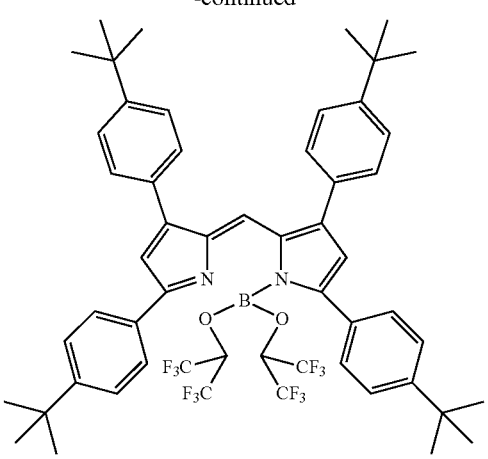
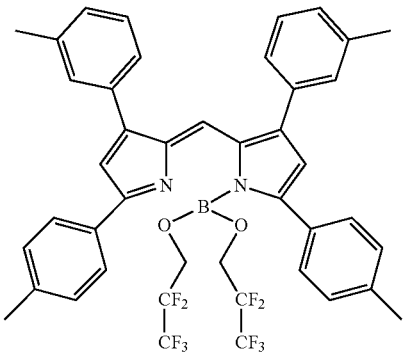
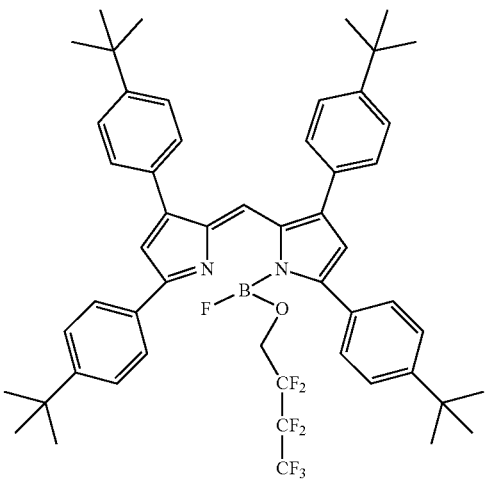

151
[Formula 85]
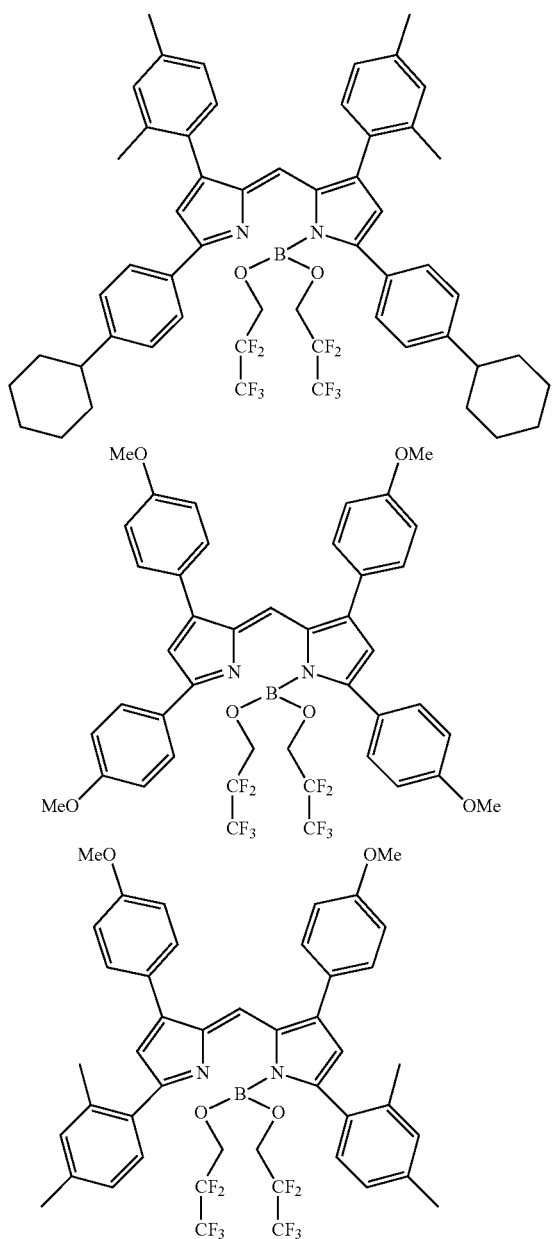
[Formula 86]
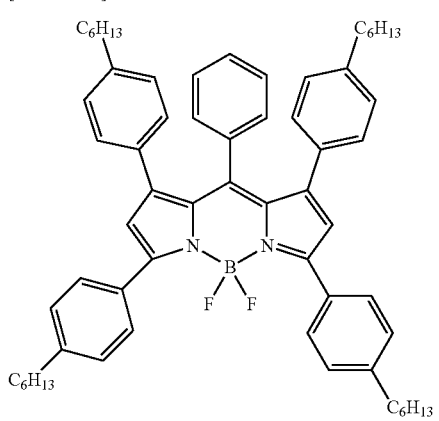
152
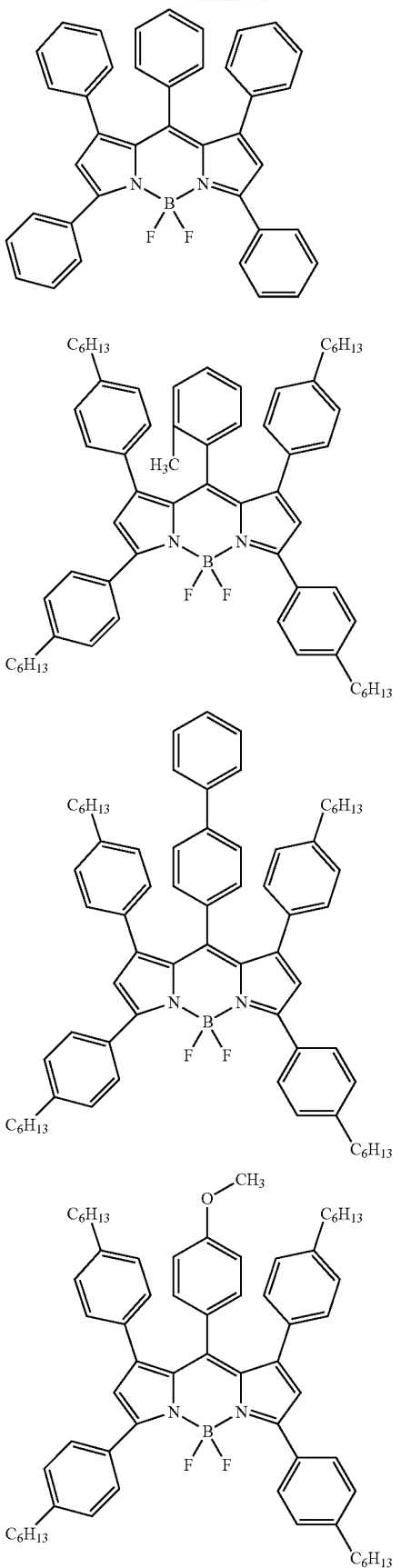

153
-continued
154
-continued
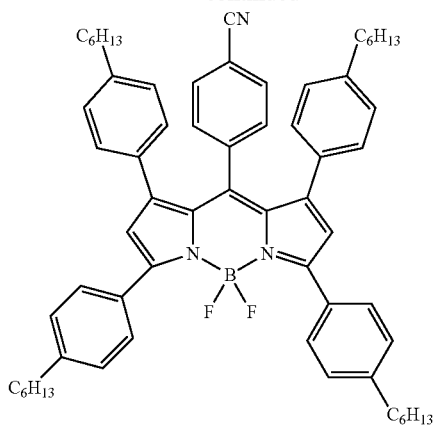
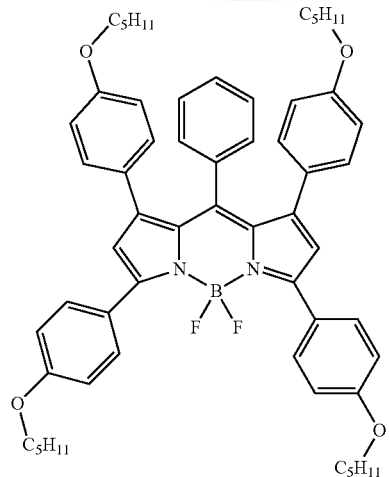
[Formula 87]
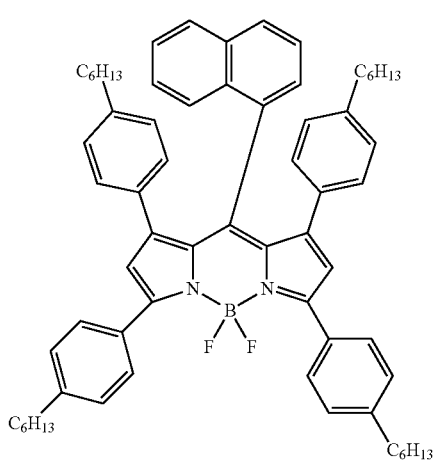
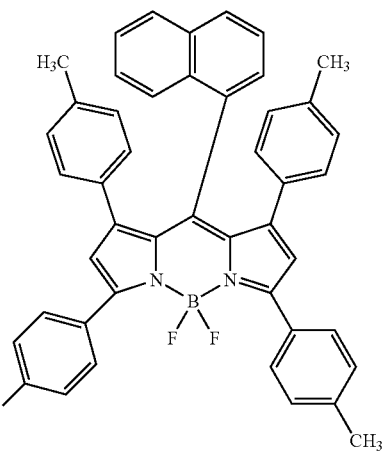
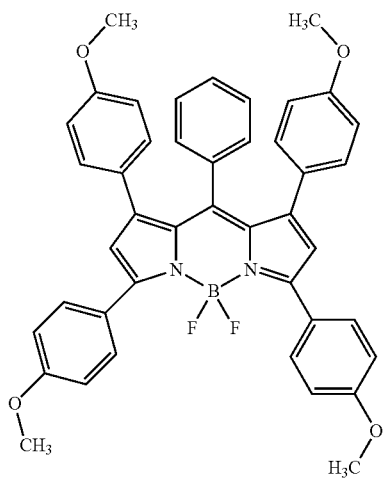
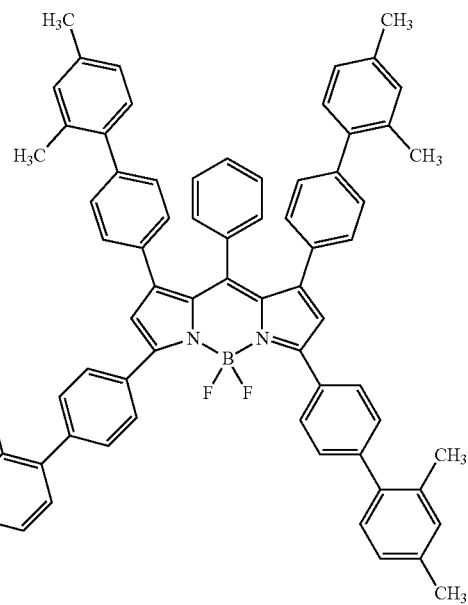

155
-continued
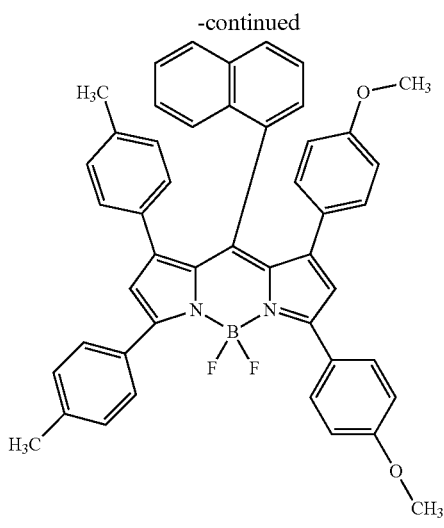
[Formula 88]
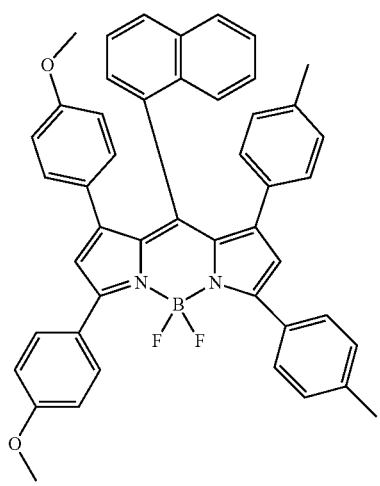
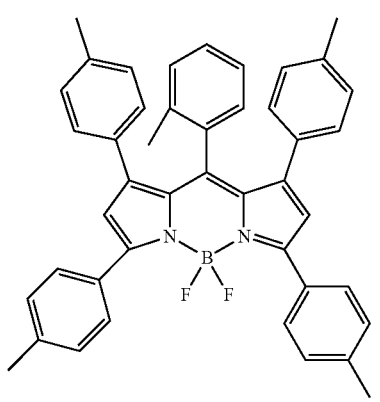
156
-continued
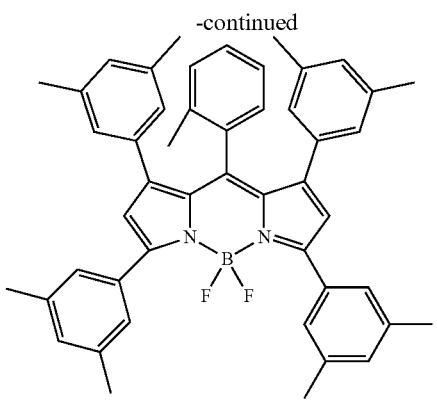
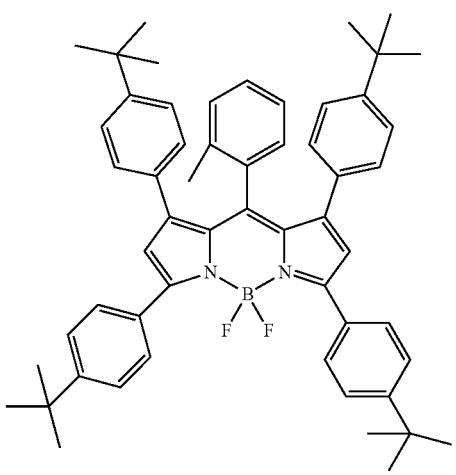
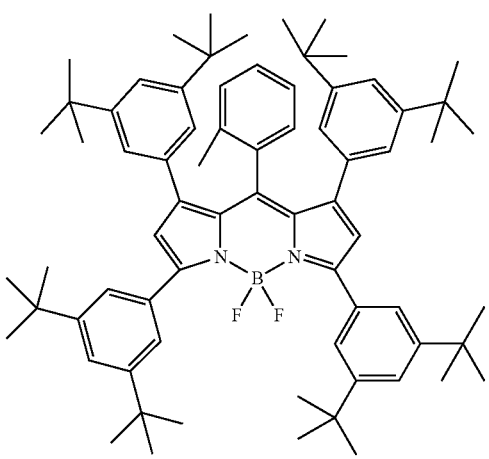

157
-continued
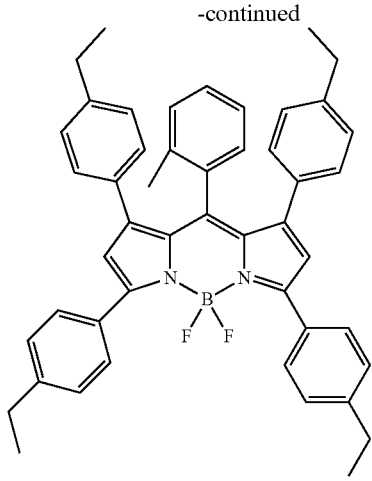
[Formula 89]
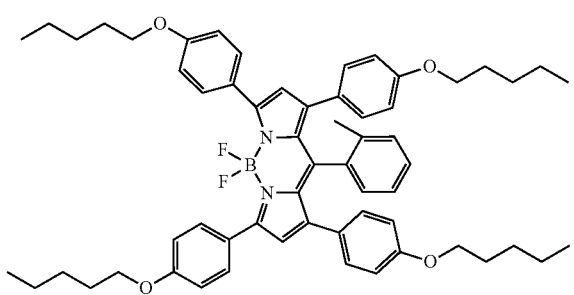
[Formula 90]
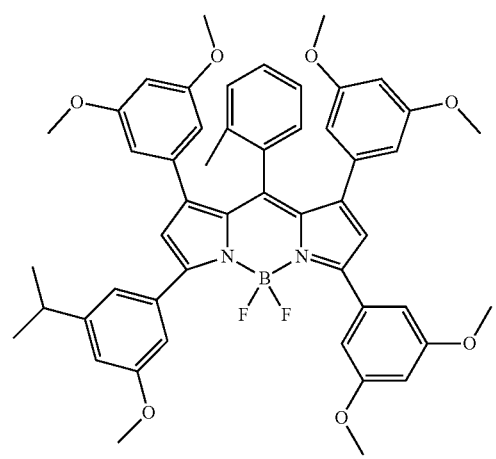
158
-continued
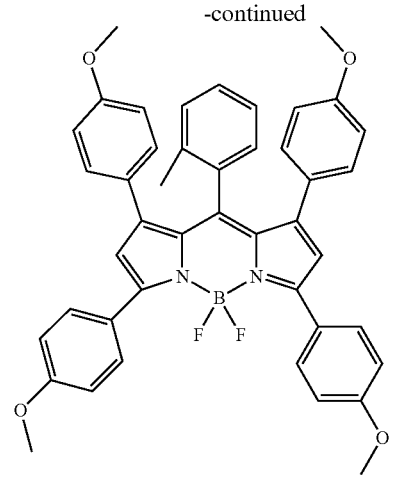
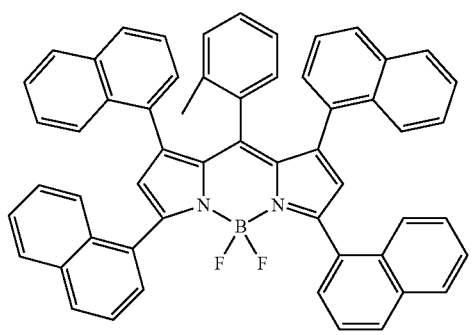
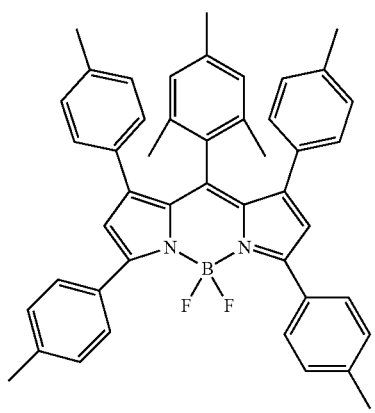
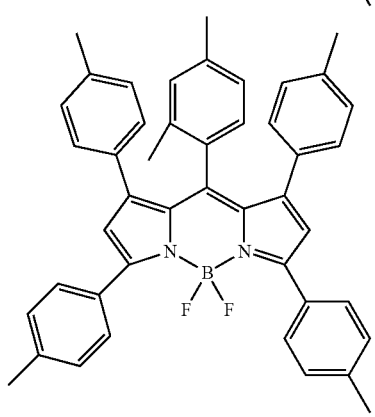

159
-continued
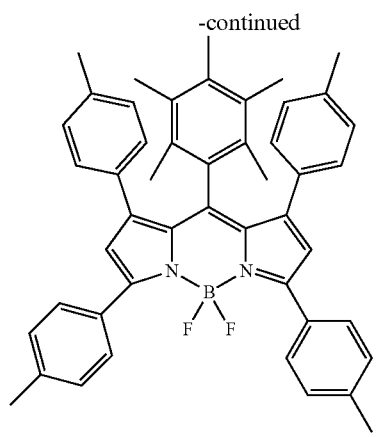
[Formula 91]
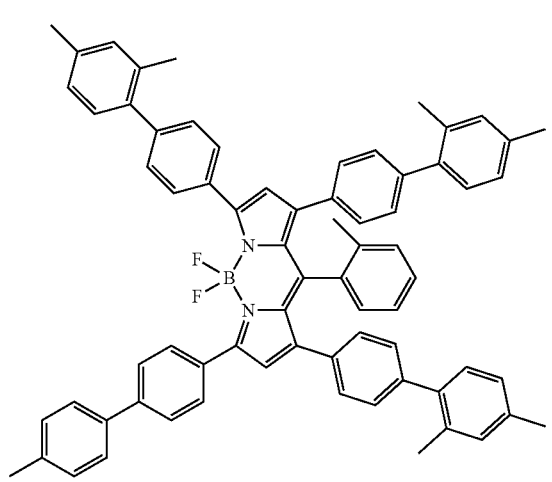
[Formula 92]
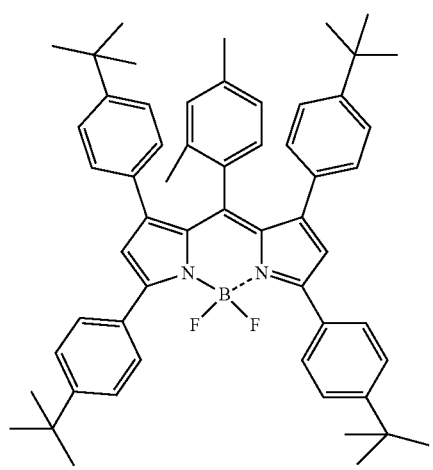
160
-continued
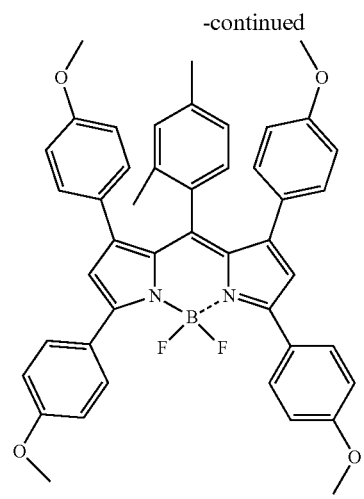
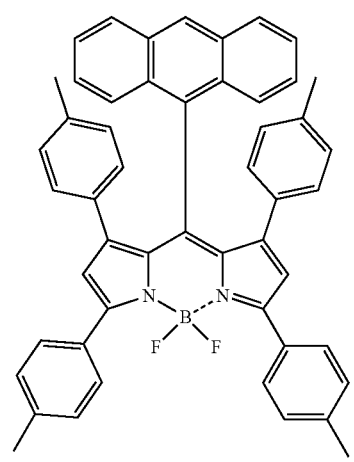
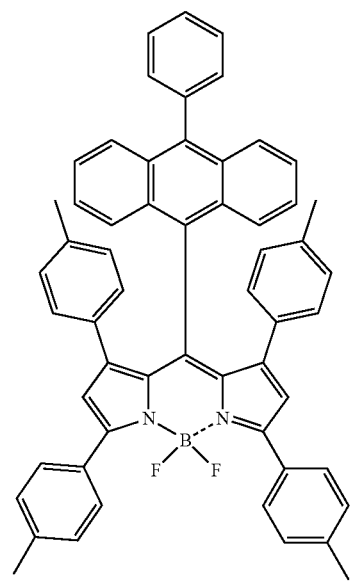

161
-continued
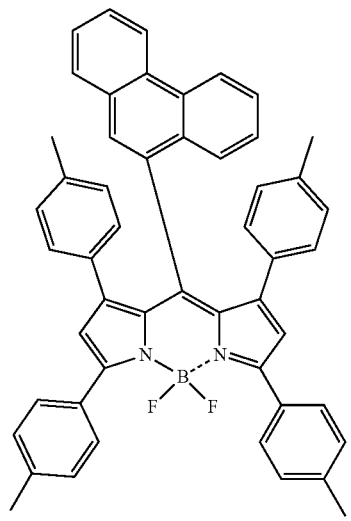
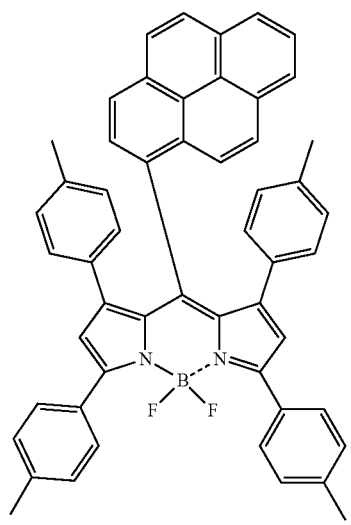
[Formula 93]
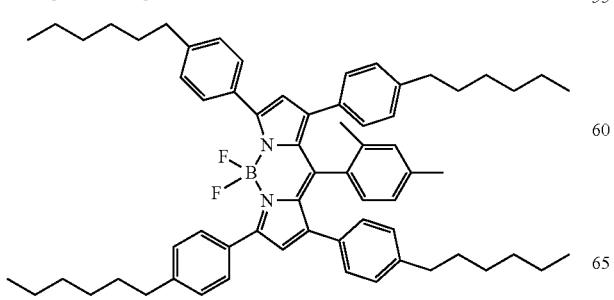
162
-continued
[Formula 94]
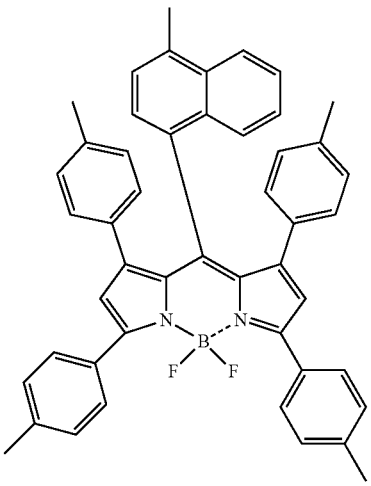
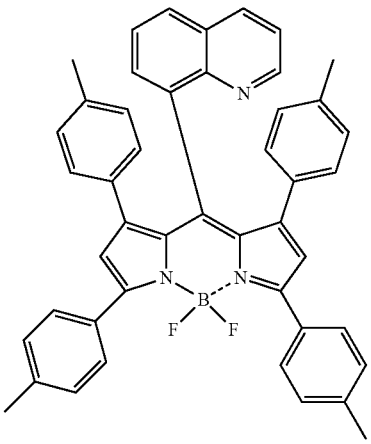
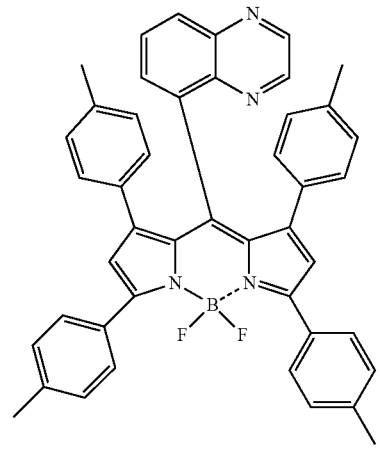

163
-continued
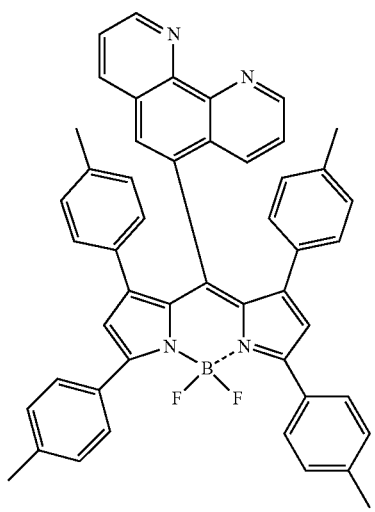
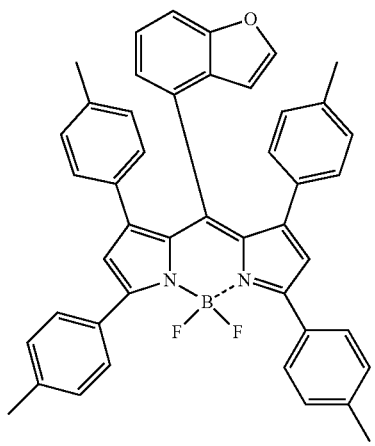
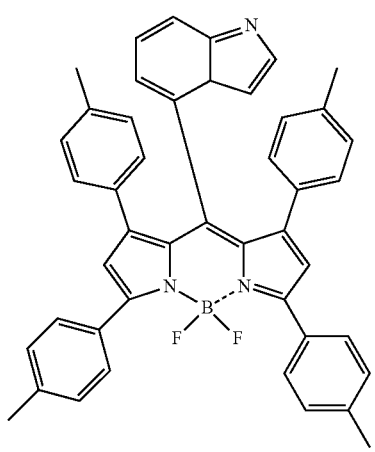
164
-continued
[Formula 95]
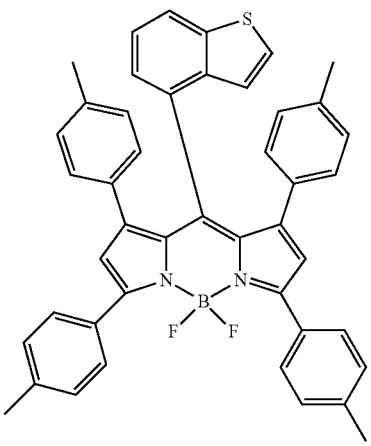
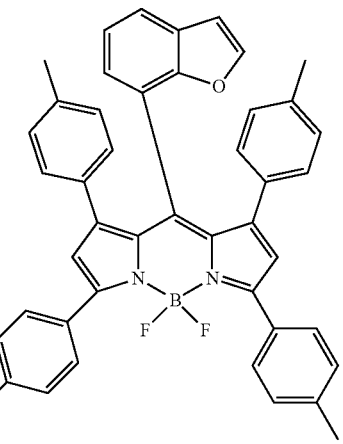
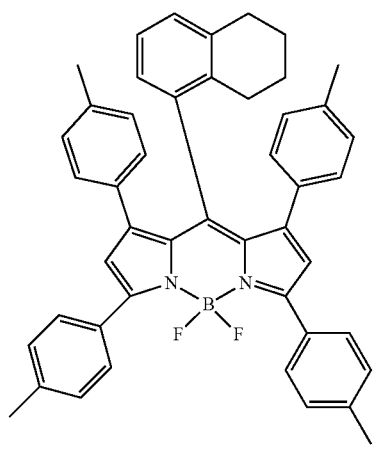

165
-continued
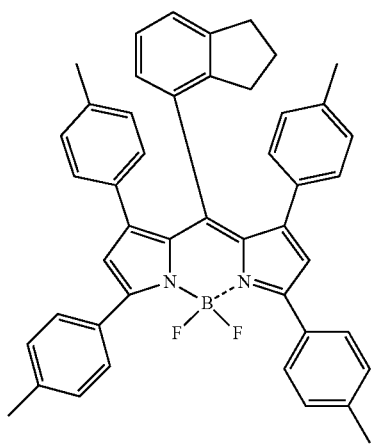
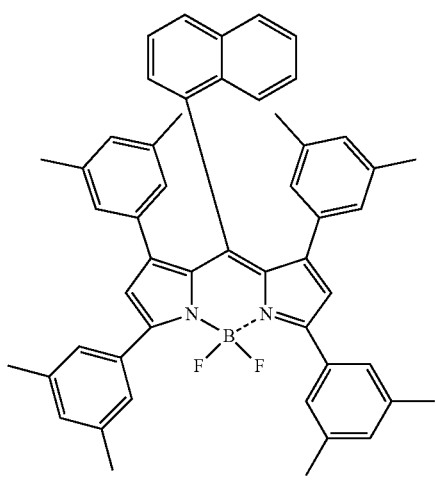
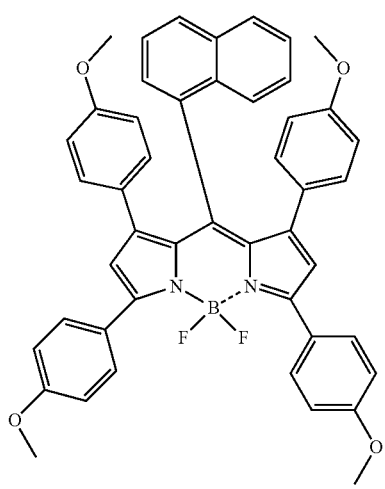
166
-continued
[Formula 96]
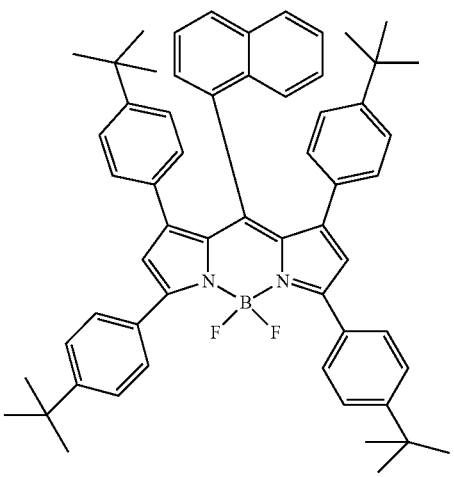
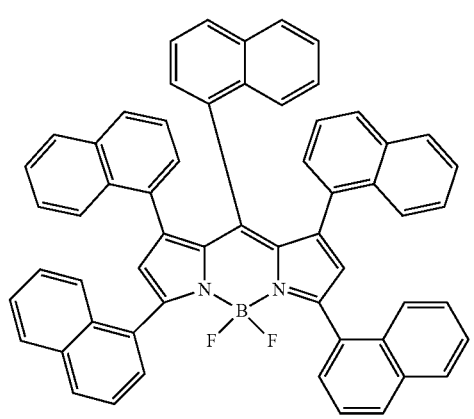
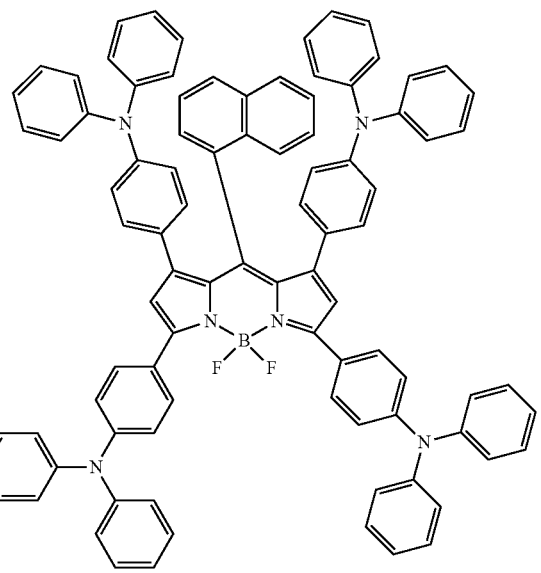

167
-continued
[Formula 97]
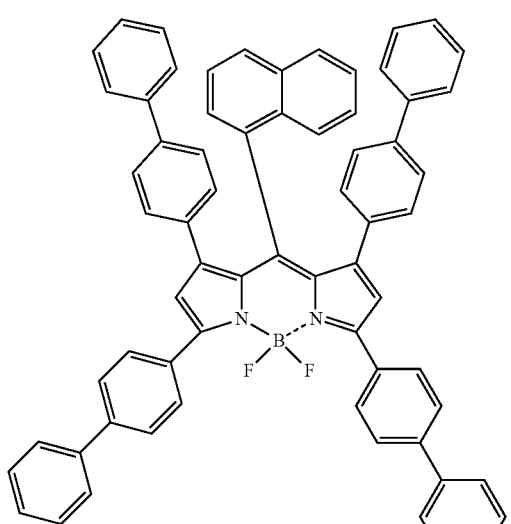
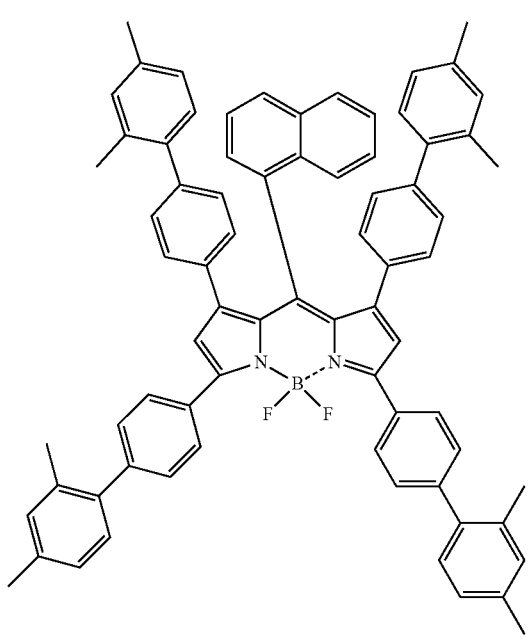
168
-continued
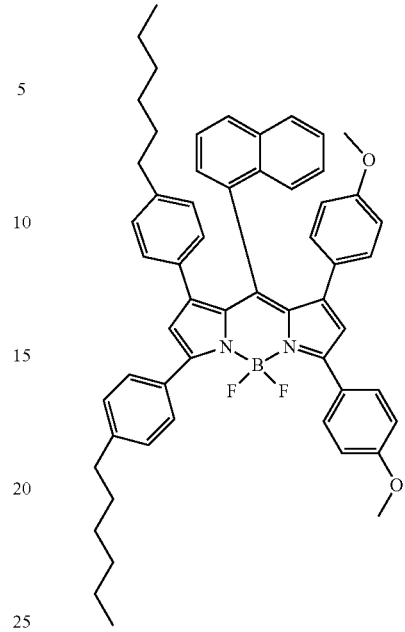
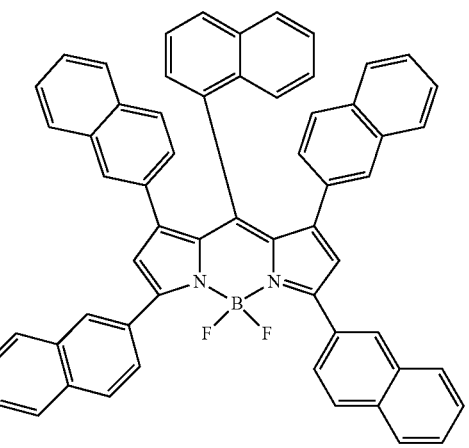
[Formula 98]
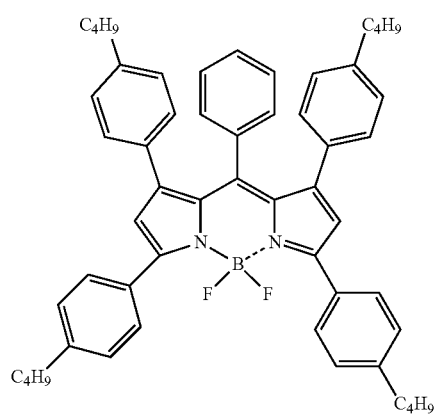

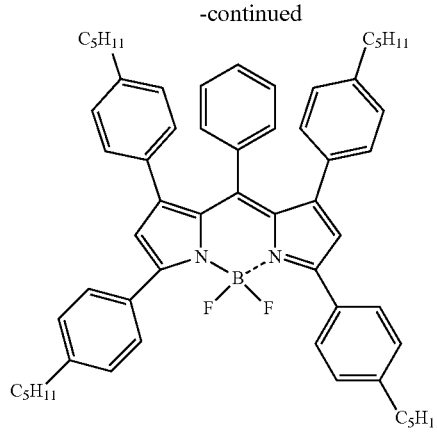
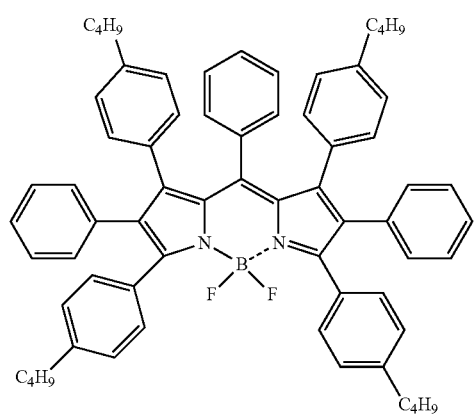
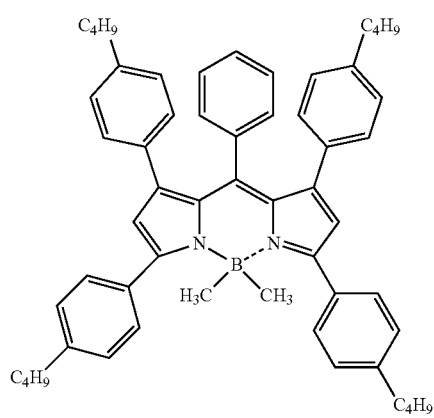
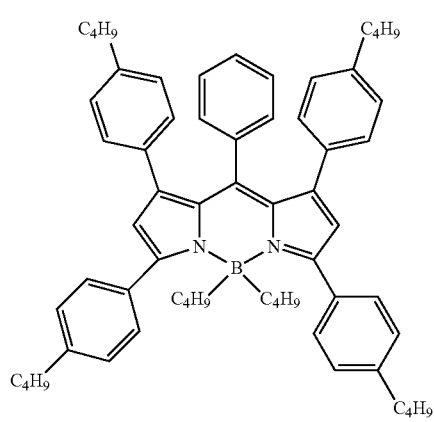
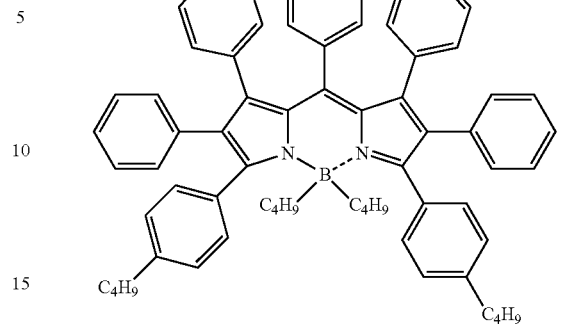
[Formula 99]
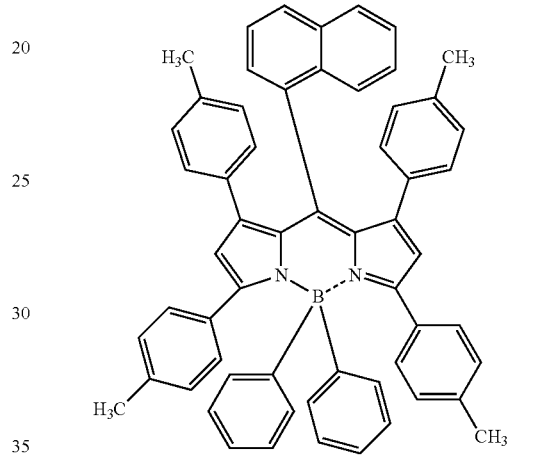

171
-continued
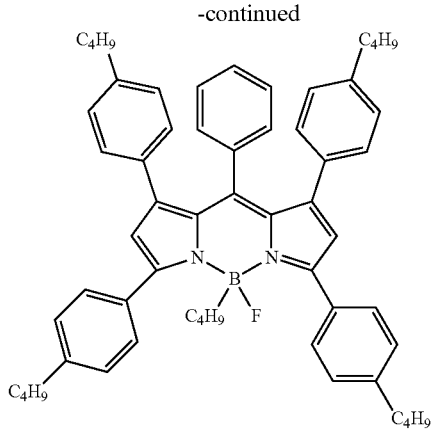
[Formula 100]
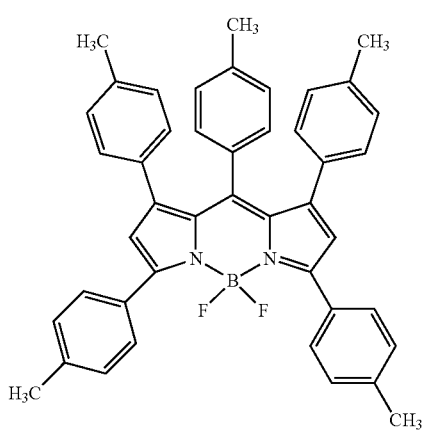
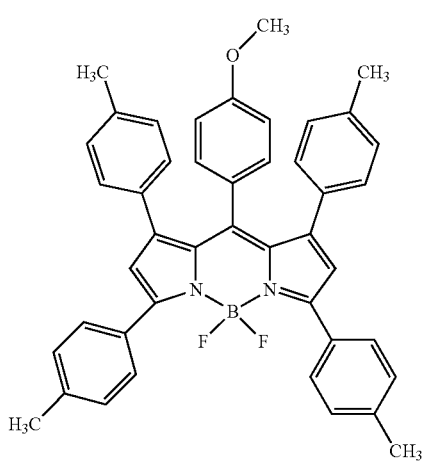
172
-continued
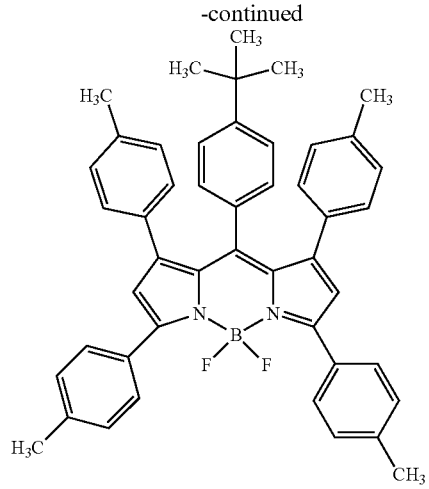
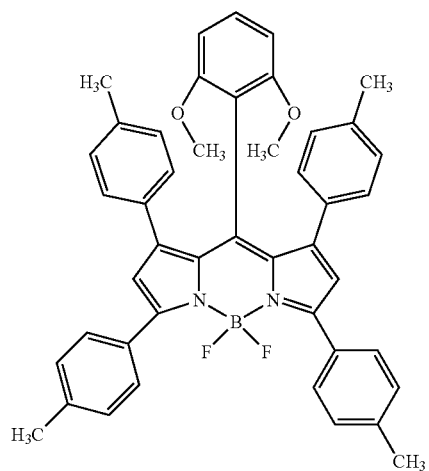
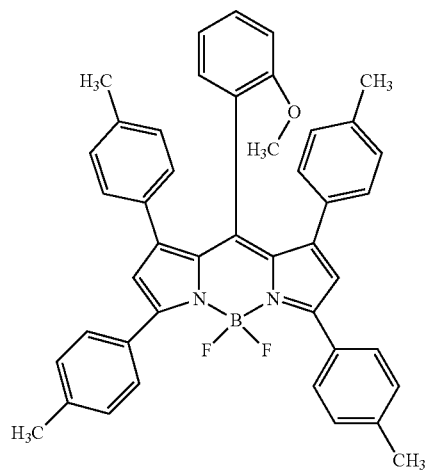

173
-continued
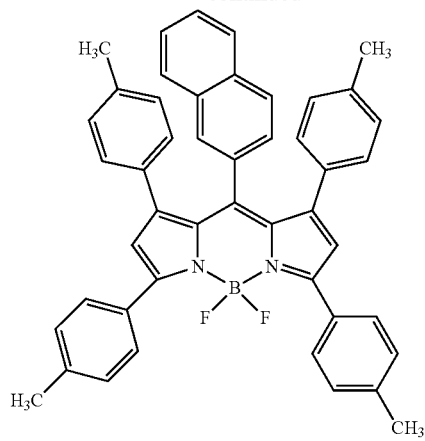
[Formula 101]
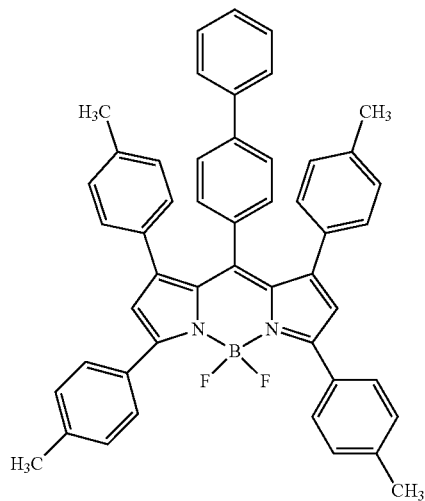
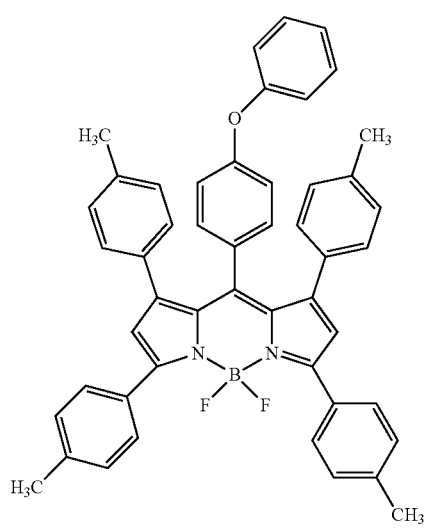
174
-continued
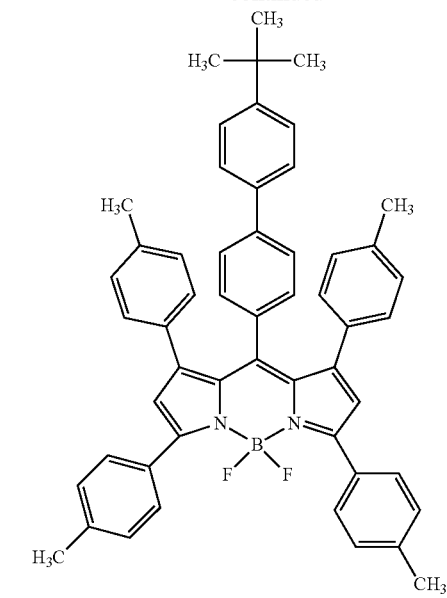
[Formula 102]
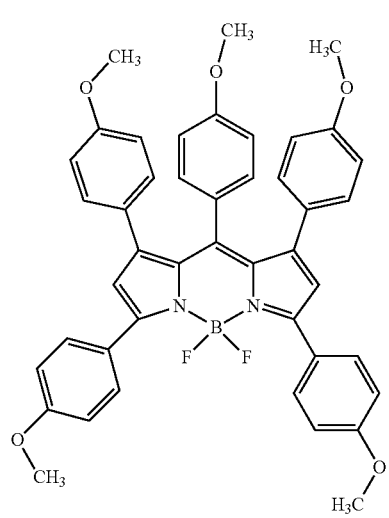

175
-continued
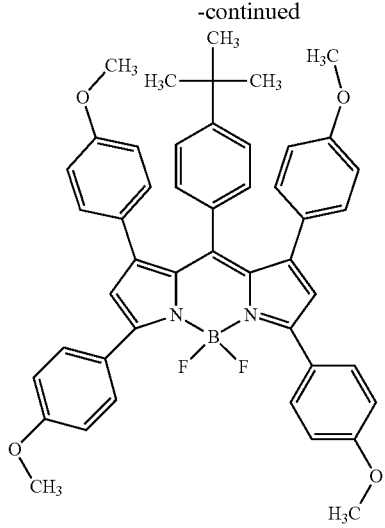
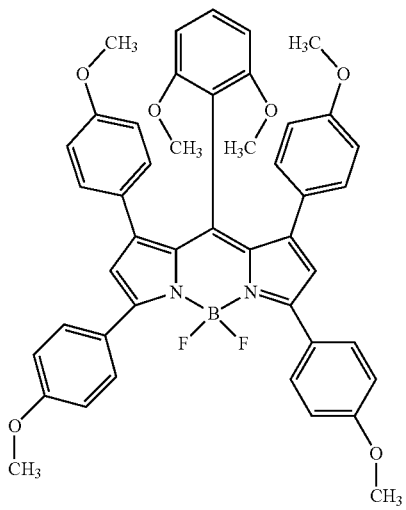
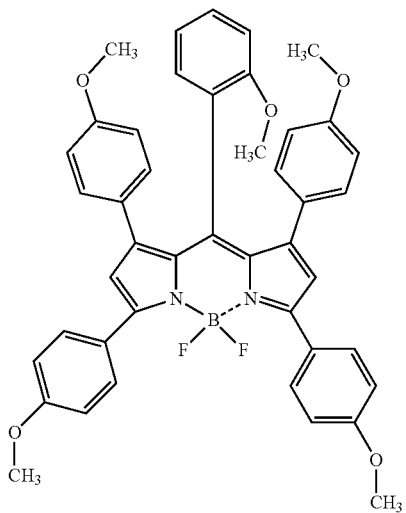
176
-continued
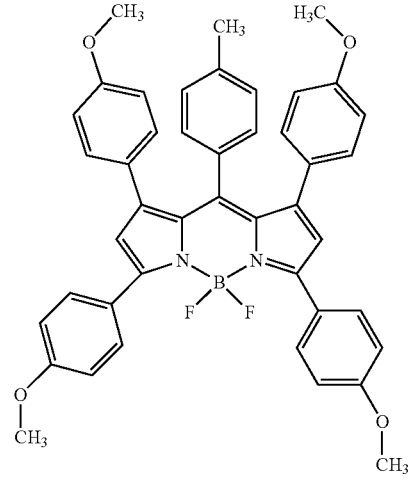
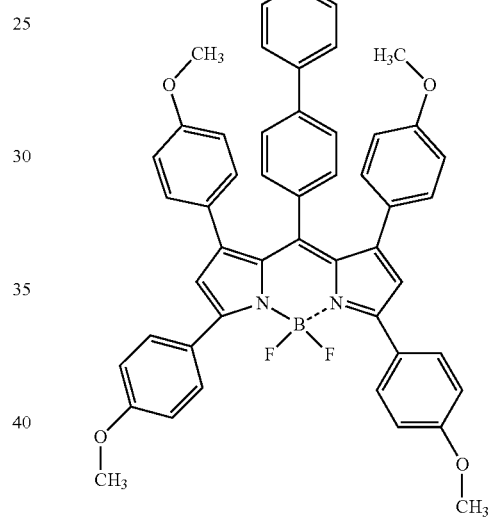
[Formula 103]
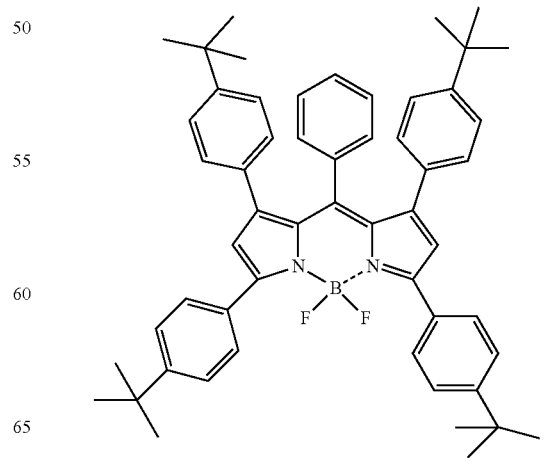

177
-continued
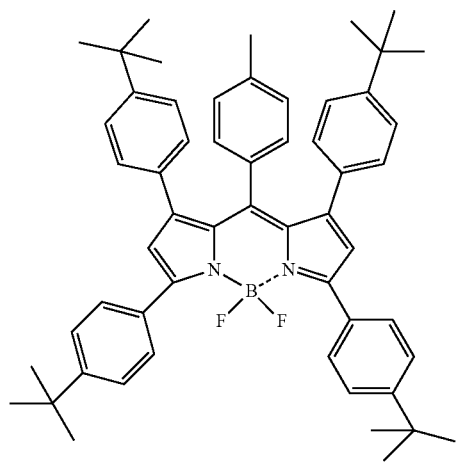
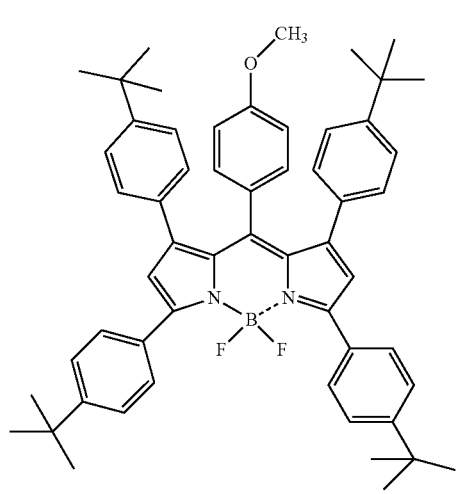
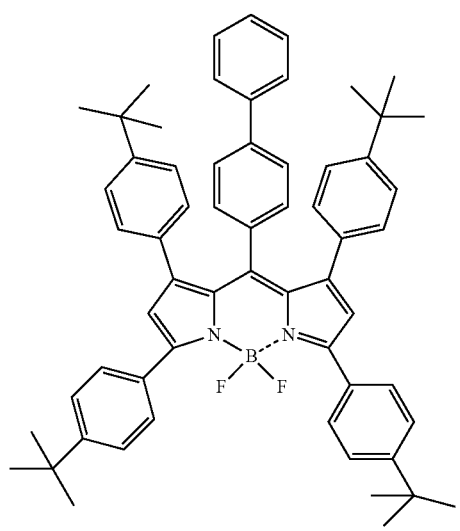
178
-continued
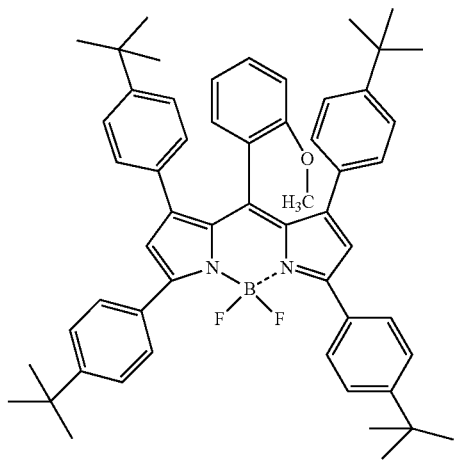
[Formula 104]
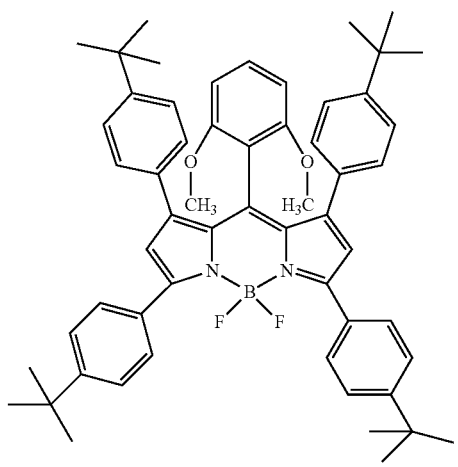
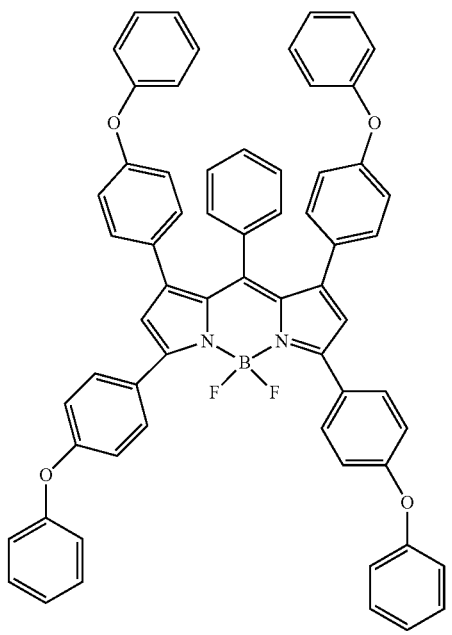

179
-continued
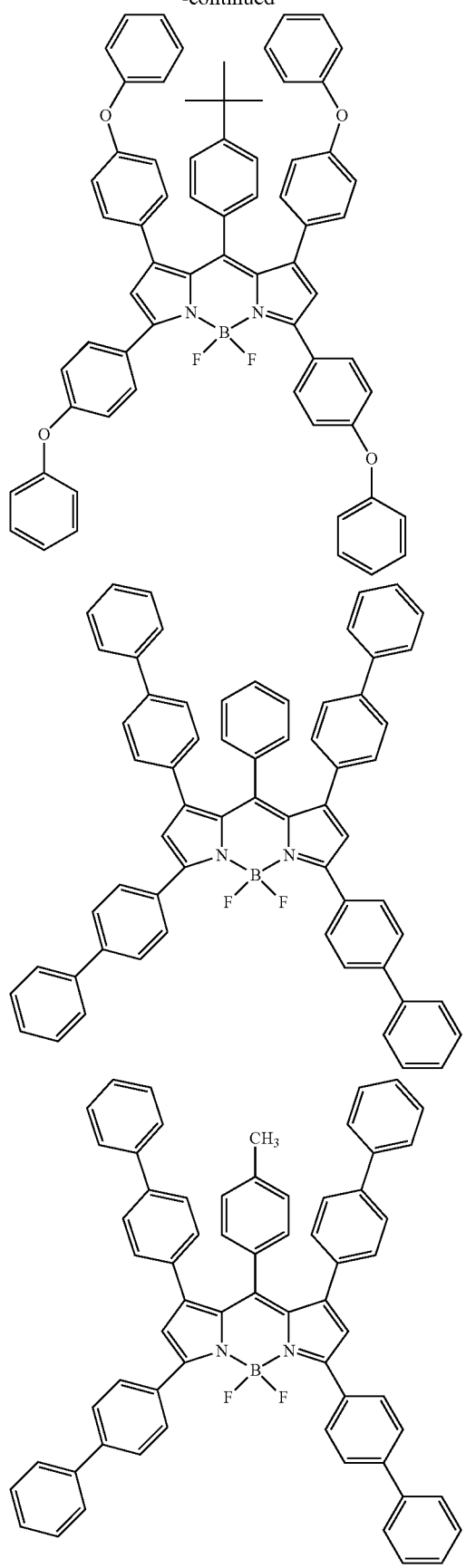
180
-continued
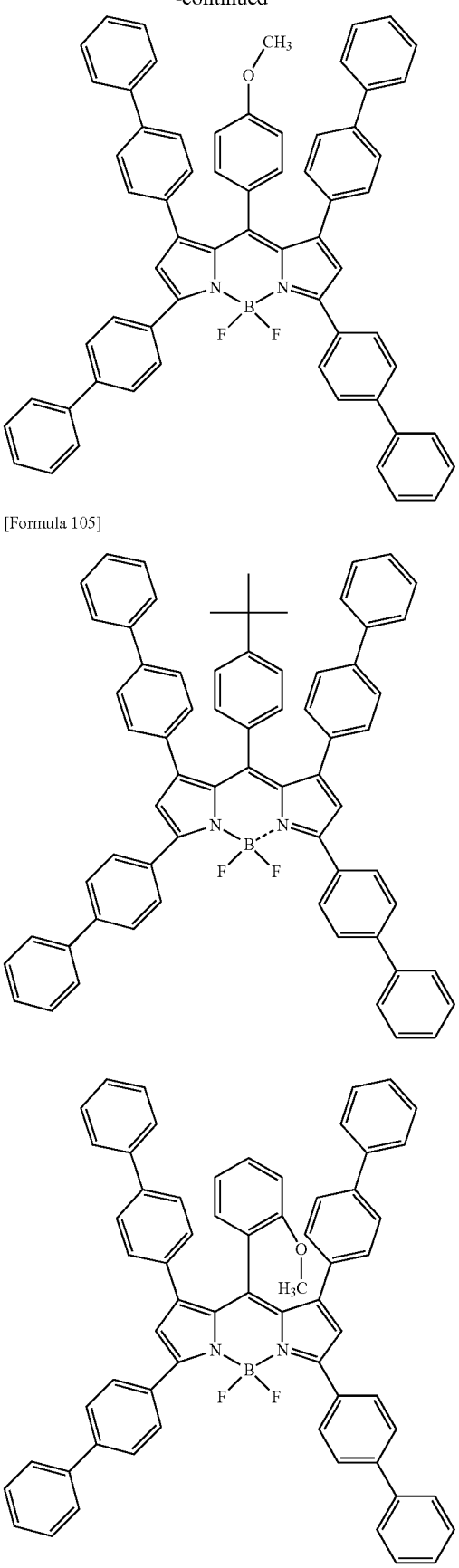
[Formula 105]

-continued
[Formula 106]
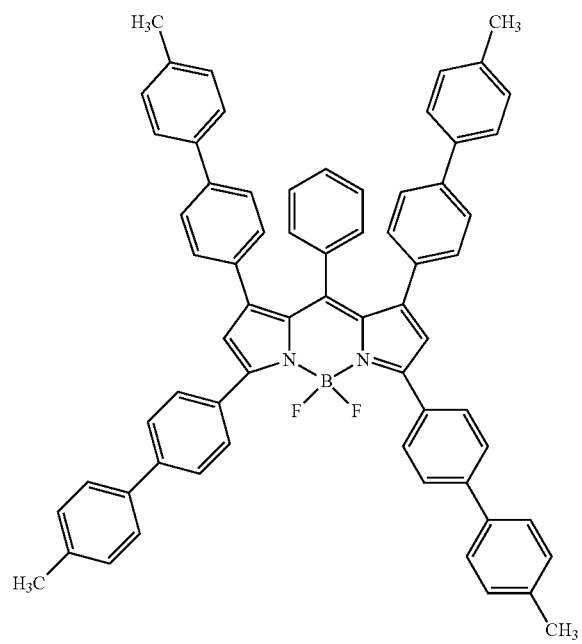
[Formula 107]
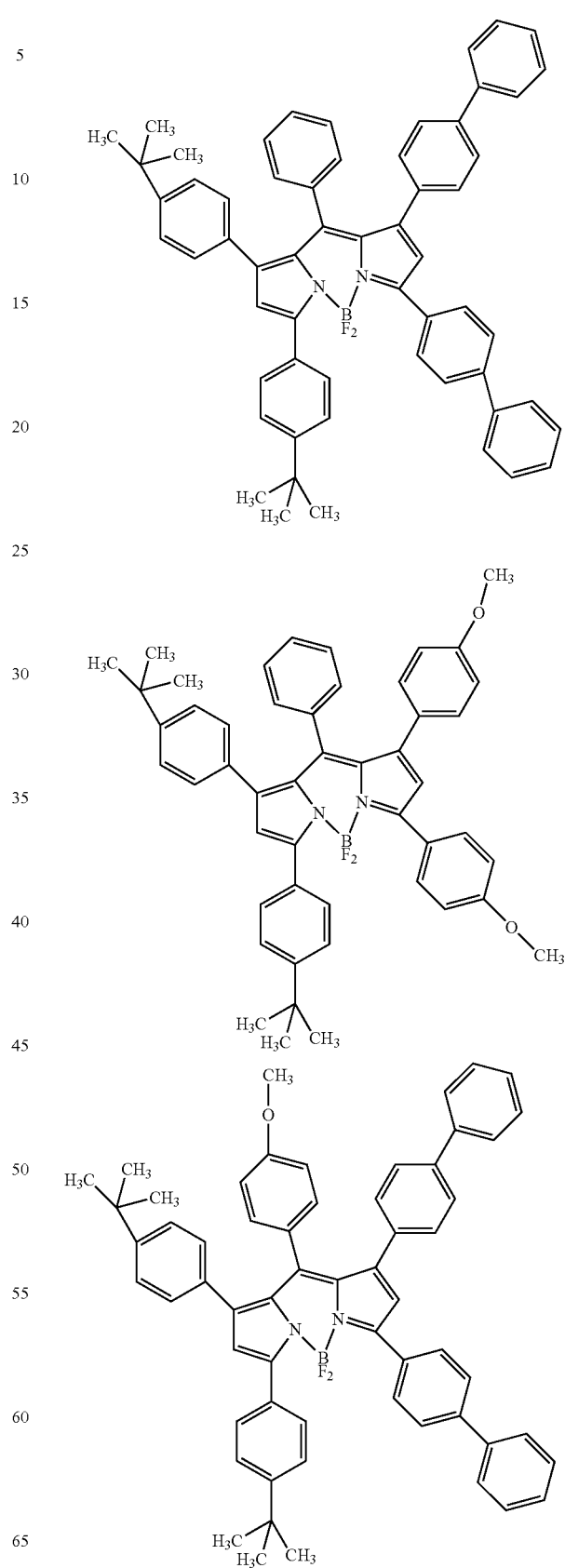
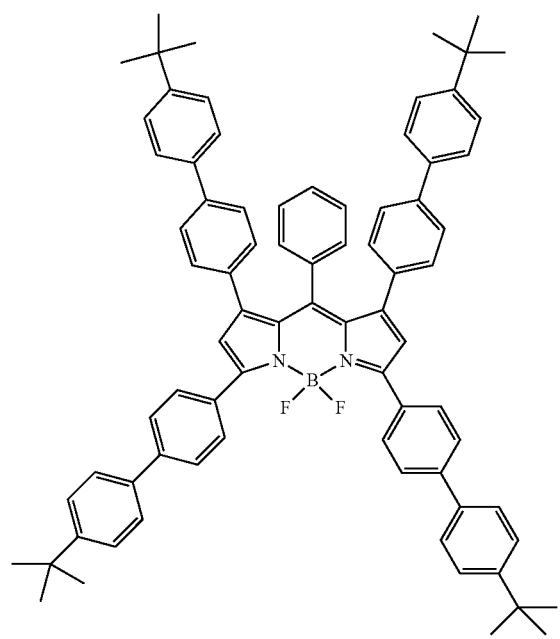

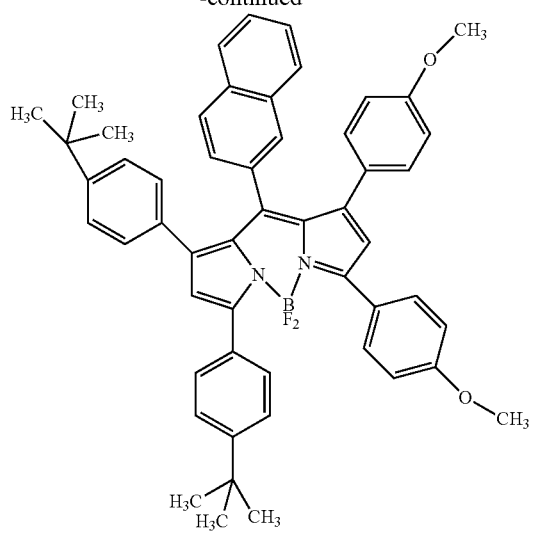
[Formula 108]
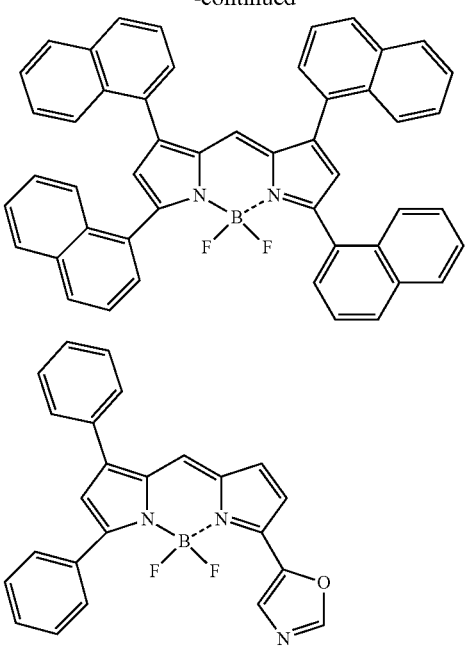
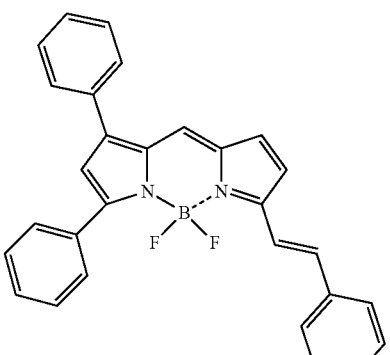
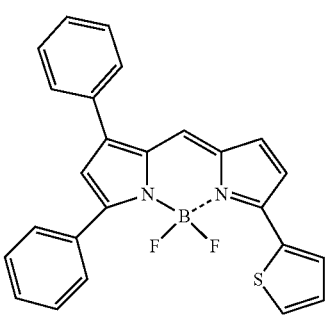
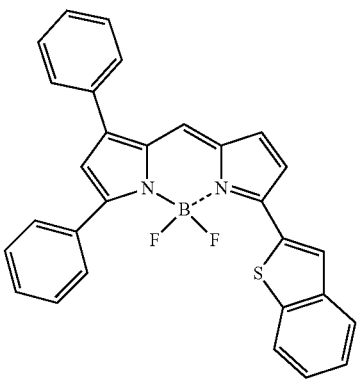

185
-continued
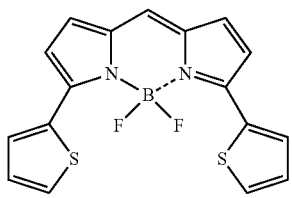
[Formula 109]
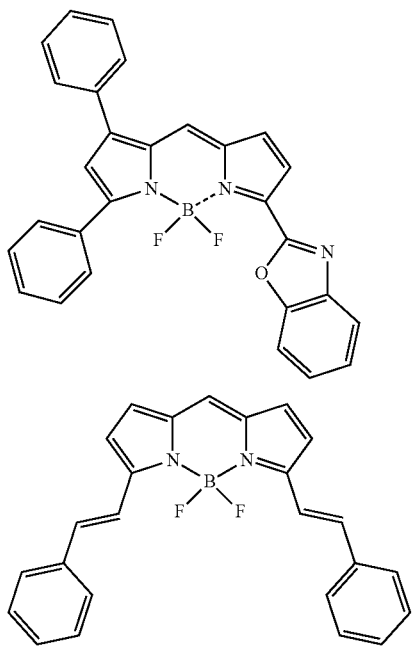
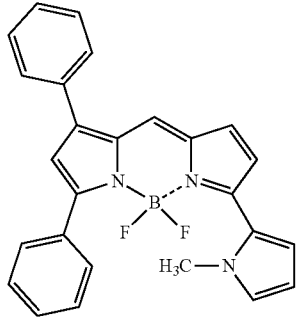
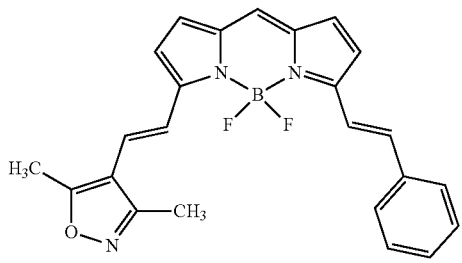
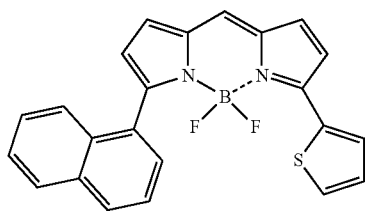
186
-continued
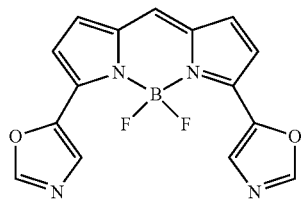
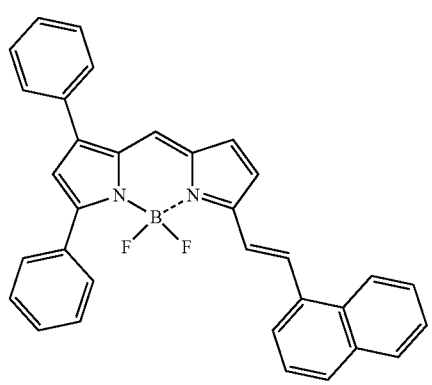
[Formula 110]
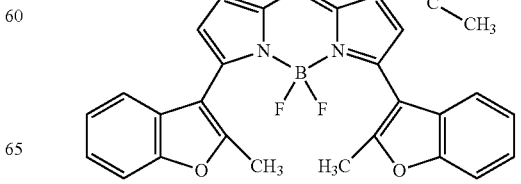

-continued
[Formula 112]
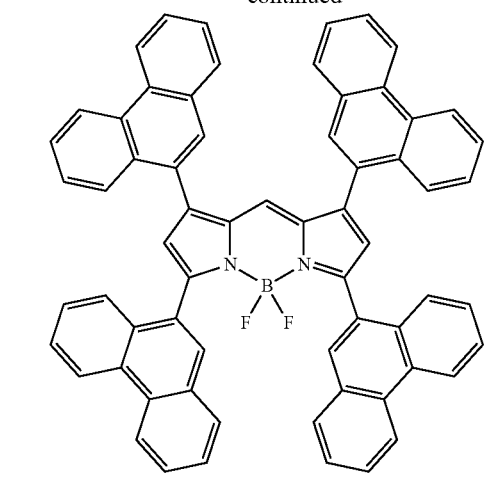
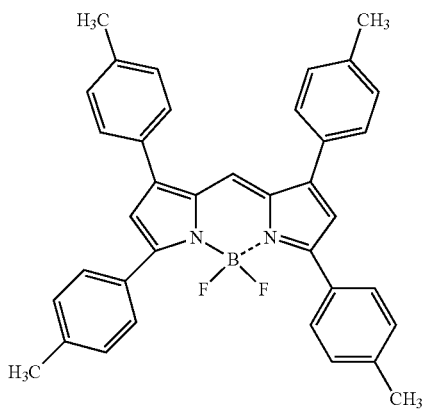
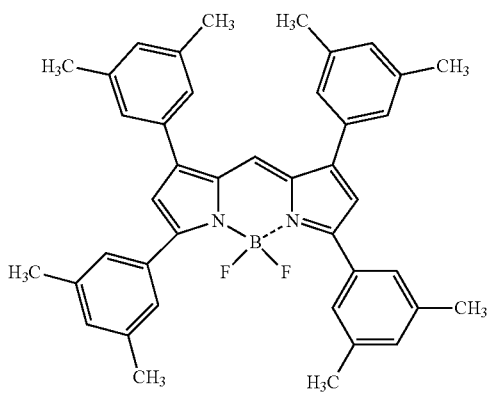
[Formula 111]
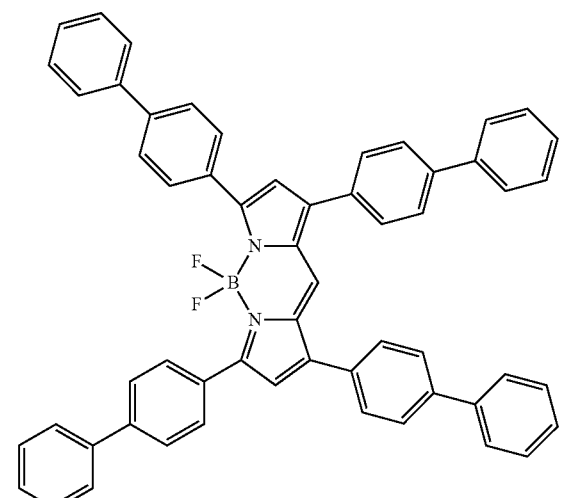
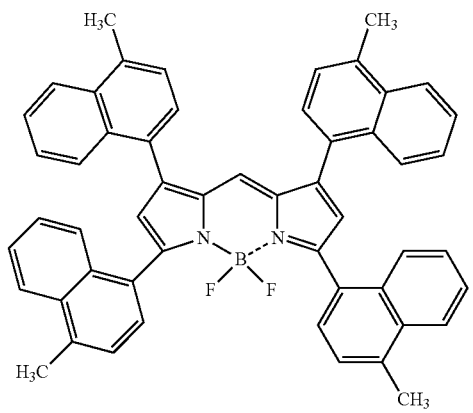
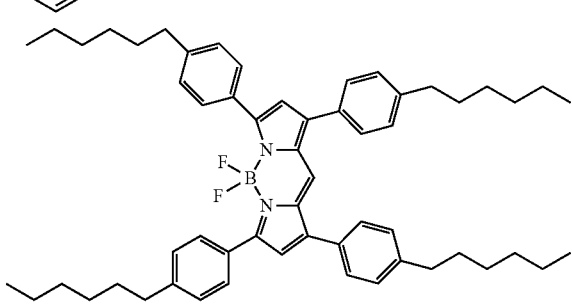
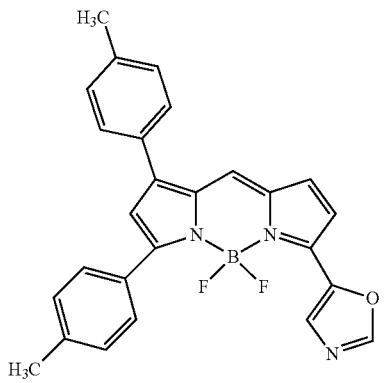

189
-continued
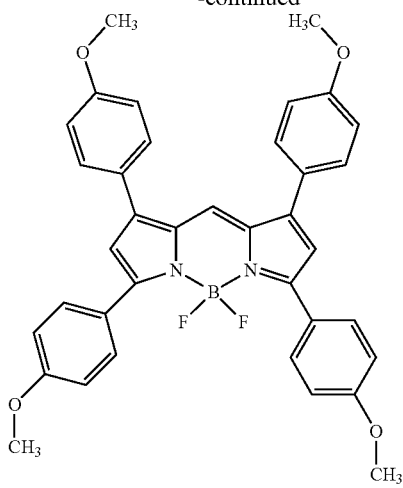
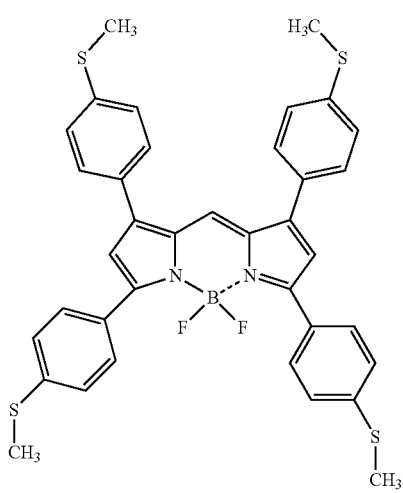
[Formula 113]
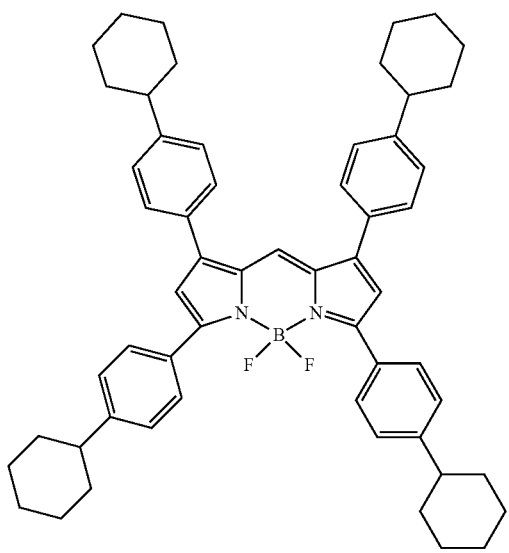
190
-continued
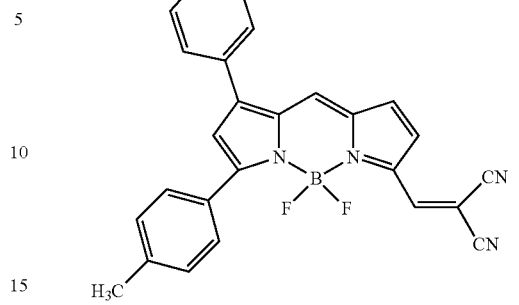
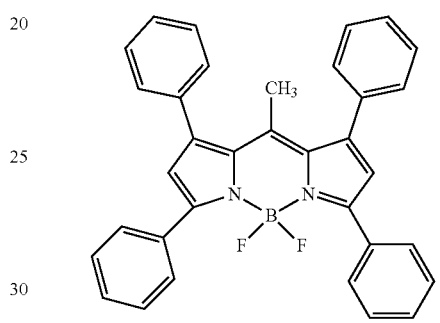
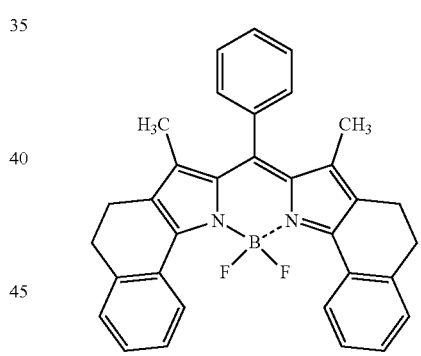
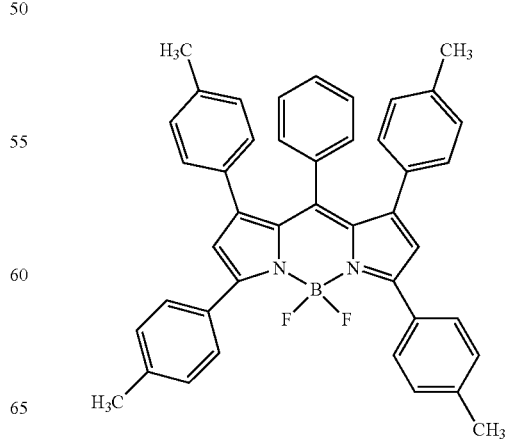

191
-continued
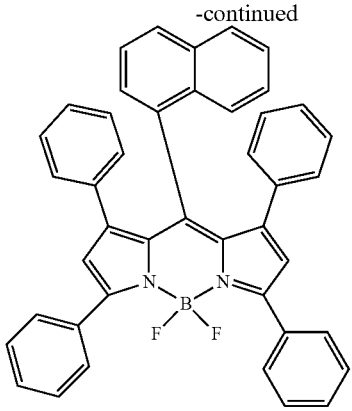
[Formula 114]
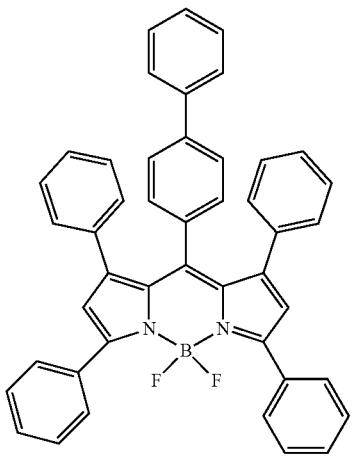
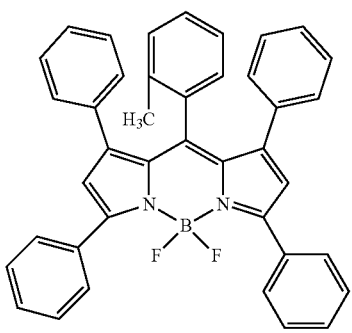
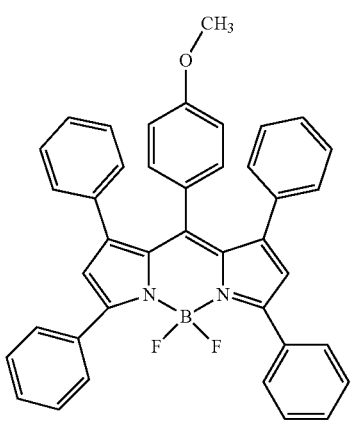
192
-continued
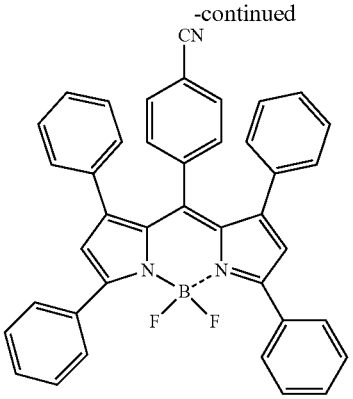
[Formula 115]
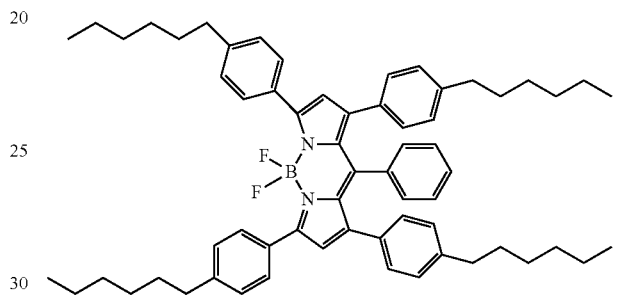
[Formula 116]
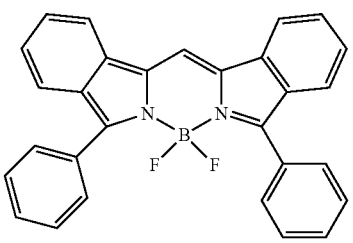
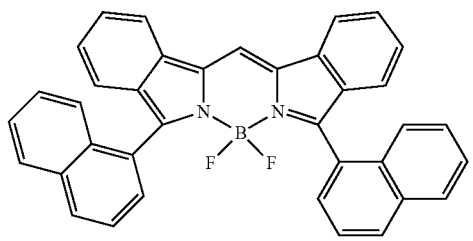

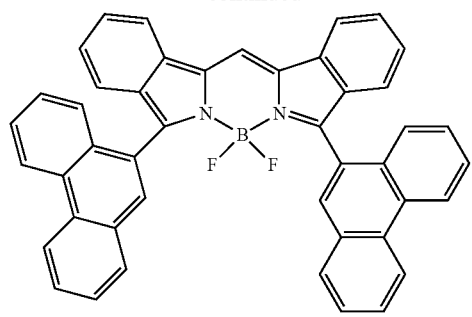
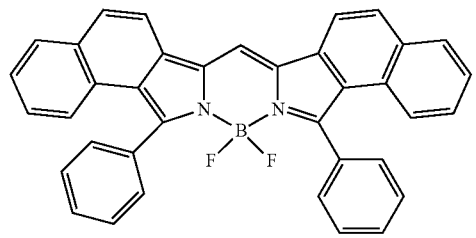
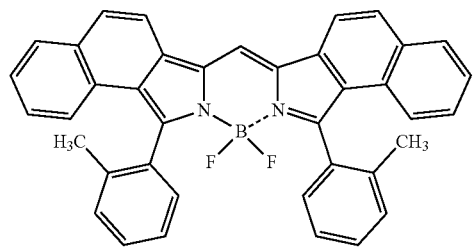
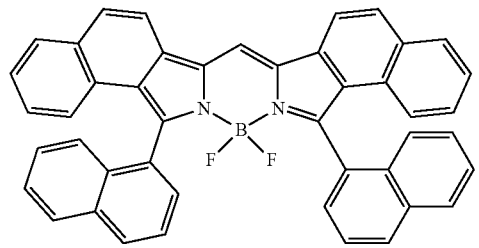
[Formula 117]
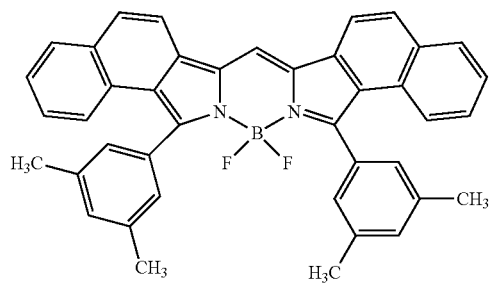
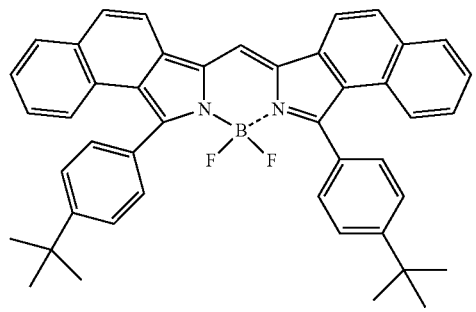
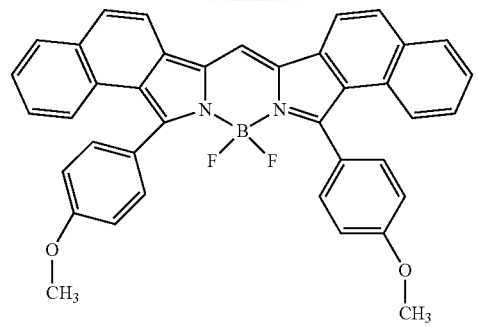
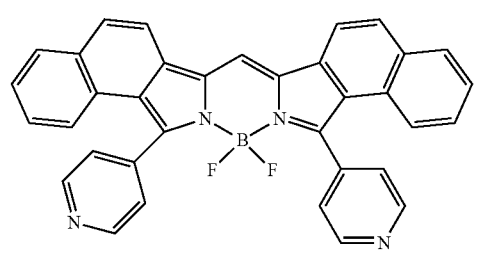
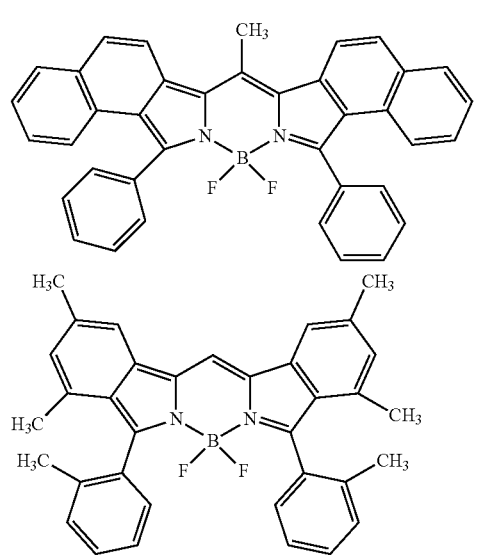
[Formula 118]
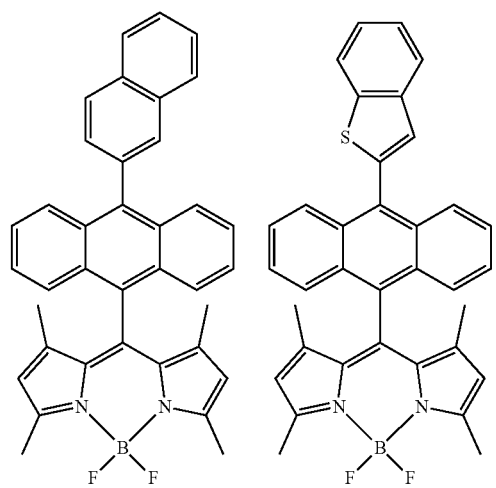

195
-continued
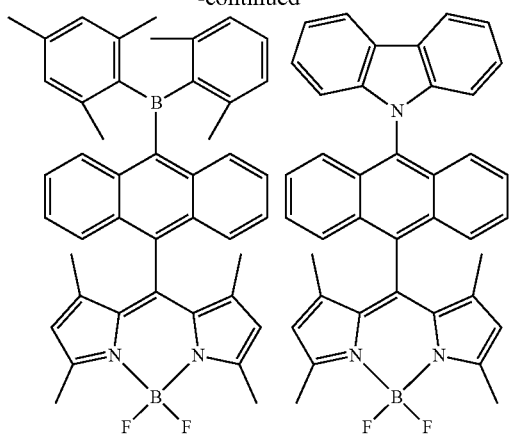
[Formula 119]
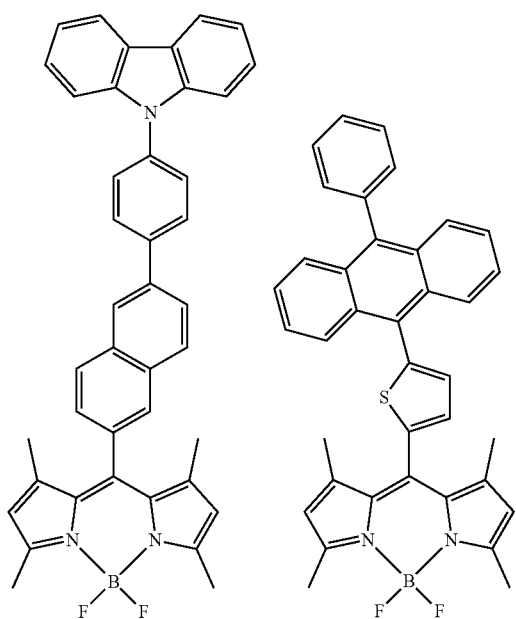
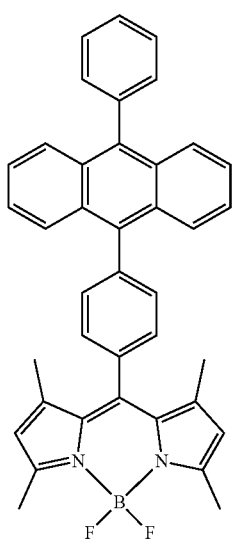
196
-continued
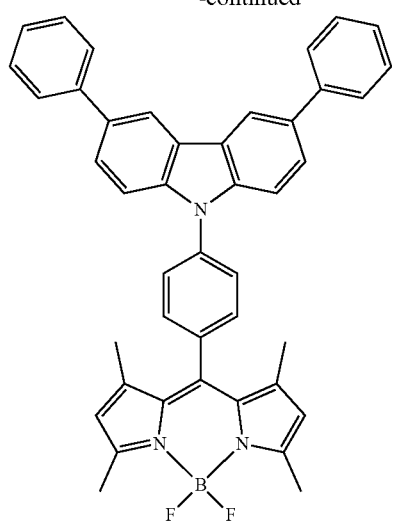
[Formula 120]
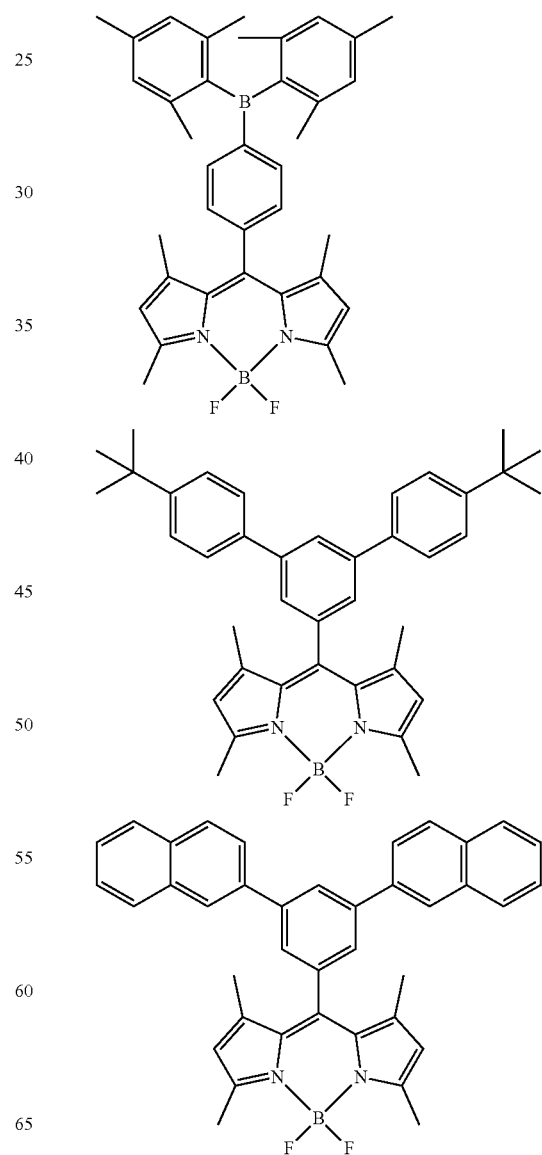

[Formula 121]
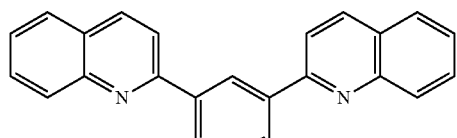
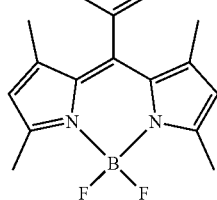
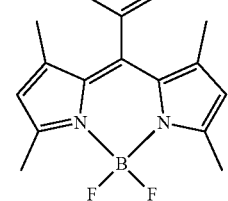
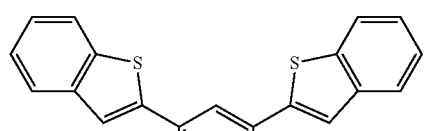
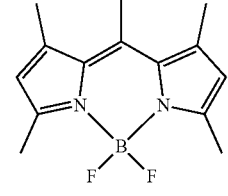
[Formula 122]
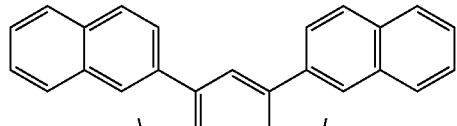
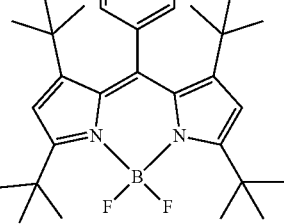
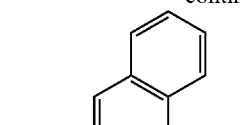
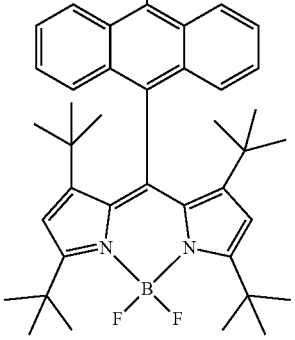
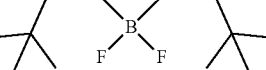
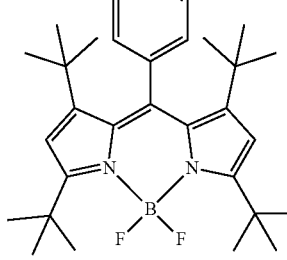
[Formula 123]
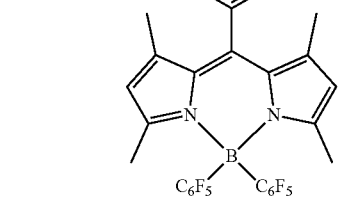

199
-continued
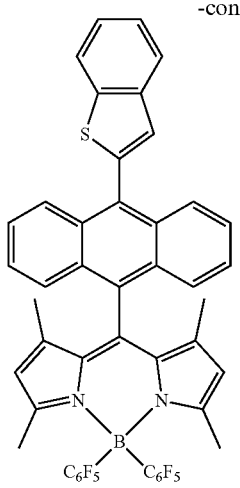
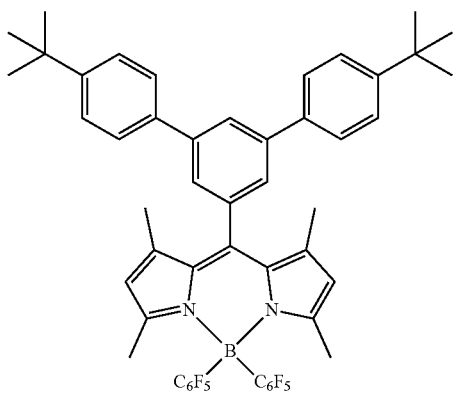
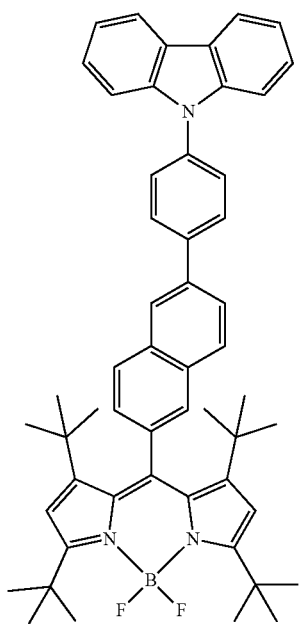
200
-continued
[Formula 124]
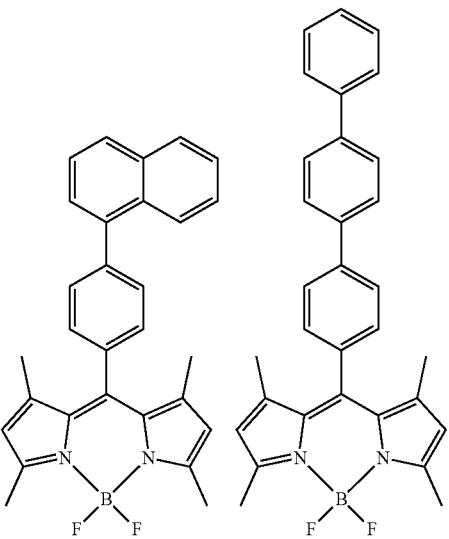
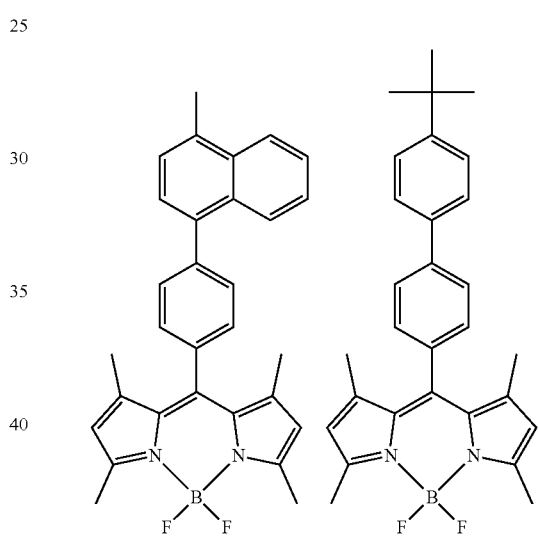
[Formula 125]
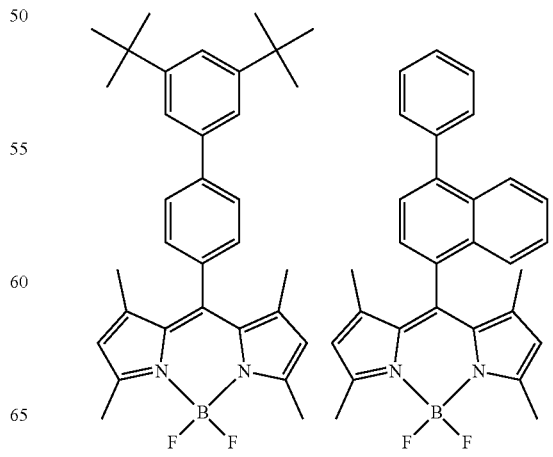

201
-continued
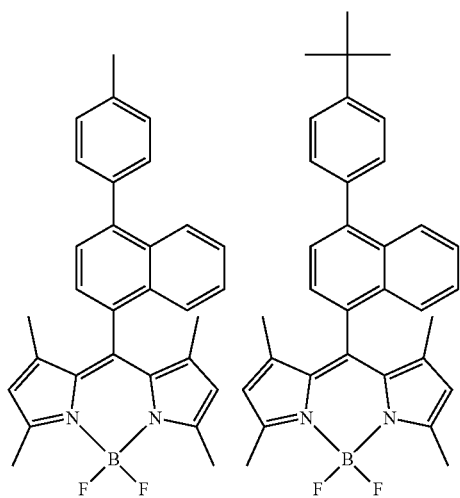
[Formula 126]
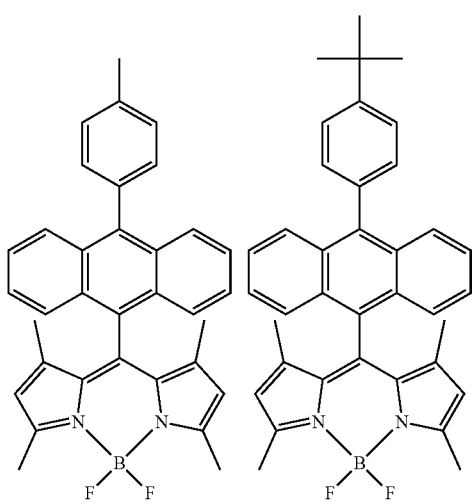
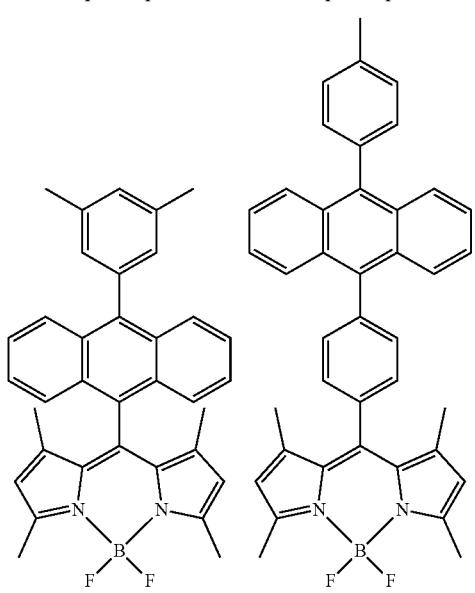
202
-continued
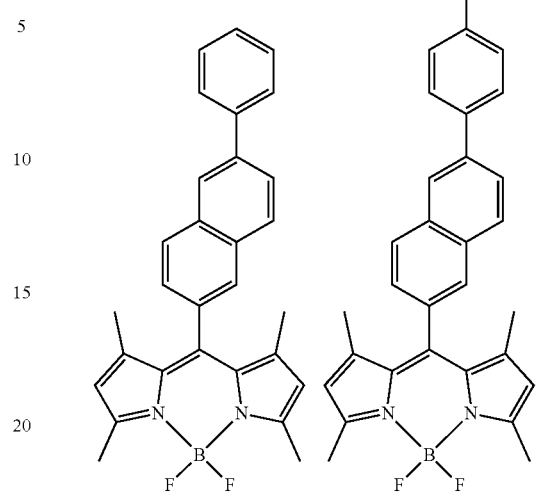
[Formula 127]
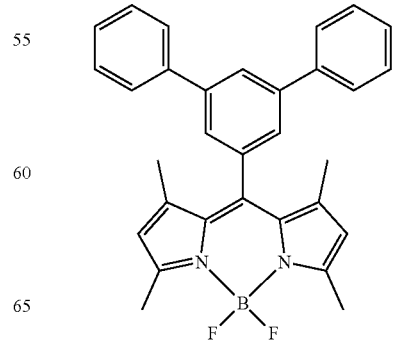

| 203 -continued | 204 -continued |
|---|---|
| 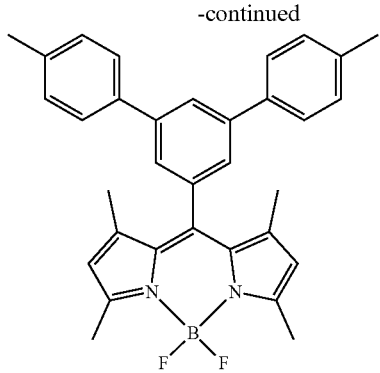 | 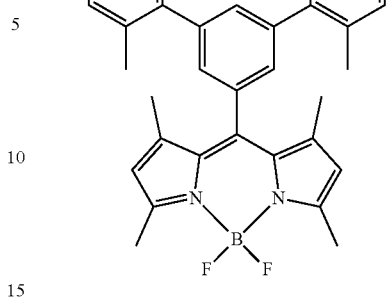 |
| 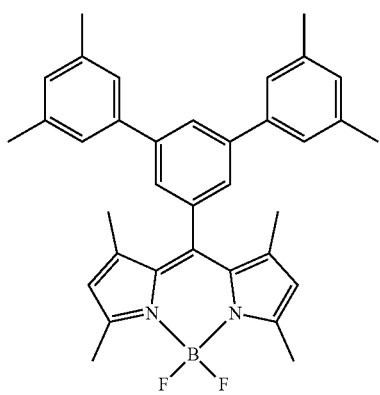 | [Formula 128]<br>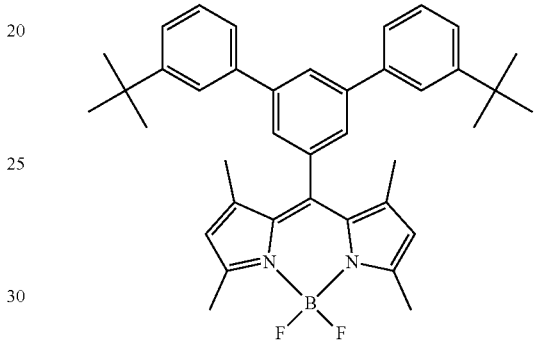 |
| 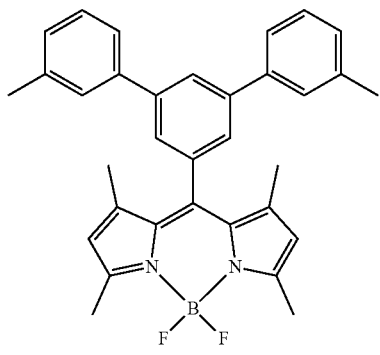 | 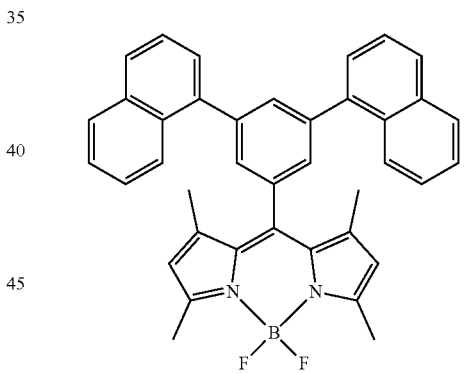 |
| 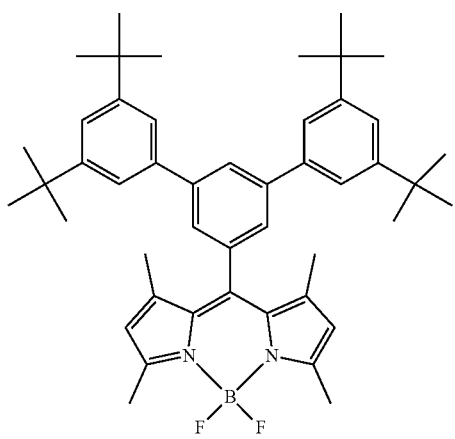 | 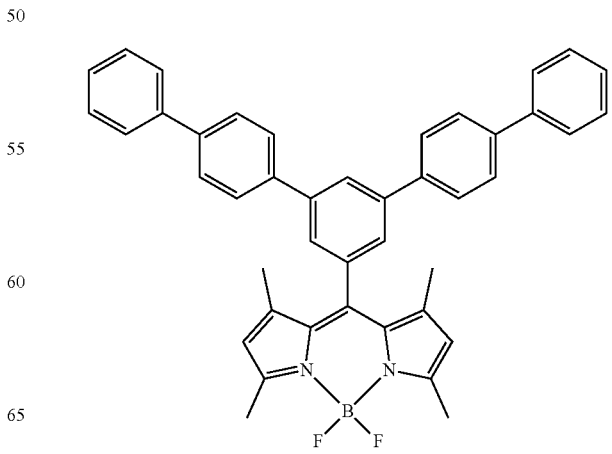 |

205
-continued
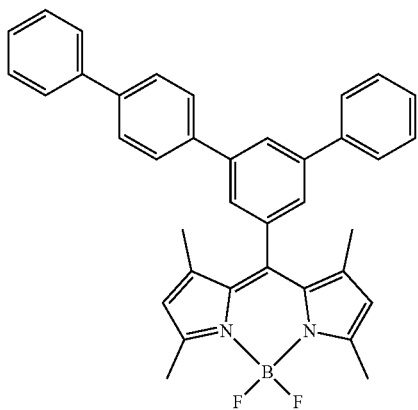
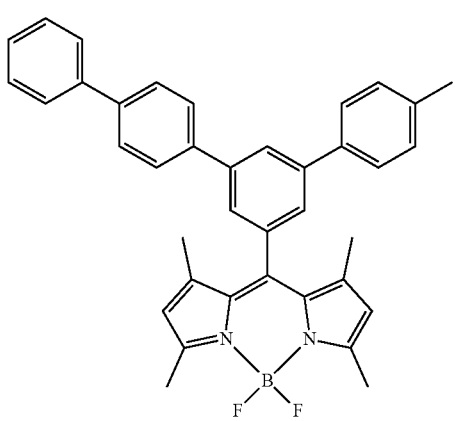
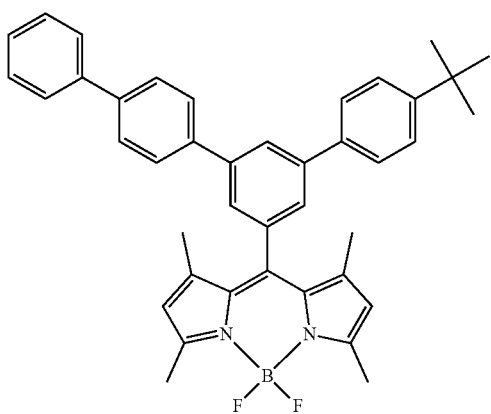
206
-continued
[Formula 129]
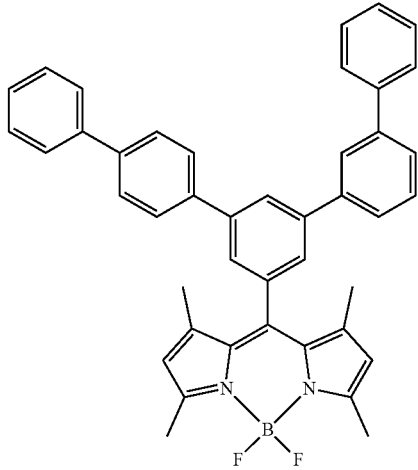
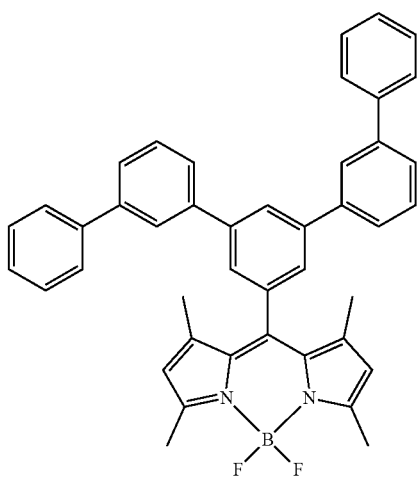
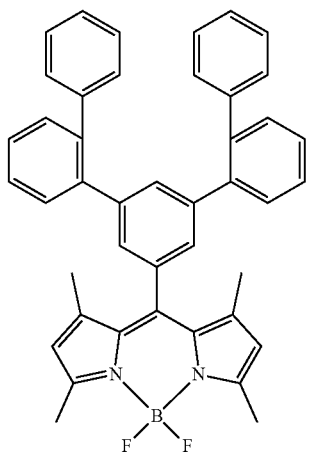

[Formula 130]
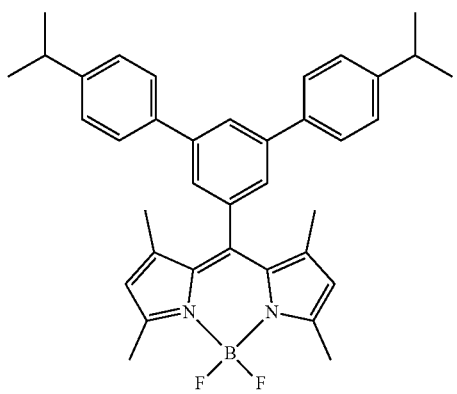
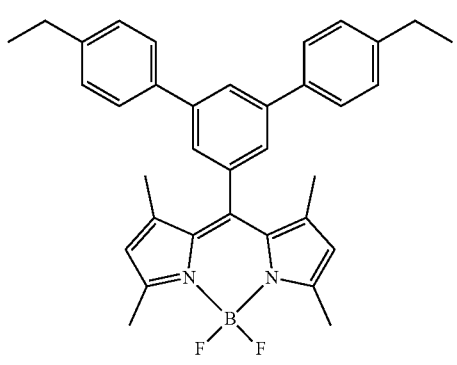
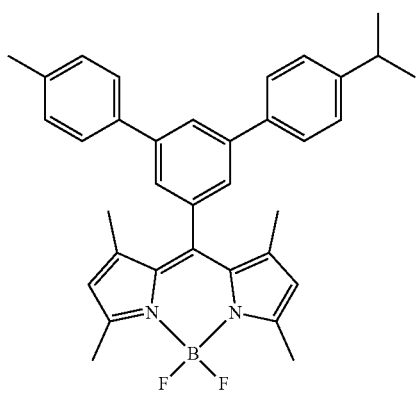
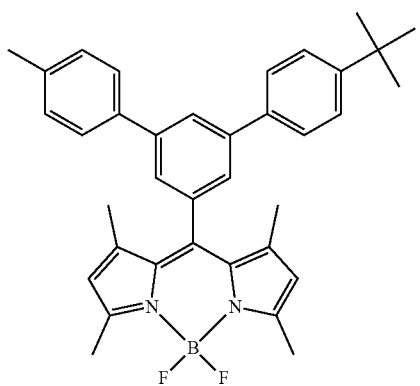
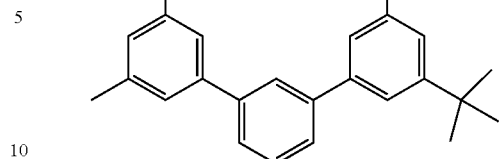
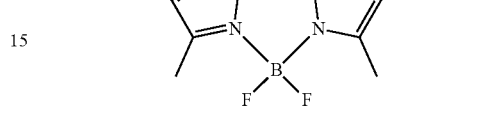
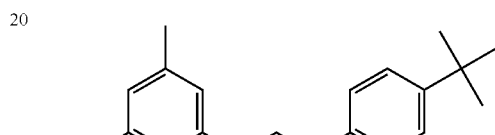
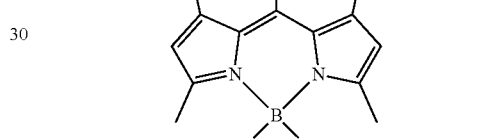
[Formula 131]
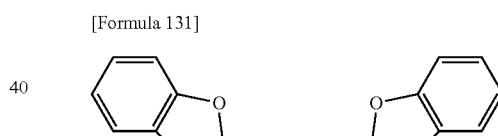
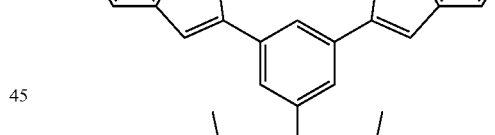
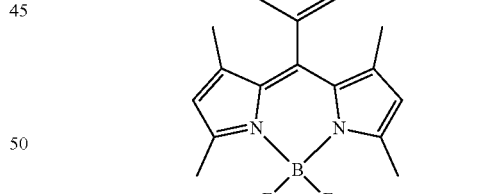
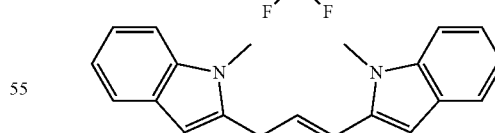
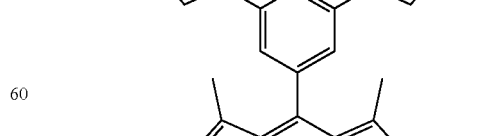
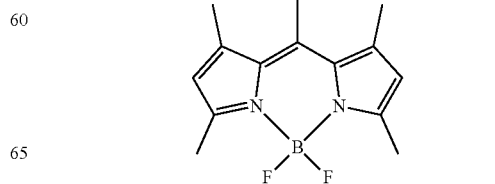

209
-continued
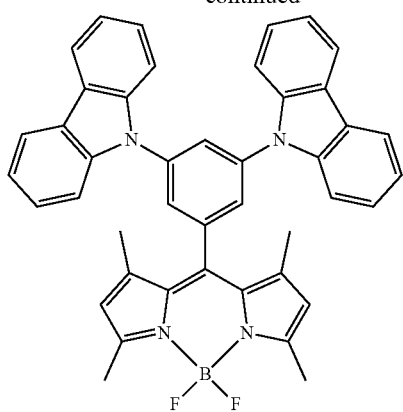
[Formula 132]
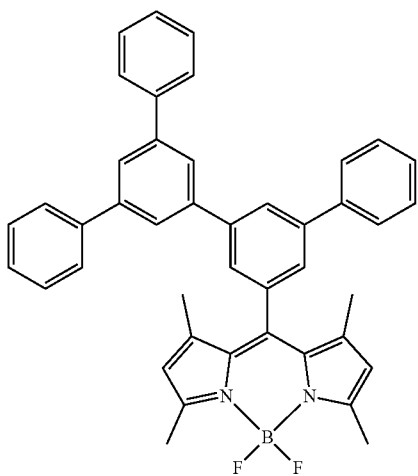
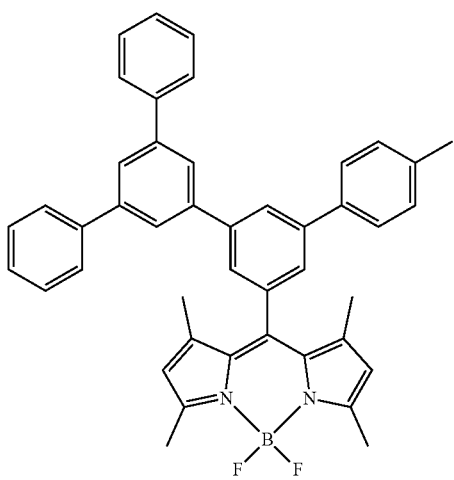
210
-continued
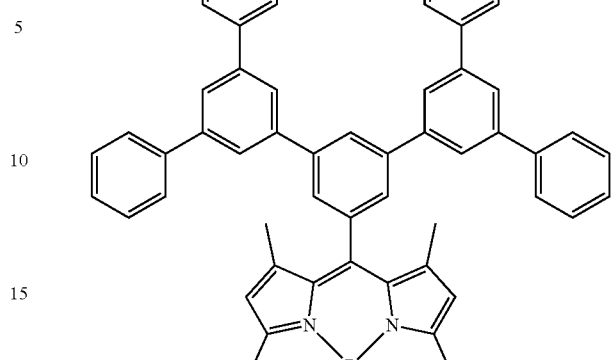
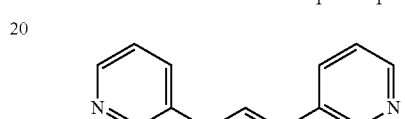
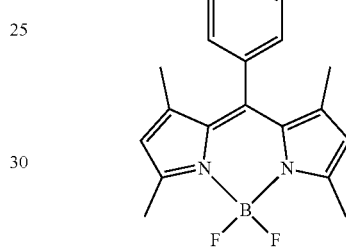
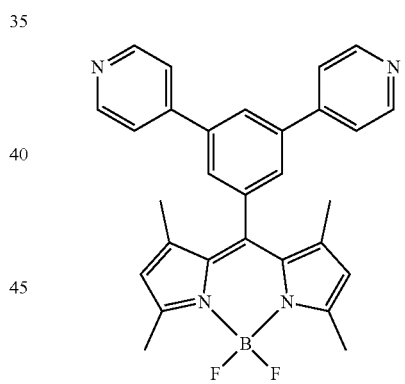
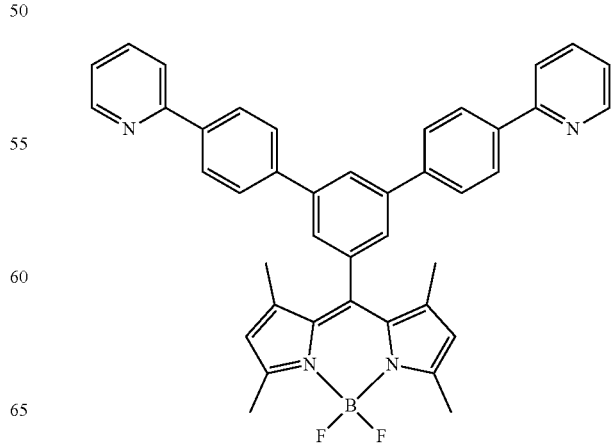

211
-continued
[Formula 133]
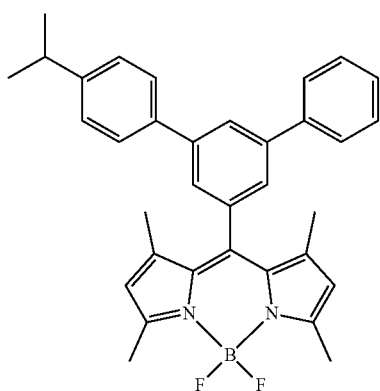
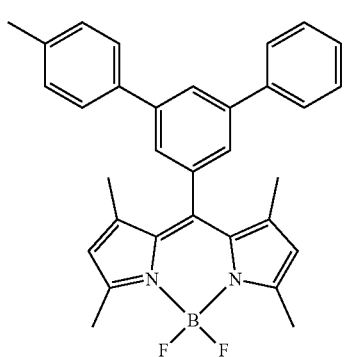
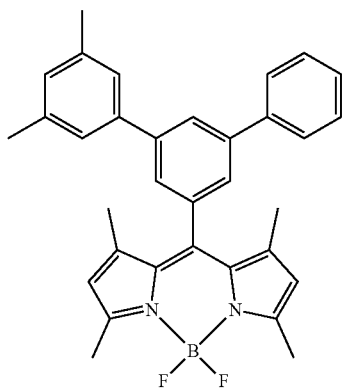
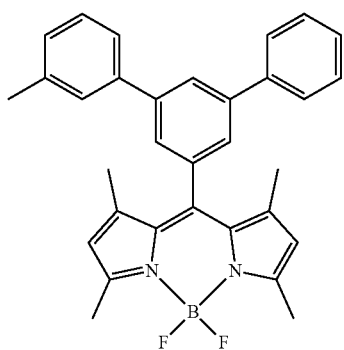
212
-continued
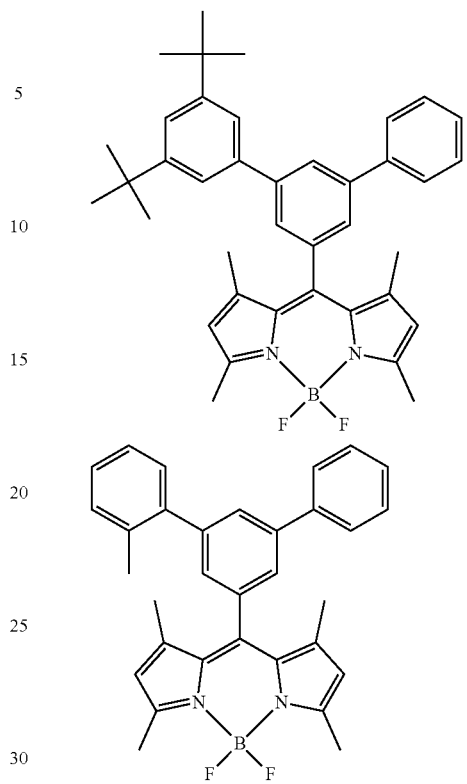
[Formula 134]
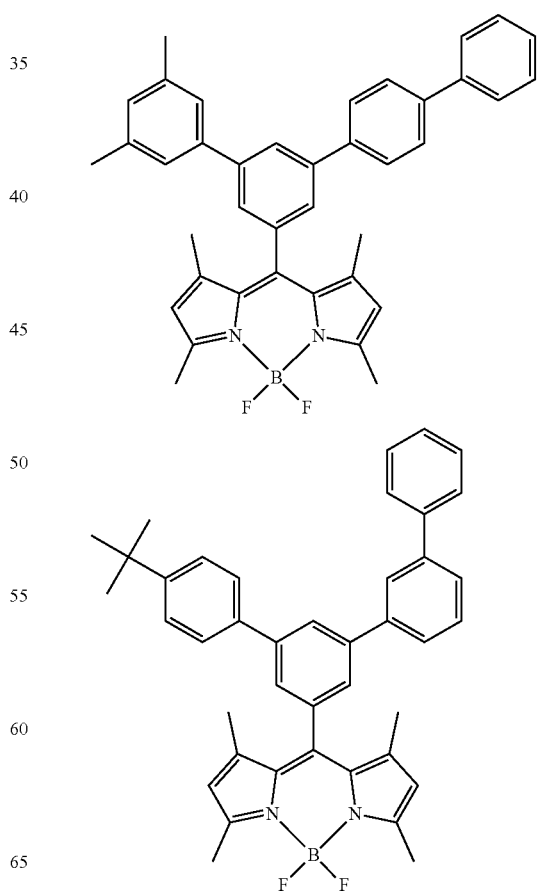

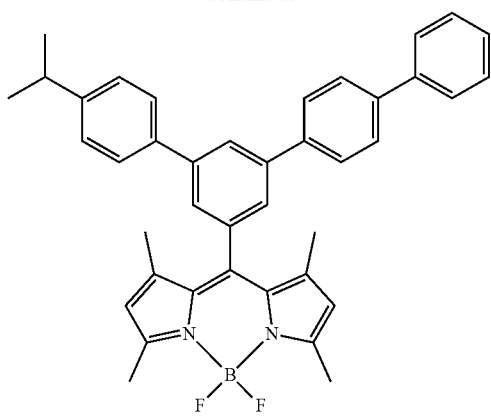
[Formula 135]
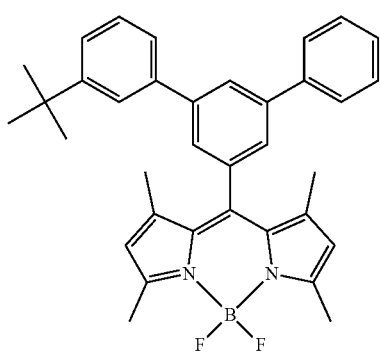
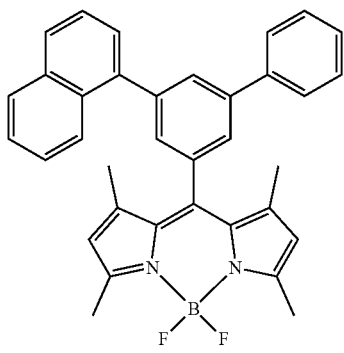
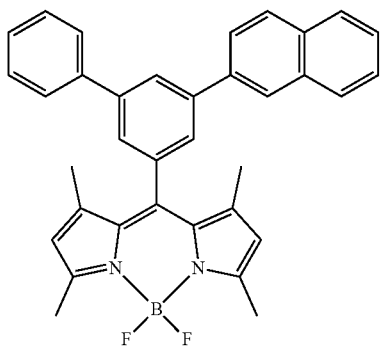
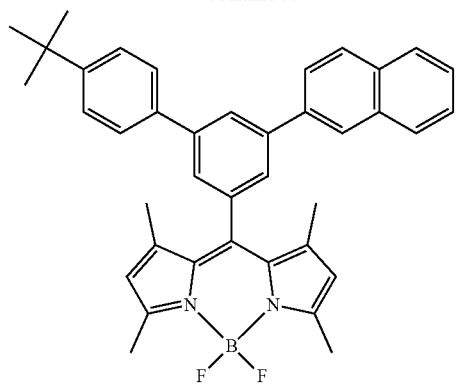
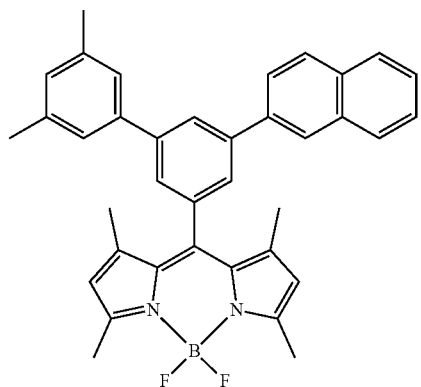
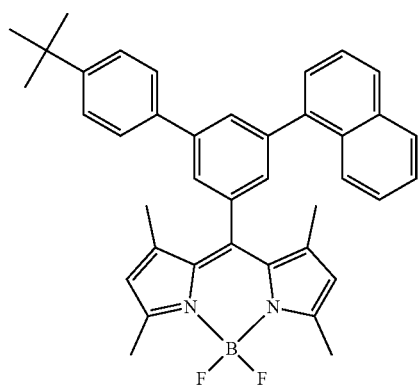
[Formula 136]
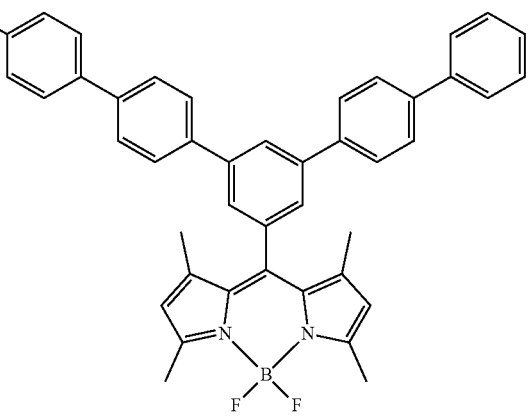

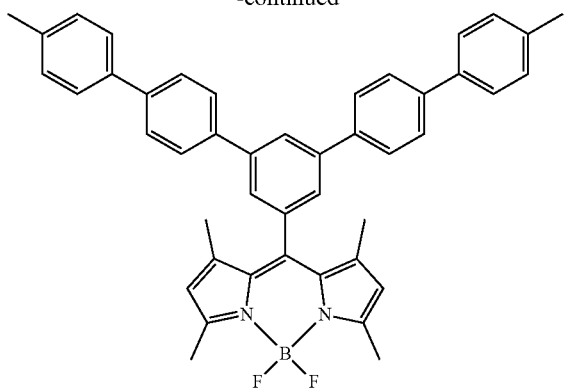
[Formula 137]
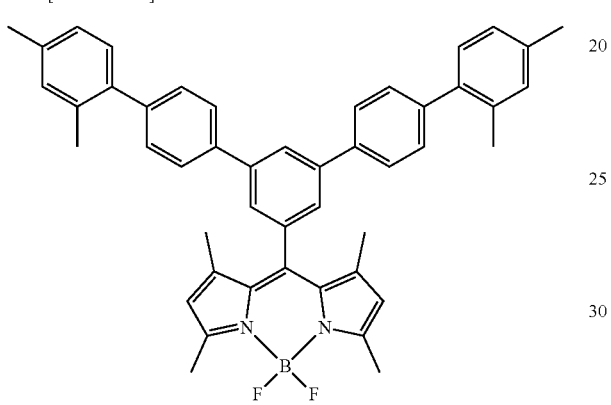
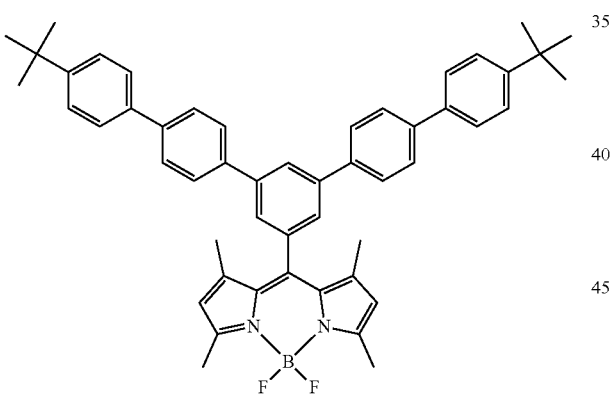
[Formula 138]
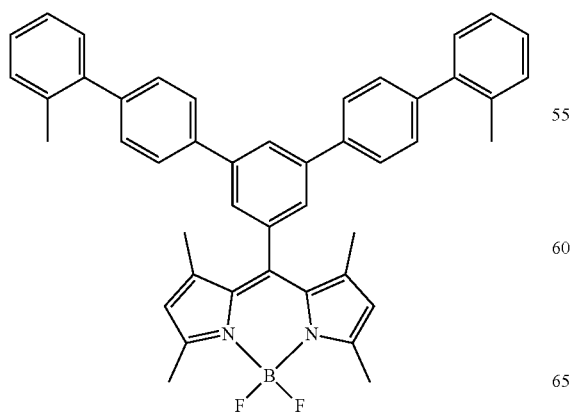
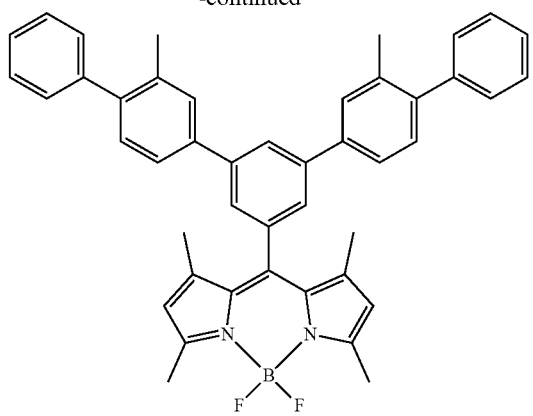
[Formula 139]
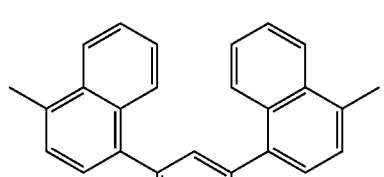
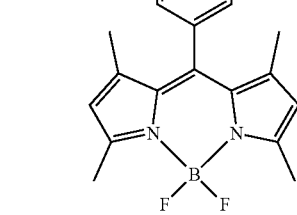
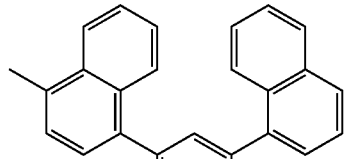
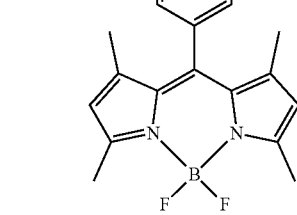
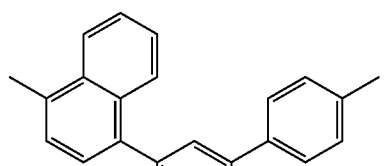
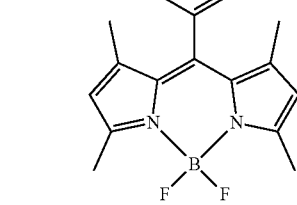

[Formula 140]

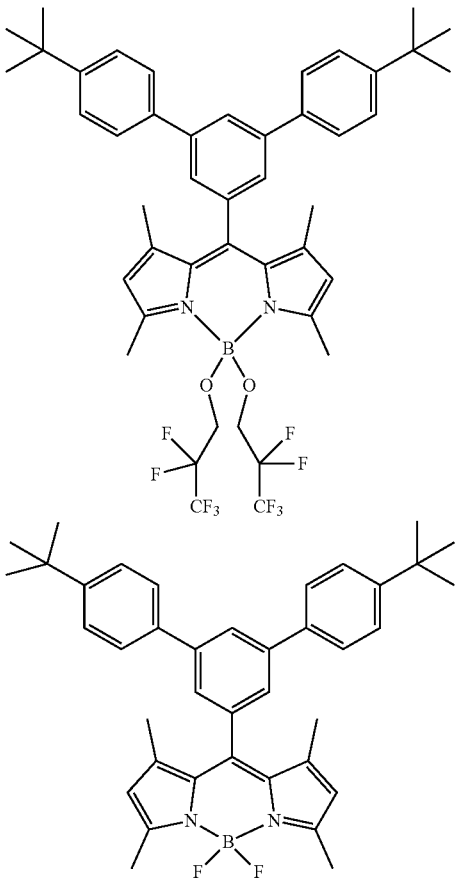

Relationship Between First Compound and Second Compound in Emitting Layer

In the organic EL device 1 of the exemplary embodiment, a singlet energy $S_1(Mat1)$ of the first compound and a singlet energy $S_1(Mat2)$ of the second compound preferably satisfy a relationship of a numerical formula (Numerical Formula 3).

$$S_1(Mat1) > S_1(Mat2) \quad \text{(Numerical Formula 3)}$$

An energy gap $T_{77K}(Mat1)$ at 77 [K] of the first compound is preferably larger than an energy gap $T_{77K}(Mat2)$ at 77 [K] of the second compound. In other words, a relationship of the following numerical formula (Numerical Formula 5) is preferably satisfied.

$$T_{77K}(Mat1) > T_{77K}(Mat2) \quad \text{(Numerical Formula 5)}$$

When the organic EL device 1 of the exemplary embodiment emits light, it is preferable that the second compound in the emitting layer 5 mainly emits light.

Relationship Between Triplet Energy and Energy Gap at 77K

Here, a relationship between a triplet energy and an energy gap at 77K will be described. In the exemplary embodiment, the energy gap at 77 [K] is different from a typical triplet energy in some aspects.

Triplet energy is measured as follows. Firstly, a solution in which a compound (measurement target) is dissolved in an appropriate solvent is encapsulated in a quartz glass tube to prepare a sample. A phosphorescent spectrum (ordinate axis: phosphorescent luminous intensity, abscissa axis: wavelength) of the sample is measured at a low temperature (77K). A tangent is drawn to the rise of the phosphorescent spectrum close to the short-wavelength region. The triplet energy is calculated by a predetermined conversion equation based on a wavelength value at an intersection of the tangent and the abscissa axis.

Here, the thermally activated delayed fluorescent compound among the compounds of the exemplary embodiment is preferably a compound having a small $\Delta ST$. When $\Delta ST$ is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the exemplary embodiment, the triplet energy is measured by the same method as a typical triplet energy T, but a value measured in the following manner is referred to as an energy gap $T_{77K}$ in order to differentiate the measured energy from the typical triplet energy in a strict meaning. The measurement target compound is dissolved in EPA (diethylether:isopentane:ethanol=5:5:2 in volume ratio) at a concentration of 10 μmol/L, and the obtained solution is encapsulated in a quartz cell to provide a measurement sample. A phosphorescent spectrum (ordinate axis: phosphorescent luminous intensity, abscissa axis: wavelength) of the sample is measured at a low temperature (77K). A tangent is drawn to the rise of the phosphorescent spectrum close to the short-wavelength region. An energy amount is calculated by a conversion equation below based on a wavelength value fledge nm at an intersection of the tangent and the abscissa axis and is defined as an energy gap $T_{77K}$ at 77K.

$$T_{77K}[eV] = 1239.85/\lambda_{edge} \quad \text{Conversion Equation (F1):}$$

The tangent to the rise of the phosphorescence spectrum close to the short-wavelength region is drawn as follows. While moving on a curve of the phosphorescence spectrum from the short-wavelength region to the maximum spectral value closest to the short-wavelength region among the maximum spectral values, a tangent is checked at each point on the curve toward the long-wavelength of the phosphorescence spectrum. An inclination of the tangent is increased along the rise of the curve (i.e., a value of the ordinate axis is increased). A tangent drawn at a point of the maximum inclination (i.e., a tangent at an inflection point) is defined as the tangent to the rise of the phosphorescence spectrum close to the short-wavelength region.

The maximum with peak intensity being 15% or less of the maximum peak intensity of the spectrum is not included in the above-mentioned maximum closest to the short-wavelength region. The tangent drawn at a point of the maximum spectral value being closest to the short-wavelength region and having the maximum inclination is defined as a tangent to the rise of the phosphorescence spectrum close to the short-wavelength region.

For phosphorescence measurement, a spectrophotofluorometer body F-4500 (manufactured by Hitachi High-Technologies Corporation) is usable. Any device for phosphorescence measurement is usable. A combination of a cooling unit, a low temperature container, an excitation light source and a light-receiving unit may be used for phosphorescence measurement.

Singlet Energy S1

A method of measuring a singlet energy $S_1$ with use of a solution (occasionally referred to as a solution method) is exemplified by a method below.

A toluene solution in which a measurement target compound is dissolved at a concentration of 10 μmol/L is prepared and is encapsulated in a quartz cell to provide a measurement sample. Absorption spectrum (ordinate axis: absorption intensity, abscissa axis: wavelength) of the sample is measured at the normal temperature (300K). A tangent is drawn to the fall of the absorption spectrum on the long-wavelength side, and a wavelength value λedge (nm) at an intersection of the tangent and the abscissa axis is assigned to a conversion equation (F2) below to calculate singlet energy.

$$S_1[eV]=1239.85/\lambda edge \quad \text{Conversion Equation (F2):}$$

Any device for measuring absorption spectrum is usable. For instance, a spectrophotometer (U3310 manufactured by Hitachi, Ltd.) is usable.

The tangent to the fall of the absorption spectrum on the long-wavelength side is drawn as follows. While moving on a curve of the absorption spectrum from the maximum spectral value closest to the long-wavelength region in a long-wavelength direction, a tangent at each point on the curve is checked. An inclination of the tangent is decreased and increased in a repeated manner as the curve fell (i.e., a value of the ordinate axis is decreased). A tangent drawn at a point of the minimum inclination closest to the long-wavelength region (except when absorbance is 0.1 or less) is defined as the tangent to the fall of the absorption spectrum close to the long-wavelength region.

The maximum absorbance of 0.2 or less is not included in the above-mentioned maximum absorbance on the long-wavelength side.

In the exemplary embodiment, a difference ($S_1$-$T_{77K}$) between the singlet energy $S_1$ and the energy gap $T_{77K}$ at 77[K] is defined as ΔST.

In the exemplary embodiment, a difference ΔST(Mat1) between the singlet energy $S_1$(Mat1) of the first compound and the energy gap $T_{77K}$(Mat1) at 77[K] of the first compound is preferably less than 0.3 eV, more preferably less than 0.2 eV, further preferably less than 0.1 eV. In other words, ΔST(Mat1) preferably satisfies a numerical formula ((Numerical Formula 1A), (Numerical Formula 1B) or (Numerical Formula 1C)) below.

$$\Delta ST(\text{Mat1})=S_1(\text{Mat1})-T_{77K}(\text{Mat1})<0.3 \text{ eV} \quad \text{(Numerical Formula 1A)}$$

$$\Delta ST(\text{Mat1})=S1(\text{Mat1})-T_{77K}(\text{Mat1})<0.2 \text{ eV} \quad \text{(Numerical Formula 1B)}$$

$$\Delta ST(\text{Mat1})=S_1(\text{Mat1})-T_{77K}(\text{Mat1})<0.1 \text{ eV} \quad \text{(Numerical Formula 1C)}$$

The organic EL device 1 in the exemplary embodiment preferably emits red light or green light.

When the organic EL device 1 in the exemplary embodiment emits green light, a main peak wavelength of the light from the organic EL device 1 is preferably in a range from 500 nm to 560 nm.

When the organic EL device 1 in the exemplary embodiment emits red light, a main peak wavelength of the light from the organic EL device 1 is preferably in a range from 600 nm to 660 nm.

When the organic EL device 1 in the exemplary embodiment emits blue light, a main peak wavelength of the light from the organic EL device 1 is preferably in a range from 430 nm to 480 nm.

A main peak wavelength of light from an organic EL device is measured as follows.

Voltage is applied on the organic EL device such that a current density was 10 mA/cm², where spectral radiance spectrum is measured by a spectroradiometer (CS-2000 manufactured by Konica Minolta, Inc.).

A peak wavelength of the emission spectrum of the measured spectral radiance spectra is measured and determined to be the main peak wavelength (unit: nm).

Film Thickness of Emitting Layer

A film thickness of the emitting layer of the organic EL device 1 in the exemplary embodiment is preferably in a range of 5 nm to 50 nm, more preferably in a range of 7 nm to 50 nm, further preferably in a range of 10 nm to 50 nm. When the film thickness of the emitting layer is 5 nm or more, the formation of the emitting layer and the adjustment of the chromaticity are easy. When the film thickness of the emitting layer is 50 nm or less, an increase in the drive voltage is likely to be reducible.

Content Ratios of Compounds in Emitting Layer

Content ratios of the first and second compounds in the emitting layer 5 are, for instance, preferably determined as follows.

The content ratio of the first compound is preferably in a range from 10 mass % to 80 mass %, more preferably in a range from 10 mass % to 60 mass %, further preferably in a range from 20 mass % to 60 mass %.

The content ratio of the second compound is preferably in a range from 0.01 mass % to 10 mass %, more preferably in a range from 0.01 mass % to 5 mass %, further preferably in a range from 0.01 mass % to 1 mass %.

It should be noted that the emitting layer 5 of the exemplary embodiment may further contain material(s) other than the first and second compounds.

The emitting layer 5 may include a single type of the first compound or may include two or more types of the first compound. The emitting layer 5 may include a single type of the second compound or may include two or more types of the second corn pound.

TADF Mechanism

Figure 4:
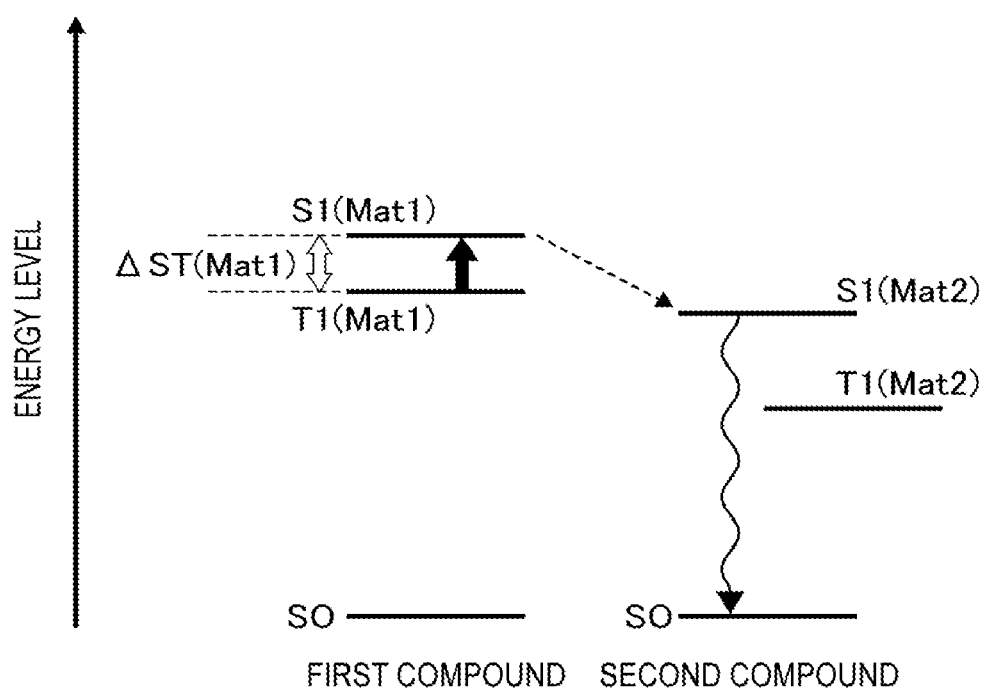
FIG. 4 shows a relationship in energy level and energy transfer between a first compound and a second compound in an emitting layer of an exemplary organic electroluminescence device according to a third exemplary embodiment of the invention.

FIG. 4 shows an example of a relationship between energy levels of the first compound and the second compound in the emitting layer. In FIG. 4, S0 represents a ground state. S1(Mat1) represents the lowest singlet state of the first compound. T1(Mat1) represents the lowest triplet state of the first compound. S1(Mat2) represents the lowest triplet state of the second compound. T1(Mat2) represents the lowest triplet state of the second compound.

A dashed arrow directed from S1(Mat1) to S1(Mat2) in FIG. 4 represents Förster energy transfer from the lowest singlet state of the first compound to the lowest singlet state of the second compound.

As shown in FIG. 4, when a compound having a small ΔST(Mat1) is used as the first compound, inverse intersystem crossing from the lowest triplet state T1(Mat1) to the lowest singlet state S1(Mat1) can be caused by a heat energy. Subsequently, Förster energy transfer from the lowest singlet state S1(Mat1) of the first compound the second compound occurs to generate the lowest singlet state S1(Mat2). Consequently, fluorescence from the lowest singlet state S1(Mat2) of the second compound can be observed. It is inferred that the internal quantum efficiency can be theoretically raised up to 100% also by using delayed fluorescence by the TADF mechanism.

The organic EL device 1 according to the third exemplary embodiment contains the first compound that is the compound according to the first exemplary embodiment (at least one of the compounds represented by the formulae (11) to (13)), and the second compound having the singlet energy smaller than that of the first compound in the emitting layer 5.

The organic EL device according to the third exemplary embodiment is applicable to an electronic device such as a display device and a light-emitting device.

Arrangement(s) of an organic EL device 1 will be detailed below. The description of the reference signs may be omitted.

Substrate

The substrate is used as a support for the organic EL device. For instance, glass, quartz, plastics and the like are usable as the substrate. A flexible substrate is also usable. The flexible substrate is a bendable substrate, which is exemplified by a plastic substrate. Examples of the material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal having a large work function (specifically, 4.0 eV or more), an alloy, an electrically conductive compound and a mixture thereof are preferably used as the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The material is typically formed into a film by a sputtering method. For instance, the indium oxide-zinc oxide can be formed into a film by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode may be formed by a vacuum deposition method, a coating method, an inkjet method, a spin coating method or the like.

Among the organic layers formed on the anode, since the hole injecting layer adjacent to the anode is formed of a composite material into which holes are easily injectable irrespective of the work function of the anode, a material usable as an electrode material (e.g., metal, an alloy, an electroconductive compound, a mixture thereof, and the elements belonging to the group 1 or 2 of the periodic table) is also usable for the anode.

A material having a small work function such as elements belonging to Groups 1 and 2 in the periodic table of the elements, specifically, an alkali metal such as lithium (Li) and cesium (Cs), an alkaline earth metal such as magnesium (Mg), calcium (Ca) and strontium (Sr), alloys (e.g., MgAg and AlLi) including the alkali metal or the alkaline earth metal, a rare earth metal such as europium (Eu) and ytterbium (Yb), alloys including the rare earth metal are also usable for the anode. It should be noted that the vacuum deposition method and the sputtering method are usable for forming the anode using the alkali metal, alkaline earth metal and the alloy thereof. Further, when a silver paste is used for the anode, the coating method and the inkjet method are usable.

Cathode

It is preferable to use metal, an alloy, an electroconductive compound, and a mixture thereof, which have a small work function (specifically, 3.8 eV or less) for the cathode. Examples of the material for the cathode include elements belonging to Groups 1 and 2 in the periodic table of the elements, specifically, the alkali metal such as lithium (Li) and cesium (Cs), the alkaline earth metal such as magnesium (Mg), calcium (Ca) and strontium (Sr), alloys (e.g., MgAg and AlLi) including the alkali metal or the alkaline earth metal, the rare earth metal such as europium (Eu) and ytterbium (Yb), and alloys including the rare earth metal.

It should be noted that the vacuum deposition method and the sputtering method are usable for forming the cathode using the alkali metal, alkaline earth metal and the alloy thereof. Further, when a silver paste is used for the cathode, the coating method and the inkjet method are usable.

By providing the electron injecting layer, various conductive materials such as Al, Ag, ITO, graphene, and indium oxide-tin oxide containing silicon or silicon oxide may be used for forming the cathode regardless of the work function. The conductive materials can be formed into a film using the sputtering method, inkjet method, spin coating method and the like.

Hole Injecting Layer

The hole injecting layer is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule organic compound, such that 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

In addition, a high polymer compound (e.g., oligomer, dendrimer and polymer) is usable as the substance exhibiting a high hole injectability. Examples of the high-molecule compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N, N'-bis(4-butylphenyl)-N, N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly(styrene sulfonic acid)(PAni/PSS) are also usable.

Hole Transporting Layer

The hole transporting layer is a layer containing a highly hole-transporting substance. An aromatic amine compound, carbazole derivative, anthracene derivative and the like are usable for the hole transporting layer. Specific examples of a material for the hole transporting layer include an aromatic amine compound such as 4,4'-bis[N-(1-naphthyl)-N-phenylamino]biphenyl (abbreviation: NPB), N,N'-bis(3-methylphenyl)-N, N'-diphenyl-[1,1'-biphenyl]-4,4'-diamine (abbreviation: TPD), 4-phenyl-4'-(9-phenylfluorene-9-yl) triphenylamine (abbreviation: BAFLP), 4,4'-bis[N-(9,9-dimethylfluorene-2-yl)-N-phenylamino]biphenyl (abbreviation: DFLDPBi), 4,4',4''-tris(N,N-diphenylamino) triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(V·s) or more.

For the hole transporting layer, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance(s).

When the hole transporting layer includes two or more layers, one of the layers with a larger energy gap is preferably provided closer to the emitting layer. An example of the material with a larger energy gap is HT-2 used in later-described Examples.

Electron Transporting Layer

The electron transporting layer is a layer containing a highly electron-transporting substance. For the electron transporting layer, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low-molecule organic compound, a metal complex such as Alq, tris(4-methyl-8-quinolinato)aluminum (abbreviation: Almq$_3$), bis(10-hydroxybenzo[h]quinolinato)beryllium (abbreviation: BeBq$_2$), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) is usable. In the exemplary embodiment, a benzimidazole compound is preferably usable. The above-described substances mostly have an electron mobility of $10^{-6}$ cm$^2$/(V·s) or more. It should be noted that any substance other than the above substance may be used for the electron transporting layer as long as the substance exhibits a higher electron transportability than the hole transportability. The electron transporting layer may be provided in the form of a single layer or a laminate of two or more layers of the above substance(s).

Moreover, a high polymer compound is usable for the electron transporting layer. For instance, poly[(9,9-dihexylfluorene-2,7-diyl)-co-(pyridine-3,5-diyl)](abbreviation: PF-Py), poly[(9,9-dioctylfluorene-2,7-diyl)-co-(2,2'-bipyridine-6,6'-diyl)](abbreviation: PF-BPy) and the like are usable.

Electron Injecting Layer

The electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride (CaF$_2$), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the anode.

Alternatively, the electron injecting layer may be provided by a composite material in a form of a mixture of the organic compound and the electron donor. Such a composite material exhibits excellent electron injectability and electron transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer are usable. As the electron donor, any substance exhibiting electron donating property to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Layer Formation Method

A method for forming each layer of the organic EL device in the third exemplary embodiment is subject to no limitation except for the above particular description. However, known methods of dry film-forming such as vacuum deposition, sputtering, plasma or ion plating and wet film-forming such as spin coating, dipping, flow coating or ink jet printing are applicable.

Film Thickness

A thickness of each of the organic layers in the organic EL device according to the third exemplary embodiment is not limited except for the above particular description. In general, the thickness preferably ranges from several nanometers to 1 μm in order to avoid defects such as a pin hole and to prevent efficiency from being deteriorated since a high voltage needs to be applied.

Fourth Exemplary Embodiment

An arrangement of an organic EL device according to a fourth exemplary embodiment will be described below. In the description of the fourth exemplary embodiment, the same components as those in the third exemplary embodiment are denoted by the same reference signs and names to simplify or omit an explanation of the components. In the fourth exemplary embodiment, any materials and compounds that are not specified may be the same as those in the third exemplary embodiment.

The organic EL device according to the fourth exemplary embodiment is different from the organic EL device according to the third exemplary embodiment in that the emitting layer further includes a third compound. The rest of the arrangement of the organic EL device according to the fifth exemplary embodiment is the same as in the third exemplary embodiment.

Specifically, in the fourth exemplary embodiment, the emitting layer as a first organic layer contains the first compound, the second compound and the third corn pound.

In the fourth exemplary embodiment, the first compound is preferably a host material, the second compound is preferably a dopant material, and the third compound is preferably a material that disperses the dopant material in the emitting layer.

Third Compound

The third compound may be a thermally activated delayed fluorescent compound or a compound exhibiting no thermally activated delayed fluorescence.

The third compound is not particularly limited, but is preferably a compound other than an amine compound. Although the third compound may be a carbazole derivative, dibenzofuran derivative, or dibenzothiophene derivative, the third compound is not limited thereto.

It is also preferable that the third compound has at least one of a partial structure represented by a formula (31), a partial structure represented by a formula (32), a partial structure represented by a formula (33) and a partial structure represented by a formula (34) in one molecule.

[Formula 141]

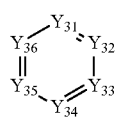

(31)

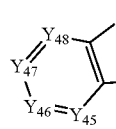

(32)

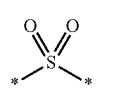

(33)

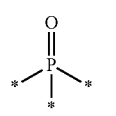

(34)

In the formula (31), $Y_{31}$ to $Y_{36}$ each independently represent a nitrogen atom or a carbon atom bonded to another atom in the molecule of the third compound.

At least one of $Y_{31}$ to $Y_{36}$ is a carbon atom bonded to another atom in the molecule of the third compound.

In the formula (32), $Y_{41}$ to $Y_{48}$ each independently represent a nitrogen atom or a carbon atom bonded to another atom in the molecule of the third compound.

At least one of $Y_{41}$ to $Y_{48}$ is a carbon atom bonded to another atom in the molecule of the third compound.

$X_{30}$ represents a nitrogen atom bonded to another atom in the molecule of the third compound, an oxygen atom, or a sulfur atom.

The mark * in the formulae (33) to (34) each independently shows a bonding position with another atom or another structure in the molecule of the third compound.

In the formula (32), it is also preferable that at least two of $Y_{41}$ to $Y_{48}$ are carbon atoms bonded to other atoms in the molecule of the third compound to form a cyclic structure including the carbon atoms.

For instance, the partial structure represented by the formula (32) is preferably any one selected from the group consisting of partial structures represented by formulae (321), (322), (323), (324), (325) and (326).

[Formula 142]

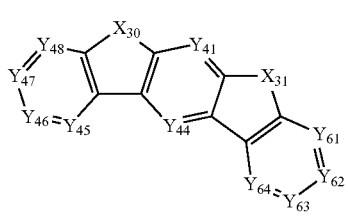

(321)

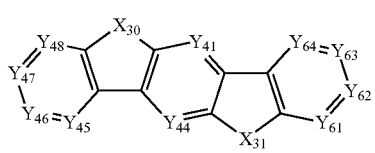

(322)

[Formula 143]

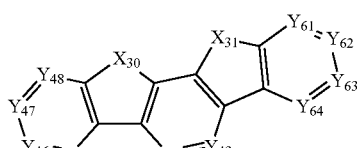

(323)

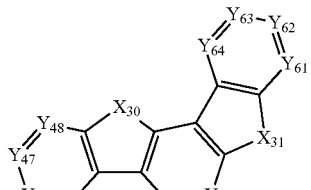

(324)

[Formula 144]

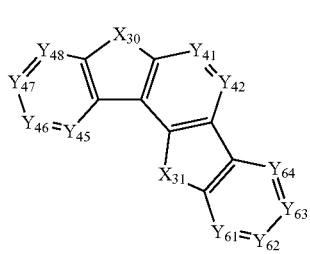

(325)

(326)

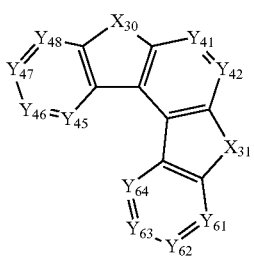

In the formulae (321) to (326), $X_{30}$ each independently represents a nitrogen atom bonded to another atom in the molecule of the third compound, an oxygen atom, or a sulfur atom.

$Y_{41}$ to $Y_{48}$ each independently represent a nitrogen atom or a carbon atom bonded to another atom in the molecule of the third compound.

$X_{31}$ each independently represents a nitrogen atom bonded to another atom in the molecule of the third compound, an oxygen atom, a sulfur atom, or a carbon atom bonded to another atom in the molecule of the third compound.

Y6 to $Y_{64}$ each independently represent a nitrogen atom or a carbon atom bonded to another atom in the molecule of the third compound.

In the exemplary embodiments, the third compound preferably has the partial structure represented by the formula (323) among those represented by the formulae (323) to (326).

The partial structure represented by the formula (31) is preferably included in the third compound as at least one group selected from the group consisting of a group represented by a formula (33) and a group represented by a formula (34) below.

It is also preferable that the third compound has at least one of the partial structures represented by the formulae (33) and (34). Since bonding positions are situated in meta positions as shown in the partial structures represented by the formulae (33) and (34), an energy gap $T_{77K}$(Mat3) at 77 [K] of the second compound can be kept high.

[Formula 145]

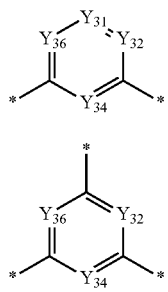

(33)

(34)

In the formula (33), $Y_{31}$, $Y_{32}$, $Y_{34}$ and $Y_{36}$ are each independently a nitrogen atom or $CR_{31}$.

In the formula (34), $Y_{32}$, $Y_{34}$ and $Y_{36}$ are each independently a nitrogen atom or $CR_{31}$.

In the formulae (33) and (34), $R_{31}$ each independently represents a hydrogen atom or a substituent.

$R_{31}$ as the substituent is each independently selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a halogen atom, a cyano group, a nitro group, and a substituted or unsubstituted carboxy group.

The substituted or unsubstituted aryl group having 6 to 30 ring carbon atoms for $R_{31}$ is preferably a non-fused ring.

The mark * in the formulae (33) and (34) each independently shows a bonding position with another atom or another structure in the molecule of the third corn pound.

In the formula (33), $Y_{31}$, $Y_{32}$, $Y_{34}$ and $Y_{36}$ are each independently preferably $CR_{31}$, in which a plurality of $R_{31}$ are the same or different.

In the formula (34), $Y_{32}$, $Y_{34}$ and $Y_{36}$ are each independently preferably $CR_{31}$, in which a plurality of $R_{31}$ are the same or different.

The substituted germanium group is preferably represented by $-Ge(R_{30}1)_3$. $R_{30}1$ is each independently a substituent. The substituent $R_{30}1$ is preferably a substituted or unsubstituted alkyl group having 1 to 30 carbon atoms or a substituted or unsubstituted aryl group having 6 to 30 ring carbon atoms. A plurality of $R_{30}1$ are mutually the same or different.

The partial structure represented by the formula (32) is preferably included in the third compound as at least one group selected from the group consisting of groups represented by formulae (35) to (39) and a group represented by a formula (30a).

[Formula 146]

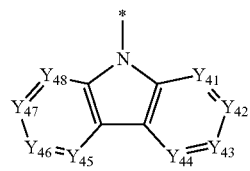

(35)

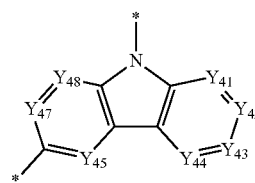

(36)

[Formula 147]

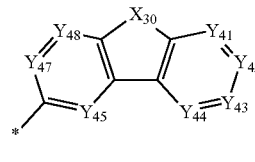

(37)

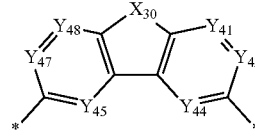

(38)

[Formula 148]

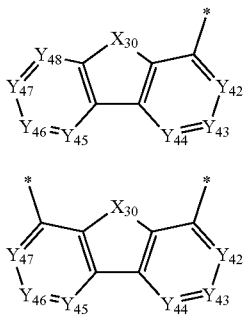

(39)

(30a)

In the formula (35), $Y_{41}$ to $Y_{48}$ are each independently a nitrogen atom or $CR_{32}$.

In the formulae (36) and (37), $Y_{41}$ to $Y_{45}$, $Y_{47}$ and $Y_{48}$ are each independently a nitrogen atom or $CR_{32}$.

In the formula (38), $Y_{41}$, $Y_{42}$, $Y_{44}$, $Y_{45}$, $Y_{47}$ and $Y_{48}$ are each independently a nitrogen atom or $CR_{32}$.

In the formula (39), $Y_{42}$ to $Y_{48}$ are each independently a nitrogen atom or $CR_{32}$.

In the formula (30a), $Y_{42}$ to $Y_{47}$ are each independently a nitrogen atom or $CR_{32}$.

In the formulae (35) to (39) and (30a), $R_{32}$ each independently represents a hydrogen atom or a substituent.

$R_{32}$ as the substituent is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a halogen atom, a cyano group, a nitro group, and a substituted or unsubstituted carboxy group.

A plurality of $R_{32}$ are the same or different.

In the formulae (37) to (39) and (30a), $X_{30}$ is $NR_{33}$, an oxygen atom or a sulfur atom.

$R_{33}$ is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a fluorine atom, a cyano group, a nitro group, and a substituted or unsubstituted carboxy group.

A plurality of $R_{33}$ are the same or different.

The substituted or unsubstituted aryl group having 6 to 30 ring carbon atoms for $R_{33}$ is preferably a non-fused ring.

The mark * in the formulae (35) to (39) and (30a) each independently shows a bonding position with another atom or another structure in the molecule of the third compound.

In the formula (35), $Y_{41}$ to $Y_{48}$ are each independently preferably $CR_{32}$. In the formulae (36) and (37), $Y_{41}$ to $Y_{45}$, $Y_{47}$ and $Y_{48}$ are each independently preferably $CR_{32}$. In the formula (38), $Y_{41}$, $Y_{42}$, $Y_{44}$, $Y_{45}$, $Y_{47}$ and $Y_{48}$ are each independently preferably $CR_{32}$. In the formula (39), $Y_{42}$ to $Y_{48}$ are each independently preferably $CR_{32}$. In the formula (30a), $Y_{42}$ to $Y_{47}$ are each independently preferably $CR_{32}$. A plurality of $R_{32}$ are the same or different.

In the third compound, $X_{30}$ is preferably an oxygen atom or a sulfur atom, more preferably an oxygen atom.

In the third compound, $R_{31}$ and $R_{32}$ each independently represent a hydrogen atom or a substituent. $R_{31}$ and $R_{32}$ as the substituents are preferably each independently a group selected from the group consisting of a fluorine atom, a cyano group, a substituted or unsubstituted alkyl group having 1 to 30 carbon atoms, a substituted or unsubstituted aryl group having 6 to 30 ring carbon atoms, and a substituted or unsubstituted heteroaryl group having 5 to 30 ring atoms. $R_{31}$ and $R_{32}$ are more preferably a hydrogen atom, a cyano group, a substituted or unsubstituted aryl group having 6 to 30 ring carbon atoms, or a substituted or unsubstituted heteroaryl group having 5 to 30 ring atoms. When $R_{31}$ and $R_{32}$ as the substituents are each a substituted or unsubstituted aryl group having 6 to 30 ring carbon atoms, the aryl group is preferably a non-fused ring.

It is also preferable that the third compound is an aromatic hydrocarbon compound or an aromatic heterocyclic compound.

Manufacturing Method of Third Compound

The third compound can be manufactured by methods disclosed in International Publication No. WO2012/153780, International Publication No. WO2013/038650, and the like. Furthermore, the second compound can be manufactured, for instance, by application of known substitution reactions and/or materials depending on a target compound.

Examples of the substituent in the third compound are shown below, but the invention is not limited thereto.

Specific examples of the aryl group (occasionally referred to as an aromatic hydrocarbon group) include a phenyl group, tolyl group, xylyl group, naphthyl group, phenanthryl group, pyrenyl group, chrysenyl group, benzo[c]phenanthryl group, benzo[g]chrysenyl group, benzoanthryl group, triphenylenyl group, fluorenyl group, 9,9-dimethylfluorenyl group, benzofluorenyl group, dibenzofluorenyl group, biphenyl group, terphenyl group, quarterphenyl group and fluoranthenyl group, among which a phenyl group, biphenyl group, terphenyl group, quarterphenyl group, naphthyl group, triphenylenyl group and fluorenyl group may be preferable.

Specific examples of the aryl group having a substituent include a tolyl group, xylyl group and 9,9-dimethylfluorenyl group.

As is understood from the specific examples, the aryl group includes both fused aryl group and non-fused aryl group.

Preferable examples of the aryl group include a phenyl group, biphenyl group, terphenyl group, quarterphenyl group, naphthyl group, triphenylenyl group and fluorenyl group.

Specific examples of the heteroaryl group (occasionally referred to as a heterocyclic group, heteroaromatic ring group or aromatic heterocyclic group) include a pyrrolyl group, pyrazolyl group, pyrazinyl group, pyrimidinyl group, pyridazynyl group, pyridyl group, triazinyl group, indolyl group, isoindolyl group, imidazolyl group, benzimidazolyl group, indazolyl group, imidazo[1,2-a]pyridinyl group, furyl group, benzofuranyl group, isobenzofuranyl group, dibenzofuranyl group, azadibenzofuranyl group, thiophenyl group, benzothienyl group, dibenzothienyl group, azadibenzothienyl group, quinolyl group, isoquinolyl group, quinoxalinyl group, quinazolinyl group, naphthyridinyl group, carbazolyl group, azacarbazolyl group, phenanthridinyl group, acridinyl group, phenanthrolinyl group, phenazinyl group, phenothiazinyl group, phenoxazinyl group, oxazolyl group, oxadiazolyl group, furazanyl group, benzoxazolyl group, thienyl group, thiazolyl group, thiadiazolyl group, benzothiazolyl group, triazolyl group and tetrazolyl group, among which a dibenzofuranyl group, dibenzothienyl group, carbazolyl group, pyridyl group, pyrimidinyl group, triazinyl group, azadibenzofuranyl group and azadibenzothienyl group may be preferable.

The heteroaryl group is preferably a dibenzofuranyl group, dibenzothienyl group, carbazolyl group, pyridyl group, pyrimidinyl group, triazinyl group, azadibenzofuranyl group or azadibenzothienyl group, and more preferably a dibenzofuranyl group, dibenzothienyl group, azadibenzofuranyl group and azadibenzothienyl group.

In the third compound, it is also preferable that the substituted silyl group is selected from the group consisting of a substituted or unsubstituted trialkylsilyl group, a substituted or unsubstituted arylalkylsilyl group, or a substituted or unsubstituted triarylsilyl group.

Specific examples of the substituted or unsubstituted trialkylsilyl group include trimethylsilyl group and triethylsilyl group.

Specific examples of the substituted or unsubstituted arylalkylsilyl group include diphenylmethylsilyl group, ditolylmethylsilyl group, and phenyldimethylsilyl group.

Specific examples of the substituted or unsubstituted triarylsilyl group include triphenylsilyl group and tritolylsilyl group.

In the third compound, it is also preferable that the substituted phosphine oxide group is a substituted or unsubstituted diary) phosphine oxide group.

Specific examples of the substituted or unsubstituted diary) phosphine oxide group include a diphenyl phosphine oxide group and ditolyl phosphine oxide group.

In the third compound, the substituted carboxy group is exemplified by a benzoyloxy group.

Specific examples of the third compound in the exemplary embodiment are shown below. It should be noted that the third compound of the invention is not limited to the specific examples.

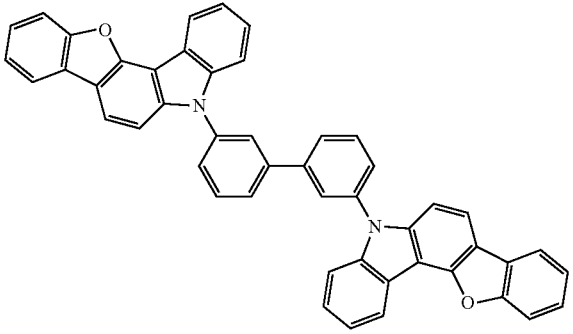

[Formula 150]

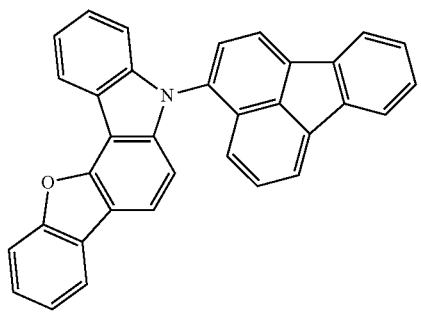

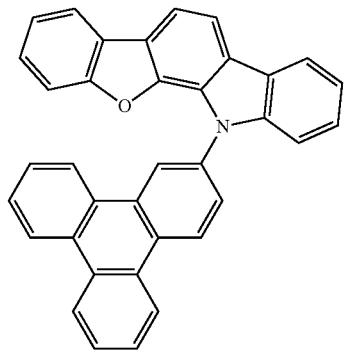

[Formula 149]

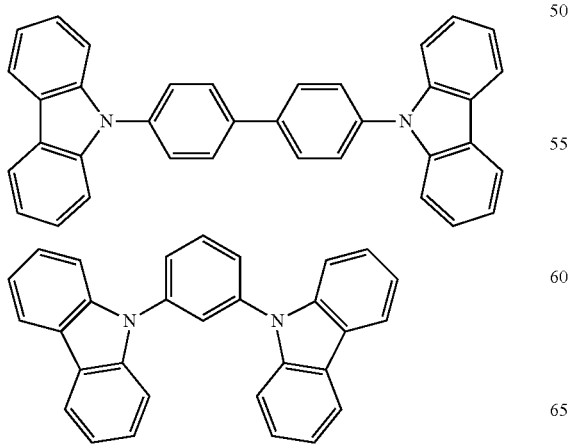

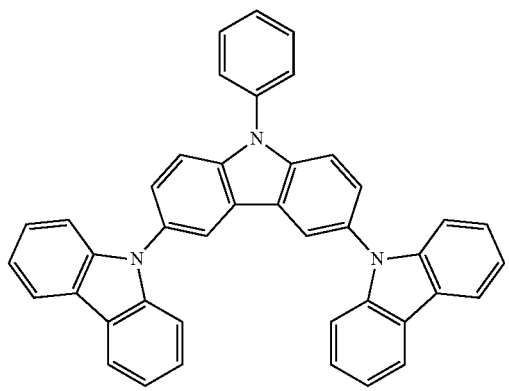

[Formula 151]

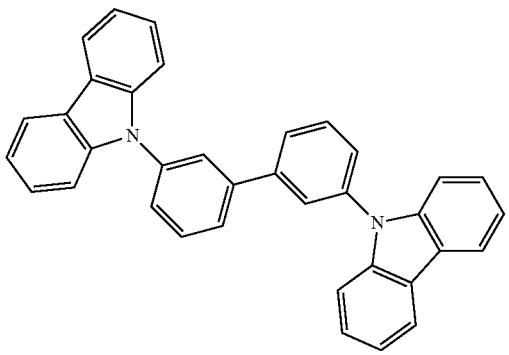

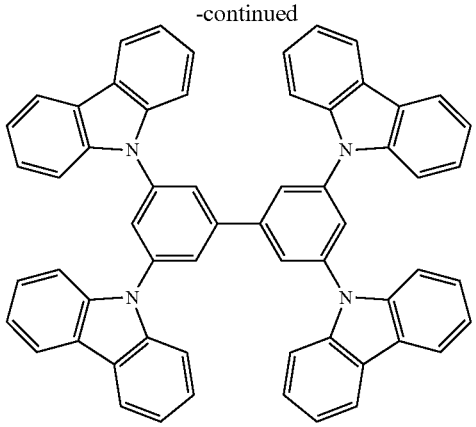

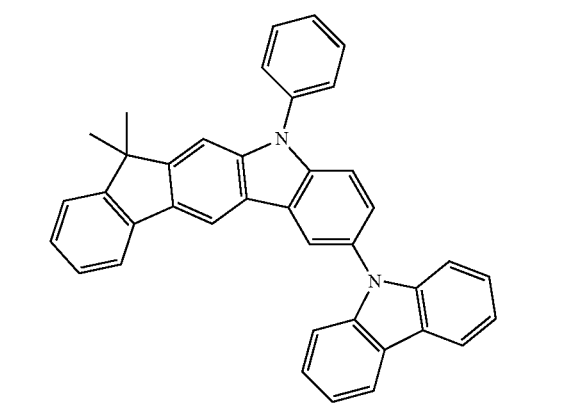

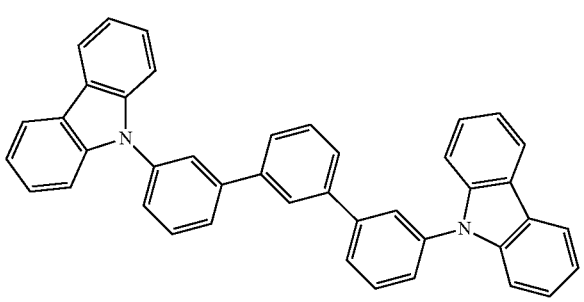

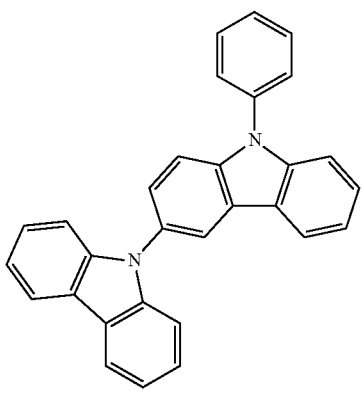

Relationship Between First Compound, Second Compound and Third Compound in Emitting Layer In the organic EL device of the exemplary embodiment, the singlet energy $S_1(Mat1)$ of the first compound and a singlet energy $S_1(Mat3)$ of the third compound preferably satisfies a relationship of Numerical Formula 2 below.

$$S_1(Mat3) > S_1(Mat1) \quad \text{(Numerical Formula 2)}$$

The energy gap $T_{77K}(Mat3)$ at 77 [K] of the third compound is preferably larger than an energy gap $T_{77K}(Mat1)$ at 77 [K] of the first compound.

The energy gap $T_{77K}(Mat3)$ at 77 [K] of the third compound is preferably larger than the energy gap $T_{77K}(Mat2)$ at 77 [K] of the second compound The singlet energy $S_1(Mat1)$ of the first compound, the singlet energy $S_1(Mat2)$ of the second compound, the singlet energy $S_1(Mat3)$ of the third compound preferably satisfy a relationship of Numerical Formula 2A.

$$S_1(Mat3) > S_1(Mat1) > S_1(Mat2) \quad \text{(Numerical Formula 2A)}$$

The energy gap $T_{77K}(Mat1)$ at 77[K] of the first compound, the energy gap $T_{77K}(Mat2)$ at 77[K] of the second compound, and the energy gap $T_{77K}(Mat3)$ at 77[K] of the third compound preferably satisfy a relationship of Numerical Formula 2B.

$$T_{77K}(Mat3) > T_{77K}(Mat1) > T_{77K}(Mat2) \quad \text{(Numerical Formula 2B)}$$

When the organic EL device of the exemplary embodiment emits light, it is preferable that the fluorescent compound in the emitting layer mainly emits light.

The organic EL device of the fourth exemplary embodiment preferably emits red light or green light in the same manner as the organic EL device of the third exemplary embodiment.

A main peak wavelength of the organic EL device can be measured by the same method as that for the organic EL device of the third exemplary embodiment.

Content Ratios of Compounds in Emitting Layer

Content ratios of the first, second and third compounds in the emitting layer are, for instance, preferably determined as follows.

The content ratio of the first compound is preferably in a range from 10 mass % to 80 mass %, more preferably in a range from 10 mass % to 60 mass %, further preferably in a range from 20 mass % to 60 mass %.

The content ratio of the second compound is preferably in a range from 0.01 mass % to 10 mass %, more preferably in a range from 0.01 mass % to 5 mass %, further preferably in a range from 0.01 mass % to 1 mass %.

The content ratio of the third compound is preferably in a range from 10 mass % to 80 mass %.

An upper limit of the total of the respective content ratios of the first, second and third compounds in the emitting layer is 100 mass %. It should be noted that the emitting layer of the exemplary embodiment may further contain material(s) other than the first, second and third compounds.

The emitting layer may include a single type of the first compound or may include two or more types of the first compound. The emitting layer may include a single of the second compound or may include two or more types of the second compound. The emitting layer may include a single of the third compound or may include two or more types of the third compound.

Figure 5:
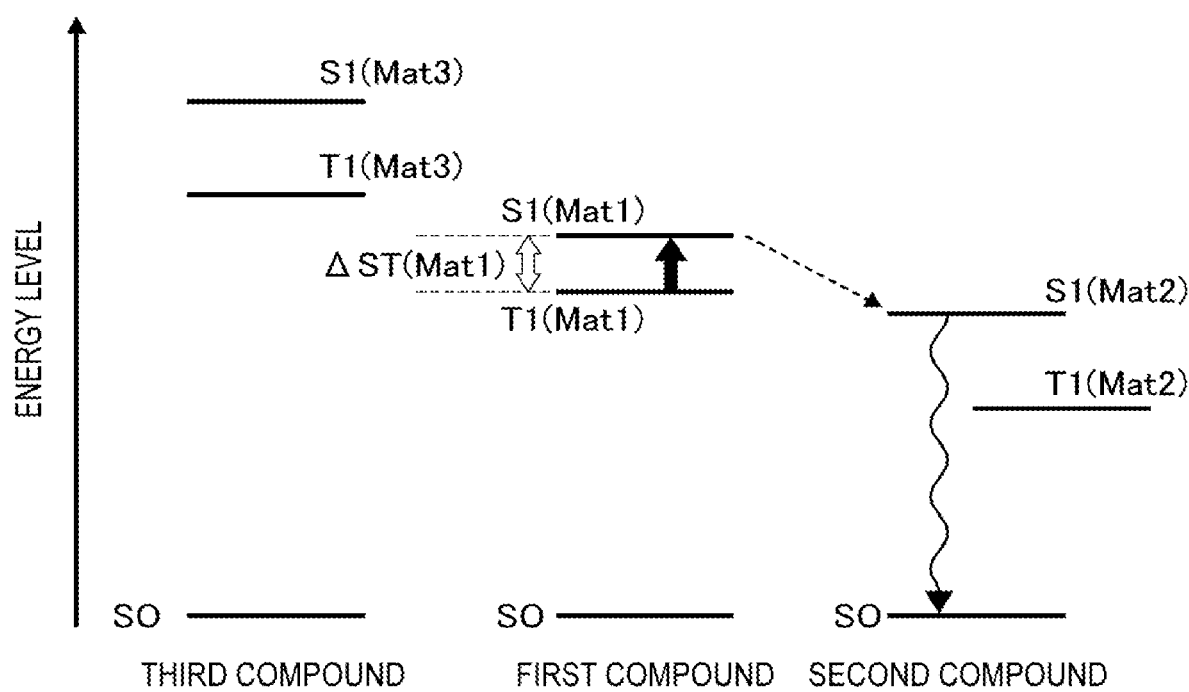
FIG. 5 shows a relationship in energy level and energy transfer between a first compound, a second compound and a third compound in an emitting layer of an exemplary organic electroluminescence device according to a fourth exemplary embodiment of the invention.

FIG. 5 shows an example of a relationship between energy levels of the first, second and third compounds in the emitting layer. In FIG. 5, S0 represents a ground state. S1(Mat1) represents the lowest singlet state of the first compound. T1(Mat1) represents the lowest triplet state of the first compound. S1(Mat2) represents the lowest singlet state of the second compound. T1(Mat2) represents the lowest triplet state of the second compound. S1(Mat3) represents the lowest singlet state of the third compound. T1(Mat3) represents the lowest triplet state of the third compound. A dashed arrow directed from S1(Mat1) to S1(Mat2) in FIG. 5 represents Forster energy transfer from the lowest singlet state of the first compound to the lowest singlet state of the second compound.

As shown in FIG. 5, when a compound having a small $\Delta ST(Mat1)$ is used as the first compound, inverse intersystem crossing from the lowest triplet state T1(Mat1) to the lowest singlet state S1(Mat1) can be caused by a heat energy. Subsequently, Forster energy transfer from the lowest singlet state S1(Mat1) of the first compound the second compound occurs to generate the lowest singlet state S1(Mat2). Consequently, fluorescence from the lowest singlet state S1(Mat2) of the second compound can be observed. It is inferred that the internal quantum efficiency can be theoretically raised up to 100% also by using delayed fluorescence by the TADF mechanism.

The organic EL device 1 according to the fourth exemplary embodiment contains the first compound that is the compound according to the first exemplary embodiment (at least one of the compounds represented by the formulae (11) to (13)), the second compound having the singlet energy smaller than that of the first compound in the emitting layer 5, and the third compound having the singlet energy larger than that of the first compound.

The organic EL device according to the fourth exemplary embodiment is applicable to an electronic device such as a display device and a light-emitting device.

Fifth Exemplary Embodiment

An arrangement of an organic EL device according to a fifth exemplary embodiment will be described below. In the description of the fifth exemplary embodiment, the same components as those in the third and fourth exemplary embodiments are denoted by the same reference signs and names to simplify or omit an explanation of the components. In the fifth exemplary embodiment, any materials and compounds that are not specified may be the same as those in the third and fourth exemplary embodiments.

The organic EL device according to the fifth exemplary embodiment is different from the organic EL device according to the third exemplary embodiment in that the emitting layer further includes a fourth compound in place of the second compound. The rest of the arrangement of the organic EL device according to the fifth exemplary embodiment is the same as in the third exemplary embodiment.

In the fifth exemplary embodiment, the emitting layer contains the first compound and the fourth compound.

In this embodiment, the first compound is preferably a dopant material (occasionally referred to as a guest material, emitter or luminescent material) and the fourth compound is preferably a host material (occasionally referred to as a matrix material).

The fourth compound may be a thermally activated delayed fluorescent compound or a compound exhibiting no thermally activated delayed fluorescence.

Although the fourth compound is not particularly limited, for instance, the third compound described in the fourth exemplary embodiment is usable as the fourth compound.

Relationship Between First Compound and Fourth Compound in Emitting Layer

In the organic EL device of the exemplary embodiment, the singlet energy $S_1(Mat1)$ of the first compound and a singlet energy $S_1(Mat4)$ of the fourth compound preferably satisfies a relationship of Numerical Formula 4 below.

$$S_1(Mat4) > S_1(Mat1) \quad \text{(Numerical Formula 4)}$$

An energy gap $T_{77K}(Mat4)$ at 77 [K] of the fourth compound is preferably larger than the energy gap $T_{77K}(Mat1)$ at 77 [K] of the first compound. In other words, a relationship of Numerical Formula 4A is preferably satisfied.

$$T_{77K}(Mat4) > T_{77K}(Mat1) \quad \text{(Numerical Formula 4A)}$$

When the organic EL device of the exemplary embodiment emits light, it is preferable that the first compound in the emitting layer mainly emits light.

Content Ratios of Compounds in Emitting Layer

Content ratios of the first and fourth compounds in the emitting layer are, for instance, preferably determined as follows.

The content ratio of the first compound is preferably in a range from 10 mass % to 80 mass %, more preferably in a range from 10 mass % to 60 mass %, further preferably in a range from 20 mass % to 60 mass %.

The content ratio of the fourth compound is preferably in a range from 20 mass % to 90 mass %, more preferably in a range from 40 mass % to 90 mass %, further preferably in a range from 40 mass % to 80 mass %.

It should be noted that the emitting layer of the exemplary embodiment may further contain material(s) other than the first and fourth compounds.

The emitting layer may include a single type of the first compound or may include two or more types of the first compound. The emitting layer may include a single type of the fourth compound or may include two or more types of the fourth compound.

Figure 6:
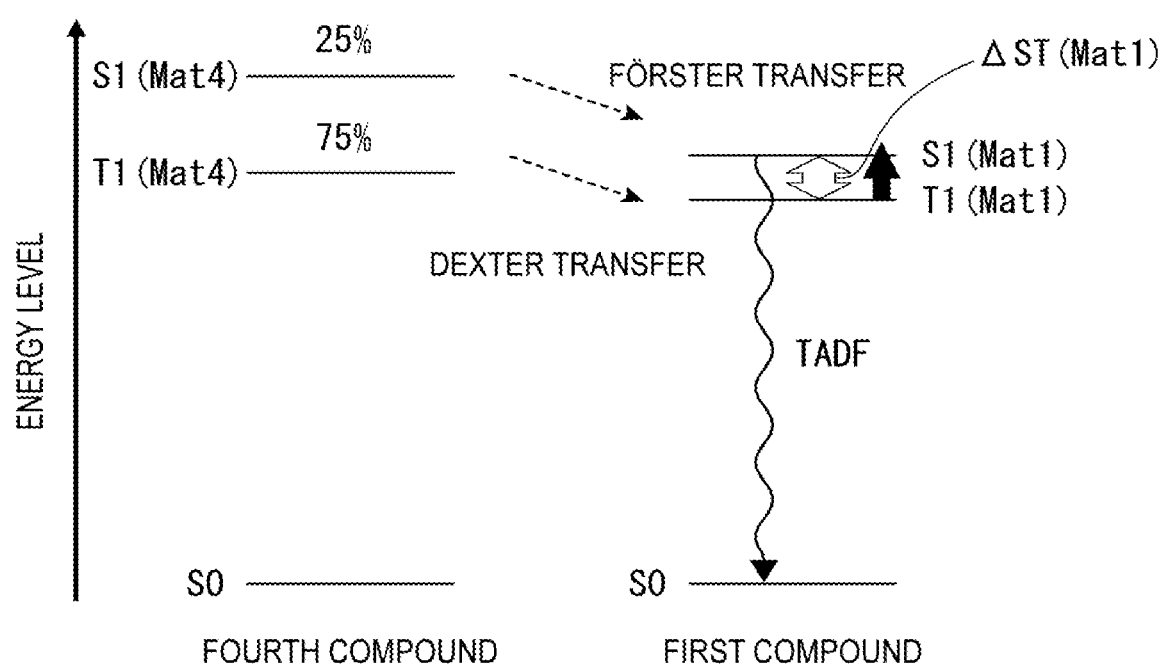
FIG. 6 shows a relationship in energy level and energy transfer between the first compound and a fourth compound in an emitting layer of an exemplary organic electroluminescence device according to a fifth exemplary embodiment of the invention.

FIG. 6 shows an example of a relationship between energy levels of the first and fourth compounds in the emitting layer. In FIG. 6, S0 represents a ground state. S1(Mat1) represents the lowest singlet state of the first compound. T1(Mat1) represents the lowest triplet state of the first compound. S1(Mat4) represents the lowest singlet state of the fourth compound. T1(Mat4) represents the lowest triplet state of the fourth compound. Dashed arrows in FIG. 6 represent energy transfer from the fourth compound to the first compound in the lowest singlet state and in the lowest triplet state, respectively. An energy transfer occurs by Forster transfer from the lowest singlet state S1 of the fourth compound to the lowest singlet state S1 of the first compound or an energy transfer occurs by Dexter transfer from the lowest triplet stateT1 of the fourth compound to the lowest triplet stateT1 of the first compound. Further, when a material having a small ΔST(Mat1) is used as the first compound, inverse intersystem crossing can be caused by a heat energy from the lowest triplet state T1 to the lowest singlet state S1 in the first compound. Consequently, fluorescence from the lowest singlet state S1 of the first compound can be observed. It is inferred that the internal quantum efficiency can be theoretically raised up to 100% also by using delayed fluorescence by the TADF mechanism.

The organic EL device according to the fifth exemplary embodiment contains the first compound that is the compound according to the first exemplary embodiment (at least one of the compounds represented by the formulae (11) to (13)), and the fourth compound having the singlet energy larger than that of the first compound in the emitting layer.

The organic EL device according to the fifth exemplary embodiment is applicable to an electronic device such as a display device and a light-emitting device.

Sixth Exemplary Embodiment

Electronic Device

An electronic device according to a sixth exemplary embodiment is installed with one of the organic EL devices according to the above exemplary embodiments. Examples of the electronic device include a display device and a light-emitting unit. Examples of the display device include a display component (e.g., an organic EL panel module), TV, mobile phone, tablet and personal computer. Examples of the light-emitting unit include an illuminator and a vehicle light.

Modification of Embodiment(s)

It should be noted that the invention is not limited to the above exemplary embodiments but may include any modification and improvement as long as such modification and improvement are compatible with the invention.

For instance, the emitting layer is not limited to a single layer, but may be provided by laminating a plurality of emitting layers. When the organic EL device has a plurality of emitting layers, it is only required that at least one of the emitting layers satisfies the conditions described in the above exemplary embodiments. For instance, the rest of the emitting layers may be a fluorescent emitting layer or a phosphorescent emitting layer with use of emission caused by electron transfer from the triplet excited state directly to the ground state.

When the organic EL device includes the plurality of emitting layers, the plurality of emitting layers may be adjacent to each other, or provide a so-called tandem-type organic EL device in which a plurality of emitting units are layered through an intermediate layer.

For instance, a blocking layer may be provided adjacent to at least one of a side near the anode and a side near the cathode of the emitting layer. The blocking layer is preferably provided in contact with the emitting layer to at least block holes, electrons or excitons.

For instance, when the blocking layer is provided in contact with the cathode-side of the emitting layer, the blocking layer permits transport of electrons, but blocks holes from reaching a layer provided near the cathode (e.g., the electron transporting layer) beyond the blocking layer. When the organic EL device includes the electron transporting layer, the organic EL device preferably includes the blocking layer between the emitting layer and the electron transporting layer.

When the blocking layer is provided in contact with the anode-side of the emitting layer, the blocking layer permits transport of holes, but blocks electrons from reaching a layer provided near the anode (e.g., the hole transporting layer) beyond the blocking layer. When the organic EL device includes the hole transporting layer, the organic EL device preferably includes the blocking layer between the emitting layer and the hole transporting layer.

Moreover, the blocking layer may abut on the emitting layer so that excited energy does not leak out from the emitting layer toward neighboring layer(s). The blocking layer blocks excitons generated in the emitting layer from being transferred to a layer(s) (e.g., the electron transporting layer and the hole transporting layer) closer to the electrode(s) beyond the blocking layer.

The emitting layer and the blocking layer are preferably bonded with each other.

Specific structure and shape of the components in the present invention may be designed in any manner as long as an object of the present invention can be achieved.

Herein, numerical ranges represented by "x to y" represents a range whose lower limit is the value (x) recited before "to" and whose upper limit is the value (y) recited after "to."

Rx and Ry are mutually bonded to form a ring, which means herein, for instance, that Rx and Ry contain a carbon atom, a nitrogen atom, an oxygen atom, a sulfur atom or a silicon atom, the atom (a carbon atom, a nitrogen atom, an oxygen atom, a sulfur atom or a silicon atom) contained in Rx and the atom (a carbon atom, a nitrogen atom, an oxygen atom, a sulfur atom or a silicon atom) contained in Ry are mutually bonded via a single bond, a double bond, a triple bond or a divalent linking group to form a ring having 5 or more ring atoms (specifically, a heterocyclic ring or an aromatic hydrocarbon ring). x represents a number, a character or a combination of a number and a character. y represents a number, a character or a combination of a number and a character.

The divalent linking group is not particularly limited and is exemplified by —O—, —CO—, —CO$_2$—, —S—, —SO—, —SO$_2$—, —NH—, —NRa—, and a group obtained by combining two or more linking groups of those.

Specific examples of the heterocyclic ring include a cyclic structure (heterocyclic ring) obtained by removing a bond from a "heteroaryl group Sub$_2$" exemplarily shown in the later-described "Description of Each Substituent in Formula." The heterocyclic ring may have a substituent.

Specific examples of the heterocyclic ring include a cyclic structure (heterocyclic ring) obtained by removing a bond from a "aryl group Sub$_1$" exemplarily shown in the later-described "Description of Each Substituent in Formula." The aromatic hydrocarbon ring may have a substituent.

Examples of Ra include a substituted or unsubstituted alkyl group Sub$_3$ having 1 to 30 carbon atoms, a substituted or unsubstituted aryl group Sub$_1$ having 6 to 30 ring carbon atoms, and a substituted or unsubstituted heteroaryl Sub$_2$ group having 5 to 30 ring atoms, which are exemplarily shown in the later-described "Description of Each Substituent in Formula."

Rx and Ry are mutually bonded to form a ring, which means, for instance, that an atom contained in Rx$_1$ and an atom contained in Ry$_1$ in a molecular structure represented by a formula (E1) below form a ring (cyclic structure) E represented by a formula (E2); that an atom contained in Rx$_1$ and an atom contained in $Ry_1$ in a molecular structure represented by a formula (F1) below form a ring (cyclic structure) F represented by a formula (F2); that an atom contained in $Rx_1$ and an atom contained in $Ry_1$ in a molecular structure represented by a formula (G1) below form a ring (cyclic structure) G represented by a formula (G2); that an atom contained in $Rx_1$ and an atom contained in $Ry_1$ in a molecular structure represented by a formula (H1) below form a ring (cyclic structure) H represented by a formula (H2); and that an atom contained in $Rx_1$ and an atom contained in $Ry_1$ in a molecular structure represented by a formula (I1) below form a ring (cyclic structure) I represented by a formula (I2).

In the formulae (E1) to (I1), * each independently represents a bonding position to another atom in a molecule. Two * in the formula (E1) correspond one-to-one to two * in the formula (E2). Two * in the formula (F1) correspond one-to-one to two * in the formula (F2). Two * in the formula (G1) correspond one-to-one to two * in the formula (G2). Two * in the formula (H1) correspond one-to-one to two * in the formula (H2). Two * in the formula (I1) correspond one-to-one to two * in the formula (I2).

[Formula 152]

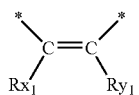
(E1)

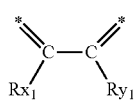
(F1)

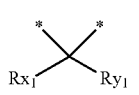
(G1)

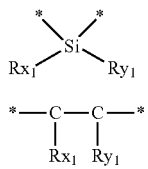
(H1)

(I1)

[Formula 153]

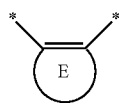
(E2)

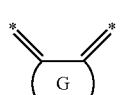
(F2)

(G2)

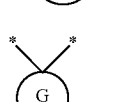
(H2)

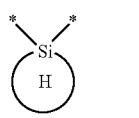

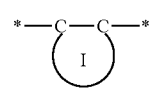
(I2)

In the molecular structures represented by the respective formulae (E2) to (I2), E to I each represent a cyclic structure (the ring having 5 or more ring atoms). In the formulae (E2) to (I2), * each independently represents a bonding position to another atom in a molecule. Two * in the formula (E2) correspond one-to-one to two * in the formula (E1). Similarly, two * in each of the formulae (F2) to (I2) correspond one-to-one to two * in in each of the formulae (F1) to (I1).

For instance, in the formula (E1), $Rx_1$ and $Ry_1$ are mutually bonded to for the ring E in the formula (E2) and the ring E is an unsubstituted benzene ring, the molecular structure represented by the formula (E1) is a molecular structure represented by a formula (E3) below. Herein, two * in the formula (E3) each independently correspond to two * in the formula (E2) and the formula (E1).

For instance, in the formula (E1), $Rx_1$ and $Ry_1$ are mutually bonded to for the ring E in the formula (E2) and the ring E is an unsubstituted pyrrole ring, the molecular structure represented by the formula (E1) is a molecular structure represented by a formula (E4) below. Herein, two * in the formula (E4) each independently correspond to two * in the formula (E2) and the formula (E1). In the formulae (E3) and (E4), * each independently represents a bonding position to another atom in a molecule.

[Formula 154]

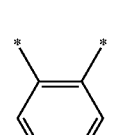
(E3)

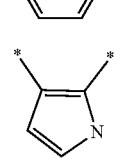
(E4)

Herein, the ring carbon atoms refer to the number of carbon atoms among atoms forming a ring of a compound (e.g., a monocyclic compound, fused-ring compound, cross-linking compound, carbon ring compound, and heterocyclic compound) in which the atoms are bonded to each other to form the ring. When the ring is substituted by a substituent(s), carbon atom(s) contained in the substituent(s) is not counted in the ring carbon atoms. Unless specifically described, the same applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring and/or a naphthalene ring is substituted by a substituent (e.g., an alkyl group), the number of carbon atoms of the alkyl group is not counted in the number of the ring carbon atoms. When a fluorene ring is substituted by a substituent (e.g., a fluorene ring) (i.e., a spirofluorene ring is included), the number of carbon atoms of the fluorene ring as the substituent is not counted in the number of the ring carbon atoms of the fluorene ring.

Herein, the ring atoms refer to the number of atoms forming a ring of a compound (e.g., a monocyclic compound, fused-ring compound, crosslinking compound, carbon ring compound, and heterocyclic compound) in which the atoms are bonded to each other to form the ring (e.g., monocyclic ring, fused ring, ring assembly). Atom(s) not forming a ring and atom(s) included in a substituent when the ring is substituted by the substituent are not counted in the number of the ring atoms. Unless specifically described, the same applies to the "ring atoms" described later. For instance, a pyridine ring has six ring atoms, a quinazoline ring has ten ring atoms, and a furan ring has five ring atoms. A hydrogen atom(s) and/or an atom(s) of a substituent which are bonded to carbon atoms of a pyridine ring and/or quinazoline ring are not counted in the ring atoms. When a fluorene ring is substituted by a substituent (e.g., a fluorene ring) (i.e., a spirofluorene ring is included), the number of atoms of the fluorene ring as the substituent is not counted in the number of the ring atoms of the fluorene ring.

Description of Each Substituent in Formula Herein

The aryl group (occasionally referred to as an aromatic hydrocarbon group) herein is exemplified by an aryl group $Sub_1$. The aryl group $Sub_1$ is at least one group selected from the group consisting of a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

Herein, the aryl group $Sub_1$ preferably has 6 to 30 ring carbon atoms, more preferably 6 to 20 ring carbon atoms, further preferably 6 to 14 ring carbon atoms, more further preferably 6 to 12 ring carbon atoms. Among the aryl group $Sub_1$, a phenyl group, biphenyl group, naphthyl group, phenanthryl group, terphenyl group and fluorenyl group are preferable. A carbon atom in a position 9 of each of 1-fluorenyl group, 2-fluorenyl group, 3-fluorenyl group and 4-fluorenyl group is preferably substituted by a substituted or unsubstituted alkyl group $Sub_3$ or a substituted or unsubstituted aryl group $Sub_1$ described later herein.

The heteroaryl group (occasionally referred to as heterocyclic group, heteroaromatic ring group or aromatic heterocyclic group) herein is exemplified by a heterocyclic group $Sub_2$. The heterocyclic group $Sub_2$ is a group containing, as a hetero atom(s), at least one atom selected from the group consisting of nitrogen, sulfur, oxygen, silicon, selenium atom and germanium atom. Preferably, the heterocyclic group $Sub_2$ contains, as a hetero atom(s), at least one atom selected from the group consisting of nitrogen, sulfur and oxygen.

Examples of the heterocyclic group $Sub_2$ herein are a pyridyl group, pyrimidinyl group, pyrazinyl group, pyridazinyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothienyl group, benzoxazolyl group, benzothiazolyl group, benzisoxazolyl group, benzisothiazolyl group, benzoxadiazolyl group, benzothiadiazolyl group, dibenzofuranyl group, dibenzothienyl group, piperidinyl group, pyrrolidinyl group, piperazinyl group, morpholyl group, phenazinyl group, phenothiazinyl group, and phenoxazinyl group.

Herein, the heterocyclic group $Sub_2$ preferably has 5 to 30 ring atoms, more preferably 5 to 20 ring atoms, further preferably 5 to 14 ring atoms. Among the above heterocyclic group $Sub_2$, a 1-dibenzofuranyl group, 2-dibenzofuranyl group, 3-dibenzofuranyl group, 4-dibenzofuranyl group, 1-dibenzothienyl group, 2-dibenzothienyl group, 3-dibenzothienyl group, 4-dibenzothienyl group, 1-carbazolyl group, 2-carbazolyl group, 3-carbazolyl group, 4-carbazolyl group, and 9-carbazolyl group are further more preferable. A nitrogen atom in position 9 of 1-carbazolyl group, 2-carbazolyl group, 3-carbazolyl group and 4-carbazolyl group is preferably substituted by the substituted or unsubstituted aryl group $Sub_1$ or the substituted or unsubstituted heterocyclic group $Sub_2$ described herein.

Herein, the heterocyclic group $Sub_2$ may be a group derived from any one of moieties represented by formulae (XY-1) to (XY-18) below.

[Formula 155]

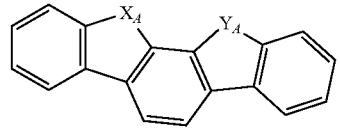

(XY-1)

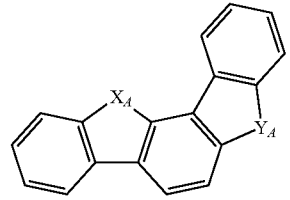

(XY-2)

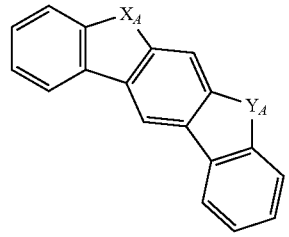

(XY-3)

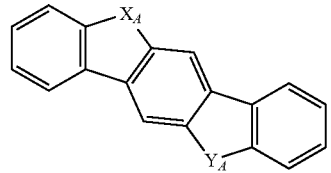

(XY-4)

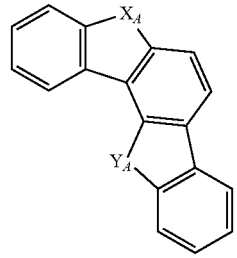

(XY-5)

(XY-6) 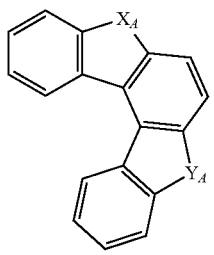

[Formula 156]

(XY-7) 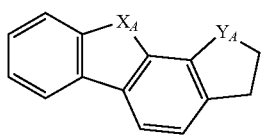

(XY-8) 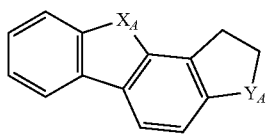

(XY-9) 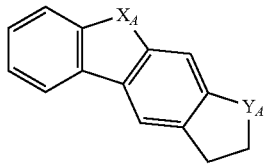

(XY-10) 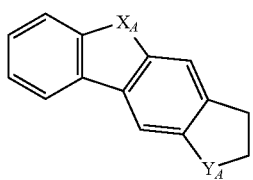

(XY-11) 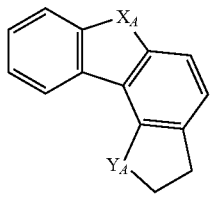

(XY-12) 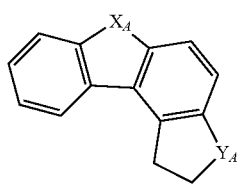

[Formula 157]

(XY-13) 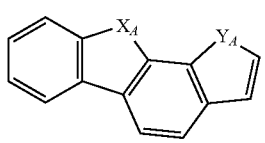

(XY-14) 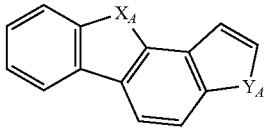

(XY-15) 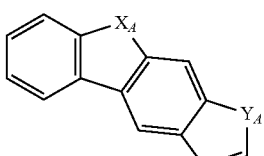

(XY-16) 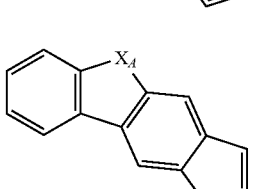

(XY-17) 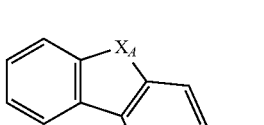

(XY-18) 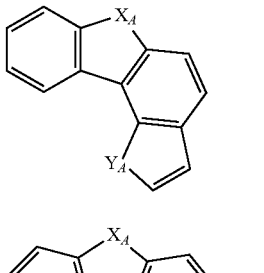

In the formulae (XY-1) to (XY-18), $X_A$ and $Y_A$ each independently represent a hetero atom, and preferably represent an oxygen atom, sulfur atom, selenium atom, silicon atom or germanium atom. Each of the moieties represented by the respective formulae (XY-1) to (XY-18) has a bond at any position to provide a heterocyclic group. The heterocyclic group may be substituted.

Herein, the heterocyclic group $Sub_2$ may be a group represented by one of formulae (XY-19) to (XY-22) below. Moreover, the position of the bond may be changed as needed

[Formula 158]

(XY-19) 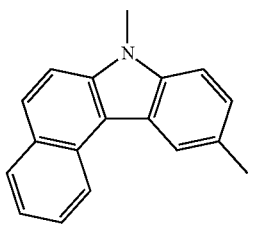

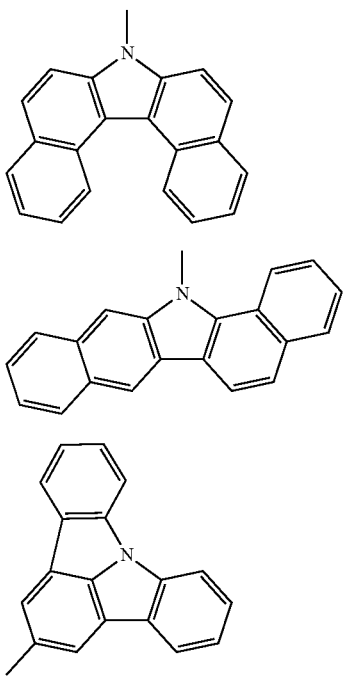

(XY-20)

(XY-21)

(XY-22)

The alkyl group herein may be any one of a linear alkyl group, branched linear alkyl group and cyclic linear alkyl group.

The alkyl group herein is exemplified by an alkyl group $Sub_3$.

The linear alkyl group herein is exemplified by a linear alkyl group $Sub_{31}$.

The branched alkyl group herein is exemplified by a branched alkyl group $Sub_{32}$.

The cyclic alkyl group herein is exemplified by a cyclic alkyl group $Sub_{33}$.

For instance, the alkyl group $Sub_3$ is at least one group selected from the group consisting of the linear alkyl group $Sub_{31}$, branched alkyl group $Sub_{32}$, and cyclic alkyl group $Sub_{33}$.

The linear alkyl group $Sub_{31}$ or branched alkyl group $Sub_{32}$ is exemplified by at least one group selected from the group consisting of a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

Herein, the linear alkyl group $Sub_{31}$ or branched alkyl group $Sub_{32}$ preferably has 1 to 30 carbon atoms, more preferably 1 to 20 carbon atoms, further preferably 1 to 10 carbon atoms, further more preferably 1 to 6 carbon atoms. The linear alkyl group $Sub_{31}$ or branched alkyl group $Sub_{32}$ is further more preferably a methyl group, ethyl group, propyl group, isopropyl group, n-butyl group, s-butyl group, isobutyl group, t-butyl group, n-pentyl group, n-hexyl group, amyl group, isoamyl group and neopentyl group.

Herein, the cyclic alkyl group is exemplified by a cycloalkyl group $Sub_{331}$.

The cycloalkyl group $Sub_{331}$ herein is exemplified by at least one group selected from the group consisting of a cyclopropyl group, cyclobutyl group, cyclopentyl group, cyclohexyl group, 4-metylcyclohexyl group, adamantyl group and norbornyl group. The cycloalkyl group $Sub_{331}$ preferably has 3 to 30 ring carbon atoms, more preferably 3 to 20 ring carbon atoms, further preferably 3 to 10 ring carbon atoms, further more preferably 5 to 8 ring carbon atoms. Among the cycloalkyl group $Sub_{331}$, a cyclopentyl group and a cyclohexyl group are further more preferable.

Herein, an alkyl halide group is exemplified by an alkyl halide group $Sub_4$. The alkyl halide group $Sub_4$ is provided by substituting the alkyl group $Sub_3$ with at least one halogen atom, preferably at least one fluorine atom.

Herein, the alkyl halide group $Sub_4$ is exemplified by at least one group selected from the group consisting of a fluoromethyl group, difluoromethyl group, trifluoromethyl group, fluoroethyl group, trifluoromethylmethyl group, trifluoroethyl group, and pentafluoroethyl group.

Herein, a substituted silyl group is exemplified by a substituted silyl group $Sub_5$. The substituted silyl group $Sub_5$ is exemplified by at least one group selected from the group consisting of an alkylsilyl group $Sub_{51}$ and an arylsilyl group $Sub_{52}$.

Herein, the alkylsilyl group $Sub_{51}$ is exemplified by a trialkylsilyl group $Sub_{511}$ having the above-described alkyl group $Sub_3$.

The trialkylsilyl group $Sub_{511}$ is exemplified by at least one group selected from the group consisting of a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups $Sub_3$ in the trialkylsilyl group $Sub_{511}$ may be mutually the same or different.

Herein, the arylsilyl group $Sub_{52}$ is exemplified by at least one group selected from the group consisting of a dialkylarylsilyl group $Sub_{521}$, alkyldiarylsilyl group $Sub_{522}$ and triarylsilyl group $Sub_{523}$.

The dialkylarylsilyl group $Sub_{521}$ is exemplified by a dialkylarylsilyl group including two alkyl groups $Sub_3$ and one aryl group $Sub_1$. The dialkylarylsilyl group $Sub_{521}$ preferably has 8 to 30 carbon atoms.

The alkyldiarylsilyl group $Sub_{522}$ is exemplified by an alkyldiarylsilyl group including one alkyl group $Sub_3$ and two aryl groups $Sub_1$. The alkyldiarylsilyl group $Sub_{522}$ preferably has 13 to 30 carbon atoms.

The triarylsilyl group $Sub_{523}$ is exemplified by a triarylsilyl group including three aryl groups $Sub_1$. The triarylsilyl group $Sub_{523}$ preferably has 18 to 30 carbon atoms.

Herein, a substituted or unsubstituted alkyl sulfonyl group is exemplified by an alkyl sulfonyl group $Sub_6$. The alkyl sulfonyl group $Sub_6$ is represented by —$SO_2R_w$. $R_w$ in —$SO_2R_w$ represents a substituted or unsubstituted alkyl group $Sub_3$ described above.

Herein, an aralkyl group (occasionally referred to as an arylalkyl group) is exemplified by an aralkyl group $Sub_7$. An aryl group in the aralkyl group $Sub_7$ includes, for instance, at least one of the above-described aryl group $Sub_1$ and the above-described heteroaryl group $Sub_2$.

The aralkyl group $Sub_7$ herein is preferably a group having the aryl group $Sub_1$ and is represented by —$Z_3$—$Z_4$. $Z_3$ is exemplified by an alkylene group corresponding to the above alkyl group $Sub_3$. $Z_4$ is exemplified by the above aryl group $Sub_1$. In this aralkyl group $Sub_7$, an aryl moiety has 6 to 30 carbon atoms (preferably 6 to 20 carbon atoms, more preferably 6 to 12 carbon atoms) and an alkyl moiety has 1 to 30 carbon atoms (preferably 1 to 20 carbon atoms, more preferably 1 to 10 carbon atoms, further preferably 1 to 6 carbon atoms). The aralkyl group $Sub_7$ is exemplified by at least one group selected from the group consisting of a benzyl group, 2-phenylpropane-2-yl group, 1-phenylethyl group, 2-phenylethyl group, 1-phenylisopropyl group, 2-phenylisopropyl group, phenyl-t-butyl group, α-naphthyl-methyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

The alkoxy group herein is exemplified by an alkoxy group $Sub_8$. The alkoxy group $Sub_8$ is represented by —$OZ_1$. $Z_1$ is exemplified by the above alkyl group $Sub_3$. The alkoxy group $Sub_8$ is exemplified by at least one group selected from the group consisting of a methoxy group, ethoxy group, propoxy group, butoxy group, pentyloxy group and hexyloxy group. The alkoxy group $Sub_8$ preferably has 1 to 30 carbon atoms, more preferably 1 to 20 carbon atoms.

Herein, an alkoxy halide group is exemplified by an alkoxy halide group $Sub_9$. The alkoxy halide group $Sub_9$ is provided by substituting the alkoxy group $Sub_8$ with at least one halogen atom, preferably at least one fluorine atom.

Herein, an aryloxy group (sometime referred to as an arylalkoxy group) is exemplified by an arylalkoxy group $Sub_{10}$. An aryl group in the arylalkoxy group $Sub_{10}$ includes at least one of the aryl group $Sub_1$ and the heteroaryl group $Sub_2$.

The arylalkoxy group $Sub_{10}$ herein is represented by —$OZ_2$. $Z_2$ is exemplified by the aryl group $Sub_1$ or the heteroaryl group $Sub_2$. The arylalkoxy group $Sub_{10}$ preferably has 6 to 30 ring carbon atoms, more preferably 6 to 20 ring carbon atoms. The arylalkoxy group $Sub_{10}$ is exemplified by a phenoxy group.

Herein, a substituted amino group is exemplified by a substituted amino group $Sub_{11}$. The substituted amino group $Sub_{11}$ is exemplified by at least one group selected from the group consisting of an arylamino group $Sub_{111}$ and an alkylamino group $Sub_{112}$.

The arylamino group $Sub_{111}$ is represented by —$NHR_{v1}$ or —$N(R_{v1})_2$. $R_{v1}$ is exemplified by the aryl group $Sub_1$. Two $R_{v1}$ in —$N(R_{v1})_2$ are mutually the same or different.

The alkylamino group $Sub_{112}$ is represented by —$NHR_{v2}$ or —$N(R_{v2})_2$. $R_{v2}$ is exemplified by the alkyl group $Sub_3$. Two $R_{v2}$ in —$N(R_{v2})_2$ are mutually the same or different.

Herein, the alkenyl group is exemplified by an alkenyl group $Sub_{12}$. The alkenyl group $Sub_{12}$, which is linear or branched, is exemplified by at least one group selected from the group consisting of a vinyl group, propenyl group, butenyl group, oleyl group, eicosapentaenyl group, docosahexaenyl group, styryl group, 2,2-diphenylvinyl group, 1,2, 2-triphenylvinyl group, and 2-phenyl-2-propenyl group.

The alkynyl group herein is exemplified by an alkynyl group $Sub_{13}$. The alkynyl group $Sub_{13}$ may be linear or branched and is at least one group selected from the group consisting of an ethynyl group, a propynyl group and a 2-phenylethynyl group.

The alkylthio group herein is exemplified by an alkylthio group $Sub_{14}$.

The alkylthio group $Sub_{14}$ is represented by —$SR_{v3}$. $R_{v3}$ is exemplified by the alkyl group $Sub_3$. The alkylthio group $Sub_{14}$ preferably has 1 to 30 carbon atoms, more preferably 1 to 20 carbon atoms.

The arylthio group herein is exemplified by an arylthio group $Sub_{15}$.

The arylthio group $Sub_{15}$ is represented by —$SR_{v4}$. $R_{v4}$ is exemplified by the aryl group $Sub_1$. The arylthio group $Sub_{15}$ preferably has 6 to 30 ring carbon atoms, more preferably 6 to 20 ring carbon atoms.

Herein, examples of the halogen atom include a fluorine atom, a chlorine atom, a bromine atom and an iodine atom, among which a fluorine atom is preferable.

A substituted phosphino group herein is exemplified by a substituted phosphino group $Sub_{16}$. The substituted phosphino group $Sub_{16}$ is exemplified by a phenyl phosphanyl group.

An arylcarbonyl group herein is exemplified by an arylcarbonyl group $Sub_{17}$. The arylcarbonyl group $Sub_{17}$ is represented by —COY'. Y' is exemplified by the aryl group $Sub_1$. Herein, the arylcarbonyl group $Sub_{17}$ is exemplified by at least one group selected from the group consisting of a phenyl carbonyl group, diphenyl carbonyl group, naphthyl carbonyl group, and triphenyl carbonyl group.

An acyl group herein is exemplified by an acyl group $Sub_{18}$. The acyl group $Sub_{18}$ is represented by —COR'. R' is exemplified by the alkyl group $Sub_3$. The acyl group $Sub_{18}$ herein is exemplified by at least one group selected from the group consisting of an acetyl group and a propionyl group.

A substituted phosphoryl group herein is exemplified by a substituted phosphoryl group $Sub_{19}$. The substituted phosphoryl group $Sub_{19}$ is represented by a formula (P) below.

[Formula 159]

(P)

In the formula (P), $Ar_{P1}$ and $Ar_{P2}$ are any one substituent selected from the group consisting of the above alkyl group $Sub_3$ and the above aryl group $Sub_1$.

An ester group herein is exemplified by an ester group $Sub_{20}$. The ester group $Sub_{20}$ is exemplified by an alkyl ester group.

An alkyl ester group herein is exemplified by an alkyl ester group $Sub_{201}$. The alkyl ester group $Sub_{201}$ is represented by —C(=O)O$R^E$. $R^E$ is exemplified by a substituted or unsubstituted alkyl group $Sub_3$ described above.

A siloxanyl group herein is exemplified by a siloxanyl group $Sub_{21}$. The siloxanyl group $Sub_{21}$ is a silicon compound group through an ether bond. The siloxanyl group $Sub_{21}$ is exemplified by a trimethylsiloxanyl group.

A carbamoyl group herein is represented by —$CONH_2$.

A substituted carbamoyl group herein is exemplified by a carbamoyl group $Sub_{22}$. The carbamoyl group $Sub_{22}$ is represented by —CONH—$Ar^C$ or —CONH—$R^C$. $Ar^C$ is exemplified by at least one group selected from the group consisting of a substituted or unsubstituted aryl group $Sub_1$ (preferably 6 to 10 ring carbon atoms) and a substituted or unsubstituted heteroaryl group $Sub_2$ (preferably 5 to 14 ring atoms). $Ar^C$ may be a group formed by bonding the aryl group $Sub_1$ and the heteroaryl group $Sub_2$.

$R^C$ is exemplified by a substituted or unsubstituted alkyl group $Sub_3$ described above (preferably having 1 to 6 carbon atoms).

Herein, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a ring including a saturated ring, unsaturated ring, or aromatic ring.

Herein, a hydrogen atom includes isotope having different numbers of neutrons, specifically, protium, deuterium and tritium.

Hereinafter, an alkyl group $Sub_3$ means at least one group of a linear alkyl group $Sub_{31}$, a branched alkyl group $Sub_{32}$, and a cyclic alkyl group $Sub_{33}$ described in "Description of Each Substituent."

Similarly, a substituted silyl group $Sub_5$ means at least one group of an alkylsilyl group $Sub_{51}$ and an arylsilyl group $Sub_{52}$.

Similarly, a substituted amino group $Sub_{11}$ means at least one group of an arylamino group $Sub_{111}$ and an alkylamino group $Sub_{112}$.

Herein, a substituent for a "substituted or unsubstituted" group is exemplified by a substituent $R_{F1}$. The substituent RFC is at least one group selected from the group consisting of an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{18}$, substituted phosphoryl group $Sub_{19}$, ester group $Sub_{20}$, siloxanyl group $Sub_{21}$, carbamoyl group $Sub_{22}$, unsubstituted amino group, unsubstituted silyl group, halogen atom, cyano group, hydroxyl group, nitro group, and carboxy group.

Herein, the substituent $R_{F1}$ for a "substituted or unsubstituted" group may be a diary) boron group $(Ar_{B1}Ar_{B2}B\text{---})$. $Ar_{B1}$ and $Ar_{B2}$ are exemplified by the above described aryl group $Sub_1$. $Ar_{B1}$ and $Ar_{B2}$ in $Ar_{B1}Ar_{B2}B\text{---}$ are the same or different.

Specific examples and preferable examples of the substituent RFC are the same as those of the substituents described in "Description of Each Substituent" (e.g., an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{18}$, substituted phosphoryl group $Sub_{19}$, ester group $Sub_{20}$, siloxanyl group $Sub_{21}$, and carbamoyl group $Sub_{22}$).

The substituent $R_{F1}$ for a "substituted or unsubstituted" group may be further substituted by at least one group (hereinafter, also referred to as a substitutent $R_{F2}$) selected from the group consisting of an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{18}$, substituted phosphoryl group $Sub_{19}$, ester group $Sub_{20}$, siloxanyl group $Sub_{21}$, carbamoyl group $Sub_{22}$, unsubstituted amino group, unsubstituted silyl group, halogen atom, cyano group, hydroxyl group, nitro group, and carboxy group. Moreover, a plurality of substituents $R_{F2}$ may be bonded to each other to form a ring.

Unsubstituted" for a "substituted or unsubstituted" group means that a group is not substituted by the above-described substituents but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of the substituent $R_{F1}$ of the substituted ZZ group.

Herein, "XX to YY atoms" in the description of "substituted or unsubstituted ZZ group having XX to YY atoms" represent carbon atoms of an unsubstituted ZZ group and do not include atoms of the substituent $R_{F1}$ of the substituted ZZ group.

The same description as the above applies to "substituted or unsubstituted" in compounds or moieties thereof described herein.

Herein, when the substituents are bonded to each other to form a ring, the ring is structured to be a saturated ring, an unsaturated ring, an aromatic hydrocarbon ring or a hetero ring.

Herein, examples of the aromatic hydrocarbon group in the linking group include a divalent or multivalent group obtained by eliminating one or more atoms from the above monovalent aryl group $Sub_1$.

Herein, examples of the heterocyclic group in the linking group include a divalent or multivalent group obtained by eliminating one or more atoms from the above monovalent heteroaryl group $Sub_2$.

EXAMPLES

Example(s) of the invention will be described below. However, the invention is not limited to Example(s).

Compounds

A compound represented by a formula (12), which is used for manufacturing an organic EL device in Example 6, is shown below.

[Formula 160]

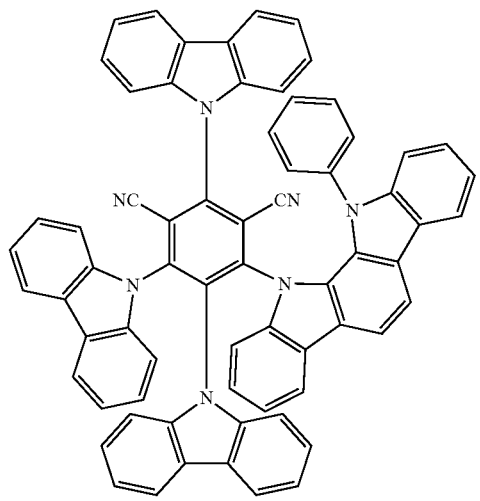

TADF3

Structures of compounds used for manufacturing organic EL devices in Comparatives 2 and 3 are shown below.

[Formula 161]
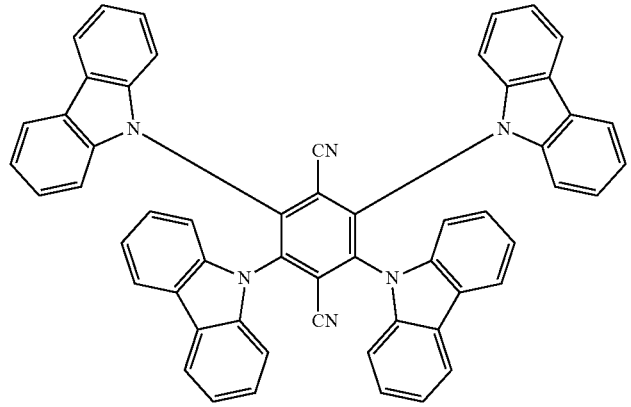
Ref-2
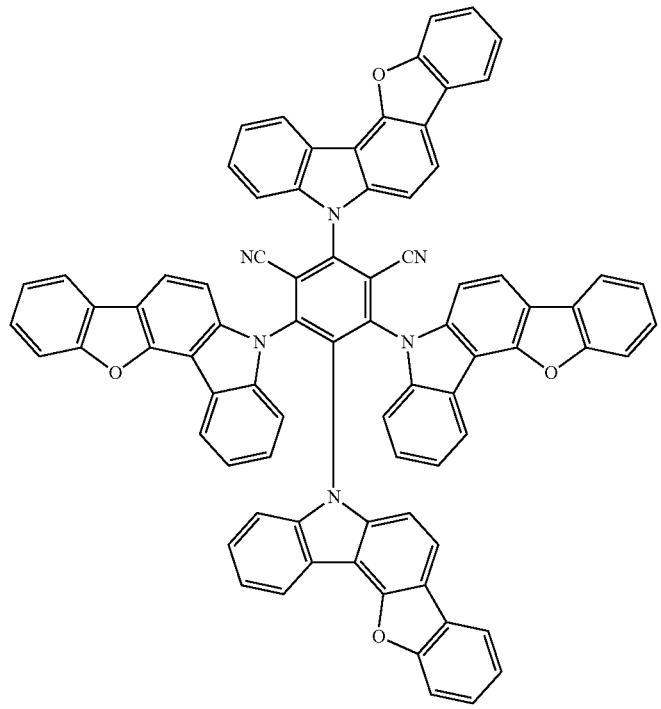
Ref-3

Structures of other compounds used for manufacturing organic EL devices in Example 6 and Comparatives 2 and 3 are shown below.
[Formula 162]
HA
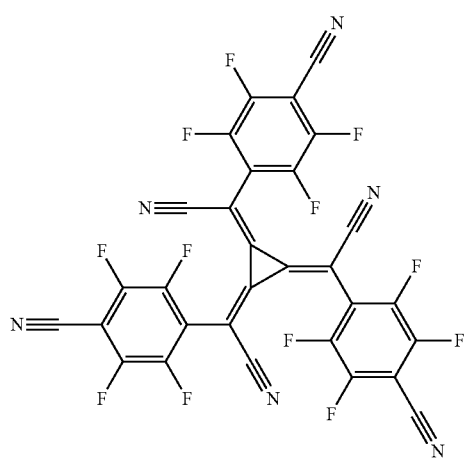
[Formula 164]
CBP
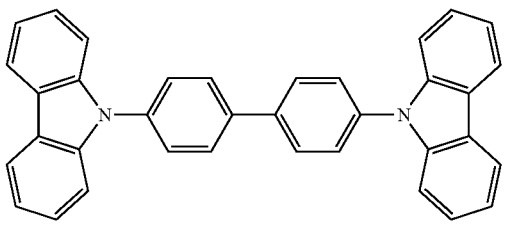
RD
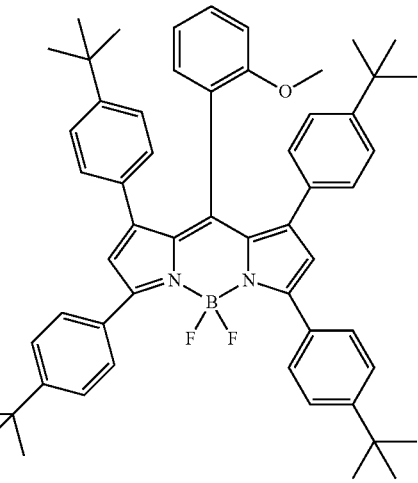
[Formula 163]
HT1
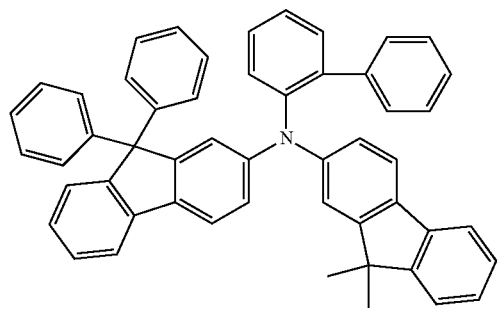
[Formula 165]
ET1
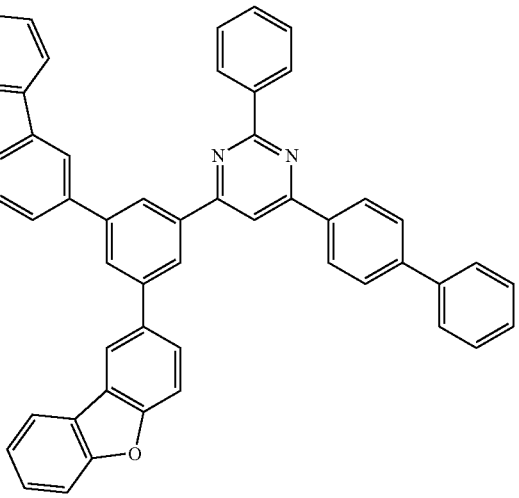
HT2
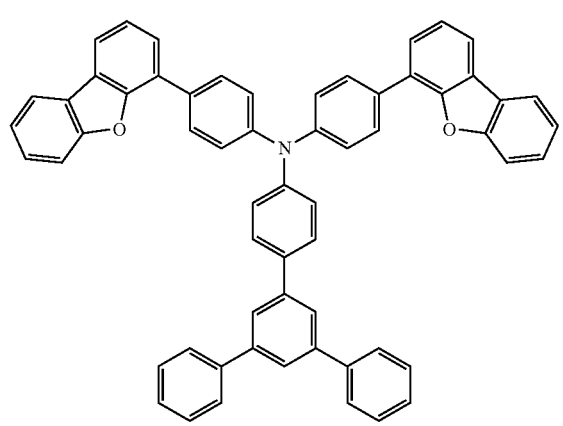
ET2
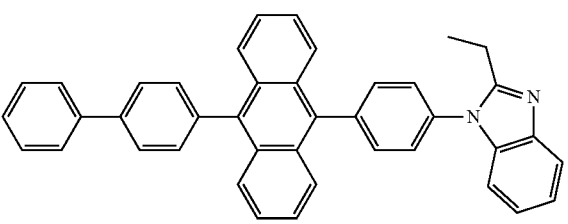
A compound represented by the formula (12) or (13), which is used for the compound evaluation in Examples 1 to 5, is shown below. It should be noted that a compound TADF3 is identical with the compound TADF3 used for manufacturing the organic EL device in Example 6.
[Formula 166]
TADF1
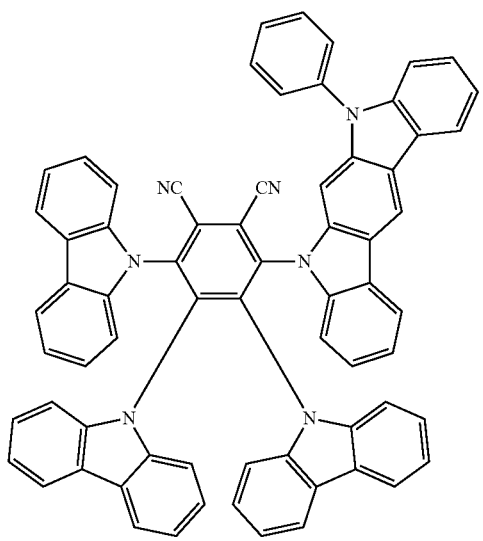
[Formula 167]
TADF3
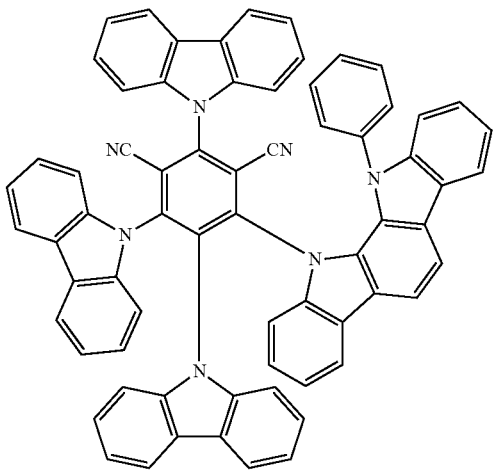
TADF2
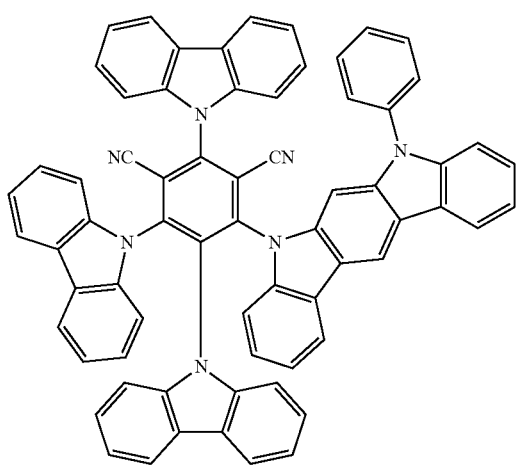
TADF4
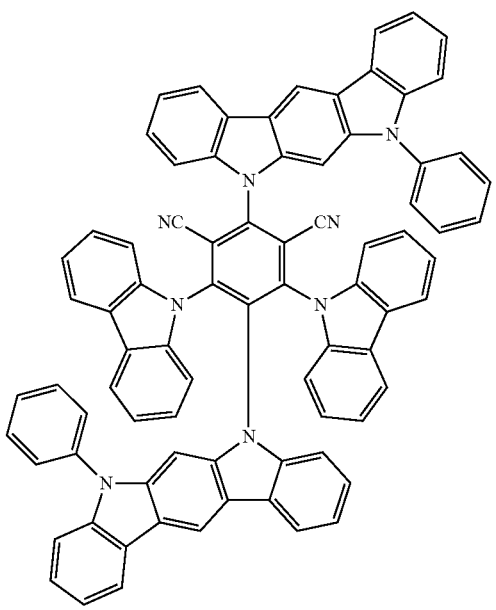

-continued

[Formula 168]

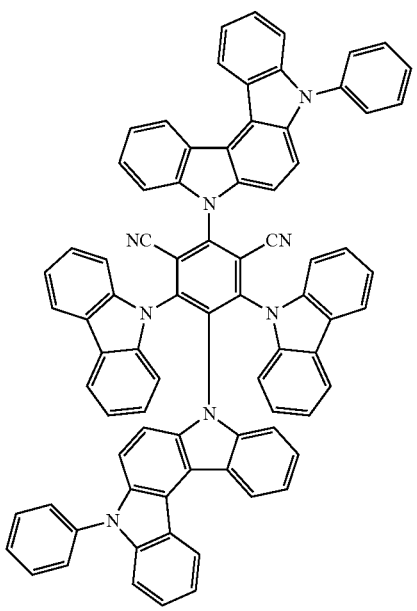

TADF5

The compound of Comparative 1 used for the compound evaluation is shown below.

[Formula 169]

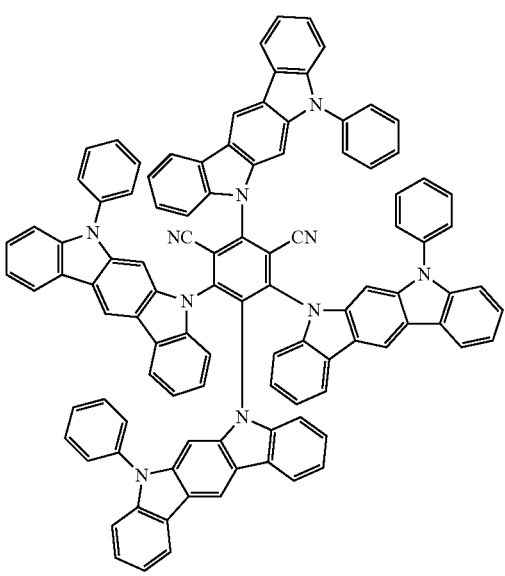

Ref-1

(Comparative Compound 1)

Preparation of Organic EL Device

The organic EL devices were prepared and evaluated as follows.

Example 6

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for one minute. A film of ITO was 130 nm thick.

After the glass substrate having the transparent electrode line was cleaned, the glass substrate was mounted on a substrate holder of a vacuum evaporation apparatus. Firstly, a compound HT1 and a compound HA were co-deposited on a surface of the glass substrate where the transparent electrode line was provided in a manner to cover the transparent electrode, thereby forming a 10-nm-thick hole injecting layer. The concentrations of the compound HT1 and the compound HA in the hole injecting layer were 97 mass % and 3 mass %, respectively.

Next, the compound HT1 was vapor-deposited on the hole injecting layer to form a 200-nm-thick first hole transporting layer.

Next, the compound HT2 was vapor-deposited on the first hole transporting layer to form a 10-nm-thick second hole transporting layer.

Next, the compound TADF3 as the first compound, a compound RD as the second compound, and a compound CBP as the third compound are co-deposited on the second hole transporting layer to form a 25-nm-thick emitting layer as the first organic layer. The concentrations of the compound TADF3, the compound RD, and the compound CBP in the emitting layer were 25 mass %, 1 mass %, and 74 mass %, respectively.

Next, a compound ET1 was vapor-deposited on the emitting layer to form a 10-nm-thick first electron transporting layer.

Next, a compound ET2 was vapor-deposited on the first electron transporting layer to form a 30-nm-thick second electron transporting layer.

Next, lithium fluoride (LiF) was vapor-deposited on the second electron transporting layer to form a 1-nm-thick electron injectable electrode (cathode).

Subsequently, metal aluminum (Al) was vapor-deposited on the electron injectable electrode to form an 80-nm-thick metal Al cathode.

A device arrangement of the organic EL device of Example 6 is roughly shown as follows.

ITO(130)/HT1:HA(10.97%:3%)/HT1(200)/HT2(10)/CBP:TADF3:RD(25.74%: 25%: 1%)/ET1(10)/ET2(30)/LiF(1)/Al(80)

Numerals in parentheses represent a film thickness (unit: nm).

The numerals (97%:3%) represented by percentage in the same parentheses each indicate a ratio (mass %) between the compound HT1 and the compound HA in the hole injecting layer, and the numerals (74%:25%:1%) represented by percentage in the same parentheses each indicate a ratio (mass %) between the third compound, the first compound, and the second compound in the emitting layer. Similar notations apply to the description below.

Comparatives 2 and 3

Organic EL devices in Comparatives 2 and 3 were manufactured in the same manner as in Example 6 except that the emitting layer in Example 6 was replaced by the emitting layers shown in Table 20.

Evaluation of Organic EL Devices

The manufactured organic EL devices were evaluated as follows. Results are shown in Table 20.

Chromaticity CIEx, CIEy, and Main Peak Wavelength $\lambda_p$

Voltage was applied on each of the organic EL devices such that a current density was 10 mA/cm$^2$, where spectral radiance spectra were measured by a spectroradiometer CS-2000 (manufactured by Konica Minolta, Inc.). The chromaticities CIEx and CIEy and main peak wavelength $\lambda_p$ (unit: nm) were calculated based on the obtained spectral-radiance spectra.

Drive Voltage

A voltage (unit: V) was measured when current was applied between the anode and the cathode such that a current density was 10 mA/cm².

TABLE 20

| | Emitting Layer | | | | | | Evaluation | | | |
|---|---|---|---|---|---|---|---|---|---|---|
| | First Compound | | Second Compound | | Third Compound | | | | $\lambda_p$ | Voltage |
| | Type | $S_1$ [eV] | Type | $S_1$ [eV] | Type | $S_1$ [eV] | CIEx | CIEy | [nm] | [V] |
| Example 6 | TADF3 | 2.48 | RD | 2.02 | CBP | 3.41 | 0.63 | 0.37 | 627 | 3.99 |
| Comparative 2 | Ref-2 | 2.62 | RD | | CBP | | 0.67 | 0.33 | 630 | 4.47 |
| Comparative 3 | Ref-3 | 2.44 | RD | | CBP | | 0.66 | 0.34 | 629 | 4.36 |

The organic EL device in Example 6 including the compound represented by the formula (12) that is the first compound, the fluorescent compound that is the second compound, and the third compound exhibited a lower drive voltage than those of the organic EL devices in Comparatives 2 and 3.

Evaluation of Compounds

Physical properties of the compounds were measured by the following method.

Weight Reduction Temperature

A 1%-weight reduction temperature and a 5%-weight reduction temperature were measured with a simultaneous thermogravimetry/differential thermal analyzer under the following conditions. Results are shown in Table 21.

Thermogravimetry-differential thermal analysis is a method of continuously measuring mass changes of a sample when the sample is heated, and used for detecting physical changes accompanied by the mass changes such as sublimation and evaporation.

Therefore, in this evaluation, a "high" weight reduction temperature and a "low" weight reduction temperature obtained by TG-DTA are regarded as a "high" sublimation temperature and a "low" sublimation temperature, respectively, under high vacuum. Herein, "under high vacuum" refers to a range from $1.0 \times 10^{-6}$ Pa to $1.0 \times 10^{-3}$ Pa.

Measurement Conditions

Device: thermogravimetry/differential thermal analyzer (STA7200RV manufactured by Hitach High-Tech Corporation)

Container: aluminum pan

Mass of Sample: 3.0 mg

Measurement Atmosphere: nitrogen gas atmosphere

Temperature Rise Rate: 10 degrees C. per minute

Measurement Range: from 35 degrees C. to 600 degrees C.

Delayed Fluorescence Properties

Delayed Fluorescence of Compound TADF1

Delayed fluorescence properties were checked by measuring transient photoluminescence (PL) using a device shown in FIG. 2. The compound TADF1 is dissolved in toluene to prepare a dilute solution with an absorbance of 0.05 or less at the excitation wavelength to eliminate the contribution of self-absorption. In order to prevent quenching due to oxygen, the sample solution was frozen and degassed and then sealed in a cell with a lid under an argon atmosphere to obtain an oxygen-free sample solution saturated with argon.

The fluorescence spectrum of the sample solution was measured with a spectrofluorometer FP-8600 (manufactured by JASCO Corporation), and the fluorescence spectrum of a 9,10-diphenylanthracene ethanol solution was measured under the same conditions. Using the fluorescence area intensities of both spectra, the total fluorescence quantum yield is calculated by an equation (1) in Morris et al. J. Phys. Chem. 80 (1976) 969.

Prompt emission was observed immediately when the excited state was achieved by exciting the compound TADF1 with a pulse beam (i.e., a beam emitted from a pulse laser) having a wavelength to be absorbed by the compound TADF1, and Delay emission was observed not immediately when the excited state was achieved but after the excited state was achieved. The delayed fluorescence in Examples means that an amount of Delay Emission is 5% or more with respect to an amount of Prompt Emission. Specifically, provided that the amount of Prompt emission is denoted by $X_P$ and the amount of Delay emission is denoted by $X_D$, the delayed fluorescence means that a value of $X_D/X_P$ is 0.05 or more.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 2.

It was confirmed that the amount of Delay Emission was 5% or more with respect to the amount of Prompt Emission in the compound TADF1.

Specifically, the value of $X_D/X_P$ was 0.05 or more in the compound TADF1.

Delayed Fluorescence Properties of Compounds TADF2 to TADF5 and Ref-1 to Ref-3

Compounds TADF2 to TADF5 and Ref-1 to Ref-3 were checked in terms of delayed fluorescence in the same manner as above except that the compound TADF1 was replaced by the compounds TADF2 to TADF5 and Ref-1 to Ref-3.

The value of $X_D/X_P$ was 0.05 or more in the compounds TADF2 to TADF5 and Ref-1 to Ref-3.

Singlet Energy $S_1$

Singlet energy $S_1$ of each of the compounds TADF1 to TADF5, RD, CBP, and Ref-1 to Ref-3 was measured according to the above-described solution method. Results are shown in Tables 20 and 21.

ΔST $T_{77K}$ of each of the compounds TADF1 to TADF5 and Ref-1 to Ref-3 was measured. ΔST was checked from the measurement results of $T_{77K}$ and the values of the singlet energy $S_1$ described above. Results are shown in Tables 20 and 21.

$T_{77K}$ of each of the compounds TADF1 to TADF5 and Ref-1 to Ref-3 was measured by the measurement method described above in "Relationship between Triplet Energy and Energy Gap at 77K."

ΔST of each of each of the compounds TADF1 to TADF5 and Ref-1 to Ref-2 was less than 0.01 eV. ΔST of the compound Ref-3 was 0.22 eV.

Main Peak Wavelength λ of Compounds

A 5-μmol/L toluene solution of each of the compounds (measurement target) was prepared and put in a quartz cell. A fluorescence spectrum (ordinate axis: fluorescence intensity, abscissa axis: wavelength) of each of the samples was measured at a normal temperature (300K). In Examples, the fluorescence spectrum was measured using a spectrophotometer (F-7000 manufactured by Hitachi, Ltd.). It should be noted that the fluorescence spectrum measuring device may be different from the above device. A peak wavelength of the fluorescence spectrum exhibiting the maximum luminous intensity was defined as a main peak wavelength. Results are shown in Table 21.

The measurement results of the compounds RD and Ref-2 were as follows.

The main peak wavelength of the compound RD was 609 nm.

The main peak wavelength of the compound Ref-2 was 499 nm.

TABLE 21

| Com-pound | Molecular Weight | Weight Reduction Temperature (° C.) TG1% | Weight Reduction Temperature (° C.) TG5% | $S_1$ [eV] | λ [nm] |
|---|---|---|---|---|---|
| Example 1 | TADF1 | 954 | 399 | 441 | 2.37 | 558 |
| Example 2 | TADF2 | 954 | 412 | 462 | 2.42 | 550 |
| Example 3 (Example 6) | TADF3 | 954 | 384 | 437 | 2.48 | 538 |
| Example 4 | TADF4 | 1119 | 462 | 509 | 2.45 | 545 |
| Example 5 | TADF5 | 1119 | 473 | 528 | 2.36 | 571 |
| Comparative 1 | Ref-1 | 1450 | 495 | 561 | 2.41 | 555 |
| Comparative 3 | Ref-3 | 1149 | 493 | 540 | 2.44 | 536 |

Description about Table

"TG1%" represents a 1%-weight reduction temperature.

"TG5%" represents a 5%-weight reduction temperature.

The compounds TADF1 to TADF5 in Examples 1 to 5 exhibited lower 1%-weight reduction temperature and 5%-weight reduction temperature than the compounds Ref-1 and Ref-3 in Comparatives 1 and 3.

The compounds TADF1 to TADF5 in Examples 1 to 5 and the compound Ref-1 were sublimated and purified under high vacuum (in a range from $1.0 \times 10^{-6}$ to $1.0 \times 10^{-3}$ Pa).

Since all of the compounds TADF1 to TADF5 in Examples 1 to 5 exhibited the lower 1%-weight reduction temperature and 5%-weight reduction temperature than the compound Ref-1, the sublimation temperature of each of the compounds TADF1 to TADF5 in Examples 1 to 5 was estimated to be lower than the sublimation temperature of the compound formed by bonding four groups each represented by one of the formulae (1-1) to (1-6) to a benzene ring of dicyanobenzene.

It should be noted that the compound Ref-1 of Comparative 1 was decomposed during sublimation purification, resulting in no sublimation purification. It is estimated from this result that the compound Ref-1 of Comparative 1 has a higher sublimation temperature than the compounds TADF1 to TADF5 in Examples 1 to 5.

Moreover, the value of $X_D/X_P$ of each of the compounds TADF1 to TADF5 in Examples 1 to 5 was 0.05 or more.

Therefore, according to Examples, the compound capable of decreasing the sublimation temperature when the compound is sublimated and purified, while maintaining the TADF properties, was obtained.

The compounds in TADF1 to TADF5 in Examples 1 to 5 and the compound Ref-1 in Comparative 1 were manufactured as follows.

Example 1

(1) Synthesis Example 1: Synthesis of Compound TADF1

(1-1) Synthesis of Intermediate A

[Formula 170]

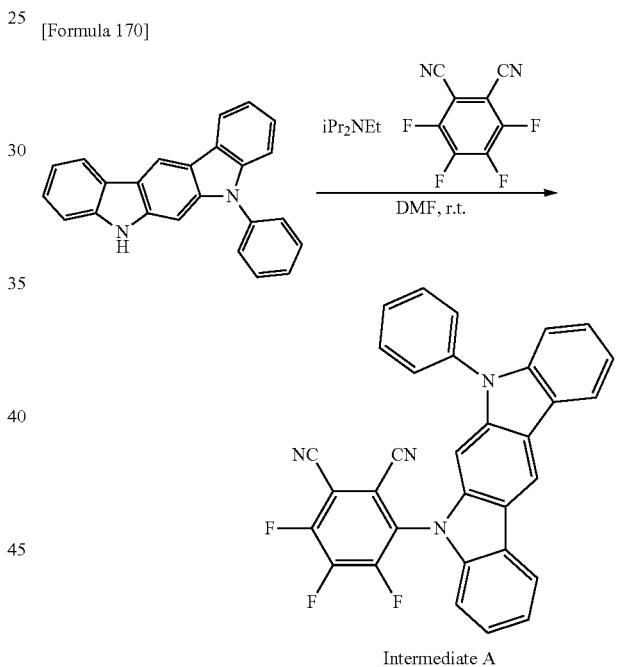

Intermediate A

Under nitrogen atmosphere, into a 300-mL three-necked flask, 5,7-dihydro-5-phenyl-Indolo[2,3-b]carbazole (8.3 g, 25 mmol), N,N-diisopropylethylamine(iPr₂NEt) (5 g, 37 mmol), tetrafluorophthalonitrile (10 g, 50 mmol), and N,N-dimethyl formamide (DMF) (120 mL) were put, and stirred at the room temperature (25 degrees C.) for 10 hours, subsequently to which 100-mL water was added. The deposited solid was purified by silica-gel column chromatography to obtain an orange solid (11.2 g). The obtained solid was identified as an intermediate according to by ASAP-MS (Atmospheric Pressure Solid Analysis Probe Mass Spectrometry) (a yield rate: 88%). In the scheme, "r.t." represents the room temperature.

(1-2) Synthesis of TADF1

[Formula 171]

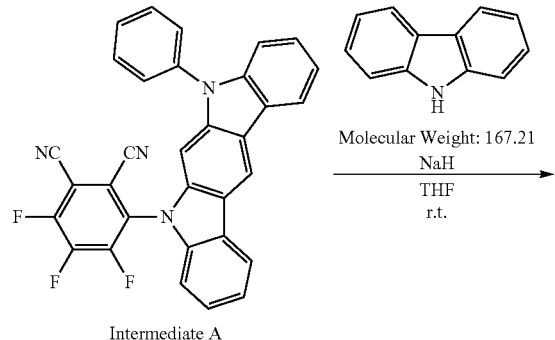

Intermediate A

(2) Synthesis Example 2: Synthesis of Compound TADF2

(2-1) Synthesis of Intermediate B

[Formula 172]

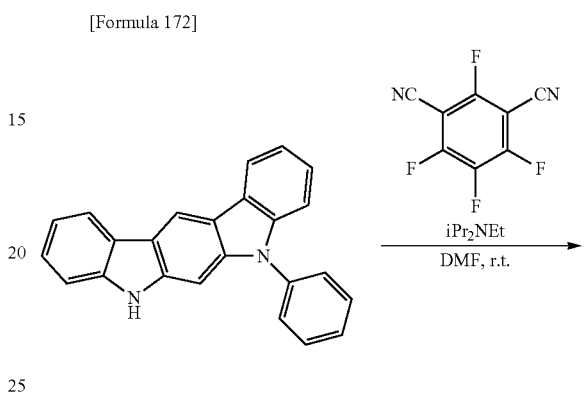

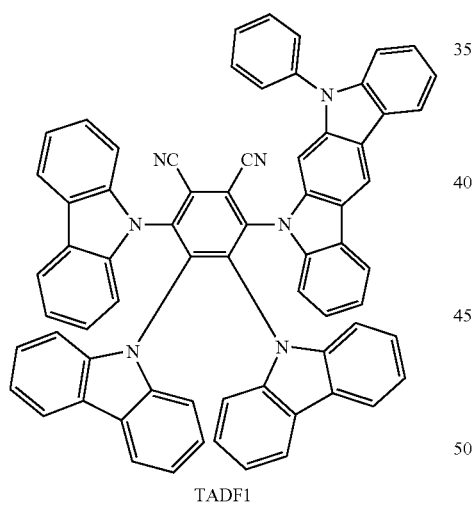

TADF1

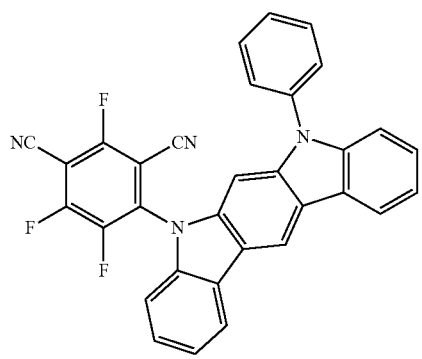

Intermediate B

Under nitrogen atmosphere, into a 100-mL three-necked flask, carbazole (3.3 g, 19.7 mmol), sodium hydride (containing oil at 40 mass %) (0.79 g, 19.7 mmol), and tetrahydrofuran (THF) (100 mL) were put, and stirred at the room temperature (25 degrees C.) for 30 minutes. Next, the intermediate A (2.6 g, 5.0 mmol) was put into the flask. Two hours later, the reaction mixture was added to 100-mL water. The deposited solid was purified by silica-gel column chromatography to obtain an orange solid (3.19 g). The obtained solid was identified as TADF1 by analysis according to ASAP-MS (a yield rate: 67%).

Under nitrogen atmosphere, into a 300-mL three-necked flask, 5,7-dihydro-5-phenyl-Indolo[2,3-b]carbazole (8.3 g, 25 mmol), N,N-diisopropylethylamine(iPr$_2$NEt) (5 g, 37 mmol), tetrafluoroisophthalonitrile (10 g, 50 mmol), and N,N-dimethyl formamide (DMF) (120 mL) were put, and stirred at the room temperature (25 degrees C.) for 10 hours, subsequently to which 100-mL water was added. The deposited solid was purified by silica-gel column chromatography to obtain an orange solid (6.5 g). The obtained solid was identified as an intermediate B according to ASAP-MS (a yield rate: 51%).

(2-2) Synthesis of TADF2

[Formula 173]

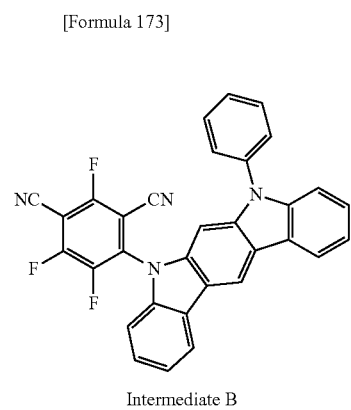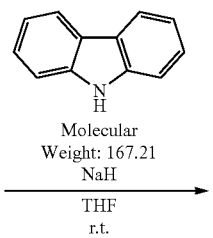

Intermediate B

Molecular Weight: 167.21
NaH
THF
r.t.

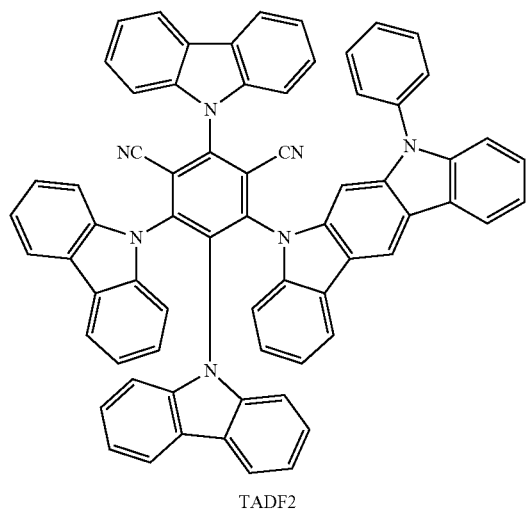

TADF2

Under nitrogen atmosphere, into a 100-mL three-necked flask, carbazole (1.7 g, 10 mmol), sodium hydride (containing oil at 40 mass %)(0.40 g, 10 mmol), and tetrahydrofuran (THF) (50 mL) were put, and stirred at the room temperature (25 degrees C.) for 30 minutes. Next, the intermediate B (1.3 g, 2.5 mmol) was put into the flask. Two hours later, the reaction mixture was added to 100-mL water. The deposited solid was purified by silica-gel column chromatography to obtain an orange solid (1.4 g). The obtained solid was identified as TADF2 by analysis according to ASAP-MS (a yield rate: 58.7%).

Example 3

(3) Synthesis Example 3: Synthesis of Compound TADF3

(3-1) Synthesis of Intermediate C

[Formula 174]

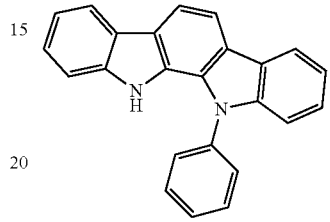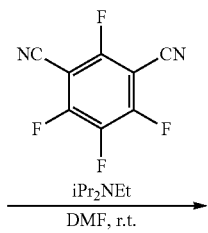

iPr₂NEt
DMF, r.t.

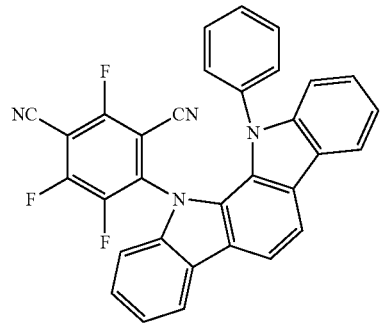

Intermediate C

Under nitrogen atmosphere, into a 300-mL three-necked flask, 11,12-dihydro-11-phenylindolo[2,3-a]carbazole (10 g, 30 mmol), N,N-diisopropylethylamine(iPr₂NEt) (8.2 g, 60 mmol), tetrafluoroisophthalonitrile (12 g, 60 mmol), and N,N-dimethyl formamide (DMF) (200 mL) were put, and stirred at the room temperature (25 degrees C.) for 6 hours, subsequently to which 100-mL water was added. The deposited solid was purified by silica-gel column chromatography to obtain an orange solid (9.7 g). The obtained solid was identified as an intermediate C according to ASAP-MS (a yield rate: 63%).

(3-2) Synthesis of TADF3

[Formula 175]

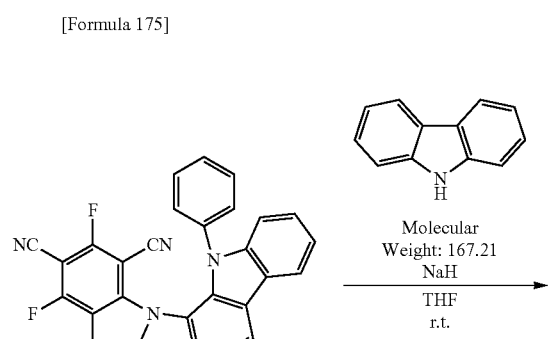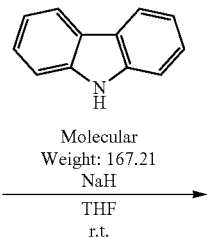

Intermediate C

Molecular Weight: 167.21
NaH
THF
r.t.

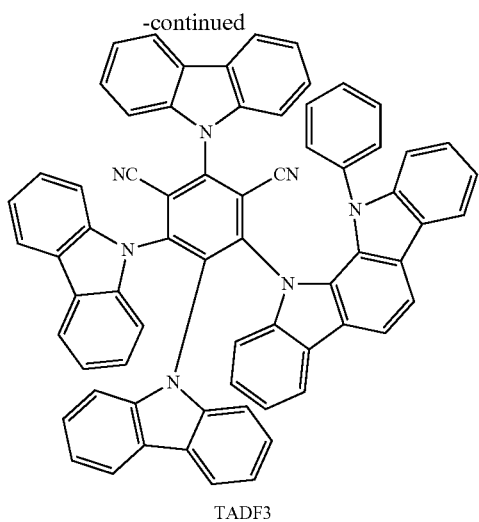

TADF3

Under nitrogen atmosphere, into a 100-mL three-necked flask, carbazole (1.7 g, 10 mmol), sodium hydride (containing oil at 40 mass %) (0.40 g, 10 mmol), and tetrahydrofuran (THF) (50 mL) were put, and stirred at the room temperature (25 degrees C.) for 30 minutes. Next, the intermediate C (1.3 g, 2.5 mmol) was put into the flask. Two hours later, the reaction mixture was added to 100-mL water. The deposited solid was purified by silica-gel column chromatography to obtain an orange solid (1.8 g). The obtained solid was identified as TADF3 by analysis according to ASAP-MS (a yield rate: 75%).

Example 4

(4) Synthesis Example 4: Synthesis of Compound TADF4

(4-1) Synthesis of Intermediate D

[Formula 176]

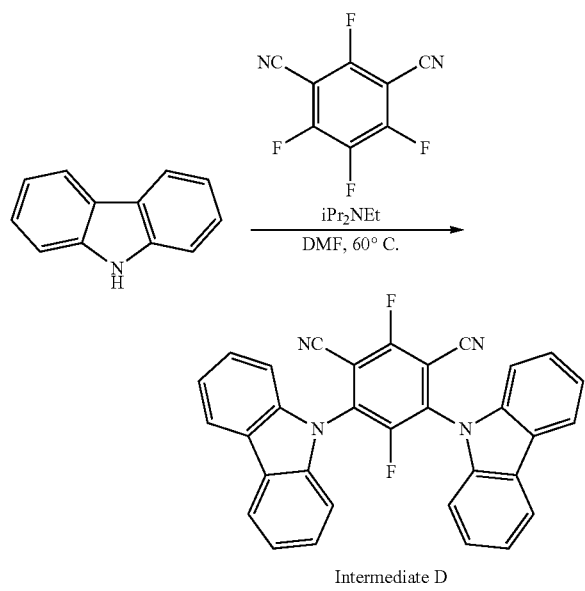

Intermediate D

Under nitrogen atmosphere, into a 500-mL three-necked flask, carbazole (17 g, 100 mmol), N,N-diisopropylethylamine(iPr$_2$NEt) (21 g, 150 mmol), tetrafluoroisophthalonitrile (8 g, 40 mmol), and N,N-dimethyl formamide (DMF) (200 mL) were put, and stirred at 60 degrees C. for 4 hours. Subsequently, the reaction mixture was added to 100-mL water. The deposited solid was purified by silica-gel column chromatography to obtain a yellow solid (7.5 g). The obtained solid was identified as an intermediate D by analysis according to ASAP-MS and $^1$H-NMR (a yield rate: 38%).

(4-2) Synthesis of TADF4

[Formula 177]

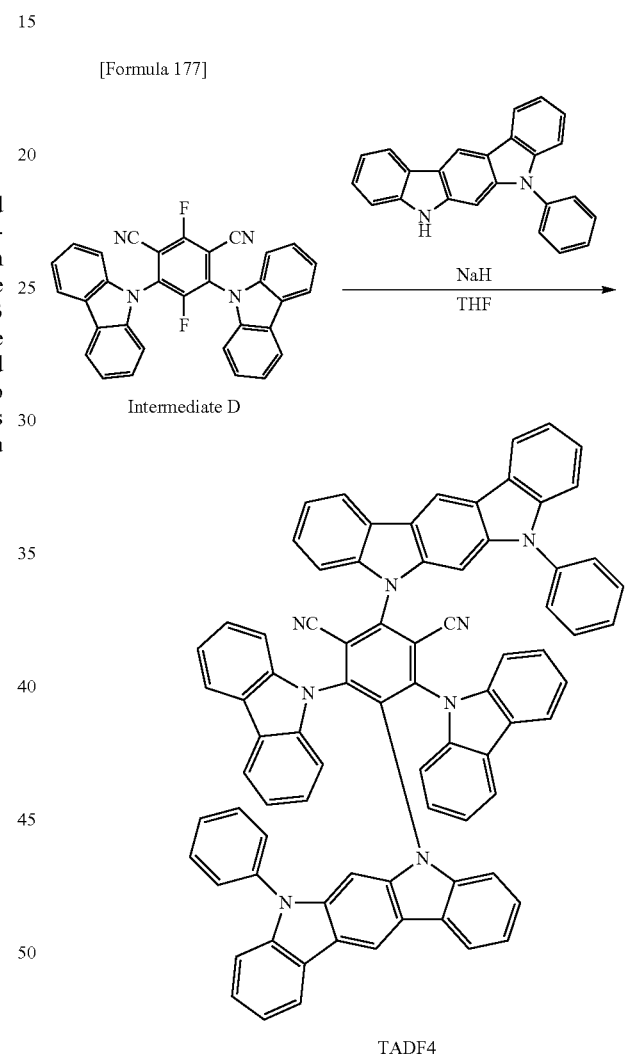

TADF4

Under nitrogen atmosphere, into a 100-mL three-necked flask, 5,7-dihydro-5-phenyl-Indolo[2,3-b]carbazole (2.5 g, 7.5 mmol), sodium hydride (containing oil at 40 mass %) (0.3 g, 7.5 mmol), and tetrahydrofuran (THF) (40 mL) were put, and stirred at the room temperature (25 degrees C.) for 30 minutes. Next, the intermediate D (1.4 g, 3 mmol) was put into the reaction mixture. Two hours later, the reaction mixture was added to 200-mL water. The deposited solid was purified by silica-gel column chromatography to obtain an orange solid (2.71 g). The obtained solid was identified as TADF4 by analysis according to ASAP-MS (a yield rate: 81%).

Example 5

(5) Synthesis Example 5: Synthesis of Compound TADF5

(5-1) Synthesis of TADF5

[Formula 178]

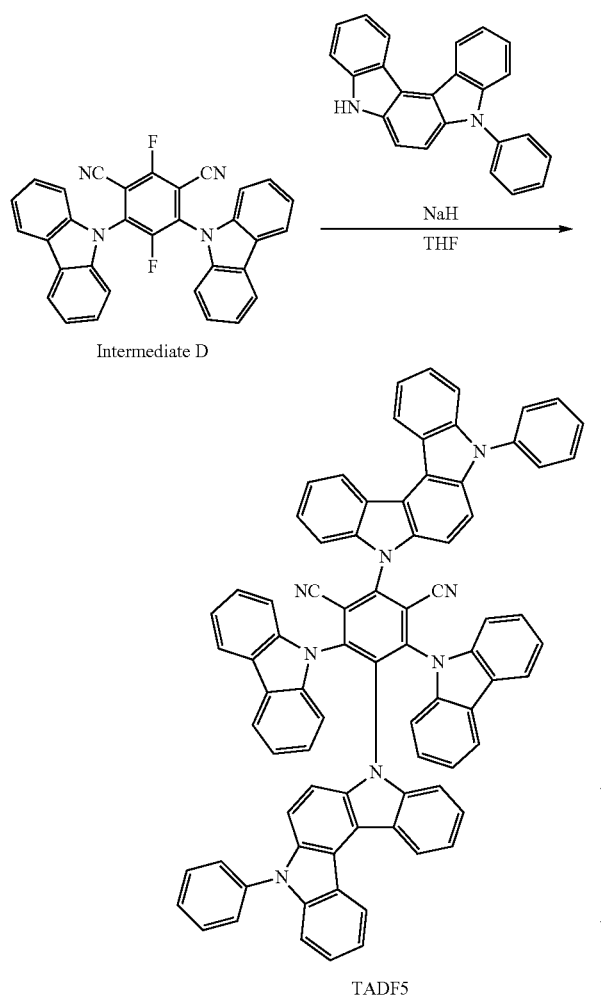

Intermediate D

TADF5

Under nitrogen atmosphere, into a 100-mL three-necked flask, 5-phenyl-5,8-dihydroindolo[2,3-c]carbazole (2.5 g, 7.5 mmol), sodium hydride (containing oil at 40 mass %) (0.3 g, 7.5 mmol), and tetrahydrofuran (THF) (40 mL) were put, and stirred at the room temperature (25 degrees C.) for 30 minutes. Next, the intermediate D (1.4 g, 3 mmol) was put into the reaction mixture. Two hours later, the reaction mixture was added to 200-mL water. The deposited solid was purified by silica-gel column chromatography to obtain an orange solid (1.7 g). The obtained solid was identified as TADF5 by analysis according to ASAP-MS (a yield rate: 54%).

Comparative 1

Under nitrogen atmosphere, into a 100-mL three-necked flask, 5,7-dihydro-5-phenyl-Indolo[2,3-b]carbazole (3.3 g, 10 mmol), sodium hydride (containing oil at 40 mass %) (0.4 g, 10 mmol), and tetrahydrofuran (THF) (50 mL) were put, and stirred at the room temperature (25 degrees C.) for 30 minutes. Next, tetrafluoroisophthalonitrile (0.44 g, 2.2 mmol) was put into the reaction mixture. Two hours later, the reaction mixture was added to 30-mL water. The deposited solid was purified by silica-gel column chromatography to obtain an orange solid (1.90 g). The obtained solid was identified as a compound Ref-1 by analysis according to ASAP-MS (a yield rate: 60%).

EXPLANATION OF CODE(S)

1 . . . organic EL device, 2 . . . substrate, 3 . . . anode, 4 . . . cathode, 5 . . . emitting layer, 6 . . . hole injecting layer, 7 . . . hole transporting layer, 8 . . . electron transporting layer, 9 . . . electron injecting layer.

The invention claimed is:
1. A compound represented by formulae (11) to (13) below,

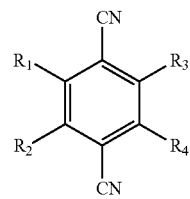
(11)

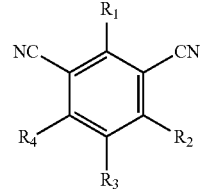
(12)

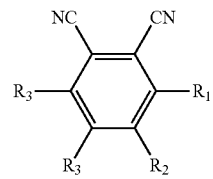
(13)

where: $R_1$ to $R_4$ each independently represent one of groups represented by formulae (1-1) to (1-6) below or one of groups represented by formulae (2-1) to (2-10) below; at least one of $R_1$ to $R_4$ is one of the groups represented by the formulae (1-1) to (1-6); and at least one of $R_1$ to $R_4$ is one of the groups represented by the formulae (2-1) to (2-10),

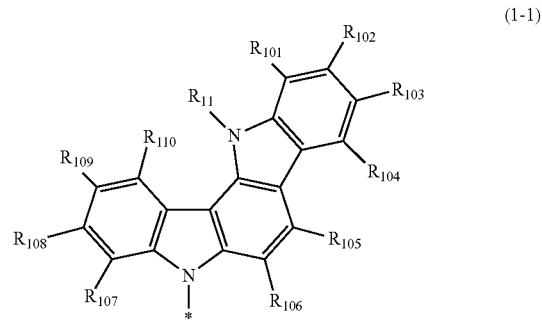
(1-1)

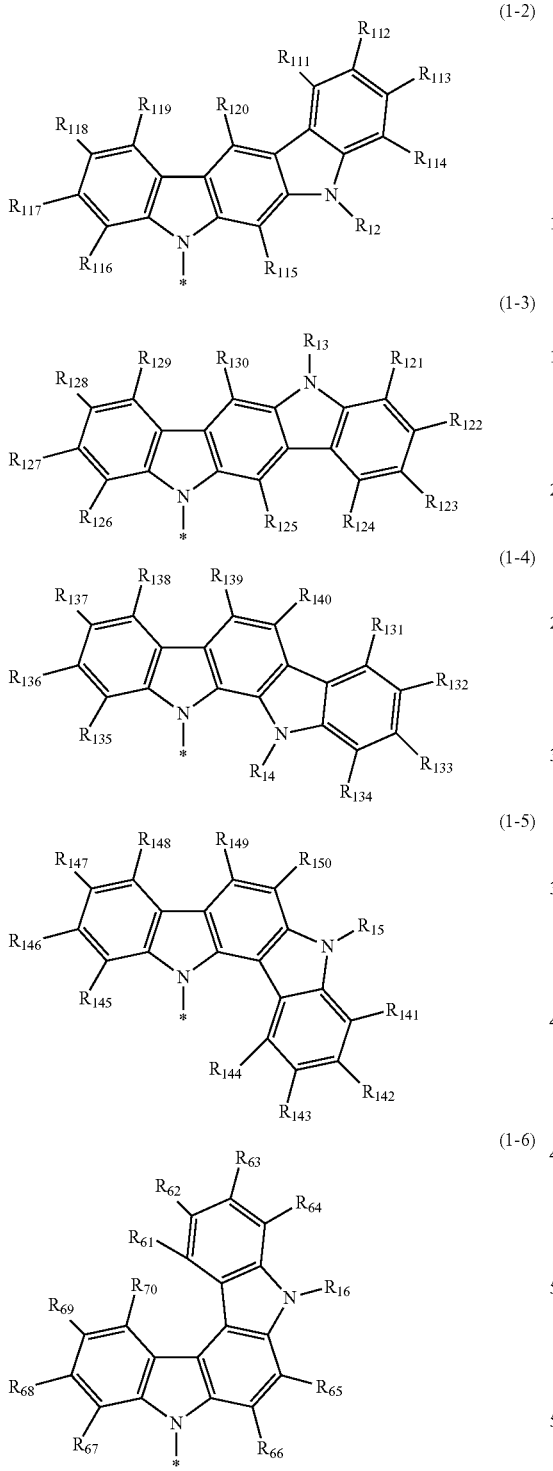

(1-2)

(1-3)

(1-4)

(1-5)

(1-6)

where: $R_{11}$ to $R_{16}$ are each a substituent; $R_{101}$ to $R_{150}$ and $R_{61}$ to $R_{70}$ are each independently a hydrogen atom or a substituent;

$R_{101}$ to $R_{150}$ and $R_{61}$ to $R_{70}$ as the substituent are each independently a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkysilyl group having 3 to 6 carbon atoms, a substituted or unsubstituted alkoxy group having 1 to 6 carbon atoms, a substituted or unsubstituted aryloxy group having 6 to 14 ring carbon atoms, a substituted or unsubstituted arylamino group having 6 to 28 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms;

$R_{11}$ to $R_{16}$ as the substituent are each independently a substituted or unsubstituted alkyl group having 1 to 6 carbon atoms, a substituted or unsubstituted aryl group having 6 to 14 ring carbon atoms, a substituted or unsubstituted heterocyclic group having 5 to 14 ring atoms, a substituted or unsubstituted alkysilyl group having 3 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms; and \* each independently represents a bonding position to a carbon atom of a benzene ring in each of the formulae (11) to (13),

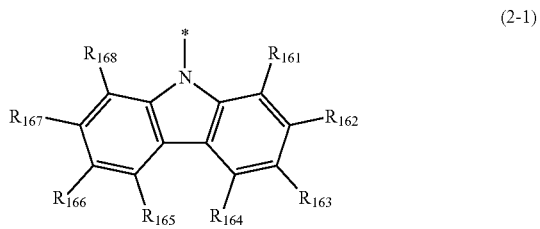

(2-1)

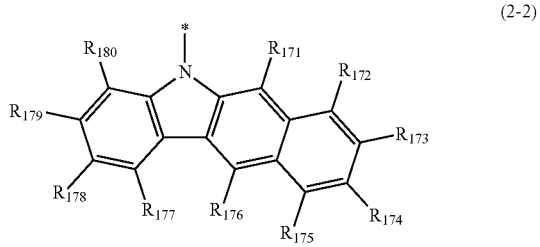

(2-2)

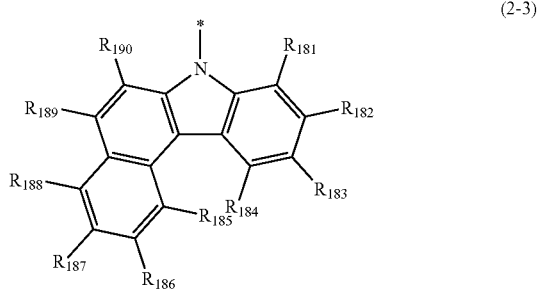

(2-3)

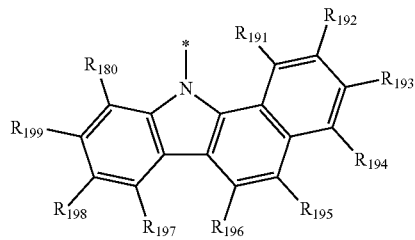

(2-4)

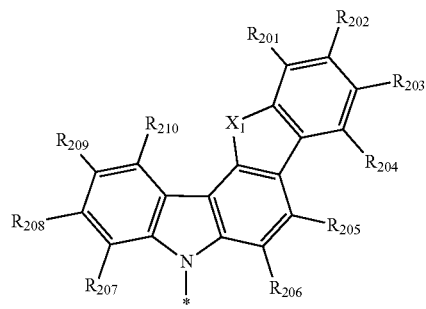

(2-5)

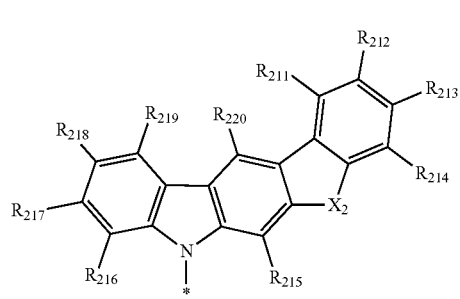

(2-6)

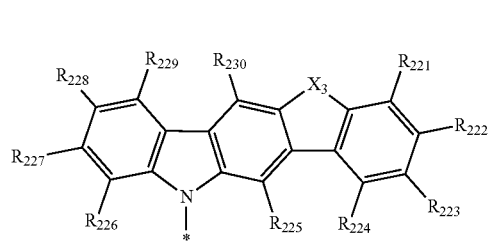

(2-7)

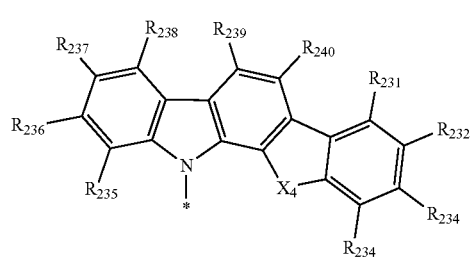

(2-8)

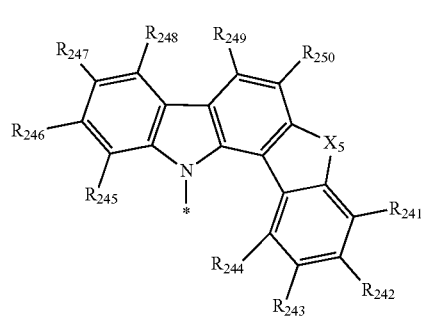

(2-9)

where: in the formula (2-1):

$R_{161}$ to $R_{168}$ each independently represent a hydrogen atom or a substituent;

$R_{161}$ to $R_{168}$ as the substituent each independently represent a halogen atom, a substituted or unsubstituted aryl group having 6 to 14 ring carbon atoms, a substituted or unsubstituted heterocyclic group having 5 to 14 ring atoms, a substituted or unsubstituted alkyl halide group having 1 to 6 carbon atoms, a substituted or unsubstituted alkysilyl group having 3 to 6 carbon atoms, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms;

in the formulae (2-2) to (2-4):

$R_{171}$ to $R_{200}$ each independently represent a hydrogen atom or a substituent;

$R_{171}$ to $R_{200}$ as the substituent are each independently a halogen atom, a substituted or unsubstituted awl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 6 carbon atoms, a substituted or unsubstituted alkysilyl group having 3 to 6 carbon atoms, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms; and

* each independently represents a bonding position to a carbon atom of a benzene ring in each of the formulae (11) to (13), and -continued (2-10)

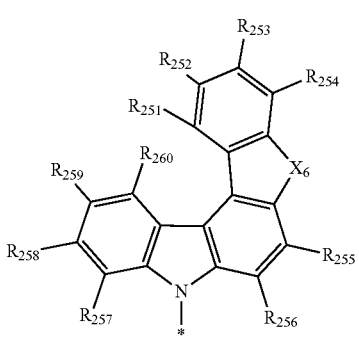

where: $X_1$ to $X_6$ each independently represent an oxygen atom, a sulfur atom, or $CR_{151}R_{152}$; $R_{201}$ to $R_{260}$ each independently represent a hydrogen atom or a substituent; and $R_{151}$ and $R_{152}$ each independently represent a hydrogen atom or a substituent or $R_{151}$ and $R_{152}$ are bonded to each other to form a ring;

$R_{201}$ to $R_{260}$, $R_{151}$ and $R_{152}$ as the substituent are each independently a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 6 carbon atoms, a substituted or unsubstituted alkysilyl group having 3 to 6 carbon atoms, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms; and

* each independently represents a bonding position to a carbon atom of a benzene ring in each of the formulae (11) to (13).

2. The compound according to claim 1, wherein
when three of the groups for $R_1$ to $R_4$ are represented by the formulae (1-1) to (1-6), all of the three groups are represented by one of the formulae (1-1) to (1-6) and are the same group including the substituent, and
when two of the groups for $R_1$ to $R_4$ are represented by the formulae (1-1) to (1-6), all of the two groups are represented by one of the formulae (1-1) to (1-6) and are the same group including the substituent.

3. The compound according to claim 1, wherein
when three of the groups for $R_1$ to $R_4$ are represented by the formulae (2-1) to (2-10), all of the three groups are represented by one of the formulae (2-1) to (2-10) and are the same group including the substituent, and
when two of the groups for $R_1$ to $R_4$ are represented by the formulae (2-1) to (2-10), all of the two groups are represented by one of the formulae (2-1) to (2-10) and are the same group including the substituent.

4. The compound according to claim 1, wherein
each of the groups that are to be represented by one of the formulae (1-1) to (1-6) is represented by the formula (1-1), (1-2), (1-4), (1-5), or (1-6).

5. The compound according to claim 1, wherein
$R_{101}$ to $R_{150}$ and $R_{61}$ to $R_{70}$ as the substituent are each independently an unsubstituted aryl group having 6 to 14 ring carbon atoms, an unsubstituted heterocyclic group having 5 to 14 ring atoms, an unsubstituted alkyl group having 1 to 6 carbon atoms, an unsubstituted alkoxy group having 1 to 6 carbon atoms, an unsubstituted aryloxy group having 6 to 14 ring carbon atoms, an unsubstituted arylamino group having 6 to 28 ring carbon atoms, or an unsubstituted alkylamino group having 2 to 12 carbon atoms,
$R_{11}$ to $R_{16}$ as the substituent are each independently an unsubstituted aryl group having 6 to 14 ring carbon atoms or an unsubstituted heterocyclic group having 5 to 14 ring atoms,
$R_{161}$ to $R_{168}$ as the substituent each independently represent a halogen atom, an unsubstituted aryl group having 6 to 14 ring carbon atoms, an unsubstituted heterocyclic group having 5 to 14 ring atoms, an unsubstituted alkyl halide group having 1 to 6 carbon atoms, an unsubstituted alkoxy group having 1 to 6 carbon atoms, an unsubstituted alkoxy halide group having 1 to 6 carbon atoms, an unsubstituted aryloxy group having 6 to 14 ring carbon atoms, or an unsubstituted alkylamino group having 2 to 12 carbon atoms,
$R_{171}$ to $R_{260}$ as the substituent are each independently a halogen atom, an unsubstituted aryl group having 6 to 14 ring carbon atoms, an unsubstituted heterocyclic group having 5 to 14 ring atoms, an unsubstituted alkyl group having 1 to 6 carbon atoms, an unsubstituted alkyl halide group having 1 to 6 carbon atoms, an unsubstituted alkoxy group having 1 to 6 carbon atoms, an unsubstituted alkoxy halide group having 1 to 6 carbon atoms, an unsubstituted aryloxy group having 6 to 14 ring carbon atoms, or an unsubstituted alkylamino group having 2 to 12 carbon atoms, and
$R_{151}$ and $R_{152}$ as the substituent are each independently an unsubstituted aryl group having 6 to 14 ring carbon atoms, or an unsubstituted alkyl group having 1 to 6 carbon atoms.

6. The compound according to claim 1, wherein
$R_{101}$ to $R_{150}$ and $R_{61}$ to $R_{70}$ as the substituent are each independently an unsubstituted aryl group having 6 to 14 ring carbon atoms or an unsubstituted alkyl group having 1 to 6 carbon atoms,
$R_{11}$ to $R_{16}$ as the substituent are each independently an unsubstituted aryl group having 6 to 14 ring carbon atoms or an unsubstituted heterocyclic group having 5 to 14 ring atoms,
$R_{161}$ to $R_{168}$ as the substituent are each independently an unsubstituted aryl group having 6 to 14 ring carbon atoms, and
$R_{171}$ to $R_{260}$, $R_{151}$ and $R_{152}$ as the substituent are each independently an unsubstituted aryl group having 6 to 14 ring carbon atoms or an unsubstituted alkyl group having 1 to 6 carbon atoms.

7. The compound according to claim 1, wherein
$R_{101}$ to $R_{150}$ and $R_{61}$ to $R_{70}$ are each a hydrogen atom,
$R_{11}$ to $R_{16}$ as the substituent are each independently an unsubstituted aryl group having 6 to 14 ring carbon atoms or an unsubstituted heterocyclic group having 5 to 14 ring atoms,
$R_{161}$ to $R_{168}$ each are a hydrogen atom,
$R_{171}$ to $R_{260}$ each are a hydrogen atom, and
$R_{151}$ and $R_{152}$ as the substituent are each independently an unsubstituted aryl group having 6 to 14 ring carbon atoms or an unsubstituted alkyl group having 1 to 6 carbon atoms.

8. The compound according to claim 1, wherein
each of the groups that are to be represented by the formulae (2-1) to (2-10) is one of the groups represented by the formulae (2-2) to (2-10).

9. The compound according to claim 8, wherein
each of the groups that are to be represented by the formulae (2-1) to (2-10) is the group represented by the formula (2-2), the group represented by the formula (2-3), or the group represented by the formula (2-4).

10. The compound according to claim 1, wherein
all of the groups that are to be represented by the formulae (2-1) to (2-10) are the groups represented by the formula (2-1).

11. The compound according to claim 1, wherein
the compound is represented by one of formulae (101), (103), (106) to (108), (110) to (112), (116) to (119), and (121) below,

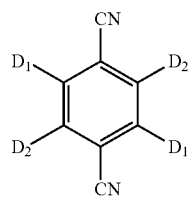
(101)

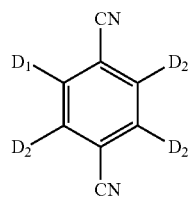
(103)

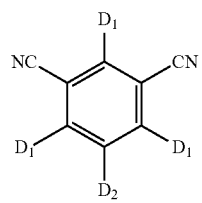
(106)

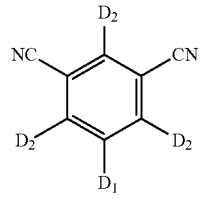
(107)

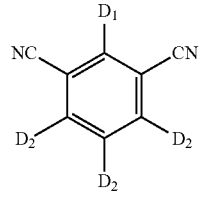
(108)

-continued

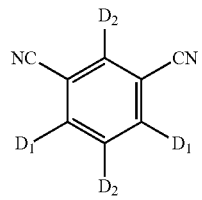
(110)

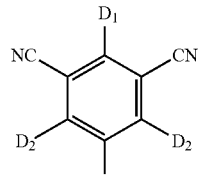
(111)

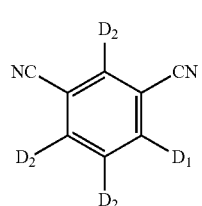
(112)

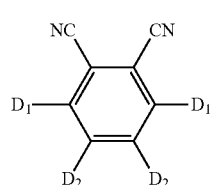
(116)

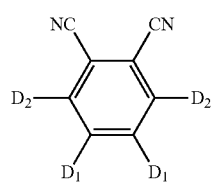
(117)

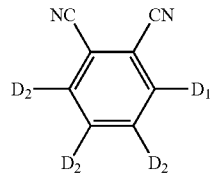
(118)

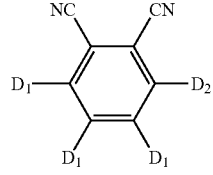
(119)

(121)

where: in the formulae (101), (103), (106) to (108), (110) to (112), (116) to (119) and (121):

$D_1$ is each independently the group represented by one of the formulae (1-1), (1-2), (1-4), (1-5), and (1-6);

$D_2$ is each independently the group represented by one of formulae (2A-1) to (2A-6) below; a plurality of $D_1$ are mutually the same or different; and a plurality of $D_2$ are mutually the same or different, and

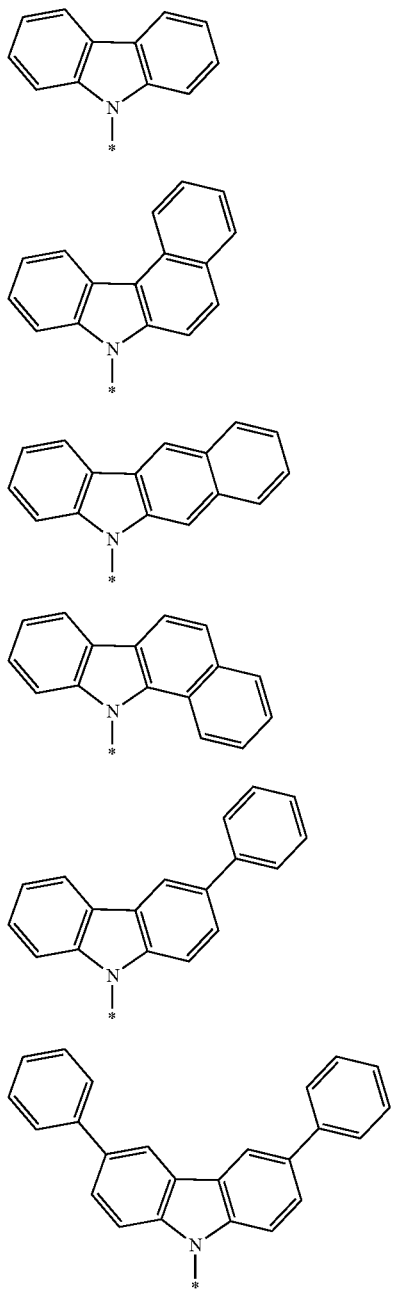

where: in the formulae (2A-1) to (2A-6):
* each independently represents a bonding position to a carbon atom of a benzene ring in each of the formulae (11) to (13).

12. The compound according to claim 11, wherein the compound is represented by the formula (103), (107), (108), (112), (118), or (121).

13. The compound according to claim 11, wherein $D_2$ is the group represented by the formula (2A-1).

14. The compound according to claim 1, wherein the compound is represented by the formula (11).

15. The compound according to claim 1, wherein the compound is represented by the formula (12).

16. The compound according to claim 1, wherein the compound is represented by the formula (13).

17. The compound according to claim 1, wherein in a calculation of a sum of an atomic weight of atoms forming each of $R_1$ to $R_4$, a minimum sum M1(min) among the sums of the groups corresponding to the groups represented by the formulae (1-1) to (1-6) and a maximum sum M2(max) among the sums of the groups corresponding to the groups represented by the formulae (2-1) to (2-10) satisfy a relationship represented by a numerical formula (Numerical Formula 1) below, $$M1(\text{min}) > M2(\text{max}) \quad \text{(Numerical Formula 1).}$$

18. An organic-electroluminescence-device material comprising the compound according to claim 1.

19. An organic electroluminescence device comprising:
an anode;
a cathode; and
a first organic layer provided between the anode and the cathode, wherein the first organic layer contains a first compound, and the first compound is the compound according to claim 1.

20. The organic electroluminescence device according to claim 19, wherein
the first organic layer is an emitting layer.

21. The organic electroluminescence device according to claim 19, wherein
the first organic layer comprises a second compound in addition to the first compound, and
the second compound is a fluorescent compound.

22. The organic electroluminescence device according to claim 21, wherein
the first organic layer comprises a third compound in addition to the first compound and the second compound, and
a singlet energy $S_1$(Mat1) of the first compound and a singlet energy $S_1$(Mat3) of the third compound satisfy a relationship of a numerical formula (Numerical Formula 2) below, $$S_1(\text{Mat3}) > S_1(\text{Mat1}) \quad \text{(Numerical Formula 2).}$$

23. The organic electroluminescence device according to claim 21, wherein
the second compound is a compound represented by a formula (20) below, and
a singlet energy $S_1$(Mat1) of the first compound and a singlet energy $S_1$(Mat2) of the second compound satisfy a relationship of a numerical formula (Numerical Formula 3) below, $$S_1(\text{Mat1}) > S_1(\text{Mat2}) \quad \text{(Numerical Formula 3),}$$

(20)

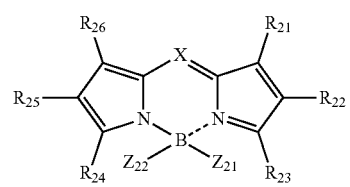

where: X is a nitrogen atom, or a carbon atom bonded to Y;

Y is a hydrogen atom or a substituent; $R_{21}$ to $R_{26}$ are each independently a hydrogen atom or a substituent, or at least one of a pair of $R_{21}$ and $R_{22}$, a pair of $R_{22}$ and $R_{23}$, a pair of $R_{24}$ and $R_{25}$, or a pair of $R_{25}$ and $R_{26}$ are mutually bonded to form a ring;

Y and $R_{21}$ to $R_{26}$ each being the substituent are each independently selected from the group consisting of a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, a substituted or unsubstituted alkylthio group having 1 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted alkenyl group having 2 to 30 carbon atoms, a substituted or unsubstituted aralkyl group having 7 to 30 carbon atoms, a substituted or unsubstituted heteroaryl group having 5 to 30 ring atoms, a halogen atom, a carboxy group, a substituted or unsubstituted ester group, a substituted or unsubstituted carbamoyl group, a substituted or unsubstituted amino group, a nitro group, a cyano group, a substituted or unsubstituted silyl group, and a substituted or unsubstituted siloxanyl group;

$Z_{21}$ and $Z_{22}$ are each independently a substituent, or are mutually bonded to form a ring; and $Z_{21}$ and $Z_{22}$ as the substituent are each independently selected from the group consisting of a halogen atom, a substituted or unsubstituted alkyl group having 1 to 30 carbon atoms, a substituted or unsubstituted alkyl halide group having 1 to 30 carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, and a substituted or unsubstituted aryloxy group having 6 to 30 ring carbon atoms.

24. The organic electroluminescence device according to claim 21, wherein
the second compound has a main peak wavelength in a range from 600 nm to 660 nm.

25. The organic electroluminescence device according to claim 21, wherein
the second compound has a main peak wavelength in a range from 500 nm to 560 nm.

26. The organic electroluminescence device according to claim 19, wherein
the first organic layer comprises a fourth compound in addition to the first compound, and
a singlet energy $S_1(Mat1)$ of the first compound and a singlet energy $S_1(Mat4)$ of the fourth compound satisfy a relationship of a numerical formula (Numerical Formula 4) below, $$S_1(Mat4) > S_1(Mat1) \qquad \text{(Numerical Formula 4)}.$$

27. The organic electroluminescence device according to claim 19, wherein
the first organic layer does not comprise a metal complex.

28. The organic electroluminescence device according to claim 19, wherein
the first compound is a delayed fluorescent compound.

29. An electronic device comprising the organic electroluminescence device according to claim 19.

* * * * *